United States Patent
Su et al.

(10) Patent No.: US 10,512,645 B2
(45) Date of Patent: Dec. 24, 2019

(54) CERTAIN TRIAZOLOPYRIDINES AND TRIAZOLOPYRAZINES, COMPOSITIONS THEREOF AND METHODS OF USE THEREFOR

(71) Applicant: Hutchison Medipharma Limited, Shanghai (CN)

(72) Inventors: Wei-Guo Su, Shanghai (CN); Hong Jia, Shanghai (CN); Guangxiu Dai, Shanghai (CN)

(73) Assignee: Hutchinson Medipharma Limited, Shanghai (CN)

(*) Notice: Subject to any disclaimer, the term of this patent is extended or adjusted under 35 U.S.C. 154(b) by 0 days.

(21) Appl. No.: 15/945,324

(22) Filed: Apr. 4, 2018

(65) Prior Publication Data

US 2018/0263977 A1  Sep. 20, 2018

Related U.S. Application Data

(63) Continuation of application No. 15/293,722, filed on Oct. 14, 2016, now Pat. No. 9,956,218, which is a continuation of application No. 14/601,674, filed on Jan. 21, 2015, now abandoned, which is a continuation of application No. 13/501,222, filed as application No. PCT/CN2010/080499 on Dec. 30, 2010, now Pat. No. 8,987,269.

(30) Foreign Application Priority Data

Dec. 31, 2009  (WO) ............... PCT/CN2009/076321

(51) Int. Cl.

| A61K 31/437 | (2006.01) |
| A61K 31/4985 | (2006.01) |
| C07D 471/04 | (2006.01) |
| C07D 487/04 | (2006.01) |
| C07D 519/00 | (2006.01) |
| A61K 31/4709 | (2006.01) |
| A61K 31/5025 | (2006.01) |
| A61K 31/519 | (2006.01) |
| A61K 31/5377 | (2006.01) |
| A61K 45/06 | (2006.01) |
| A61K 31/4375 | (2006.01) |
| A61K 31/4545 | (2006.01) |

(52) U.S. Cl.
CPC ........ *A61K 31/4985* (2013.01); *A61K 31/437* (2013.01); *A61K 31/4375* (2013.01); *A61K 31/4545* (2013.01); *A61K 31/4709* (2013.01); *A61K 31/5025* (2013.01); *A61K 31/519* (2013.01); *A61K 31/5377* (2013.01); *A61K 45/06* (2013.01); *C07D 471/04* (2013.01); *C07D 487/04* (2013.01); *C07D 519/00* (2013.01)

(58) Field of Classification Search
CPC ............... A61K 31/437; C07D 471/04

USPC .......................................... 514/300; 544/117
See application file for complete search history.

(56) References Cited

U.S. PATENT DOCUMENTS

| 8,507,487 B2 | 8/2013 | Su et al. |
| 2007/0265272 A1 | 11/2007 | Cheng et al. |
| 2010/0298315 A1 | 11/2010 | Albert et al. |
| 2011/0135600 A1 | 6/2011 | Stieber et al. |
| 2011/0281865 A1 | 11/2011 | Muthuppalaniappan et al. |
| 2012/0245178 A1 | 9/2012 | Su et al. |
| 2015/0368271 A1 | 12/2015 | Su et al. |

FOREIGN PATENT DOCUMENTS

| WO | 2004/092177 A1 | 10/2004 |
| WO | 2005/004607 A1 | 1/2005 |
| WO | 2005/010005 A1 | 2/2005 |
| WO | 2005/028480 A2 | 3/2005 |
| WO | 2006/015123 A1 | 2/2006 |
| WO | 2006/018735 A2 | 2/2006 |
| WO | 2006/087538 A1 | 8/2006 |
| WO | 2007/064797 A2 | 6/2007 |
| WO | 2007/075567 A1 | 7/2007 |
| WO | 2007/132308 A1 | 11/2007 |
| WO | 2007/138472 A2 | 12/2007 |
| WO | 2008/008539 A2 | 1/2008 |
| WO | 2008/021781 A1 | 2/2008 |
| WO | 2008/036272 A1 | 3/2008 |
| WO | 2008/051808 A2 | 5/2008 |
| WO | 2008/064157 A1 | 5/2008 |
| WO | 2008/124848 A1 | 10/2008 |
| WO | 2008/138842 A1 | 11/2008 |
| WO | 2009/056692 A2 | 5/2009 |
| WO | 2009/091374 A2 | 5/2009 |
| WO | 2009/106577 A1 | 9/2009 |
| WO | 2009/143477 A1 | 11/2009 |
| WO | 2010/017870 A1 | 2/2010 |
| WO | 2010/019899 A1 | 2/2010 |
| WO | 2011/020861 A1 | 2/2011 |

OTHER PUBLICATIONS

Diamond et al., "Species-Specific Metabolism of SGX523 by Aldehyde Oxidase and the Toxicological Implications", Drug Metabolism and Disposition, 2010, pp. 1277-1285, vol. 38, No. 8.
Jiang et al., "Hepatocyte growth factor/scatter factor, its molecular, cellular and clinical implications in cancer", Critical Reviews in Oncology/Haematology, 1999, pp. 209-248, vol. 29.
Ma et al, "c-Met: Structure, functions and potential for therapeutic inhibition", Cancer and Metastasis Review, 2003, pp. 309-325, vol. 22.
Ma et al., "c-Met Mutational Analysis in Small Cell Lung Cancer: Novel Juxtamembrane Domain Mutations Regulating Cytoskeletal Functions", Cancer Research, 2003, pp. 6272-6281, vol. 63.
Maulik et al., "Role of the hepatocyte growth factor receptor, c-Met, in oncogenesis and potential for therapeutic inhibition", Cytokine & Growth Factor Reviews, 2002, pp. 41-59, vol. 13.

*Primary Examiner* — Jeffrey H Murray
(74) *Attorney, Agent, or Firm* — Meaghan Richmond

(57) ABSTRACT

Provided are certain triazolopyridines and triazolopyrazines, compositions thereof and methods of use therefor.

18 Claims, No Drawings

CERTAIN TRIAZOLOPYRIDINES AND TRIAZOLOPYRAZINES, COMPOSITIONS THEREOF AND METHODS OF USE THEREFOR

This application is a continuation of U.S. patent application Ser. No. 15/293,722 filed Oct. 14, 2016 which is a continuation of U.S. patent application Ser. No. 14/601,674, filed Jan. 21, 2015 (abandoned), which is a continuation of U.S. patent application Ser. No. 13/501,222, filed Jun. 18, 2012 (now granted as U.S. Pat. No. 8,987,269), which is a national stage application under 35 U.S.C. § 371 of International Application No. PCT/CN2010/080499, filed Dec. 30, 2010, which claims priority to PCT/CN2009/076321, filed Dec. 31, 2009. This application is also related to U.S. patent application Ser. No. 13/501,224, filed Apr. 10, 2012, now U.S. Pat. No. 8,507,487, issued Aug. 13, 2013. The contents of each of the foregoing applications are hereby incorporated by reference in their entirety.

The c-Met protein, also known as the hepatocyte growth factor (HGF) receptor, is a transmembrane 190 kDa heterodimer with tyrosine kinase activity, encoded by the c-met oncogene. The HGF/c-Met signalling pathway has been shown to demonstrate various cellular responses, including mitogenic, proliferative, morphogenic and angiogenic activities. The inhibition of the HGF/c-Met pathway has significant potential for the treatment of cancer.

Provided is at least one compound of formula 1:

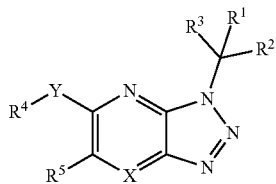

and/or at least one pharmaceutically acceptable salt thereof wherein

X is N, Y is selected from —O—, —S—, and —N($R^7$)— and $R^1$ is selected from aryl and heteroaryl, each of which is optionally substituted with one or more groups selected from halo, —$CF_3$, —$CF_2H$, cycloalkyl, —C(O)$R^{11}$, —C(O)O$R^{11}$, —CN, —C(O)N$R^{13}R^{14}$, —N$R^{13}R^{14}$, —N$R^{13}$C(O)$R^{11}$, —N$R^{13}$S(O)$_n R^{12}$, —N$R^{13}$S(O)$_n$N$R^{13}R^{14}$, —N$R^{13}$C(O)O$R^{12}$, —N$R^{13}$C(O)N$R^{13}R^{14}$, —$NO_2$, —S(O)$_n R^{12}$, —S(O)$_n$N$R^{13}R^{14}$, heterocycle, heteroaryl, aryl, alkenyl, alkynyl, lower alkyl, lower alkyl substituted with hydroxy, lower alkyl substituted with lower alkoxy, lower alkyl substituted with —N$R^{13}R^{14}$, and lower alkyl substituted with heterocycle; or X is N, Y is absent and $R^1$ is a fused bicyclic heteroaryl optionally substituted with one or more groups selected from halo, —$CF_3$, —$CF_2H$, cycloalkyl, —C(O)$R^{11}$, —C(O)O$R^{11}$, —CN, —C(O)N$R^{13}R^{14}$, —N$R^{13}R^{14}$, —N$R^{13}$C(O)$R^{11}$, —N$R^{13}$S(O)$_n R^{12}$, —N$R^{13}$S(O)$_n$N$R^{13}R^{14}$, —N$R^{13}$C(O)O$R^{12}$, —N$R^{13}$C(O)N$R^{13}R^{14}$, —$NO_2$, —S(O)$_n R^{12}$, —S(O)$_n$N$R^{13}R^{14}$, heterocycle, heteroaryl, aryl, alkenyl, alkynyl, lower alkyl, lower alkyl substituted with hydroxy, lower alkyl substituted with lower alkoxy, lower alkyl substituted with —N$R^{13}R^{14}$, and lower alkyl substituted with heterocycle; or X is C($R^6$), Y is selected from —O—, —S—, and —N($R^7$)— or Y is absent, and $R^1$ is heteroaryl optionally substituted with one or more groups selected from halo, —$CF_3$, —$CF_2H$, cycloalkyl, —C(O)$R^{11}$, —C(O)O$R^{11}$, —CN, —C(O)N$R^{13}R^{14}$, —N$R^{13}R^{14}$, —N$R^{13}$C(O)$R^{11}$, —N$R^{13}$S(O)$_n R^{12}$, —N$R^{13}$S(O)$_n$N$R^{13}R^{14}$, —N$R^{13}$C(O)O$R^{12}$, —N$R^{13}$C(O)N$R^{13}R^{14}$, —$NO_2$, —S(O)$_n R^{12}$, —S(O)$_n$N$R^{13}R^{14}$, heterocycle, heteroaryl, aryl, alkenyl, alkynyl, lower alkyl, lower alkyl substituted with hydroxy, lower alkyl substituted with lower alkoxy, lower alkyl substituted with —N$R^{13}R^{14}$, and lower alkyl substituted with heterocycle;

$R^2$ and $R^3$ are independently selected from hydrogen and alkyl, or $R^2$ and $R^3$, together with the carbon to which they are attached, form a ring chosen from 3- to 7-membered cycloalkyl and 3- to 7-membered heterocycle;

$R^4$ is selected from halo, alkyl, cycloalkyl, heterocycle, aryl and heteroaryl, each of which, except for halo, is optionally substituted with one or more groups selected from
  lower alkyl optionally substituted with one or more groups selected from hydroxy, lower alkoxy, cyano, halo, —C(O)O$R^{11}$, —C(O)N$R^{13}R^{14}$, —N$R^{13}R^{14}$, —OC(O)$R^{11}$, —N$R^{13}$C(O)$R^{11}$, —N$R^{13}$S(O)$_n R^{12}$, —N$R^{13}$S(O)$_n$N$R^{13}R^{14}$, —N$R^{13}$C(O)O$R^{12}$, and —N$R^{13}$C(O)N$R^{13}R^{14}$,
  lower alkoxy optionally substituted with one or more groups selected from halo, hydroxy, and lower alkoxy,
  cycloalkoxy optionally substituted with one or more groups selected from halo, hydroxy, and lower alkoxy,
  heterocycloalkoxy optionally substituted with one or more groups selected from halo, hydroxy, and lower alkoxy,
  heterocycle optionally substituted with one or more groups selected from lower alkyl, halo, hydroxy, and lower alkoxy,
  heteroaryloxy optionally substituted with one or more groups selected from lower alkyl, halo, hydroxy, and lower alkoxy,
  aryl optionally substituted with one or more groups selected from lower alkyl, halo, hydroxy, and lower alkoxy,
  heteroaryl optionally substituted with one or more groups selected from lower alkyl, halo, hydroxy, and lower alkoxy,
  halo, cyano, —C(O)$R^{11}$, —C(O)O$R^{11}$, —N$R^{13}R^{14}$, —N$R^{13}$C(O)$R^{11}$, —N$R^{13}$S(O)$_n R^{12}$, —N$R^{13}$S(O)$_n$N$R^{13}R^{14}$, —N$R^{13}$C(O)O$R^{12}$, —N$R^{13}$C(O)N$R^{13}R^{14}$, —C(O)N$R^{13}R^{14}$, —S(O)$_n R^{12}$, and —S(O)$_n$N$R^{13}R^{14}$;

$R^5$ is selected from hydrogen, halo, OH, $NH_2$, $CF_3$, —$CF_2H$, alkyl, alkenyl, and alkynyl;

$R^6$ is selected from hydrogen, —OH, —$NH_2$, —NHC(O)$R^{11}$, halo and alkyl;

$R^7$ is selected from hydrogen and lower alkyl;

each n is independently 0, 1, or 2;

$R^{11}$, $R^{12}$, $R^{13}$, and $R^{14}$ are independently selected from hydrogen, alkyl, alkenyl, alkynyl, cycloalkyl, aryl, heteroaryl, and heterocycle, each of which except for hydrogen, is optionally substituted with one or more groups selected from halo, lower alkyl, hydroxy, and lower alkoxy, or $R^{13}$ and $R^{14}$, with the nitrogen to which they are attached, combine to form a heterocycle ring, which is optionally substituted with one or more groups selected from halo, lower alkyl, hydroxy, and lower alkoxy and further optionally includes one or two additional heteroatoms in the heterocycle ring wherein the one or two additional heteroatoms are selected from —O—, —S—, and —N($R^{15}$)—; and $R^{15}$ is selected from hydrogen, lower alkyl, —C(O)$R^{11}$, —C(O)O$R^{11}$, —C(O)N$R^{13}R^{14}$, —S(O)$_n R^{12}$, and —S(O)$_n$N$R^{13}R^{14}$ provided that R$^1$ is not optionally substituted phenyl or optionally substituted 4-pyridinyl;

when X is N, R$^2$ is hydrogen or methyl, R$^3$ and R$^5$ are hydrogen, and Y is absent, then R$^1$ is not quinolin-6-yl, 7-fluoroquinolin-6-yl, 3-quinazolin-6-yl, 2-3-dihydro-benzofuran-5-yl, or 2,3-dihydro-benzo[1,4]dioxin-6-yl; and when X is N, R$^2$, R$^3$ and R$^5$ are hydrogen, and Y is —O— or —N(R$^7$)—, and R$^1$ is quinolin-6-yl, 7-fluoroquinolin-6-yl, 3-quinazolin-6-yl, 2-3-dihydro-benzofuran-5-yl, or 2,3-dihydro-benzo[1,4]dioxin-6-yl; then R$^4$ is optionally substituted heteroaryl.

Also provided is a composition comprising at least one compound and/or at least one pharmaceutically acceptable salt described herein and at least one pharmaceutically acceptable carrier.

Also provided is a method of inhibiting the activity of c-Met comprising contacting the receptor with an effective amount of at least one compound and/or at least one pharmaceutically acceptable salt described herein.

Also provided is a method of treating cancer responsive to inhibition of c-Met comprising administering to a subject in need thereof an effective amount of at least one compound and/or at least one pharmaceutically acceptable salt described herein.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

The term "alkyl" herein refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. "Lower alkyl" refers to a straight or branched hydrocarbon, containing 1-4 carbon atoms.

By "alkoxy" is meant a straight or branched alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. ""Lower alkoxy" refers to a straight or branched alkoxy, wherein the alkyl portion contains 1-4 carbon atoms.

The term "alkenyl" herein refers to a C$_{2-10}$ straight or branched hydrocarbon, containing one or more C=C double bonds. Examples of alkenyl groups include, but are not limited to, vinyl, 2-propenyl, and 2-butenyl.

The term "alkynyl" herein refers to a C$_{2-10}$ straight or branched hydrocarbon, containing one or more C≡C triple bonds. Examples of alkynyl groups include, but are not limited to, ethynyl, 2-propynyl, and 2-butynyl.

The term "cycloalkyl" refers to a saturated and partially unsaturated cyclic hydrocarbon group having 3 to 12 carbons. Examples of cycloalkyl groups include, but are not limited to, cyclopropyl, cyclobutyl, cyclopentyl, cyclopentenyl, cyclohexyl, cyclohexenyl, cycloheptyl, and cyclooctyl. The ring may be saturated or have one or more double bonds (i.e. partially unsaturated), but not fully conjugated.

"Aryl" encompasses:

5- and 6-membered carbocyclic aromatic rings, for example, benzene;

bicyclic ring systems wherein at least one ring is carbocyclic and aromatic, for example, naphthalene, indane, and 1,2,3,4-tetrahydroquinoline; and tricyclic ring systems wherein at least one ring is carbocyclic and aromatic, for example, fluorene.

For example, aryl includes 5- and 6-membered carbocyclic aromatic rings fused to a 5- to 7-membered heterocyclic ring containing one or more heteroatoms selected from N, O, and S, provided that the point of attachment is at the carbocyclic aromatic ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings are fused with a heterocyclic aromatic ring, the resulting ring system is heteroaryl, not aryl, as defined herein.

The term "halo" includes fluoro, chloro, bromo, and iodo, and the term "halogen" includes fluorine, chlorine, bromine, and iodine.

The term "heteroaryl" refers to 5- to 8-membered aromatic, monocyclic rings containing one or more, for example, from 1 to 4, or, in some embodiments, from 1 to 3, heteroatoms selected from N, O, and S, with the remaining ring atoms being carbon;

8- to 12-membered bicyclic rings containing one or more, for example, from 1 to 4, or, in some embodiments, from 1 to 3, heteroatoms selected from N, O, and S, with the remaining ring atoms being carbon and wherein at least one heteroatom is present in an aromatic ring; and 11- to 14-membered tricyclic rings containing one or more, for example, from 1 to 4, or in some embodiments, from 1 to 3, heteroatoms selected from N, O, and S, with the remaining ring atoms being carbon and wherein at least one heteroatom is present in an aromatic ring.

For example, heteroaryl includes a 5- to 7-membered heterocyclic aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 1-pyrazolyl, 2,3-pyrazolyl, 2,4-imidazolinyl, isoxazolyl, oxazolyl, thiazolyl, thiadiazolyl, tetrazolyl, thienyl, benzothienyl, furyl, benzofuryl, benzoimidazolinyl, indolinyl, pyridizinyl, triazolyl, quinolinyl, pyrazolyl, and 5,6,7,8-tetrahydroisoquinoline.

Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O$^-$) substituents, such as pyridinyl N-oxides.

By "heterocycle" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. "Heterocycle" also refers to 5- to 7-membered heterocyclic ring containing one or more heteroatoms selected from N, O, and S fused with 5- and 6-membered carbocyclic aromatic ring, provided that the point of attachment is at the heterocyclic ring. The rings may be saturated or have one or more double bonds (i.e. partially unsaturated). The heterocycle can be substituted by oxo. The point of the attachment may be carbon or heteroatom in the heterocyclic ring.

Suitable heterocycles include, for example (as numbered from the linkage position assigned priority 1), 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, and 2,5-piperazinyl. Morpholinyl groups are also contemplated, including 2-morpholinyl and 3-morpholinyl (numbered wherein the oxygen is assigned priority 1). Substituted heterocycle also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

In some embodiments, "substituted with one or more groups" refers to two hydrogens on the designated atom or group being independently replaced with two selections from the indicated group of substituents. In some embodiments, "substituted with one or more groups" refers to three hydrogens on the designated atom or group being independently replaced with three selections from the indicated group of substituents. In some embodiments, "substituted with one or more groups" refers to four hydrogens on the designated atom or group being independently replaced with four selections from the indicated group of substituents.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates or mixtures of diastereomers. Resolution of the racemates or mixtures of diastereomers can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, the term "compound" is intended to include all tautomeric forms of the compound. Such compounds also include crystal forms including polymorphs and clathrates. Similarly, the term "salt" is intended to include all isomers, racemates, other mixtures, Z- and E-forms, tautomeric forms and crystal forms of the salt of the compound.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium.

In addition, if a compound described herein is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A "solvate," such as a "hydrate," is formed by the interaction of a solvent and a compound. The term "compound" is intended to include solvates, including hydrates, of compounds. Similarly, "salts" includes solvates, such as hydrates, of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound'.

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

As used herein the terms "group", "radical" or "fragment" are synonymous and are intended to indicate functional groups or fragments of molecules attachable to a bond or other fragments of molecules.

The term "active agent" is used to indicate a chemical substance which has biological activity. In some embodiments, an "active agent" is a chemical substance having pharmaceutical utility.

"Treating" or "treatment" or "alleviation" refers to administering at least one compound and/or at least one pharmaceutically acceptable salt described herein to a subject that has cancer, or has a symptom of cancer, or has a predisposition toward cancer, with the purpose to cure, heal, alleviate, relieve, alter, remedy, ameliorate, improve, or affect cancer, the symptoms of cancer, or the predisposition toward cancer.

The term "effective amount" refers to an amount of at least one compound and/or at least one pharmaceutically acceptable salt described herein effective to "treat" a disease or disorder in a subject. In the case of cancer, the effective amount may cause any of the changes observable or measurable in a subject as described in the definition of "treating," "treatment" and "alleviation" above. For example, the effective amount can reduce the number of cancer or tumor cells; reduce the tumor size; inhibit or stop tumor cell infiltration into peripheral organs including, for example, the spread of tumor into soft tissue and bone; inhibit and stop tumor metastasis; inhibit and stop tumor growth; relieve to some extent one or more of the symptoms associated with the cancer, reduce morbidity and mortality; improve quality of life; or a combination of such effects. An effective amount may be an amount sufficient to decrease the symptoms of a disease responsive to inhibition of c-Met activity. For cancer therapy, efficacy in vivo can, for example, be measured by assessing the duration of survival, time to disease progression (TTP), the response rates (RR), duration of response, and/or quality of life. Effective amounts may vary, as recognized by those skilled in the art, depending on route of administration, excipient usage, and co-usage with other agents.

The term "inhibition" indicates a decrease in the baseline activity of a biological activity or process. "Inhibition of c-Met activity" refers to a decrease in the activity of c-Met as a direct or indirect response to the presence of at least one at least one compound and/or at least one pharmaceutically acceptable salt described herein, relative to the activity of c-Met in the absence of the at least one compound and/or the at least one pharmaceutically acceptable salt thereof. The decrease in activity may be due to the direct interaction of the at least one compound and/or at least one pharmaceutically acceptable salt described herein with c-Met, or due to the interaction of the at least one compound and/or at least one pharmaceutically acceptable salt described herein, with one or more other factors that in turn affect c-Met activity. For example, the presence of at least one compound and/or at least one pharmaceutically acceptable salt described herein, may decrease c-Met activity by directly binding to the c-Met, by causing (directly or indirectly) another factor to decrease c-Met activity, or by (directly or indirectly) decreasing the amount of c-Met present in the cell or organism.

The details of one or more embodiments of the invention are set forth below.

Provided is at least one compound of formula 1:

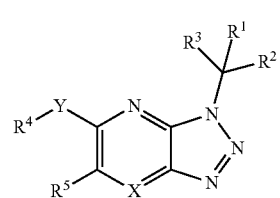

and/or at least one pharmaceutically acceptable salt thereof wherein

X is N, Y is selected from —O—, —S—, and —N(R$^7$)— and R$^1$ is selected from aryl and heteroaryl, each of which is optionally substituted with one or more groups selected from halo, —CF$_3$, —CF$_2$H, cycloalkyl, —C(O)R$^{11}$, —C(O)OR$^{11}$, —CN, —C(O)NR$^{13}$R$^{14}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —NO$_2$, —S(O)$_n$R$^{12}$, —S(O)$_n$NR$^{13}$R$^{14}$, heterocycle, heteroaryl, aryl, alkenyl, alkynyl, lower alkyl, lower alkyl substituted with hydroxy, lower alkyl substituted with lower alkoxy, lower alkyl substituted with —NR$^{13}$R$^{14}$, and lower alkyl substituted with heterocycle; or X is N, Y is absent and R$^1$ is a fused bicyclic heteroaryl optionally substituted with one or more groups selected from halo, —CF$_3$, —CF$_2$H, cycloalkyl, —C(O)R$^{11}$, —C(O)OR$^{11}$, —CN, —C(O)NR$^{13}$R$^{14}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —NO$_2$, —S(O)$_n$R$^{12}$, —S(O)$_n$NR$^{13}$R$^{14}$, heterocycle, heteroaryl, aryl, alkenyl, alkynyl, lower alkyl, lower alkyl substituted with hydroxy, lower alkyl substituted with lower alkoxy, lower alkyl substituted with —NR$^{13}$R$^{14}$, and lower alkyl substituted with heterocycle; or X is C(R$^6$), Y is selected from —O—, —S—, and —N(R$^7$)— or Y is absent, and R$^1$ is heteroaryl optionally substituted with one or more groups selected from halo, —CF$_3$, —CF$_2$H, cycloalkyl, —C(O)R$^{11}$, —C(O)OR$^{11}$, —CN, —C(O)NR$^{13}$R$^{14}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —NO$_2$, —S(O)$_n$R$^{12}$, —S(O)$_n$NR$^{13}$R$^{14}$, heterocycle, heteroaryl, aryl, alkenyl, alkynyl, lower alkyl, lower alkyl substituted with hydroxy, lower alkyl substituted with lower alkoxy, lower alkyl substituted with —NR$^{13}$R$^{14}$, and lower alkyl substituted with heterocycle;

R$^2$ and R$^3$ are independently selected from hydrogen and alkyl, or R$^2$ and R$^3$, together with the carbon to which they are attached, form a ring chosen from 3- to 7-membered cycloalkyl and 3- to 7-membered heterocycle;

R$^4$ is selected from halo, alkyl, cycloalkyl, heterocycle, aryl and heteroaryl, each of which, except for halo, is optionally substituted with one or more groups selected from lower alkyl optionally substituted with one or more groups selected from hydroxy, lower alkoxy, cyano, halo, —C(O)OR$^{11}$, —C(O)NR$^{13}$R$^{14}$, —NR$^{13}$R$^{14}$, —OC(O)R$^{11}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, and —NR$^{13}$C(O)NR$^{13}$R$^{14}$, lower alkoxy optionally substituted with one or more groups selected from halo, hydroxy, and lower alkoxy, cycloalkoxy optionally substituted with one or more groups selected from halo, hydroxy, and lower alkoxy, heterocycloalkoxy optionally substituted with one or more groups selected from halo, hydroxy, and lower alkoxy, heterocycle optionally substituted with one or more groups selected from lower alkyl, halo, hydroxy, and lower alkoxy, heteroaryloxy optionally substituted with one or more groups selected from lower alkyl, halo, hydroxy, and lower alkoxy, aryl optionally substituted with one or more groups selected from lower alkyl, halo, hydroxy, and lower alkoxy, heteroaryl optionally substituted with one or more groups selected from lower alkyl, halo, hydroxy, and lower alkoxy, halo, cyano, —C(O)R$^{11}$, —C(O)OR$^{11}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —C(O)NR$^{13}$R$^{14}$, —S(O)$_n$R$^{12}$, and —S(O)$_n$NR$^{13}$R$^{14}$;

R$^5$ is selected from hydrogen, halo, OH, NH$_2$, CF$_3$, —CF$_2$H, alkyl, alkenyl, and alkynyl;

R$^6$ is selected from hydrogen, —OH, —NH$_2$, —NHC(O)R$^{11}$, halo and alkyl;

R$^7$ is selected from hydrogen and lower alkyl;

each n is independently 0, 1, or 2;

R$^{11}$, R$^{12}$, R$^{13}$, and R$^{14}$ are independently selected from hydrogen, alkyl, alkenyl, alkynyl, cycloalkyl, aryl, heteroaryl, and heterocycle, each of which except for hydrogen, is optionally substituted with one or more groups selected from halo, lower alkyl, hydroxy, and lower alkoxy, or R$^{13}$ and R$^{14}$, with the nitrogen to which they are attached, combine to form a heterocycle ring, which is optionally substituted with one or more groups selected from halo, lower alkyl, hydroxy, and lower alkoxy and further optionally includes one or two additional heteroatoms in the heterocycle ring wherein the one or two additional heteroatoms are selected from —O—, —S—, and —N(R$^{15}$)—; and R$^{15}$ is selected from hydrogen, lower alkyl, —C(O)R$^{11}$, —C(O)OR$^{11}$, —C(O)NR$^{13}$R$^{14}$, —S(O)$_n$R$^{12}$, and —S(O)$_n$NR$^{13}$R$^{14}$ provided that R$^1$ is not optionally substituted phenyl or optionally substituted 4-pyridinyl;

when X is N, R$^2$ is hydrogen or methyl, R$^3$ and R$^5$ are hydrogen, and Y is absent, then R$^1$ is not quinolin-6-yl, 7-fluoroquinolin-6-yl, 3-quinazolin-6-yl, 2-3-dihydro-benzofuran-5-yl, or 2,3-dihydro-benzo[1,4]dioxin-6-yl; and when X is N, R$^2$, R$^3$ and R$^5$ are hydrogen, and Y is —O— or —N(R$^7$)—, and R$^1$ is quinolin-6-yl, 7-fluoroquinolin-6-yl, 3-quinazolin-6-yl, 2-3-dihydro-benzofuran-5-yl, or 2,3-dihydro-benzo[1,4]dioxin-6-yl; then R$^4$ is optionally substituted heteroaryl.

In some embodiments, X is N. In some embodiments, X is C(R$^6$). In some embodiments, R$^6$ is selected from hydrogen, halo and lower alkyl. In some embodiments, R$^6$ is hydrogen.

In some embodiments, Y is —O—. In some embodiments, Y is —S—. In some embodiments, Y is —N(R$^7$)—. In some embodiments, R$^7$ is hydrogen or methyl. In some embodiments, R$^7$ is hydrogen. In some embodiments, Y is absent.

In some embodiments, R$^1$ is 8-10 membered heteroaryl optionally substituted with one or more groups selected from halo, —CF$_3$, —CF$_2$H, cycloalkyl, —C(O)R$^{11}$, —C(O)OR$^{11}$, —CN, —C(O)NR$^{13}$R$^{14}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —NO$_2$, —S(O)$_n$R$^{12}$, —S(O)$_n$NR$^{13}$R$^{14}$, heterocycle, heteroaryl, aryl, alkenyl, alkynyl, lower alkyl, lower alkyl substituted with hydroxy, lower alkyl substituted with lower alkoxy, lower alkyl substituted with —NR$^{13}$R$^{14}$, and lower alkyl substituted with heterocycle. In some embodiments, R$^1$ is 8-10 membered heteroaryl optionally substituted with one or more groups selected from halo, lower alkyl, lower alkyl substituted with hydroxy, and lower alkyl substituted with lower alkoxy.

In some embodiments, R$^1$ is selected from quinolin-6-yl, thieno[3,2-c]pyridin-2-yl, benzo[d]thiazol-6-yl, and imidazo[1,2-a]pyridin-6-yl, each of which is optionally substituted with one or more groups selected from halo, lower alkyl, lower alkyl substituted with hydroxy, and lower alkyl substituted with lower alkoxy. In some embodiments, R$^1$ is selected from quinolin-6-yl optionally substituted with one or more groups selected from halo, lower alkyl, lower alkyl substituted with hydroxy, and lower alkyl substituted with lower alkoxy.

In some embodiments, R$^1$ is a ring system selected from

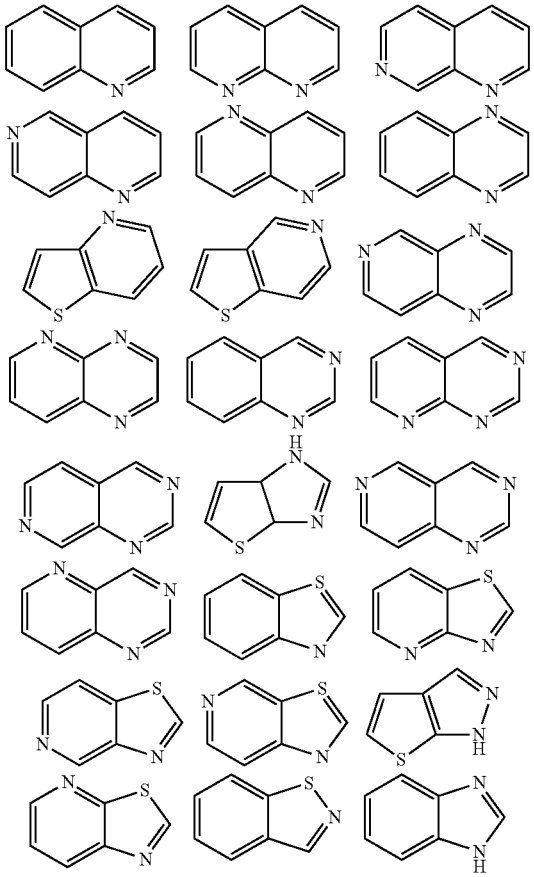

-continued

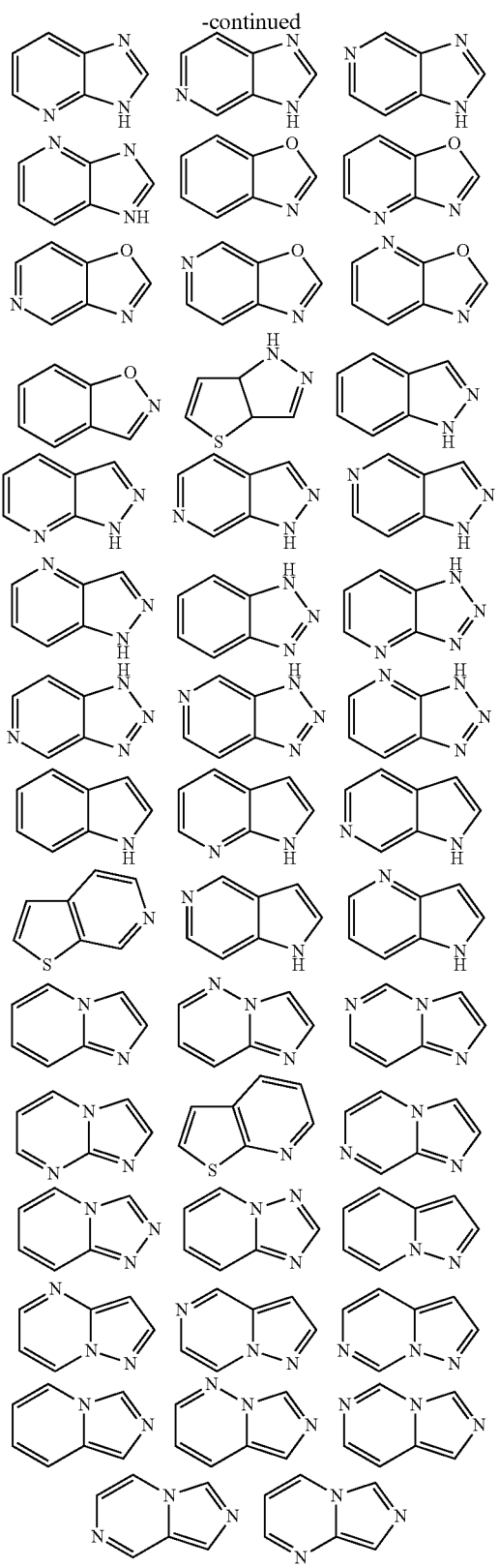

wherein each of said ring systems is optionally substituted with one or more groups selected from halo, $CF_3$, —$CF_2H$, cycloalkyl, —$C(O)R^{11}$, $C(O)OR^{11}$, —CN, —$C(O)NR^{13}R^{14}$, —$NR^{13}R^{14}$, —$NR^{13}C(O)R^{11}$, —$NR^{13}S(O)_nR^{12}$, —$NR^{13}S(O)_nNR^{13}R^{14}$, —$NR^{13}C(O)OR^{12}$, —$NR^{13}C(O)NR^{13}R^{14}$, —$NO_2$, —$S(O)_nR^{12}$, —$S(O)_nNR^{13}R^{14}$, heterocycle, heteroaryl, aryl, alkenyl, alkynyl, lower alkyl, lower alkyl substituted with hydroxy, lower alkyl substituted with lower alkoxy, lower alkyl substituted with —$NR^{13}R^{14}$, and lower alkyl substituted with heterocycle. For avoidance of doubt, each of said ring systems may be appended to the carbon bearing $R^2$ and $R^3$ at any open valence on either of the rings in the ring systems.

In some embodiments, $R^1$ is a ring system selected from

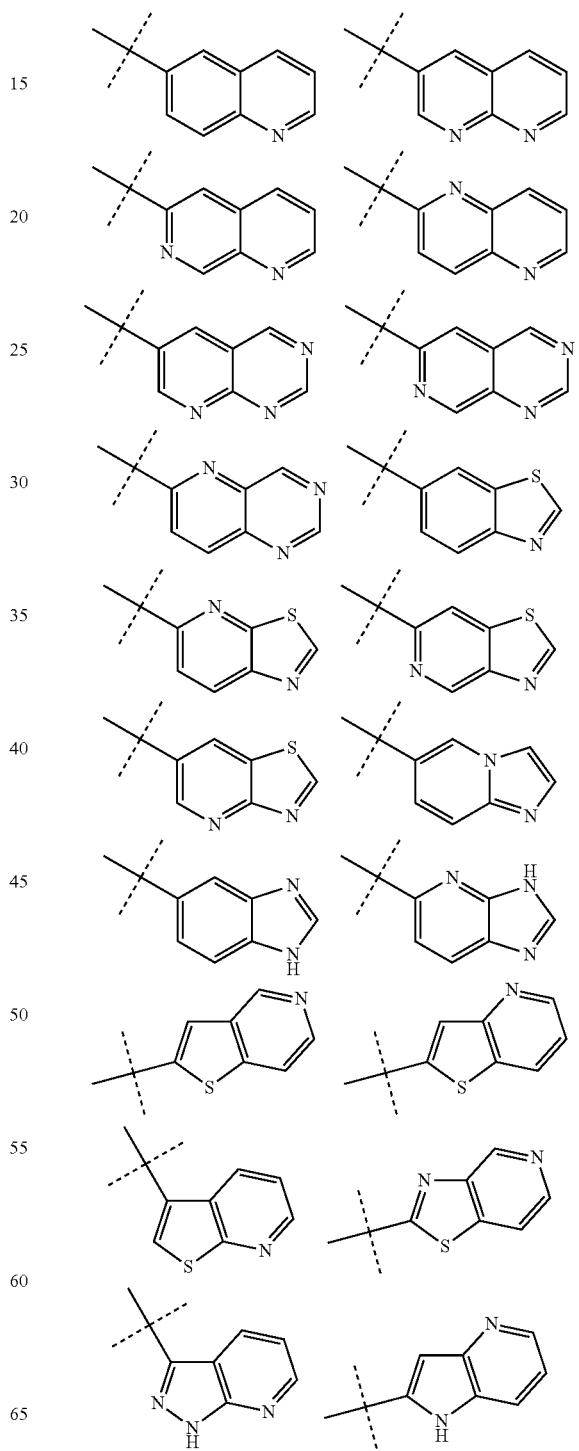

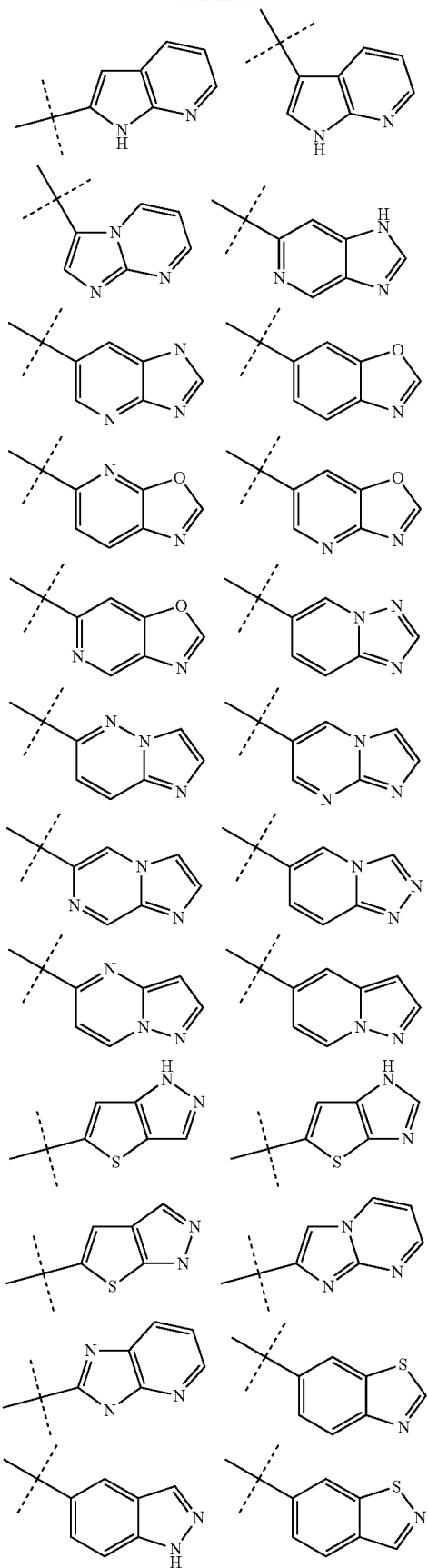
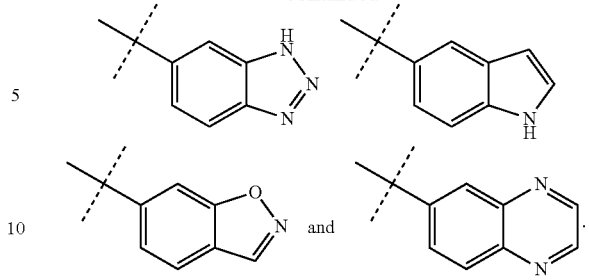

wherein each of said ring systems is optionally substituted with one or more groups selected from halo, $CF_3$, $-CF_2H$, cycloalkyl, $-C(O)R^{11}$, $C(O)OR^{11}$, $-CN$, $-C(O)NR^{13}R^{14}$, $-NR^{13}R^{14}$, $-NR^{13}C(O)R^{11}$, $-NR^{13}S(O)_nR^{12}$, $-NR^{13}S(O)_nNR^{13}R^{14}$, $-NR^{13}C(O)OR^{12}$, $-NR^{13}C(O)NR^{13}R^{14}$, $-NO_2$, $-S(O)_nR^{12}$, $-S(O)_nNR^{13}R^{14}$, heterocycle, heteroaryl, aryl, alkenyl, alkynyl, lower alkyl, lower alkyl substituted with hydroxy, lower alkyl substituted with lower alkoxy, lower alkyl substituted with $-NR^{13}R^{14}$, and lower alkyl substituted with heterocycle. For avoidance of doubt, each of said ring systems depicted above is appended to the carbon bearing $R^2$ and $R^3$ at the position indicated.

In some embodiments, $R^2$ and $R^3$ are independently selected from hydrogen and $C_1$-$C_6$ alkyl or $R^2$ and $R^3$, together with the carbon to which they are attached, form a 3-membered cycloalkyl. In some embodiments, $R^2$ is hydrogen and $R^3$ is selected from hydrogen and $C_1$-$C_6$ alkyl. In some embodiments, $R^2$ is hydrogen and $R^3$ is selected from hydrogen and methyl. In some embodiments, $R^2$ and $R^3$ are hydrogen. In some embodiments, $R^2$ and $R^3$, together with the carbon to which they are attached, form a 3-membered cycloalkyl.

In some embodiments, $R^4$ is aryl optionally substituted with one or more groups selected from
  lower alkyl optionally substituted with one or more groups selected from hydroxy, lower alkoxy, cyano, halo, $-C(O)OR^{11}$, $-C(O)NR^{13}R^{14}$, $-NR^{13}R^{14}$, $-OC(O)R^{11}$, $-NR^{13}C(O)R^{11}$, $-NR^{13}S(O)_nR^{12}$, $-NR^{13}S(O)_nNR^{13}R^{14}$, $-NR^{13}C(O)OR^{12}$, and $-NR^{13}C(O)NR^{13}R^{14}$,
  lower alkoxy optionally substituted with one or more groups selected from halo, hydroxy, and lower alkoxy,
  heterocycle optionally substituted with one or more groups selected from lower alkyl, halo, hydroxy, and lower alkoxy,
  heteroaryloxy optionally substituted with one or more groups selected from lower alkyl, halo, hydroxy, and lower alkoxy,
  aryl optionally substituted with one or more groups selected from lower alkyl, halo, hydroxy, and lower alkoxy,
  heteroaryl optionally substituted with one or more groups selected from lower alkyl, halo, hydroxy, and lower alkoxy,
  halo, cyano, $-C(O)R^{11}$, $-C(O)OR^{11}$, $-NR^{13}R^{14}$, $-NR^{13}C(O)R^{11}$, $-NR^{13}S(O)_nR^{12}$, $-NR^{13}S(O)_nNR^{13}R^{14}$, $-NR^{13}C(O)OR^{12}$, $-NR^{13}C(O)NR^{13}R^{14}$, $-C(O)NR^{13}R^{14}$, $-S(O)_nR^{12}$, and $-S(O)_nNR^{13}R^{14}$.

In some embodiments, $R^4$ is aryl optionally substituted with one or more groups selected from halo, hydroxy, $-NR^{13}S(O)_nR^{12}$, lower alkoxy, lower alkyl, lower alkyl substituted with hydroxy, lower alkyl substituted with lower alkoxy, lower alkoxy substituted with hydroxy, and lower alkoxy substituted with lower alkyl.

In some embodiments, $R^4$ is phenyl optionally substituted with one or more groups selected from lower alkoxy, lower alkoxy substituted with hydroxy, and lower alkoxy substituted with lower alkoxy.

In some embodiments, $R^4$ is heterocycle optionally substituted with one or more groups selected from
- lower alkyl optionally substituted with one or more groups selected from hydroxy, lower alkoxy, cyano, halo, —C(O)OR$^{11}$, —C(O)NR$^{13}$R$^{14}$, NR$^{13}$R$^{14}$, —OC(O)R$^{11}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, and —NR$^{13}$C(O)NR$^{13}$R$^{14}$,
- lower alkoxy optionally substituted with one or more groups selected from halo, hydroxy, and lower alkoxy,
- heterocycle optionally substituted with one or more groups selected from lower alkyl, halo, hydroxy, and lower alkoxy,
- halo, cyano, —C(O)R$^{11}$, —C(O)OR$^{11}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, C(O)NR$^{13}$R$^{14}$, —S(O)$_n$R$^{12}$, and —S(O)$_n$NR$^{13}$R$^{14}$.

In some embodiments, $R^4$ is selected from pyrrolidin-1-yl, piperidin-1-yl, tetrahydro-2H-pyran-4-yl, morpholin-4-yl, and 6,7-dihydrothieno[3,2-c]pyridin-5(4H)-yl, each of which is optionally substituted with one or more groups selected from
- lower alkyl optionally substituted with one or more groups selected from hydroxy, lower alkoxy, cyano, halo, —C(O)OR$^{11}$, —C(O)NR$^{13}$R$^{14}$, NR$^{13}$R$^{14}$, —OC(O)R$^{11}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, and —NR$^{13}$C(O)NR$^{13}$R$^{14}$,
- lower alkoxy optionally substituted with one or more groups selected from halo, hydroxy, and lower alkoxy,
- heterocycle optionally substituted with one or more groups selected from lower alkyl, halo, hydroxy, and lower alkoxy,
- halo, cyano, —C(O)R$^{11}$, —C(O)OR$^{11}$, —NR$^{13}$R$^{14}$, —NR$^{13}$C(O)R$^{11}$, —NR$^{13}$S(O)$_n$R$^{12}$, NR$^{13}$S(O)$_n$NR$^{13}$R$^{14}$, —NR$^{13}$C(O)OR$^{12}$, —NR$^{13}$C(O)NR$^{13}$R$^{14}$, C(O)NR$^{13}$R$^{14}$, —S(O)$_n$R$^{12}$, and —S(O)$_n$NR$^{13}$R$^{14}$.

In some embodiments, $R^4$ is selected from pyrrolidin-1-yl, piperidin-1-yl, tetrahydro-2H-pyran-4-yl, morpholin-4-yl, and 6,7-dihydrothieno[3,2-c]pyridin-5(4H)-yl, each of which is optionally substituted with one or more groups selected from halo, CF$_3$, —CF$_2$H, hydroxy, lower alkyl, lower alkyl substituted with hydroxy, and lower alkyl substituted with lower alkoxy.

In some embodiments, $R^4$ is heteroaryl optionally substituted with one or more groups selected from
- lower alkyl optionally substituted with one or more groups selected from hydroxy, lower alkoxy, cyano, halo, —C(O)OR$^{11}$, —C(O)NR$^{13}$R$^{14}$, NR$^{13}$R$^{14}$, —OC(O)R$^{11}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, and —NR$^{13}$C(O)NR$^{13}$R$^{14}$,
- lower alkoxy optionally substituted with one or more groups selected from halo, hydroxy, and lower alkoxy,
- heterocycle optionally substituted with one or more groups selected from lower alkyl, halo, hydroxy, and lower alkoxy,
- halo, cyano, —C(O)R$^{11}$, —C(O)OR$^{11}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —C(O)NR$^{13}$R$^{14}$, —S(O)$_n$R$^{12}$, and —S(O)$_n$NR$^{13}$R$^{14}$.

In some embodiments, $R^4$ is selected from 1H-pyrazol-1-yl, 1H-pyrazol-3-yl, 1H-pyrazol-4-yl, 1H-imidazol-1-yl, 1H-imidazol-4-yl, oxazol-2-yl, thiazol-2-yl, isoxazol-3-yl, isoxazol-5-yl, 1H-pyrrol-2-yl, 1H-pyrrol-3-yl, thiophen-2-yl, thiophen-3-yl, pyridin-2-yl, pyridin-3-yl, and pyridin-4-yl, each of which is optionally substituted with one or more groups selected from
- lower alkyl optionally substituted with one or more groups selected from hydroxy, lower alkoxy, cyano, halo, —C(O)OR$^{11}$, —C(O)NR$^{13}$R$^{14}$, NR$^{13}$R$^{14}$, —OC(O)R$^{11}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, and —NR$^{13}$C(O)NR$^{13}$R$^{14}$,
- lower alkoxy optionally substituted with one or more groups selected from halo, hydroxy, and lower alkoxy,
- heterocycle optionally substituted with one or more groups selected from lower alkyl, halo, hydroxy, and lower alkoxy,
- halo, cyano, —C(O)R$^{11}$, —C(O)OR$^{11}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —C(O)NR$^{13}$R$^{14}$, —S(O)$_n$R$^{12}$, and —S(O)$_n$NR$^{13}$R$^{14}$.

In some embodiments, $R^4$ is selected from 1H-pyrazol-1-yl, 1H-pyrazol-3-yl, 1H-pyrazol-4-yl, 1H-imidazol-1-yl, 1H-imidazol-4-yl, oxazol-2-yl, thiazol-2-yl, isoxazol-3-yl, isoxazol-5-yl, 1H-pyrrol-2-yl, 1H-pyrrol-3-yl, thiophen-2-yl, thiophen-3-yl, pyridin-2-yl, pyridin-3-yl, and pyridin-4-yl, each of which is optionally substituted with one or more groups selected from
- lower alkyl optionally substituted with one or more groups selected from hydroxy, lower alkoxy, cyano, halo, —C(O)OR$^{11}$, —C(O)NR$^{13}$R$^{14}$, NR$^{13}$R$^{14}$, —OC(O)R$^{11}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, and —NR$^{13}$C(O)NR$^{13}$R$^{14}$, and
- heterocycle optionally substituted with one or more groups selected from lower alkyl, halo, hydroxy, and lower alkoxy, In some embodiments, $R^4$ is selected from 1H-pyrazol-1-yl, 1H-pyrazol-3-yl, 1H-pyrazol-4-yl, 1H-imidazol-1-yl, 1H-imidazol-4-yl, oxazol-2-yl, thiazol-2-yl, isoxazol-3-yl, isoxazol-5-yl, 1H-pyrrol-2-yl, 1H-pyrrol-3-yl, thiophen-2-yl, thiophen-3-yl, pyridin-2-yl, pyridin-3-yl, and pyridin-4-yl, each of which is optionally substituted with one or more groups selected from lower alkyl optionally substituted with one or more groups selected from hydroxy, lower alkoxy, cyano, and halo.

In some embodiments, $R^4$ is lower alkyl.

In some embodiments, $R^5$ is hydrogen.

In some embodiments, n is 0. In some embodiments, n is 1. In some embodiments, n is 2.

Also provided is at least one compound selected from compounds 1 to 332 and/or at least one pharmaceutically acceptable salt described herein.

The compounds described herein, and/or the pharmaceutically acceptable salts thereof, can be synthesized from commercially available starting materials by methods well known in the art. The following schemes illustrate methods for most of compound preparation. In each of the schemes, LG and LG' are leaving groups that can be same or different. Y' is —NHR$^7$, —OH, —SH, —B(OH)$_2$, or B(OR')$_2$, and R$^1$, R$^2$, R$^3$, R$^4$, R$^5$ and Y are as defined herein.

Scheme I

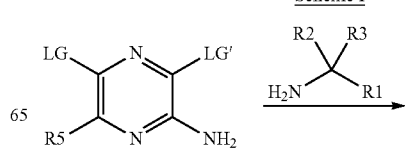

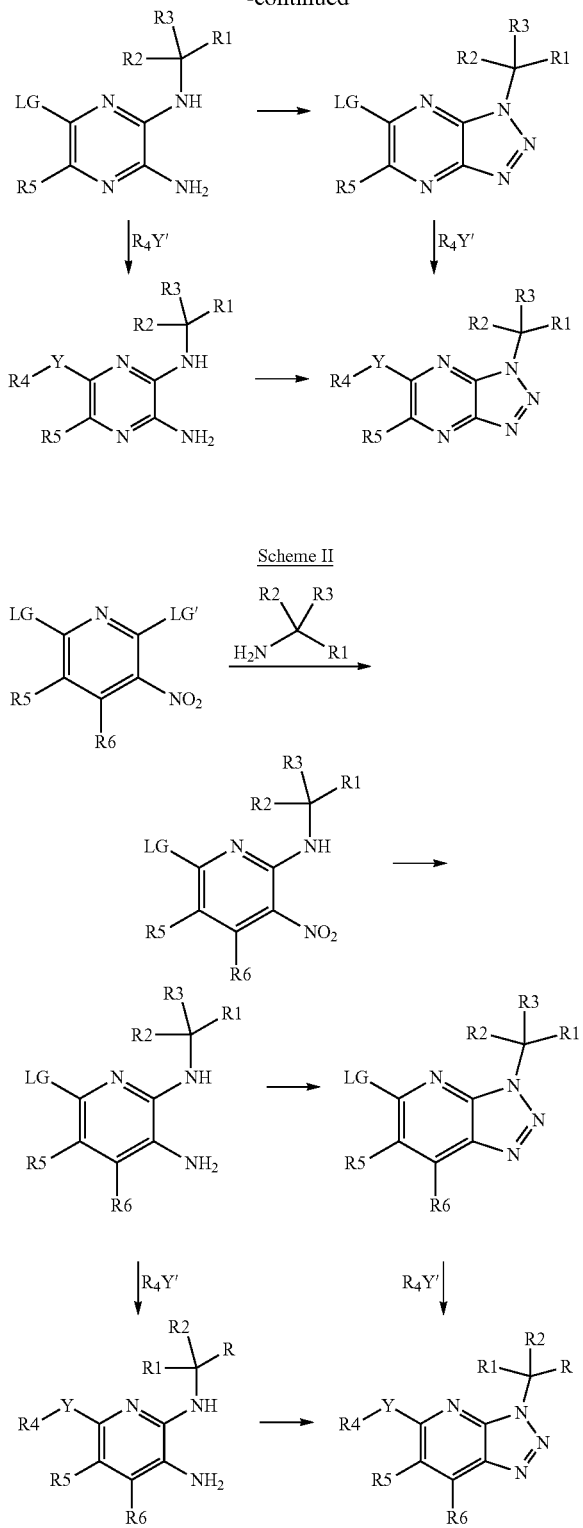

Scheme II

The compounds thus obtained can be further modified at their peripheral positions to provide the desired compounds. Synthetic chemistry transformations are described, for example, in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Before use, the at least one compound and/or at least one pharmaceutically acceptable salt described herein, can be purified by column chromatography, high performance liquid chromatography, crystallization, or other suitable methods.

Also provided is a composition containing at least one compound and/or at least one pharmaceutically acceptable salt described herein, and at least one pharmaceutically acceptable carrier.

A composition comprising at least one compound and/or at least one pharmaceutically acceptable salt described herein, can be administered in various known manners, such as orally, parenterally, by inhalation spray, or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

An oral composition can be any orally acceptable dosage form including, but not limited to, tablets, capsules, emulsions, and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the pharmaceutically acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A topical composition can be formulated in form of oil, cream, lotion, ointment and the like. Suitable carriers for the composition include vegetable or mineral oils, white petrolatum (white soft paraffin), branched chain fats or oils, animal fats and high molecular weight alcohols (greater than C12). In some embodiments, the pharmaceutically acceptable carrier is one in which the active ingredient is soluble. Emulsifiers, stabilizers, humectants and antioxidants may also be included as well as agents imparting color or fragrance, if desired. Additionally, transdermal penetration enhancers may be employed in these topical formulations. Examples of such enhancers can be found in U.S. Pat. Nos. 3,989,816 and 4,444,762.

Creams may be formulated from a mixture of mineral oil, self-emulsifying beeswax and water in which mixture the active ingredient, dissolved in a small amount of an oil, such as almond oil, is admixed. An example of such a cream is one which includes about 40 parts water, about 20 parts beeswax, about 40 parts mineral oil and about 1 part almond oil. Ointments may be formulated by mixing a solution of the active ingredient in a vegetable oil, such as almond oil, with warm soft paraffin and allowing the mixture to cool. An example of such an ointment is one which includes about 30% by weight almond and about 70% by weight white soft paraffin.

A pharmaceutically acceptable carrier refers to a carrier that is compatible with active ingredients of the composition (and in some embodiments, capable of stabilizing the active ingredients) and not deleterious to the subject to be treated. For example, solubilizing agents, such as cyclodextrins (which form specific, more soluble complexes with the at least one compound and/or at least one pharmaceutically acceptable salt described herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10.

Suitable in vitro assays can be used to preliminarily evaluate the efficacy of the at least one compound and/or at least one pharmaceutically acceptable salt described herein, in inhibiting the activity of c-Met. The at least one compound and/or at least one pharmaceutically acceptable salt described herein, can further be examined for efficacy in treating cancer by in vivo assays. For example, the compounds described herein, and/or the pharmaceutically acceptable salts thereof, can be administered to an animal (e.g., a mouse model) having cancer and its therapeutic effects can be accessed. Based on the results, an appropriate dosage range and administration route for animals, such as humans, can also be determined.

Also provided is a method of inhibiting the activity of c-Met. The method comprises contacting the receptor with an amount of at least one compound and/or at least one pharmaceutically acceptable salt described herein effective to inhibit the activity of c-Met.

The at least one compound and/or at least one pharmaceutically acceptable salt described herein can be used to achieve a beneficial therapeutic or prophylactic effect, for example, in subjects with cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; skin cancer, including e.g., malignant melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; soft tissue sarcoma; and thyroid carcinoma.

Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, the examples of the cancer to be treated include, but are not limited to, lung cancer, head and neck cancer, colorectal cancer, pancreatic cancer, colon cancer, breast cancer, ovarian cancer, prostate cancer, stomach cancer, kidney cancer, liver cancer, brain cancer, bone cancer, and leukemia.

In some embodiments, the at least one compound and/or at least one pharmaceutically acceptable salt described herein, is administered in conjunction with another therapeutic agent. In some embodiments, the other therapeutic agent is one that is normally administered to patients with the disease or condition being treated. The at least one compound and/or at least one pharmaceutically acceptable salt described herein, may be administered with the other therapeutic agent in a single dosage form or as a separate dosage form. When administered as a separate dosage form, the other therapeutic agent may be administered prior to, at the same time as, or following administration of the at least one compound and/or at least one pharmaceutically acceptable salt described herein.

In some embodiments, at least one compound and/or at least one pharmaceutically acceptable salt described herein, is administered in conjunction with an anti-neoplastic agent. As used herein, the term "anti-neoplastic agent" refers to any agent that is administered to a subject with cancer for purposes of treating the cancer. Nonlimiting examples anti-neoplastic agents include: radiotherapy; immunotherapy; DNA damaging chemotherapeutic agents; and chemotherapeutic agents that disrupt cell replication.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide and related analogs (e.g., CC-5013 and CC-4047); protein tyrosine kinase inhibitors (e.g., imatinib mesylate and gefitinib);

proteasome inhibitors (e.g., bortezomib); NF-kappa B inhibitors, including inhibitors of I kappa B kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which downregulates cell replication.

EXAMPLES

The examples below are intended to be purely exemplary and should not be considered to be limiting in any way. Efforts have been made to ensure accuracy with respect to numbers used (for example, amounts, temperature, etc.) but some experimental errors and deviations should be accounted for. Unless indicated otherwise, parts are parts by weight, temperature is in degrees Centigrade, and pressure is at or near atmospheric. All MS data were checked by agilent 6120 agilent 1100. All reagents, except intermediates, used in this invention are commercially available. All compound names except the reagents were generated by Chemdraw 8.0.

In the following examples, the abbreviations below are used:
AIBN a,a'-azo-isobutyronnitrile
BINAP 2,2'-Bis(diphenylphosphino)-1,1'-binaphthyl
Boc tert-butoxycarbonyl
Boc₂O di-t-butyl-dicarbonate
i-BuNO₂ Isobutylnitrite
DCM dichloromethane
DMF N,N-dimethylformamide
DMAP 4-Dimethylaminopyridine
DPPA Diphenylphosphoryl azide
DBU 1,8-Diazabicyclo[5.4.0]undec-7-ene
DEA N, N-diethylamine
ee enantiomeric excess
Et₃N triethylamine
h hour
HATU O-(7-Azabenzotriazol-1-yl)-N,N,N',N'-tetra-methyl-uronium hexafluorophosphate
HMTA Hexamethylenetetramine
HOAc acetic acid
Lawesson's reagent 2,4-Bis(4-methoxyphenyl)-2,4-dithi-oxo-1,3,2,4-dithiadiphosphetane
mL milliliter(s)
min minute(s)
MeOH methanol
MsCl methanesulfonyl chloride
NBS N-Bromosuccinimide
Pd(dppf)Cl₂ 1,1'-Bis(diphenylphosphino)ferrocene-palladium(II)dichloride dichloromethane complex
Pd₂(dba)₃ Tris(dibenzylideneacetone)dipalladium (0)
Pd(PPh₃)₄ Tetrakis(triphenylphosphine)palladium(0)
PPh₃ Triphenylphosphine
THF tetrahydrofuran
Ti(i-OPr)₄ Titanium(IV) isopropoxide
Xantphos 9-Dimethyl-4,5-bis(diphenylphosphino)xanthene Synthesis of Amine (NH₂CR¹R²R³ in Scheme I and II)

Intermediate A:

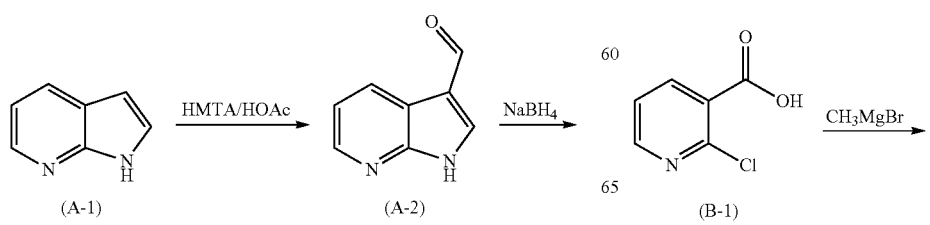

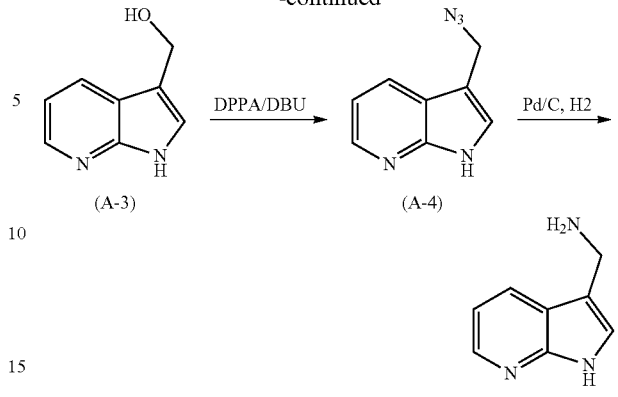

1H-Prrolo[2,3-b]pyridine-3-carbaldehyde (A-2)

To a solution of 1H-pyrrolo[2,3-b]pyridine (A-1) (7.23 g, 61.2 mmol) in acetic acid (20 mL) and water (40 mL) was added HMTA (9.42 g, 67.3 mmol). The reaction mixture was stirred at 120° C. for 6 h. It was cooled with an ice bath, and the resulting precipitate was collected and dried to afford the title compound (7.90 g) MS (m/z): 147 (M+1)⁺.

(1H-Prrolo[2,3-b]pyridin-3-yl)methanol (A-3)

To a solution of 1H-pyrrolo[2,3-b]pyridine-3-carbaldehyde (A-2) (5.0 g, 34.21 mmol) in EtOH (150 mL) was added NaBH₄ (1.30 g, 34.21 mmol). The reaction mixture was stirred at room temperature for 0.5 h. It was concentrated and purified by chromatography on silica gel to afford the title compound (5.0 g). MS (m/z): 149 (M+1)⁺.

3-(Aidomethyl)-1H-pyrrolo[2,3-b]pyridine (A-4)

To a mixture of 1H-pyrrolo[2,3-b]pyridin-3-yl)methanol (A-3) (1.0 g, 6.75 mmol) in anhydrous THF (50 mL) were added DPPA (3.71 g, 13.5 mmol) and DBU (0.821 g, 5.4 mmol) respectively. It was refluxed under N₂ for 6 h, and then concentrated under vacuo. The resulting residue was dissolved in EtOAc (50 mL), washed with brine, dried over sodium sulfate and concentrated under vacuo, to obtain the crude product. The crude product was purified by chromatography on silica gel to afford the title compound (0.587 g). MS (m/z): 174 (M+1)⁺.

(1H-Prrolo[2,3-b]pyridin-3-yl)methanamine (A)

To a mixture of 3-(azidomethyl)-1H-pyrrolo[2,3-b]pyridine (A-4) (1.50 g, 8.63 mmol) in EtOAc (150 mL) was added 10% Pd/C (1.10 g). The resulting reaction mixture was stirred under one atmosphere of H₂ at room temperature for 3 h. The mixture was filtered, and the filtrate was concentrated to afford the title compound (1.15 g).

Intermediate B:

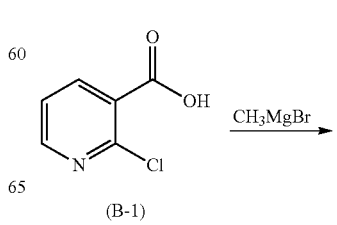

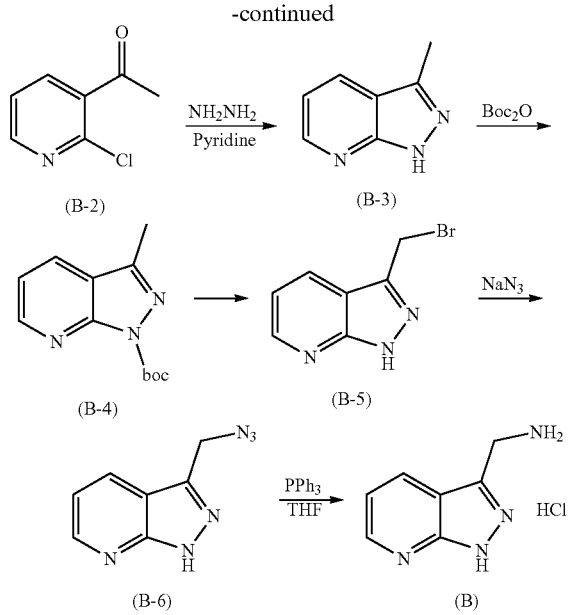

1-(2-Cloropyridin-3-yl)ethanone (B-2)

To a solution of 2-chloronicotinic acid (B-1) (7.88 g, 50.0 mmol) in THF (100 mL) was added methyl magnesium bromide (42 mL, 3M ethyl ether solution) dropwise under 0° C. Upon completion of the addition, the reaction mixture was stirred at 0° C. for 0.5 h and then at room temperature overnight. The reaction mixture was added into ice/water (150 mL), and extracted with ethyl acetate. The combined organic layers were dried over $Na_2SO_4$ and concentrated to afford the title compound 1-(2-chloropyridin-3-yl)ethanone (B-2). MS (m/z): 156 $(M+1)^+$.

3-Methyl-1H-pyrazolopyrrolo[3,4-b]pyridine (B-3)

A solution of 1-(2-chloropyridin-3-yl)ethanone (B-2) (6 g, 38.6 mmol) and hydrazine (85%, 9.1 g, 154.4 mmol) in pyridine (80 mL) was stirred under reflux overnight. The mixture was cooled to room temperature, concentrated, diluted with water (80 mL) and then extracted with ethyl acetate (100 mL×3). The combined organic layers were washed with brine, dried over $Na_2SO_4$, and concentrated under vacuo. The resulting residue was used for the next step without further purification. MS (m/z): 134 $(M+1)^+$.

tert-Butyl 3-methyl-1H-pyrazolo[3,4-b]pyridine-1-carboxylate (B-4)

To a solution of 3-methyl-1H-pyrazolo[3,4-b]pyridine (B-3) in EtOAc (300 mL) were added $(Boc)_2O$ (16.4 g, 75 mmol), DMAP (610 mg, 5 mmol), and $Et_3N$ (10 g, 100 mmol). The reaction mixture was stirred at room temperature overnight. Solvent was removed in vacuo, and the residue was purified by chromatography on silica gel to afford the title compound (5.3 g, 45.5% by two steps). MS (m/z): 134.

3-(Bomomethyl)-1H-pyrazolo[3,4-b]pyridine (B-5)

To a solution of tert-butyl 3-methyl-1H-pyrazolo[3,4-b]pyridine-1-carboxylate (B-4) (699 mg, 3 mmol) in $CCl_4$ (15 mL) were added NBS (641 mg, 3.6 mmol) and AIBN (70 mg, 0.3 mmol). The reaction mixture was stirred under reflux overnight and then filtered. The filtrate was washed with saturated aqueous $Na_2CO_3$ (15 mL). The organic layer was dried over $Na_2SO_4$ and concentrated to afford the crude product. The crude product was used for next step without further purification. MS (m/z): 212 $(M+1)^+$.

3-(Aidomethyl)-1H-pyrazolo[3,4-b]pyridine (B-6)

A mixture of 3-(bromomethyl)-1H-pyrazolo[3,4-b]pyridine (B-5) and $NaN_3$ (390 mg, 6 mmol) in DMF (6 mL) was stirred at 80° C. for 1.5 h. After the mixture was cooled to room temperature, water (25 mL) was added. The resulting mixture was extracted with ethyl acetate (40 mL×3). The combined organic layers were washed with brine (40 mL) and dried over $Na_2SO_4$. Solvent was removed in vacuo, and the residue was purified by chromatography on silica gel. A solid was obtained (152 mg, 29.1% by two steps).

(1H-Pzolo[3,4-b]pyridin-3-yl)methanaminium chloride (B)

A mixture of 3-(azidomethyl)-1H-pyrazolo[3,4-b]pyridine (B-6) (152 mg, 0.87 mmol), $PPh_3$ (465 mg, 1.74 mmol) and 1 mL of $NH_4OH$ in THF (20 mL) was stirred at room temperature overnight. The solution was concentrated, and the resulting residue was dissolved in ethyl acetate. The solution was treated with 2M HCl, which resulted in precipitates. The precipitates were collected by filtration to afford the title compound (121 mg). MS (m/z): 149 $(M+1)^+$. Intermediate C:

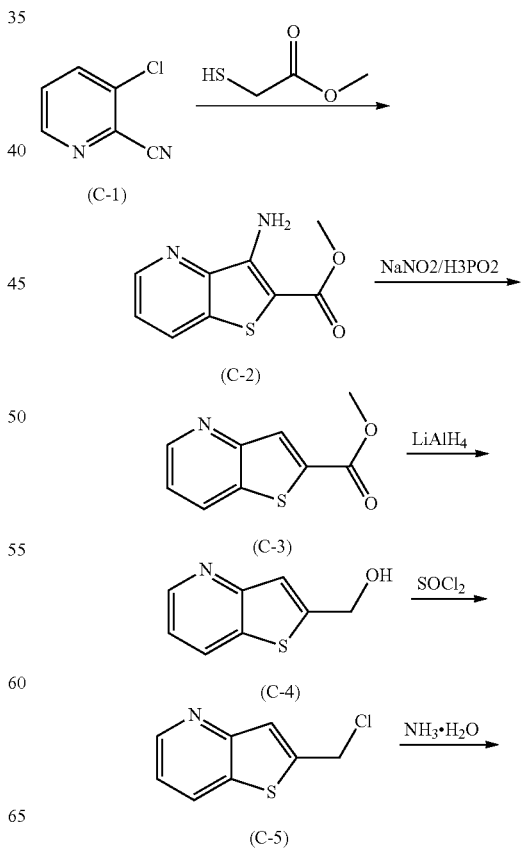

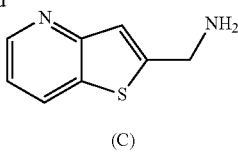

(C)

Methyl 3-aminothieno[3,2-b]pyridine-2-carboxylate (C-2)

To a mixture of 3-chloropyridine-2-carbonitrile (C-1) (1.01 g, 7.29 mmol) and K$_2$CO$_3$ (1.10 g, 7.96 mmol) in DMF (10 mL) and water (1 mL) was added methyl thioglycolate (0.709 mL, 7.93 mmol) dropwise. The reaction mixture was stirred at 40° C. for 3 h. The mixture was quenched with cold water (70 mL) and placed on ice to enhance precipitation. The precipitate was collected by filtration to afford the title compound. MS (m/z): 209 (M+1)$^+$.

Methyl thieno[3,2-b]pyridine-2-carboxylate (C-3)

To a solution of methyl 3-aminothieno[3,2-b]pyridine-2-carboxylate (C-2) (930 mg, 4.47 mmol) in hypophosphorous acid (35 mL) chilled in an ice bath was added sodium nitrite (620 mg, 8.98 mmol) in a minimal amount of water. The reaction mixture was stirred for 3 h in an ice bath, and then the pH was adjusted to about 7.0 with 30% aqueous sodium hydroxide solution. The resulting mixture was extracted with EtOAc. The combined organic layers were dried and concentrated to afford the title compound. MS (m/z): 194 (M+1)$^+$.

Thieno[3,2-b]pyridin-2-ylmethanol (C-4)

To a solution of methyl thieno[3,2-b]pyridine-2-carboxylate (C-3) (600 mg, 3.1 mmol) in 30 mL of anhydrous THF at 0° C. was added LiAlH$_4$ (472 mg, 12.4 mmol) in anhydrous THF (25 mL) dropwise over 20 mins. The reaction mixture was stirred at 0° C. for 30 mins. MeOH was added and the resulting mixture was purified by chromatography to afford the title compound. MS (m/z): 166 (M+1)$^+$.

2-(Cloromethyl)thieno[3,2-b]pyridine (C-5)

To a solution of thieno[3,2-b]pyridin-2-ylmethanol (C-4) (17 mg, 0.1 mmol) in anhydrous dichloromethane (10 mL) was added SOCl$_2$ (120 mg). After the mixture was stirred at room temperature for 2 hours, it was concentrated and used for the next step without further purification. MS (m/z): 184 (M+1)$^+$.

Thieno[3,2-b]pyridin-2-ylmethanamine (C)

2-(Chloromethyl)thieno[3,2-b]pyridine (C-5) (183 mg, 1 mmol) was dissolved in NH$_3$/methanol (7 N, 10 mL). The resulting mixture was stirred at 50° C. for 16 hours and concentrated. The residue was purified by chromatography. MS (m/z): 165 (M+1)$^+$.

Intermediates D and D'

Methyl thieno[3,2-c]pyridine-2-carboxylate (D-2)

To a solution of 4-chloropyridine-3-carboxaldehyde (D-1) (1.4 g, 10 mmol) dissolved in DMF (10 mL) and water (1 mL) were added K$_2$CO$_3$ (1.66 g, 12 mmol) and methyl thioglycolate (1.07 mL, 12 mmol) portion-wise. The reaction mixture was stirred at 45° C. overnight and then quenched with cold water. The flask was placed on ice to enhance precipitation. The precipitate was collected by filtration and air-dried to afford the title compound (1.23 g). MS (m/z): 194 (M+1)$^+$.

Thieno[3,2-c]pyridin-2-ylmethanol (D-3)

To a solution of methyl thieno[3,2-c]pyridine-2-carboxylate (D-2) (15 g, 77.6 mmol) in anhydrous THF (250 mL) was added LiAlH$_4$ (4.42 g, 116.4 mmol) in portions at 0° C. The suspension was stirred at 0° C. for 1 h and then quenched by adding saturated aqueous NH$_4$Cl and filtered. The filtrate was washed with brine and concentrated. The residue was used in the next step without any further purification (10.3 g).

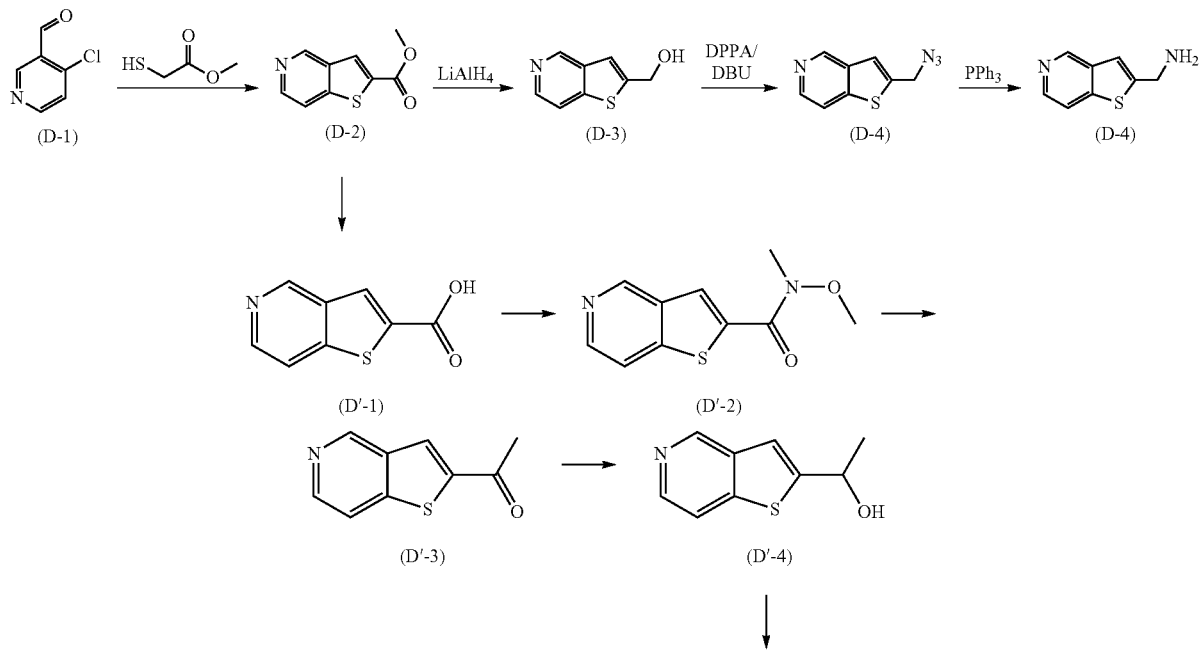

-continued

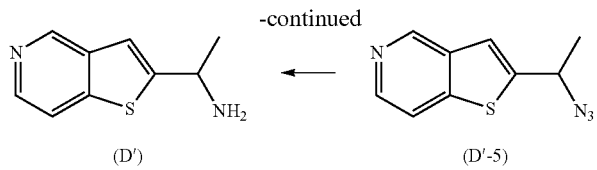

2-(Azidomethyl)thieno[3,2-c]pyridine (D-4)

To a flame-dried round-bottomed flask containing thieno[3,2-c]pyridin-2-ylmethanol (D-3) (3.2 g, 19.4 mmol) was added DPPA (8 g, 6.26 mL, 29.1 mmol) in THF (50 mL). The reaction mixture was stirred for 5 mins and cooled to 0° C., followed by adding DBU (4.43 g, 4 mL, 29.1 mmol) via syringe. The mixture was allowed to stir at reflux overnight. The reaction was then partitioned between water and ethyl ether. The aqueous layer was extracted with ethyl ether. The combined organic layers were washed with brine, dried over $Na_2SO_4$, concentrated, and purified by chromatography to afford the product (3.27 g). MS (m/z): 191 $(M+1)^+$.

Thieno[3,2-c]pyridin-2-ylmethanamine hydrochloride (D)

To a solution of 2-(azidomethyl)thieno[3,2-c]pyridine (D-4) (3 g, 15.8 mmol) in anhydrous THF (50 mL) was added $Ph_3P$ (8.27 g, 31.5 mmol), followed by $NH_4OH$ (2 mL). The solution was stirred at room temperature overnight. Solvent was removed, and the residue was purified by chromatography to afford the title compound (2.5 g).

Thieno[3,2-c]pyridine-2-carboxylic acid (D'-1)

To a solution of methyl thieno[3,2-c]pyridine-2-carboxylate (D-2) (12 g, 62.1 mmol) in MeOH (150 mL) and $H_2O$ (15 mL) was added $LiOH.H_2O$ (5.2 g, 124.2 mmol). The solution was stirred at room temperature overnight, and then acidified with 1N aqueous HCl. The resulting white precipitate was collected by filtration and air-dried to afford the title compound. MS (m/z): 179 $(M)^+$.

N-Methoxy-N-methylthieno[3,2-c]pyridine-2-carboxamide (D'-2)

To a solution of thieno[3,2-c]pyridine-2-carboxylic acid (D'-1) (11.5 g, 64.2 mmol) in DCM (200 mL) and DMF (50 mL) was added $Et_3N$ (19.5 g, 26.6 mL, 192.6 mmol) followed by HATU (36.6 g, 96.3 mmol). The reaction solution was stirred at room temperature for 20 mins, and then treated with N,O-dimethylhydroxylamine hydrochloride (6.9 g, 70.6 mmol). Stirring continued overnight at room temperature. The solvent was removed. The residue was dissolved in EtOAc and washed with water and brine. The organic layer was dried and concentrated. The residue was purified by chromatography on silica gel to give the title compound. MS (m/z): 223 $(M+1)^+$.

1-(Thieno[3,2-c]pyridin-2-yl)ethanone (D'-3)

To a solution of N-methoxy-N-methylthieno[3,2-c]pyridine-2-carboxamide (D'-2) (11.1 g, 50 mmol) in anhydrous THF (150 mL) was added MeMgBr (3M in ethyl ether, 25 mL, 75 mmol) at 0° C. under $N_2$. The reaction mixture was allowed to warm to the ambient temperature and stirred overnight. Saturated aqueous $NH_4Cl$ solution was added to quench the reaction. The resulting mixture was then extracted with EtOAc. The combined organic layers were dried over $Na_2SO_4$, filtered, and concentrated to afford the title compound. MS (m/z): 178 $(M+1)^+$.

1-(Thieno[3,2-c]pyridin-2-yl)ethanol (D'-4)

To a solution of 1-(thieno[3,2-c]pyridin-2-yl)ethanone (D'-3) (3.5 g, 1 mmol) in anhydrous THF (50 mL) was added $LiAlH_4$ (1.13 g, 1.5 mmol) in portions at 0° C. The suspension was stirred under this temperature for 1 h. The reaction mixture was quenched with saturated aqueous $NH_4Cl$ solution and filtered. The filtrate was washed with brine, concentrated, and then used for the next step without any further purification.

1-(Thieno[3,2-c]pyridin-2-yl)ethanamine (D')

Intermediate D' was prepared from 1-(thieno[3,2-c]pyridin-2-yl)ethanol (D'-4) following similar procedures for synthesizing intermediate A from A-3, as described above.

Intermediate E:

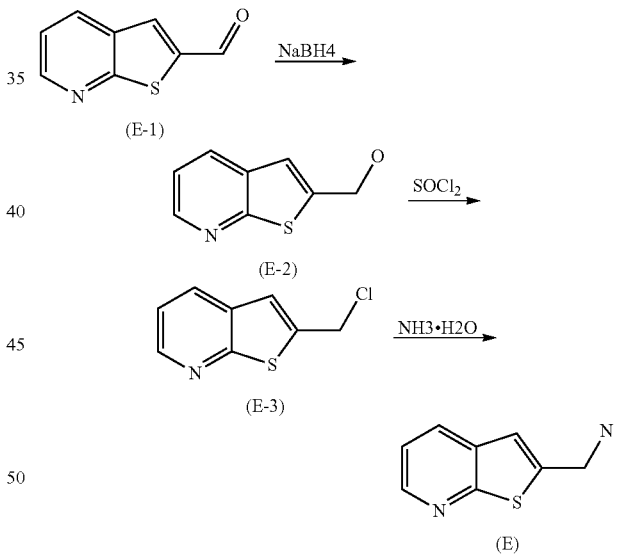

Thieno[2,3-b]pyridin-2-ylmethanol (E-2)

E-2 was prepared from thieno[2,3-b]pyridine-2-carbaldehyde (E-1) following similar procedures for synthesizing intermediate A-3 from A-2, as described above. MS (m/z): 166 $(M+1)^+$.

Thieno[2,3-b]pyridin-2-ylmethanamine (E)

Intermediate E was prepared from thieno[2,3-b]pyridine-2-ylmethanol (E-2) following similar procedures for synthesizing intermediate C from C-4, as described above. MS (m/z): 165 $(M+1)^+$.

Intermediate F:

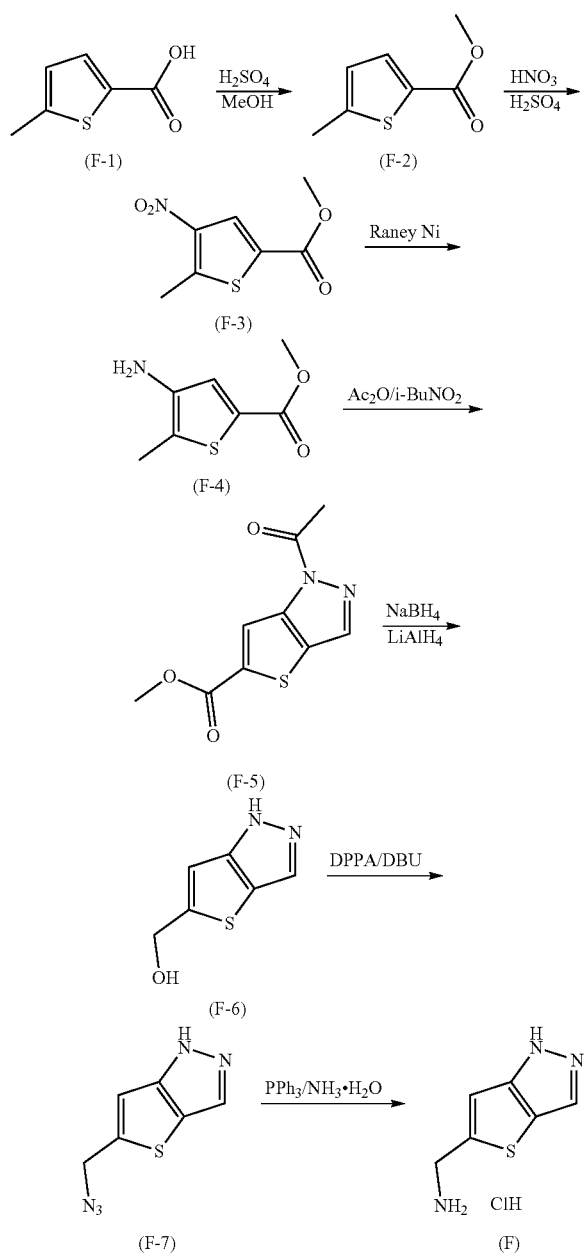

Methyl 5-methylthiophene-2-carboxylate (F-2)

To a solution of 5-methylthiophene-2-carboxylic acid (F-1) (14.0 g, 0.1 mol) in MeOH (250 mL) was added concentrated $H_2SO_4$ (2.0 mL). The reaction mixture was stirred under reflux for 60 h. The solvent was removed in vacuo. Ethyl acetate was added to dilute the reaction mixture. Then the organic solution was washed with a saturated aqueous $Na_2CO_3$ solution, and dried over $Na_2SO_4$. The solvent was removed to afford the title compound (13.4 g).

Methyl 5-methyl-4-nitrothiophene-2-carboxylate (F-3)

A solution of concentrated $HNO_3$ (7.2 mL, 111.5 mmol) in concentrated $H_2SO_4$ (20 mL) was added dropwise to the solution of methyl 5-methylthiophene-2-carboxylate (F-2) (13.4 g, 86.0 mmol) in concentrated $H_2SO_4$ (30 mL) at 0° C. The reaction mixture was stirred at 0° C. for 30 mins and poured into ice-water. The precipitate was filtered and washed with water. A solid was collected as the product (14.8 g).

Methyl 4-amino-5-methylthiophene-2-carboxylate (F-4)

To a solution of methyl 5-methyl-4-nitrothiophene-2-carboxylate (F-3) (14.8 g, 73.6 mmol) in MeOH/THF (1:1, 300 mL) was added Raney Ni. The reaction mixture was degassed and charged with hydrogen 3 times, and then stirred at room temperature for 36 h under 1 atmosphere of hydrogen. Raney Ni was filtered, and the filtrate was concentrated. The residue was treated with aqueous HCl (1 N, 150 mL) and filtered. The filtrate was treated with aqueous NaOH (1 N) to bring pH to about 8 to 9. Then the mixture was extracted with ethyl acetate. The combined organic layers were dried over $Na_2SO_4$, and the solvent was removed to give the title compound (8.1 g).

Methyl 1-acetyl-1H-thieno[3,2-c]pyrazole-5-carboxylate (F-5)

To a solution of methyl 4-amino-5-methylthiophene-2-carboxylate (F-4) (5.1 g, 30 mmol) in toluene (120 mL) were added acetic anhydride (16.0 g, 0.12 mol) and potassium acetate (1.5 g, 15.1 mmol). The reaction mixture was stirred at 100° C. for 3 h. After cooled to room temperature, the reaction mixture was treated with isobutyl nitrite (10.5 g, 90.0 mmol), and then stirred at 1000° C. overnight. Water was added, and then the mixture was extracted with ethyl acetate. The combined organic layers were washed with brine, dried over $Na_2SO_4$ and concentrated. The residue was purified by chromatography eluting with Pet/EtOAc=10/1 to afford the title compound (5.3 g) as the product.

(1H-Thieno[3,2-c]pyrazol-5-yl)methanol (F-6)

To a solution of methyl 1-acetyl-1H-thieno[3,2-c]pyrazole-5-carboxylate (F-5) (4.5 g, 20.0 mmol) in MeOH (30 mL) was slowly added $NaBH_4$ (836 mg, 22.0 mmol). The mixture was stirred at room temperature for 30 mins, and then concentrated. The residue was dissolved in anhydrous THF (80 mL) and then $LiAlH_4$ (1.5 g, 40.0 mmol) was slowly added at 0° C. The reaction mixture was stirred at 0° C. for 30 min. Aqueous $NH_4Cl$ solution was added dropwise to quench the reaction. The resulting mixture was filtered, and the filtrate was extracted with ethyl acetate. The combined organic layers were washed with brine, dried over $Na_2SO_4$, and concentrated in vacuo to give the title compound (2.9 g).

(1H-Thieno[3,2-c]pyrazol-5-yl)methanaminium chloride (F)

Intermediate F was prepared from (1H-thieno[3,2-c]pyrazol-5-yl)methanol (F-6) following similar procedures for synthesizing intermediate D from D-3, as described above.

Intermediate G and G':

1H-Thieno[3,2-c]pyrazole-5-carboxylic acid (G-1)

To a solution of methyl 1-acetyl-1H-thieno[3,2-c]pyrazole-5-carboxylate (F-5) (4.9 g, 21.8 mmol) in MeOH (15 mL) was added an aqueous KOH solution (6 N, 10 mL). The reaction mixture was stirred at room temperature for 2 h, and then concentrated in vacuo. Aqueous HCl (6 N) was added to adjust pH to 5-6. The precipitates were collected by filtration to afford the title compound (3.0 g).

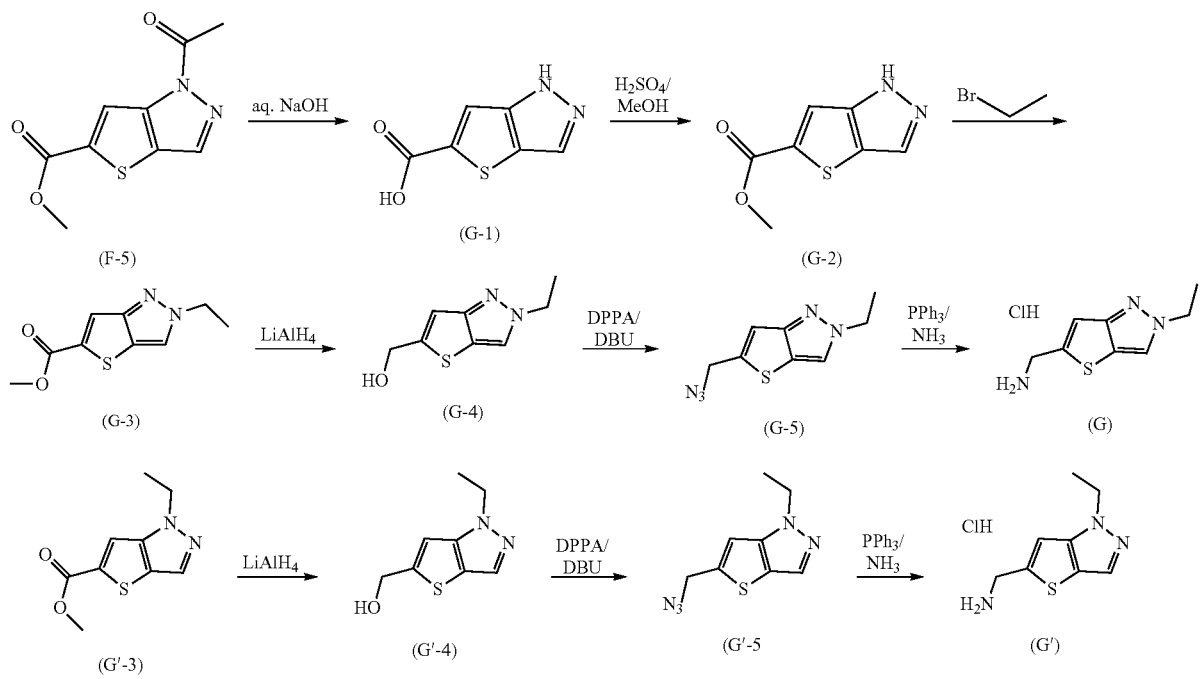

Methyl 1H-thieno[3,2-c]pyrazole-5-carboxylate (G-2)

To a solution of 1H-thieno[3,2-c]pyrazole-5-carboxylic acid (G-1) (3.0 g, 17.9 mmol) in MeOH (50 mL) was added concentrated $H_2SO_4$ (0.3 mL). The reaction mixture was stirred at reflux for 60 h. Solvent was removed in vacuo. Ethyl acetate was added to dilute the mixture. The mixture was washed with aqueous $NaHCO_3$ solution, dried over $Na_2SO_4$, and concentrated in vacuo to afford the title compound (2.4 g).

Methyl 2-ethyl-2H-thieno[3,2-c]pyrazole-5-carboxylate (G-3) and Methyl 1-ethyl-1H-thieno[3,2-c]pyrazole-5-carboxylate (G'-3)

To a solution of methyl 1H-thieno[3,2-c]pyrazole-5-carboxylate (G-2) (760 mg, 4.2 mmol) in DMF (4 mL) were added bromoethane (915 mg, 8.3 mmol) and $K_2CO_3$ (1.7 g, 12.6 mmol). The reaction mixture was stirred at 110° C. for 3 h in a sealed tube. After cooled to room temperature, the mixture was concentrated and purified by chromatography to afford two products:

Methyl 2-ethyl-2H-thieno[3,2-c]pyrazole-5-carboxylate (351 mg) (G-3). MS (m/z): 211 (M+1)$^+$.
Methyl 1-ethyl-1H-thieno[3,2-c]pyrazole-5-carboxylate (272 mg) (G'-3). MS (m/z): 211 (M+1)$^+$.

(2-Ethyl-2H-thieno[3,2-c]pyrazol-5-yl)methanaminium chloride (G)

Intermediate G was prepared from methyl 2-ethyl-2H-thieno[3,2-c]pyrazole-5-carboxylate (G-3) following similar procedures for synthesizing intermediate D from D-2, as described above. MS (m/z): 182 (M+1)$^+$.

(1-Ethyl-1H-thieno[3,2-c]pyrazol-5-yl)methanamine chloride (G')

Intermediate G' was prepared from methyl 1-ethyl-1H-thieno[3,2-c]pyrazole-5-carboxylate (G'-3) following similar procedures for synthesizing intermediate D from D-2, as described above. MS (m/z): 182 (M+1)$^+$.
Intermediate H and H':

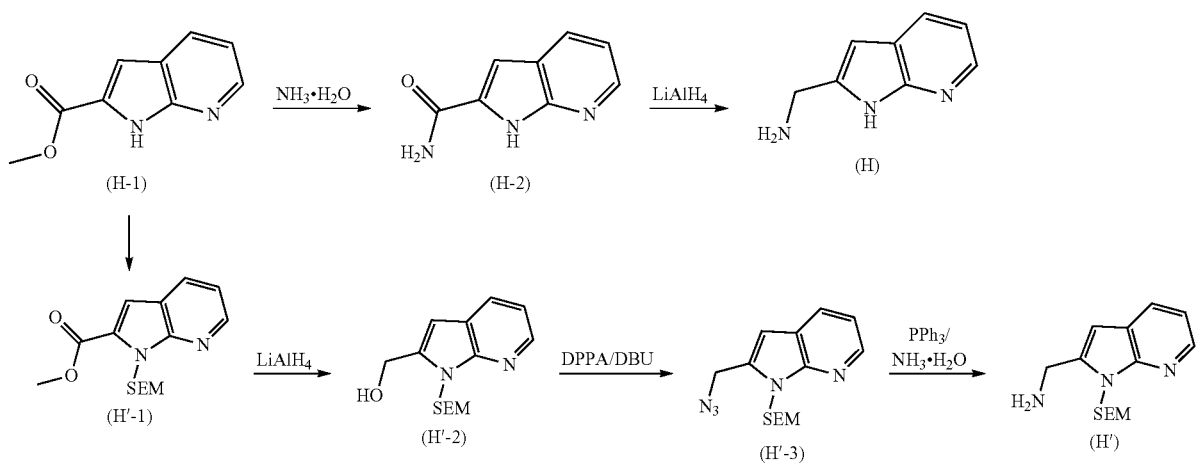

1H-Pyrrolo[2,3-b]pyridine-2-carboxamide (H-2)

To a solution of methyl 1H-pyrrolo[2,3-b]pyridine-2-carboxylate (H-1) (880 mg, 5.0 mmol) in MeOH (2 mL) was added $NH_3 \cdot H_2O$ (6 mL). The reaction was heated at 80° C. overnight. After being cooled to room temperature, the mixture was concentrated in vacuo to afford the title compound (805 mg) as a yellow solid, which was used for the next step without further purification. MS (m/z): 162 (M+1)$^+$.

(1H-Pyrrolo[2,3-b]pyridin-2-yl)methanamine (H)

To a solution of 1H-pyrrolo[2,3-b]pyridine-2-carboxamide (H-2) (805 mg, 5.0 mmol) in dried THF (10 mL) at 0° C. under 1 atm of $N_2$ was slowly added $LiAlH_4$ (570 mg, 15 mmol). The mixture was stirred at 80° C. overnight. The mixture was then cooled to 000° C. concentrated, and then purified by chromatography on silica gel to afford the title compound (720 mg). MS (m/z): 148 (M+1)$^+$.

Methyl 1-((2-(trimethylsilyl)ethoxy)methyl)-$^1$H-pyrrolo[2,3-b]pyridine-2-carboxylate (H'-1)

To a solution of methyl 1H-pyrrolo[2,3-b]pyridine-2-carboxylate (H-1) (528 mg, 3 mmol) in dried THF (5 mL) at 0° C. was added NaH (240 mg, 6 mmol). The reaction was stirred for 0.5 h under $N_2$, and then SEMCl (526 mg, 3 mmol) was added dropwise. The mixture was stirred at room temperature for 2 h. $H_2O$ was added to quench the reaction. The resulting mixture was extracted with EtOAc. The organic layer was dried over $Na_2SO_4$, and concentrated to afford the title compound (750 mg), which was used for the next step without purification. MS (m/z): 307 (M+1)$^+$.

(1-((2-(Trimethylsilyl)ethoxy)methyl)-1H-pyrrolo[2,3-b]pyridin-2-yl)methanamine (H')

Intermediate H' was prepared from methyl 1-((2-(trimethylsilyl)ethoxy)methyl)-$^1$H-pyrrolo[2,3-b]pyridine-2-carboxylate (H'-1) following similar procedures for synthesizing intermediate D from D-2, as described above. MS (m/z): 278 (M+1)$^+$.

Intermediate I:

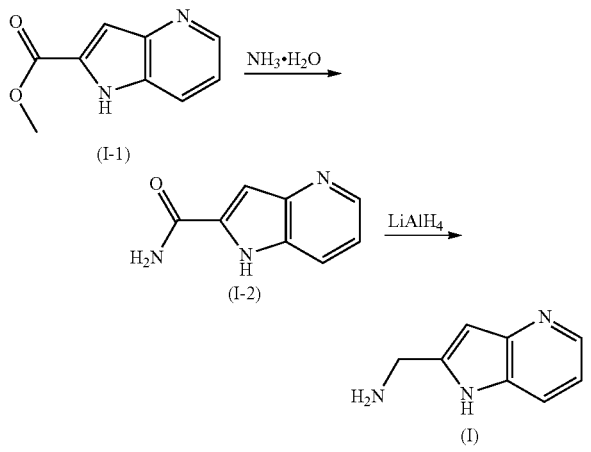

(1H-Pyrrolo[3,2-b]pyridin-2-yl)methanamine (I)

Intermediate I was prepared from methyl 1H-pyrrolo[3,2-b]pyridine-2-carboxylate (I-1) following similar procedures for synthesizing intermediate H, as described above. MS (m/z): 148 (M+1)$^+$.

Intermediate J:

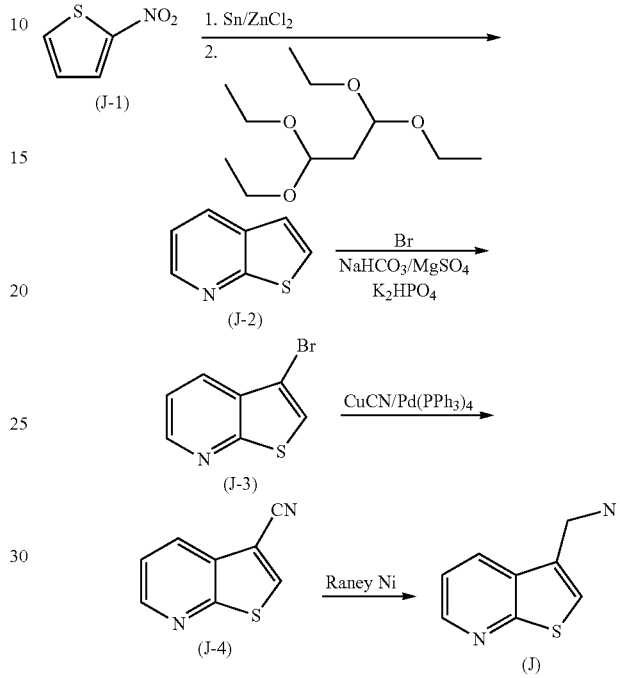

Thieno[2,3-b]pyridine (J-2)

To a vigorously stirred mixture of 2-nitrothiophene (J-1) (13 g, 0.1 mol) and concentrated hydrochloric acid (195 mL) was added tin (25 g) at 0° C. After most of the tin was dissolved, EtOH (70 mL) and anhydrous $ZnCl_2$ (6 g) were added. The mixture was heated to 85° C., and then treated with malonaldehyde bis(diethyl acetal) (17.2 g, 0.078 mol) in EtOH (30 mL). The resulting reaction was maintained at 85° C. for 1 h, then poured onto ice (100 g), basified with $NH_3 \cdot H_2O$, and extracted with DCM (75 mL×3). The combined organic layers were concentrated and purified by chromatography on silica gel to give the title compound. MS (m/z): 135 (M)$^+$.

3-Bromothieno[2,3-b]pyridine (J-3)

Bromine (2.08 g, 13 mmol) was dropwise added to a mixture of thieno[2,3-b]pyridine (J-2) (1.35 g, 10 mmol), dipotassium monohydrogen orthophosphate (940 mg, 5.4 mmol), sodium bicarbonate (840 mg 10 mmol), and magnesium sulfate (2.0 g, 16.7 mmol) in chloroform (40 mL) which has been stirred at reflux for 16 h, the resulting mixture was stirred under reflux for 24 h, then filtered and washed with DCM. The filtrate was concentrated, and purified by chromatography. MS (m/z): 214 (M+1)$^+$.

Thieno[2,3-b]pyridine-3-carbonitrile (J-4)

To a stirred solution of 3-bromothieno[2,3-b]pyridine (J-3) (107 mg, 0.5 mmol) and CuCN (60 mg, 0.67 mmol) in anhydrous DMF (4 mL) was added Pd(PPh$_3$)$_4$ (57 mg, 0.05 mmol). The reaction was degassed with nitrogen and stirred at 120° C. for 5 h. Then the cooled mixture was concentrated and purified by chromatography to afford the title compound. MS (m/z): 161 (M+1)$^+$.

Thieno[2,3-b]pyridin-3-ylmethanamine (J)

To a solution of thieno[2,3-b]pyridine-3-carbonitrile (J-4) (320 mg, 2 mmol) in NH$_3$.EtOH (25 mL) was added Ranye/Ni (about 300 mg). The reaction was degassed with hydrogen and stirred at room temperature for 2 h. Then the mixture was filtered, and the filtrate was concentrated to give the title compound, which was used for next step without purification. MS (m/z): 165 (M+1)$^+$.

Intermediate K:

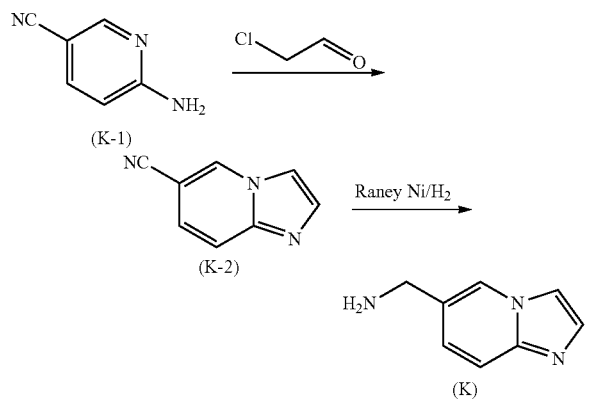

H-Imidazo[1,2-a]pyridine-6-carbonitrile (K-2)

To a solution of 6-aminonicotinonitrile (K-1) (4.0 g, 33.6 mmol) in anhydrous EtOH (160 mL) was added 2-chloroacetaldehyde (40% in H$_2$O, 27.5 mL, 168 mmol). The reaction was refluxed for 4 h, and then concentrated. The resulting residue was dissolved in water and adjusted to pH>7 with a saturated NaHCO$_3$ solution. The precipitate was collected and dried to afford the title compound (4.80 g).

(H-Imidazo[1,2-a]pyridin-6-yl)methanamine (K)

Intermediate K was prepared from H-imidazo[1,2-a]pyridine-6-carbonitrile (K-2) following similar procedures for synthesizing intermediate J from J-4, as described above.

Intermediate L:

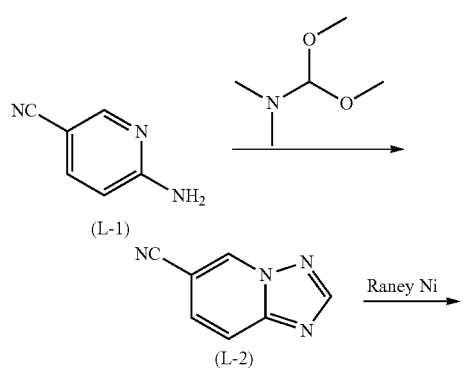

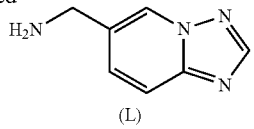

[1,2,4]triazolo[1,5-a]pyridine-6-carbonitrile (L-2)

To a stirred solution of 6-aminonicotinonitrile (L-1) (8.7 g, 73 mmol) in DMF (35 mL) was added N,N-dimethylformamide dimethyl acetal (35 mL, 294 mmol). The reaction mixture was heated to 130° C. overnight. After cooled to room temperature, the volatiles were removed under reduced pressure to afford the desired intermediate N-(5-cyanopyridin-2-yl)-N,N-dimethylformamidine.

To an ice-cooled, stirred solution of the above product in methanol (200 mL) and pyridine (11.5 mL, 143 mmol) was added hydroxylamine-O-sulfonic acid (11.3 g, 100 mmol). The reaction mixture was allowed to warm to room temperature and was stirred overnight. Then the volatiles were removed under reduced pressure, and the residue was partitioned between aqueous sodium bicarbonate solution and ethyl acetate. The aqueous layer was further extracted with ethyl acetate. The combined organic layers were washed sequentially with water and brine, dried over anhydrous Na$_2$SO$_4$, filtered, and concentrated. The resulting residue was purified by chromatography on silica gel to give the title compound (5.5 g). MS (m/z): 145 (M+1)$^+$.

[1,2,4]Triazolo[1,5-a]pyridin-6-ylmethanamine (L)

Intermediate L was prepared from [1,2,4]triazolo[1,5-a]pyridine-6-carbonitrile (L-2) following similar procedures for synthesizing intermediate J from J-4, as described above.

Intermediate M:

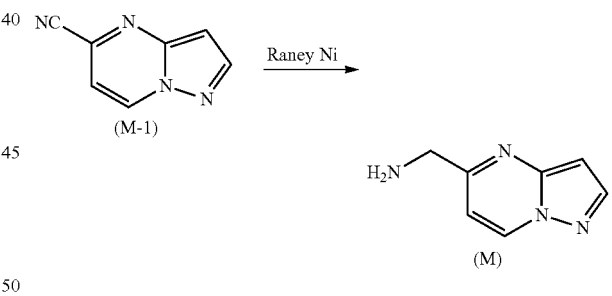

Pyrazolo[1,5-a]pyrimidin-5-ylmethanamine (M)

Intermediate M was prepared from pyrazolo[1,5-a]pyrimidine-5-carbonitrile (M-1) following similar procedures for synthesizing intermediate J from J-4, as described above. MS (m/z): 149 (M+1)$^+$.

Intermediate N:

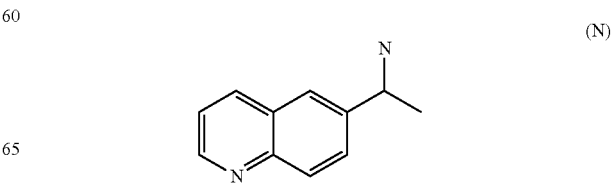

Intermediate N was prepared from quinoline-6-carboxylic acid as described in US2007/0265272.

Intermediate O:

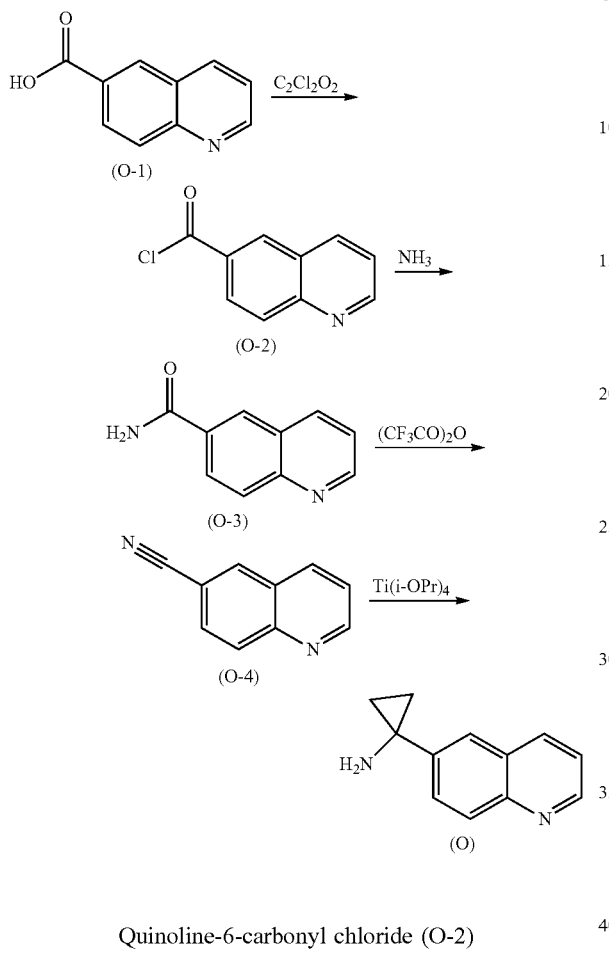

Quinoline-6-carbonyl chloride (O-2)

To a mixture of quinoline-6-carboxylic acid (O-1) (2.0 g, 11.5 mmol) in $CH_2Cl_2$ (250 mL) was added 3 drops of DMF at 0° C., followed by oxalyl chloride (7.3 g, 57.5 mmol) dropwise. The resulting reaction was stirred at room temperature overnight, and then concentrated to afford the title compound (2.2 g).

Quinoline-6-carboxamide (O-3)

To a solution of quinoline-6-carbonyl chloride (O-2) (2.2 g, 10.5 mmol) in THF (100 mL) was added ammonia (5 mL) at 0° C. The mixture was stirred at room temperature for 1 h, then concentrated and washed with water (15 mL) to afford the title compound (1.5 g). MS (m/z): 173 $(M+1)^+$.

Quinoline-6-carbonitrile (O-4)

To a mixture of quinoline-6-carboxamide (O-3) (1.2 g, 7.2 mmol) and triethylamine (2.2 g, 21.8 mmol) in DCM (50 mL) at 0° C. was added trifluoroacetic acid anhydride (1.9 g, 8.9 mmol). The reaction was stirred for 10 mins at 0° C., then quenched with water. The resulting mixture was extracted with DCM. The organic layer was dried over anhydrous $Na_2SO_4$, and concentrated to afford the desired title compound (1.0 g). MS (m/z): 154 $(M)^+$.

1-(Quinolin-6-yl)cyclopropanamine (O)

Ethylmagnesium bromide (7.7 mmol, 3 M in ethyl ether) was added to a solution of quinoline-6-carbonitrile (O-4) (540 mg, 3.5 mmol) and Ti(Oi-Pr)$_4$ (3.9 mmol, 1.16 mL) in Et$_2$O (15 mL) at −70° C. The resulting yellow solution was stirred for 10 mins, warmed to room temperature over 1.5 h, and then was treated with BF$_3$.OEt$_2$ (7 mmol, 0.88 mL). The resulting mixture was stirred for 1 h. Then 1N aqueous HCl (11 mL) and ethyl ether (40 mL) were added, followed by NaOH (10% aq, 30 mL). The mixture was extracted with ethyl ether. The combined ethyl ether layers were dried over anhydrous Na$_2$SO$_4$, filtered, and concentrated in vacuo to afford the crude title compound, which was used for the next step without further purification. MS (m/z): 185 $(M+1)^+$.

Intermediate P

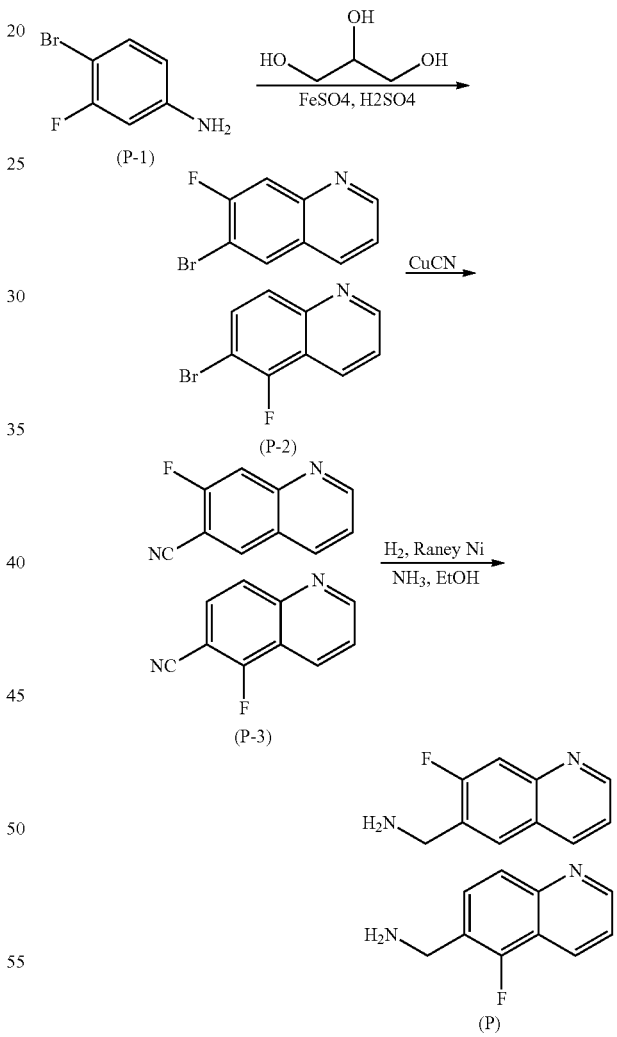

6-Bromo-7-fluoroquinoline and
6-bromo-5-fluoroquinoline (P-2)

A mixture of 4-bromo-3-fluoroaniline (P-1) (5.7 g, 30 mmol), propane-1,2,3-triol (11.04 g, 120 mmol), FeSO$_4$.7H$_2$O (1.92 g, 6.9 mmol), and nitrobenzene (2.22 g, 18 mmol) was stirred at room temperature for 10 mins, then concentrated H$_2$SO$_4$ (9.7 g, 9.9 mmol) was added. The resulting mixture was stirred at reflux for 7 h. After cooling to room temperature, the reaction was poured into water, basified with NH$_3$.H$_2$O to pH about 8, and extracted with DCM. The concentrated organic layer was purified by chromatography on silica gel (eluted with Pet/EtOAc=15/1) to afford the title compound mixture. 6.78 g. MS (m/z): 226 (M+1)$^+$.

(7-Fluoroquinolin-6-yl)methanamine and (5-fluoroquinolin-6-yl)methanamine (P)

These compounds were prepared from 6-bromo-7-fluoroquinoline and 6-bromo-5-fluoroquinoline (P-2) following similar procedures for synthesizing Intermediate J from J-3, as described above. MS (m/z): 177 (M+1)$^+$.

Intermediate Q:

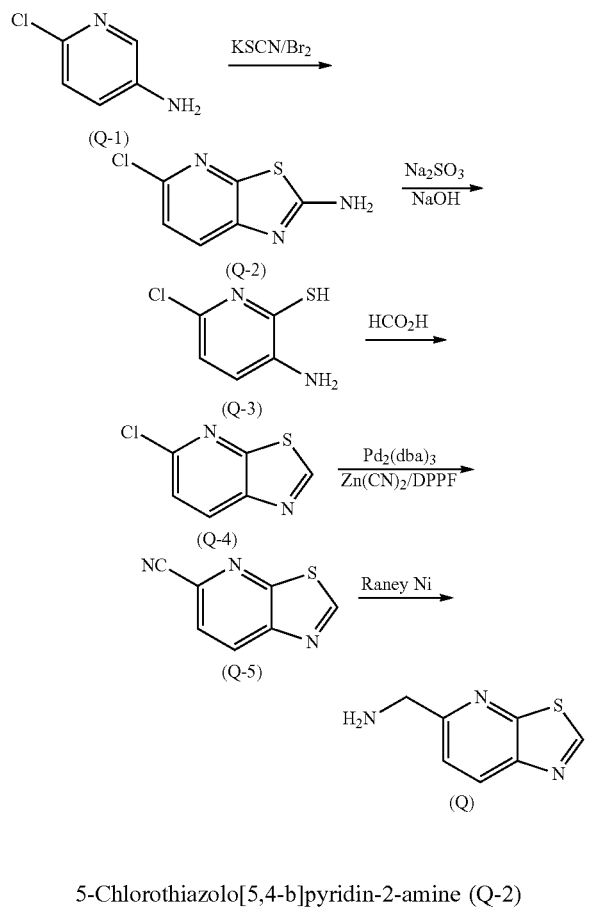

5-Chlorothiazolo[5,4-b]pyridin-2-amine (Q-2)

To glacial acetic acid (125 mL) pre-cooled to 5° C. were added potassium thiocyanate (93 g, 961 mmol) and 6-chloropyridin-3-amine (Q-1) (15 g, 117 mmol). The mixture was placed in a freezing mixture of ice and salt and stirred, while 10 mL of bromine in glacial acetic acid (30 mL) was added from an addition funnel at such a rate that the temperature never rose beyond 0° C. After all the bromine had been added, the solution was stirred for an additional 2 h at 0° C. and at room temperature overnight. Water (60 mL) was added quickly, and the slurry maintained at 90° C. was filtered hot. The orange filter cake was placed in the reaction flask. Glacial acetic acid (60 mL) was added to the flask. The mixture in the flask was maintained at 85° C. was filtered hot once again. The combined filtrates were cooled and neutralized with concentrated ammonia solution to pH 6. A precipitate was collected as the title compound (19 g). MS (m/z): 186 (M+1)$^+$.

3-Amino-6-chloropyridine-2-thiol (Q-3)

5-Chlorothiazolo[5,4-b]pyridin-2-amine (Q-2) (19 g, 103 mmol) containing sodium sulfite (2 g) was refluxed in 20% aqueous sodium hydroxide solution (150 mL) overnight. The solids were completely dissolved after 1 h, then cooled to room temperature. The solution was neutralized with formic acid. A precipitate was collected by filtration as the title compound (16.4 g).

5-Chlorothiazolo[5,4-b]pyridine (Q-4)

3-Amino-6-chloropyridine-2-thiol (Q-3) (16.4 g, 103 mmol) in formic acid (80 mL) was refluxed at 110° C. for 2 h. The reaction mixture was cooled and neutralized with concentrated ammonia to pH 7. A precipitate was collected by filtration as the title compound (14.5 g). MS (m/z): 171 (M+1)$^+$.

Thiazolo[5,4-b]pyridine-5-carbonitrile (Q-5)

To an 8 mL screw cap vial equipped with a magnetic stirring bar were added 5-chlorothiazolo[5,4-b]pyridine (Q-4) (460 mg, 2.7 mmol), Zn(CN)$_2$ (316 mg, 2.7 mmol), Pd$_2$(dba)$_3$ (123 mg, 0.13 mmol), DPPF (150 mg, 0.27 mmol) and DMF (5 mL, wet, containing 1% of H$_2$O). The vial was flushed with nitrogen, then sealed with the screw cap. The mixture was stirred at 120° C. for overnight, and then concentrated in vacuo. The resulting residue was purified by chromatography on silica gel to give the title compound (151 mg).

Thiazolo[5,4-b]pyridin-5-ylmethanamine (Q)

Intermediate Q was prepared from thiazolo[5,4-b]pyridine-5-carbonitrile (Q-5) following similar procedures for synthesizing intermediate J from J-4, as described above. MS (m/z): 166 (M+1)$^+$.

Intermediate R:

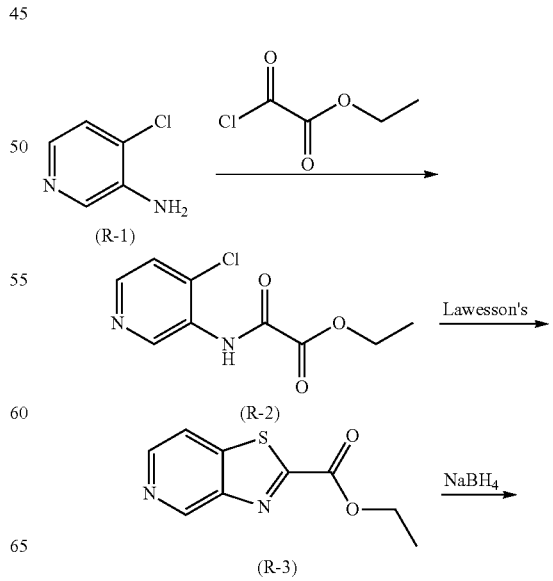

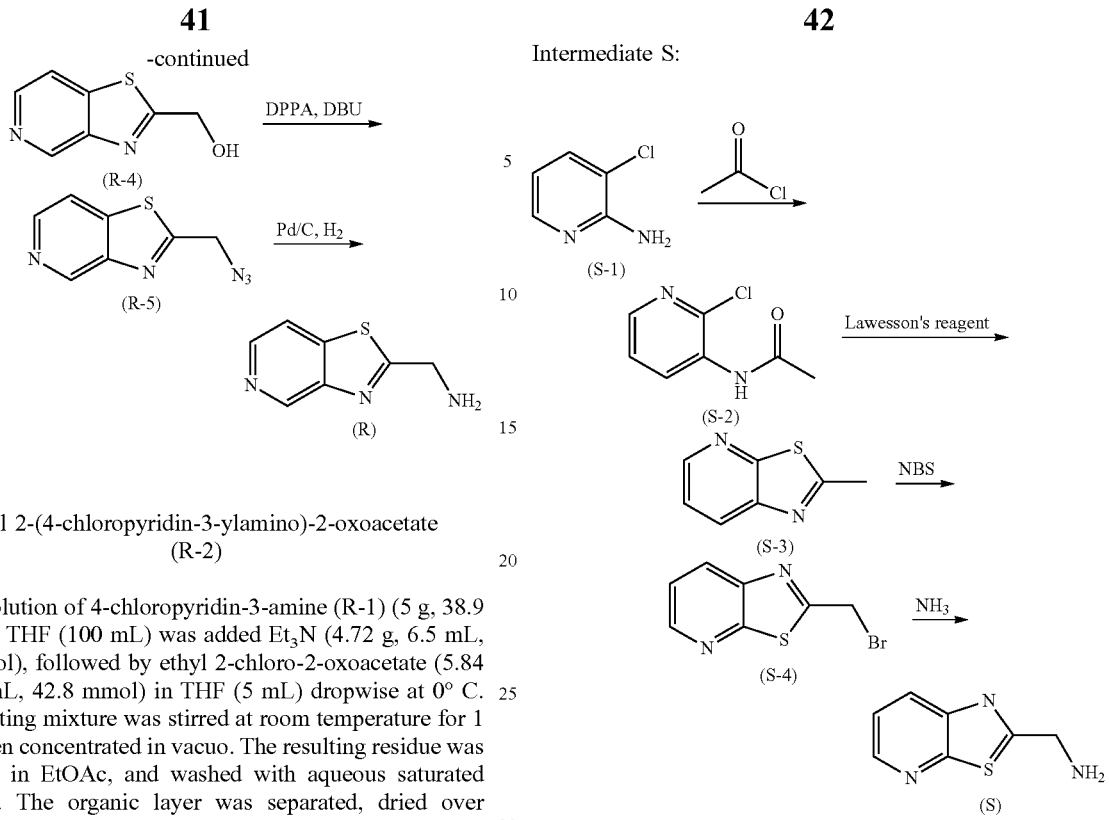

Ethyl 2-(4-chloropyridin-3-ylamino)-2-oxoacetate (R-2)

To a solution of 4-chloropyridin-3-amine (R-1) (5 g, 38.9 mmol) in THF (100 mL) was added $Et_3N$ (4.72 g, 6.5 mL, 46.7 mmol), followed by ethyl 2-chloro-2-oxoacetate (5.84 g, 4.78 mL, 42.8 mmol) in THF (5 mL) dropwise at 0° C. The resulting mixture was stirred at room temperature for 1 h, and then concentrated in vacuo. The resulting residue was dissolved in EtOAc, and washed with aqueous saturated $NaHCO_3$. The organic layer was separated, dried over $Na_2SO_4$, and concentrated to give the title compound, which was used for the next step without further purification. MS (m/z): 229 $(M+1)^+$.

Ethyl thiazolo[4,5-c]pyridine-2-carboxylate (R-3)

A solution of ethyl 2-(4-chloropyridin-3-ylamino)-2-oxoacetate (R-2) (8 g, 35 mmol) and Lawesson's reagent (8.5 g, 21 mmol) in toluene (100 mL) was refluxed for 2 h, and then concentrated in vacuo. The residue was purified by chromatography on silica gel to give the title compound. MS (m/z): 209 $(M+1)^+$.

Thiazolo[4,5-c]pyridin-2-ylmethanol (R-4)

To a solution of ethyl thiazolo[4,5-c]pyridine-2-carboxylate (R-3) (5 g, 24 mmol) in ethanol (100 mL) was added $NaBH_4$ (0.9 g, 24 mmol) in portions at 0° C. The suspension was stirred at room temperature for 1 h, and then concentrated. The resulting residue was dissolved in EtOAc, washed with water. The organic layer was separated, dried over $Na_2SO_4$, concentrated in vacuo and purified by chromatography on silica gel to give the title compound. MS (m/z): 167 $(M+1)^+$.

Thiazolo[4,5-c]pyridin-2-ylmethanamine (R)

Intermediate R was prepared from thiazolo[4,5-c]pyridin-2-ylmethanol (R-4) following similar procedures for synthesizing intermediate A from A-3, as described above. MS (m/z): 165 $(M)^+$.

Intermediate S:

N-(2-Chloropyridin-3-yl)acetamide (S-2)

To a mixture of 3-chloropyridin-2-amine (S-1) (12.8 g, 100 mmol) and $Et_3N$ (3 mL) in dried DCM (50 mL) was added acetyl chloride (8 mL) dropwise. The reaction was stirred at room temperature overnight, then adjusted to pH about 7 with an aqueous $NaHCO_3$ solution, and extracted with DCM. The organic layer was washed with water, dried over $Na_2SO_4$, and concentrated to afford the title compound (17.1 g). MS (m/z): 171.6 $(M+1)^+$.

2-Methylthiazolo[5,4-b]pyridine (S-3)

Intermediate S-3 was prepared from N-(2-chloropyridin-3-yl)acetamide (S-2) following similar procedures for synthesizing intermediate R-3 from R-2, as described above. MS (m/z): 151.6 $(M+1)^+$.

2-(Bromomethyl)thiazolo[5,4-b]pyridine (S-4)

Intermediate S-4 was prepared from 2-methylthiazolo[5,4-b]pyridine (S-3) following similar procedures for synthesizing intermediate B-5 from B-4, as described above.

Thiazolo[5,4-b]pyridin-2-ylmethanamine(S)

Intermediate S was prepared from 2-(bromomethyl)thiazolo[5,4-b]pyridine (S-4) following similar procedured for synthesizing intermediate C from C-5, as described above. MS (m/z): 166 $(M+1)^+$.

Intermediate T and T'

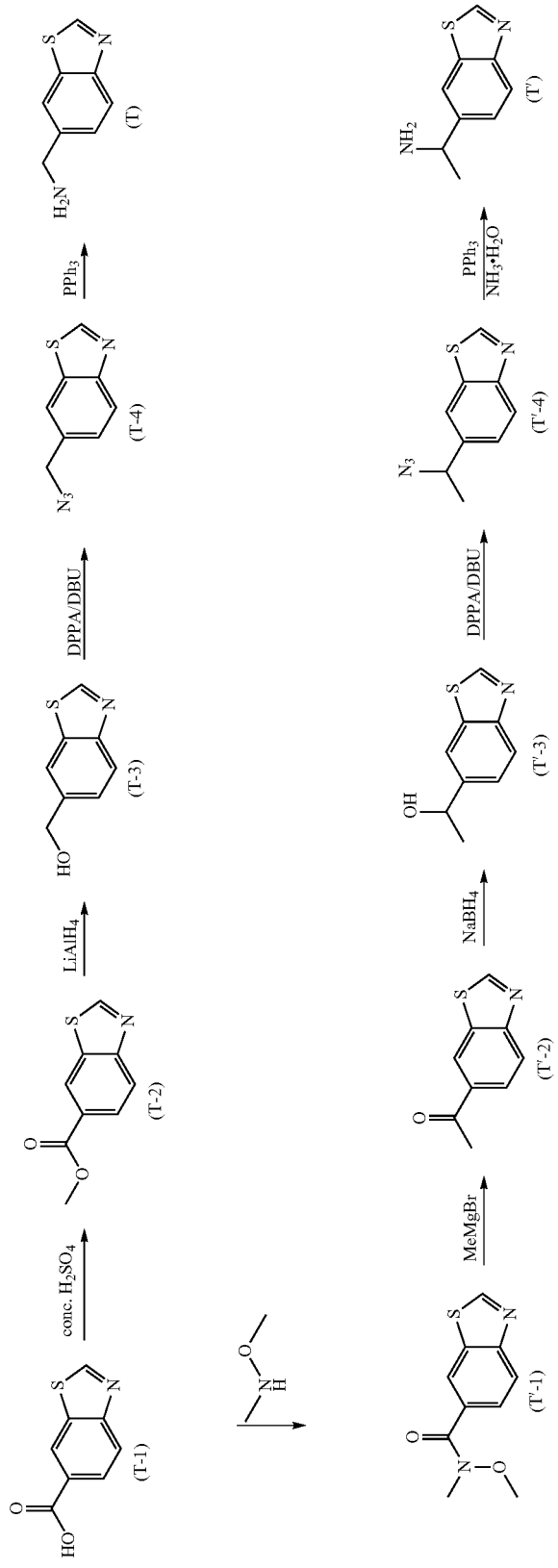

Methyl benzo[d]thiazole-6-carboxylate (T-2)

Intermediate T2 was prepared from benzo[d]thiazole-6-carboxylic acid (T-1) following similar procedures for synthesizing intermediate F-2 from F-1, as described above.

Benzo[d]thiazol-6-ylmethanamine (T)

Intermediate T was prepared from methyl benzo[d]thiazole-6-carboxylate (T-2) following similar procedures for synthesizing intermediate D from D-2, as described above. MS (m/z): 165 (M+1)$^+$.

1-(Benzo[d]thiazol-6-yl)ethanamine (T')

Intermediate T' was prepared from benzo[d]thiazole-6-carboxylic acid (T-1) following similar procedures for synthesizing intermediate D'-5 from D'-1, as described above, and intermediate D from D-4 as described above. MS (m/z): 179 (M+1)$^+$.

Synthesis of Boric Acid or Ester Intermediates

Intermediate U

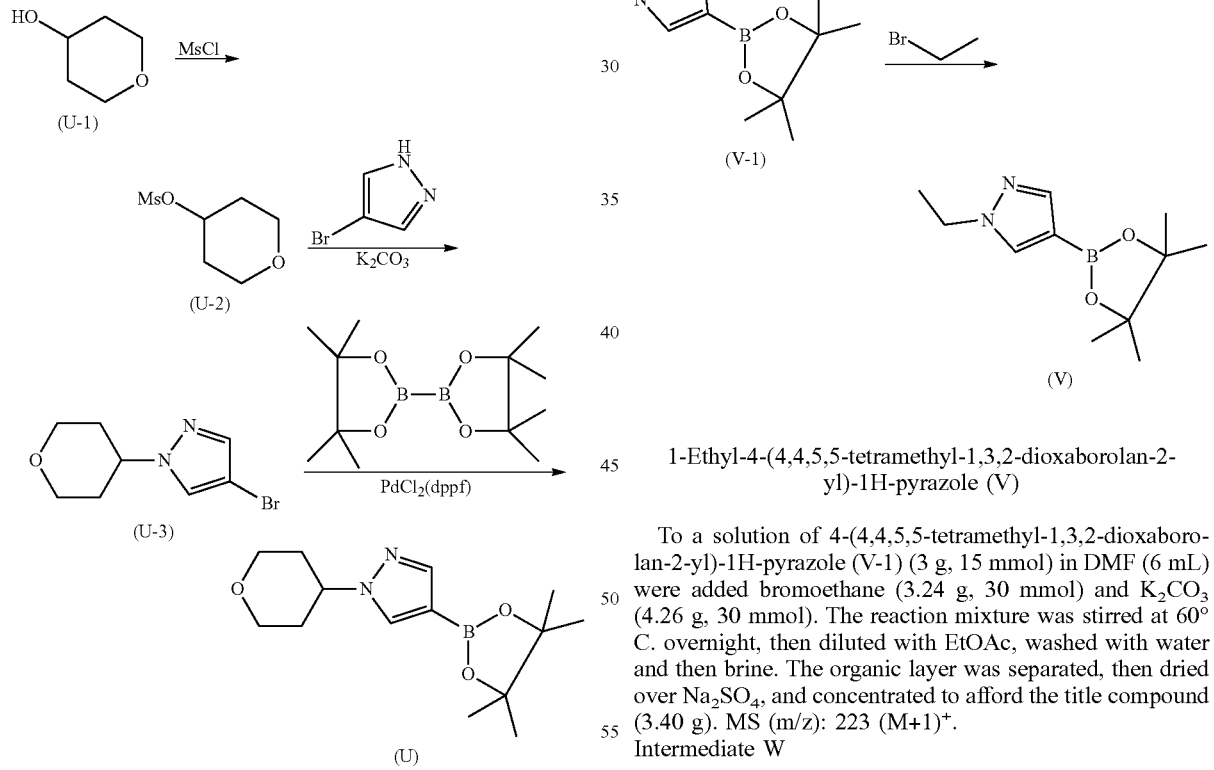

Tetrahydro-2H-pyran-4-yl methanesulfonate (U-2)

To a mixture of tetrahydro-2H-pyran-4-ol (U-1) (1.02 g, 10 mmol) and Et$_3$N (1 mL) in dried DCM (20 mL) was added MsCl (2 mL) dropwise. The reaction was stirred at room temperature for 1 h, then washed with water. The organic layer was separated, dried over Na$_2$SO$_4$, and concentrated to afford the title compound (1.8 g).

4-Bromo-1-(tetrahydro-2H-pyran-4-yl)-1H-pyrazole (U-3)

The mixture of tetrahydro-2H-pyran-4-yl methanesulfonate (U-2) (1.8 g, 10 mmol), 4-bromo-1H-pyrazole (1.46 g, 10 mmol) and K$_2$CO$_3$ (1.4 g, 10 mmol) in DMF (10 mmol) was stirred at 80° C. overnight, then purified by chromatography to afford the title compound (861 mg). MS (m/z): 231 (M+1)$^+$.

1-(Tetrahydro-2H-pyran-4-yl)-4-(4,4,5,5-tetramethyl-1,3,2-dioxaborolan-2-yl)-1H-pyrazole (U)

To a mixture of 4-bromo-1-(tetrahydro-2H-pyran-4-yl)-1H-pyrazole (U-3) (1.13 g, 4.48 mmol), 4,4,5,5-tetramethyl-2-(4,4,5,5-tetramethyl-1,3,2-dioxaborolan-2-yl)-1,3,2-dioxaborolane (861 mg, 3.73 mmol) and KOAc (12.43 g, 12.68 mmol) in DMSO (5 mL) was added Pd (dppf)C$_2$ (172 mg, 0.21 mmol) under N$_2$. The mixture was stirred overnight at 80° C. under N$_2$. After cooling to room temperature, the reaction mixture was poured into water, and extracted with EtOAc. The organic phase was separated, concentrated in vacuo and then purified by chromatography to afford the title compound (170 mg). MS (m/z): 279 (M+1)$^+$.

Intermediate V

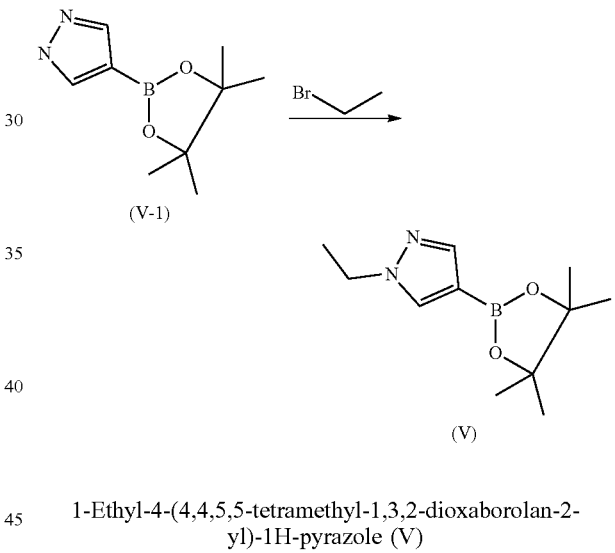

1-Ethyl-4-(4,4,5,5-tetramethyl-1,3,2-dioxaborolan-2-yl)-1H-pyrazole (V)

To a solution of 4-(4,4,5,5-tetramethyl-1,3,2-dioxaborolan-2-yl)-1H-pyrazole (V-1) (3 g, 15 mmol) in DMF (6 mL) were added bromoethane (3.24 g, 30 mmol) and K$_2$CO$_3$ (4.26 g, 30 mmol). The reaction mixture was stirred at 60° C. overnight, then diluted with EtOAc, washed with water and then brine. The organic layer was separated, then dried over Na$_2$SO$_4$, and concentrated to afford the title compound (3.40 g). MS (m/z): 223 (M+1)$^+$.

Intermediate W

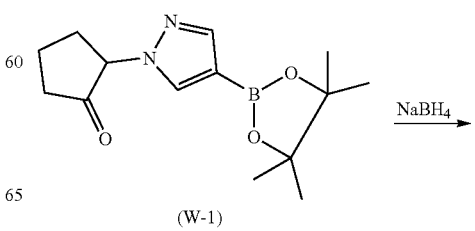

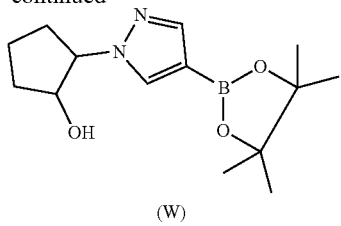

(W)

2-(4-(4,4,5,5-tetramethyl-1,3,2-dioxaborolan-2-yl)-1H-pyrazol-1-yl)cyclopentanone (W-1)

Intermediate W-1 was prepared from 2-chlorocyclopentanone (1.06 g, 9 mmol) following the similar procedures of synthesizing intermediate (V), as described above. MS (m/z): 277 (M+1)$^+$.

2-(4-(4,4,5,5-Tetramethyl-1,3,2-dioxaborolan-2-yl)-1H-pyrazol-1-yl)cyclopentanol (W)

To a solution of 2-(4-(4,4,5,5-tetramethyl-1,3,2-dioxaborolan-2-yl)-1H-pyrazol-1-yl)cyclopentanone (W-1) (550 mg, 2 mmol) in methanol (5 mL) was added NaBH$_4$ (150 mg, 4 mmol). The reaction was stirred at room temperature for 1 h. The solvent was removed in vacuo, and the residue was extracted with EtOAc, washed with water, and purified by chromatography on silica gel to afford the title compound (200 mg). MS (m/z): 279 (M+1)$^+$.

Intermediate X

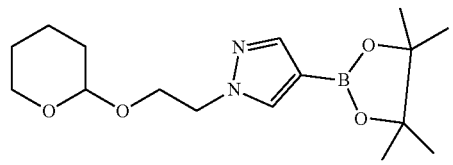

(X)

This intermediate was prepared from 4-bromo-1H-pyrazole as described in US2007/0265272.

Other Pyrazole Boric Acids or Esters were Prepared According to the Procedures of Intermediates (U-X)

Intermediate Y:

2-(2,4-Dinitrophenoxy)isoindoline-1,3-dione (Y-2)

To a suspension of 2-hydroxyisoindoline-1,3-dione (20.0 g, 0.12 mol) in acetone (400 mL) was added Et$_3$N (14.9 g, 0.15 mol), the mixture was stirred at room temperature until it became a homogeneous solution, then 1-bromo-2,4-dinitrobenzene Y-1 (30.2 g, 0.12 mol) was added. The reaction was stirred at room temperature for 3 h, then poured into ice-water, the resulting precipitate was filtered and washed three times with cold MeOH, dried in vacuum to afford the title compound (38.1 g).

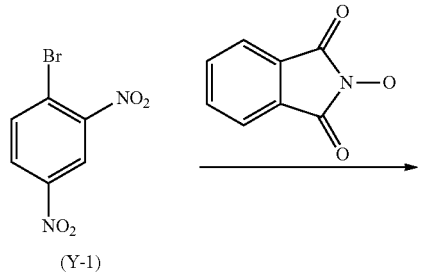

(Y-1)

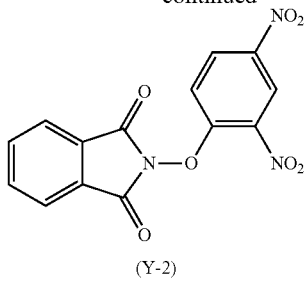

(Y-2)

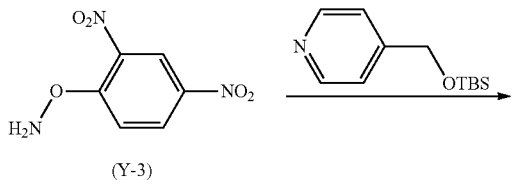

(Y-3)

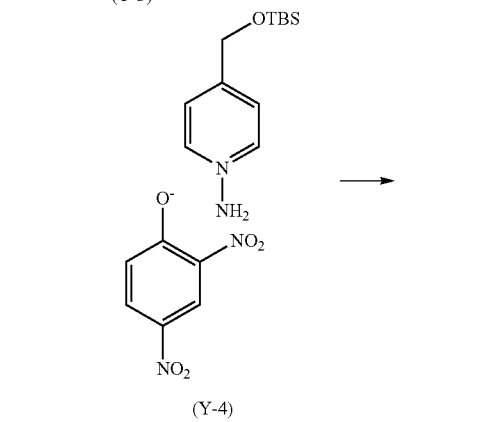

(Y-4)

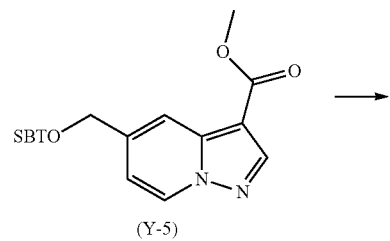

(Y-5)

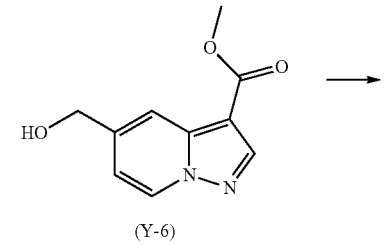

(Y-6)

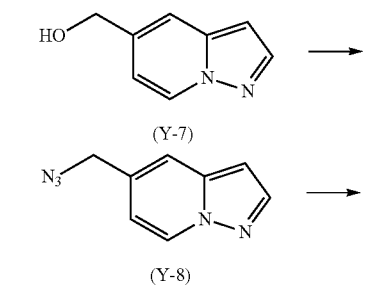

(Y-7)

(Y-8)

-continued

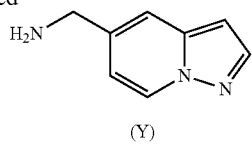

(Y)

2-(2,4-Dinitrophenyl)hydroxylamine (Y-3)

To a solution of 2-(2,4-dinitrophenoxy)isoindoline-1,3-dione Y-2 (20.0 g, 60.7 mmol) in $CH_2Cl_2$ (400 ml) was added a solution of hydrazine hydrate (10.0 mL, 85%, 177 mmol) in MeOH (60 ml) at 0° C. The reaction mixture was stirred at 0° C. for 6 h, then treated with cold aqueous HCl (1N, 400 ml). The resulting mixture was rapidly filtered and washed with MeCN. The filtrate was transferred into a funnel. The organic phase was separated. The aqueous layer was extracted with $CH_2Cl_2$. The combined organic layers were dried over anhydrous $Na_2SO_4$, then concentrated to afford the title compound (7.9 g). MS (m/z): 183 (M−16)$^-$.

1-Amino-4-((tert-butyldimethylsilyloxy)methyl) pyridinium 2,4-dinitrophenolate (Y-4)

To a solution of pyridin-4-ylmethanol (21.8 g, 0.20 mol) in $CH_2Cl_2$ (200 mL) were added $Et_3N$ (30.0 g, 0.30 mmol) and TBSCl (45.0 g, 0.30 mmol) at 0° C. The reaction mixture was stirred at room temperature for 4 h, then quenched with water. The organic phase was separated, and the aqueous layer was extracted with $CH_2Cl_2$. The combined organic layers were washed with brine, dried over $Na_2SO_4$ and concentrated. The residue was purified by silica gel chromatography to afford 4-((tert-butyldimethylsilyloxy) methyl)-pyridine.

A mixture of 4-((tert-butyldimethylsilyloxy)methyl)pyridine (8.9 g, 39.7 mmol) and 0-(2,4-dinitrophenyl)hydroxylamine Y-3 (7.9 g, 39.7 mmol) in MeCN (27 ml) was stirred at 40° C. for 24 h, then concentrated to afford the title compound (17.1 g), used in next step without further purification. MS (m/z): 239 (M−183)$^+$.

Methyl 5-((tert-butyldimethylsilyloxy)methyl)pyrazolo[1,5-a]pyridine-3-carboxylate (Y-5)

To a solution of 1-amino-4-((tert-butyldimethylsilyloxy) methyl)pyridinium 2,4-dinitrophenolate Y-4 (13.4 g, 31.6 mmol) in DMF (60 mL) were added methyl propiolate (2.7 g, 31.6 mmol) and $K_2CO_3$ (6.5 g, 47.4 mmol). The reaction was stirred at room temperature for 24 h, then treated with water. The resulting mixture was extracted with ethyl acetate (100 ml×3), the combined organic layers were washed with water, brine and dried over $Na_2SO_4$, then concentrated in vacuo, the residue was purified by silica gel chromatography to afford the title compound (2.9 g). MS (m/z): 321 (M+1)$^+$.

Methyl 5-(hydroxymethyl)pyrazolo[1,5-a]pyridine-3-carboxylate (Y-6)

To a solution of methyl 5-((tert-butyldimethylsilyloxy) methyl)pyrazolo[1,5-a]pyridine-3-carboxylate Y-5 (2.9 g, 9.1 mmol) in dry THF (20 mL) was added TBAF (3.5 g, 13.7 mmol). The reaction mixture was stirred at room temperature for 10 mins, then treated with ethyl acetate. The resulting mixture was washed with brine, dried over $Na_2SO_4$ and concentrated to afford the title compound (1.9 g).

Pyrazolo[1,5-a]pyridin-5-ylmethanol (Y-7)

A suspension of methyl 5-(hydroxymethyl)pyrazolo[1,5-a]pyridine-3-carboxylate Y-6 (1.9 g, 9.1 mmol) in 40% $H_2SO_4$ was stirred at 80° C. for 24 h, then neutralized with 3N NaOH to pH=7-8. The resulting mixture was extracted with ethyl acetate. The combined organic layers were washed with brine, dried over $Na_2SO_4$ and concentrated. The residue was purified by silica gel chromatography to afford the title compound (1.1 g). MS (m/z): 149 (M+1)$^+$.

Intermediate (Y)

Intermediate Y was prepared from pyrazolo[1,5-a]pyridin-5-ylmethanol (Y-7) following similar procedures for synthesizing intermediate D from D-3.

Intermediate Z

Methyl H-imidazo[1,2-a]pyridine-6-carboxylate (Z-2)

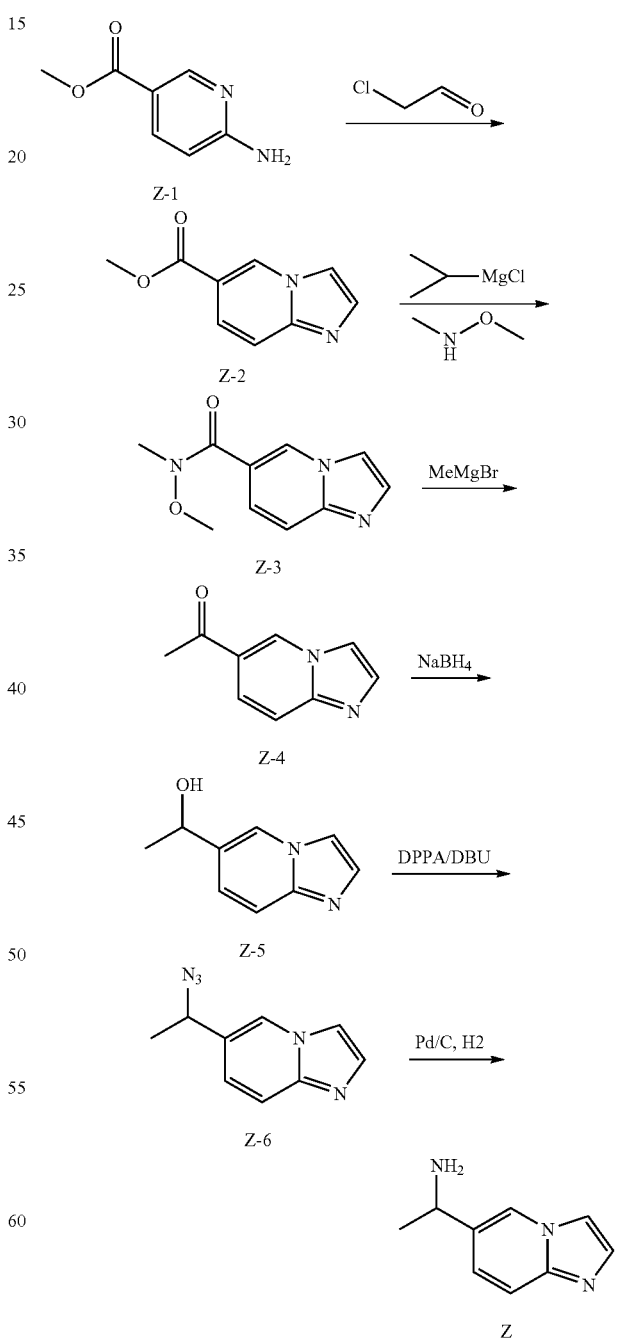

To a solution of Z-1 (9.0 g, 59.21 mmol) in anhydrous EtOH (160 ml) was added chloroacetaldehyde (40% in $H_2O$, 48.6 mL, 296 mmol). The reaction mixture was refluxed for 4 h, then concentrated. The residue was dissolved in water and adjusted to pH>7 with a saturated NaHCO3 solution, extracted with EtOAc and purified by silica gel chromatography to afford the title compound (6.60 g). MS (m/z): 177 (M+1)$^+$.

N-Methoxy-N-methylH-imidazo[1,2-a]pyridine-6-carboxamide (Z-3)

To a mixture of Z-2 (5.0 g, 28.4 mmol) and N-methoxymethanamine (5.54 g, 56.8 mmol) in dry THF (50 ml) at −20° C. under $N_2$ was added isopropylmagnesium chloride (56.8 mL, 113.6 mmol) over 30 mins. The resulting mixture was stirred at −20° C. for 30 mins, then quenched with 20% NH$_4$Cl solution, and extracted with EtOAc (50 mL×3). The combined organic layers were dried over Na$_2$SO$_4$, concentrated and purified by silicon gel chromatography to afford the title compound (3.0 g). MS (m/z): 206 (M+1)$^+$.

1-(H-imidazo[1,2-a]pyridin-6-yl)ethanamine (Z)

It was prepared from compound Z-3 following similar procedures for synthesizing intermediate D' from D'-2.

Intermediate 1

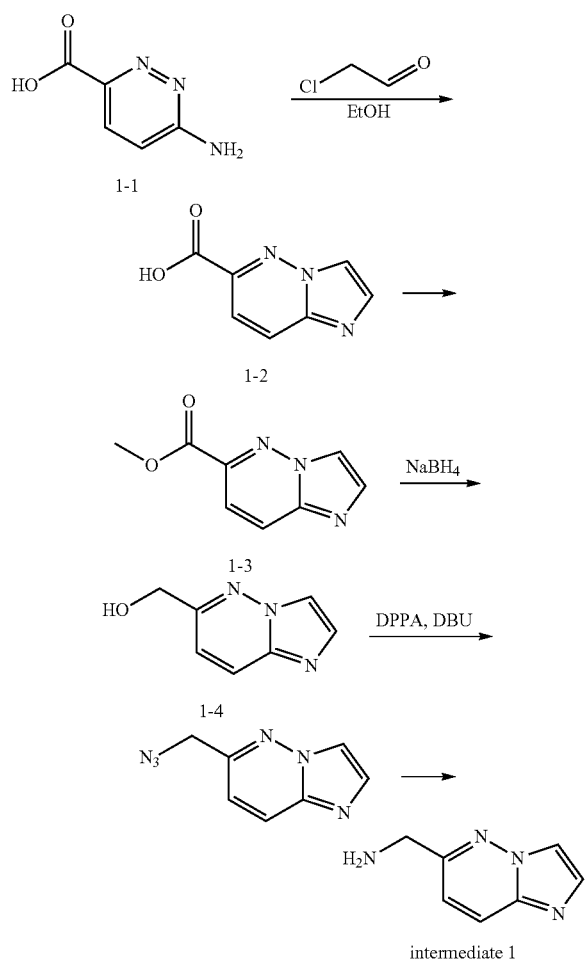

intermediate 1

Imidazo[1,2-b]pyridazine-6-carboxylic acid (1-2)

To a mixture of 6-aminopyridazine-3-carboxylic acid (1-1) (1.39 g, 10 mmol) in ethanol in a sealed flask was added 2-chloroacetaldehyde (4 mL, 40% aqueous). The reaction mixture was stirred at room temperature for 5 min, then heated at 100° C. overnight. After cooled to room temperature, the mixture was concentrated to afford the title compound (1.63 g). MS (m/z): 164 (M+1)

Methyl imidazo[1,2-b]pyridazine-6-carboxylate (1-3)

To a mixture of imidazo[1,2-b]pyridazine-6-carboxylic acid (1-2) (1.63 g, 10 mmol) in SOCl$_2$ (15 mL) was added 10 drops of DMF at room temperature. The resulting solution was heated at reflux for 3 h. After cooled to room temperature, the reaction was concentrated, and the resulting solid was dissolved in methanol, and stirred for a while, then treated with an aqueous saturated NaHCO$_3$ solution to pH7. The mixture was purified by silica gel chromatography to afford the title compound (891 mg). MS (m/z): 178 (M+1)

Imidazo[1,2-b]pyridazin-6-ylmethanol (1-4)

To a solution of methyl imidazo[1,2-b]pyridazine-6-carboxylate (1-3) (891 mg, 5.03 mmol) in ethanol (25 mL) was added NaBH$_4$ (420 mg, 11.1 mmol) at room temperature. The suspension was stirred at room temperature for 2 h. The reaction mixture was concentrated in vacuum. The residue was purified by chromatography on silica gel to afford the title compound (630 mg). MS (m/z): 150 (M+1)$^+$ Imidazo[1,2-b]pyridazin-6-ylmethanamine (Intermediate 1)

Intermediate 1 was prepared from imidazo[1,2-b]pyridazin-6-ylmethanol (1-4) following the procedures similar to procedure of intermediate D from D-3. MS (m/z): 149 (M+1)

Intermediate 2

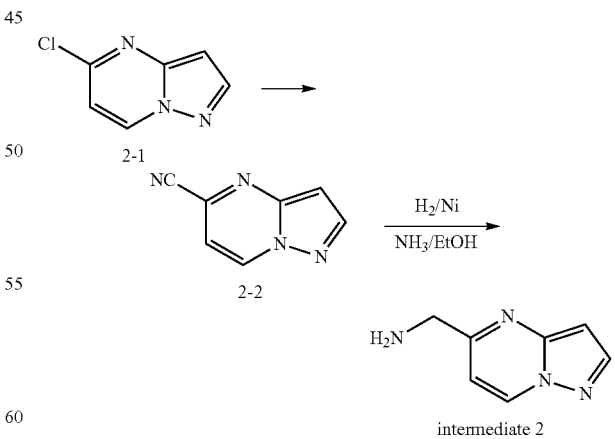

intermediate 2

Pyrazolo[1,5-a]pyrimidine-5-carbonitrile (2-2)

To a mixture of 5-chloropyrazolo[1,5-a]pyrimidine (2-1) (1.0 g, 6.45 mmol) and Zn(CN)$_2$ (770 mg, 6.58 mmol) in dried DMF (20 mL) exchanged by $N_2$ was added $Pd(PPh_3)_4$ (400 mg, 3.46 mmol). The reaction mixture was stirred at 110° C. overnight. After cooled to the room temperature, the solution was concentrated and purified by chromatography on silica gel to afford the title compound (620 mg)

Pyrazolo[1,5-a]pyrimidin-5-ylmethanamine (Intermediate 2)

To a solution of pyrazolo[1,5-a]pyrimidine-5-carbonitrile (2-2) (620 mg, 4.31 mmol) in $NH_3$ in MeOH (5 mL) was added Raney Ni (100 mg). The reaction mixture was stirred at room temperature for 3 h under $H_2$. The mixture was filtered, and the filtrate was concentrated to afford the title compound (600 mg). MS (m/z): 149 $(M+1)^+$.

Intermediate 3

(3-1)
To a solution of 1-(pyridin-4-yl)ethanone (100 mg, 0.82 mmol) dissolved in $CH_3CN$ (3 mL) was added Y-3 (180 mg, 0.9 mmol). The reaction mixture was heated to 40° C. and stirred at 40° C. for 24 h. Solvent was removed in vacuum. The residue was used in next step without further purification (225 mg).

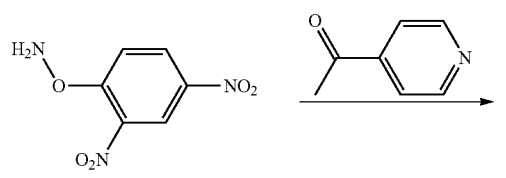

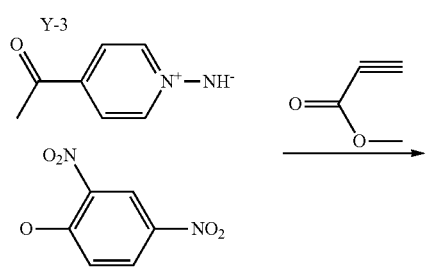

3-1

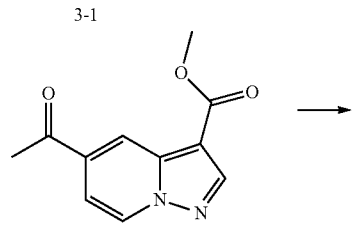

3-2

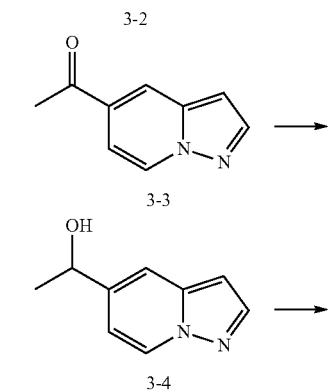

3-3

OH 3-4

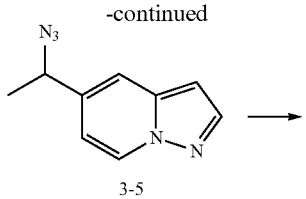

3-5

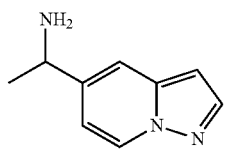

intermediate 3

Methyl 5-acetylpyrazolo[1,5-a]pyridine-3-carboxylate (3-2)

To a mixture of (3-1) (100 mg, 0.31 mmol) and $K_2CO_3$ (60 mg, 0.43 mmol) in DMF (1 mL) was added methyl propiolate (29 mg, 0.34 mmol) dropwise. The reaction mixture was stirred vigorously at room temperature for 24 h. The suspension was filtered. The filtrate was concentrated. The resulting residue was dissolved in $Et_2O$ and washed with water. The organic layer was separated, concentrated and purified by chromatography on silica gel to afford the title compound (20 mg). MS (m/z): 219 $(M+1)^+$.

1-(Pyrazolo[1,5-a]pyridin-5-yl)ethanone (3-3)

A suspension of methyl 5-acetylpyrazolo[1,5-a]pyridine-3-carboxylate (3-2) (90 mg, 0.41 mmol) dissolved in 50% $H_2SO_4$ (2 mL) was stirred at 80° C. for 3 h. After cooled to 0° C., the solution was treated with 5N NaOH solution, and then extracted with $Et_2O$. The organic layer was separated, dried, concentrated and purified by flash chromatography to afford the title compound (25 mg).

1-(Pyrazolo[1,5-a]pyridin-5-yl)ethanamine (Intermediate 3)

Intermediate 3 was prepared from 1-(pyrazolo[1,5-a]pyridin-5-yl)ethanone (3-3) following the procedures similar to the procedures of intermediate D' from D'-3. MS (m/z): 162 $(M+1)^+$.

Intermediate 4

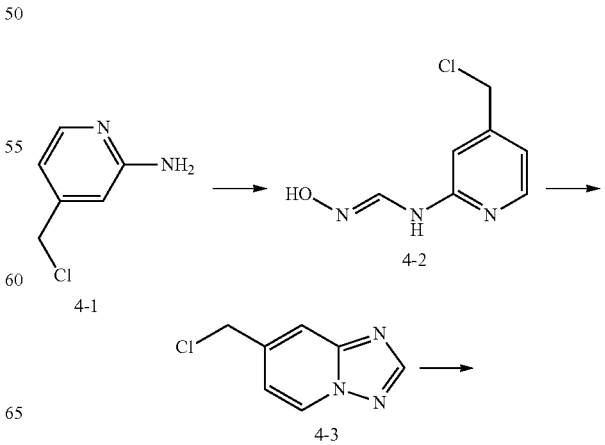

4-1

4-2

4-3

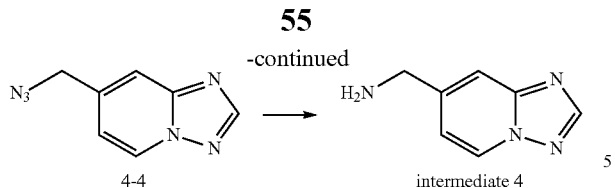

N-(4-(Chloromethyl)pyridin-2-yl)-N-hydroxyformimidamide (4-2)

To a solution of 4-(chloromethyl)pyridin-2-amine (4-1) (1.56 g, 8.7 mmol) in propan-2-ol (15 mL) was added DMF-DMA (1.56 mL, 11.3 mmol) at room temperature under $N_2$. The reaction mixture was heated to 90° C. for 3 h. After cooled to 50° C., the mixture was treated with $NH_2OH \cdot HCl$ (0.781 g, 11.3 mmol), then stirred at 50° C. overnight. After cooled to room temperature, the mixture was concentrated and purified by chromatography on silica gel to afford the title compound (820 mg). MS (m/z): 186 $(M+1)^+$.

7-(Chloromethyl)-[1,2,4]triazolo[1,5-a]pyridine (4-3)

To a solution of N-(4-(chloromethyl)pyridin-2-yl)-N-hydroxyformimidamide (4-2) (820 mg, 4.4 mmol) in anhydrous THF (5 mL) cooled to 0° C. was added TFAA (1.1 g, 5.28 mmol) dropwise under $N_2$. The reaction mixture was stirred at room temperature for 3 h. Then the mixture was treated with aqueous $NaHCO_3$ to pH 8, concentrated and purified by chromatography on silica gel to afford the title compound (400 mg). MS (m/z): 168 $(M+1)^+$.

7-(Azidomethyl)-[1,2,4]triazolo[1,5-a]pyridine (4-4)

To a solution of 7-(chloromethyl)-[1,2,4]triazolo[1,5-a]pyridine (4-3) (400 mg, 2.4 mmol) in dried DMF (5 mL) was added $NaN_3$ (250 mg, 3.6 mmol) under $N_2$. The reaction mixture was stirred at 80° C. for 2 h, then quenched with aqueous $Na_2S_2O_3$. The resulting mixture was extracted with EtOAc, dried on $Na_2SO_4$, and concentrated to afford the title compound (340 mg), which was used in next step without further purification. MS (m/z): 175 $(M+1)^+$.

Triazolo[1,5-a]pyridin-7-ylmethanamine (Intermediate 4)

To a solution of 7-(azidomethyl)-[1,2,4]triazolo[1,5-a]pyridine (4-4) (340 mg, 1.9 mmol) in methanol (20 mL) was added Pd/C (30 mg). The reaction mixture was stirred at room temperature under $H_2$ (1 atm) for 2 h. The mixture was filtered to remove Pd/C. The filtrate was concentrated to afford the title compound (300 mg) MS (m/z): 149 $(M+1)^+$.

Intermediate 5

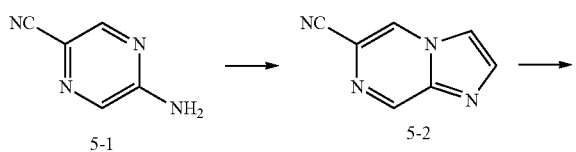

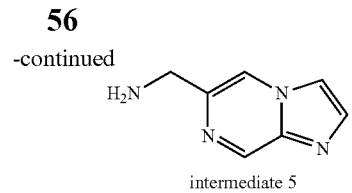

Imidazo[1,2-a]pyrazine-6-carbonitrile (5-2)

To a solution of 5-aminopyrazine-2-carbonitrile (5-1) (350 mg, 2.92 mmol) in ethanol (15 mL) was added 2-chloroacetaldehyde (4 mL, 40% in water). The mixture was stirred at 110° C. overnight. The solution was concentrated, then purified by chromatography on silica gel to afford the title compound (280 mg). MS (m/z): 145.1 $(M+H)^+$.

Imidazo[1,2-a]pyrazin-6-ylmethanamine (Intermediate 5)

To a solution of imidazo[1,2-a]pyrazine-6-carbonitrile (5-1) (180 mg, 1.25 mmol) in methanol (15 mL) were added Raney nickel (slurry in water, 150 mg) and 1 N ammonia. The reaction mixture was stirred under $H_2$ (1 atm) for 2 h. The mixture was filtered, and the filtrate was concentrated to afford the title compound (160 mg). MS (m/z): 149.1 $(M+H)^+$

Intermediate 6

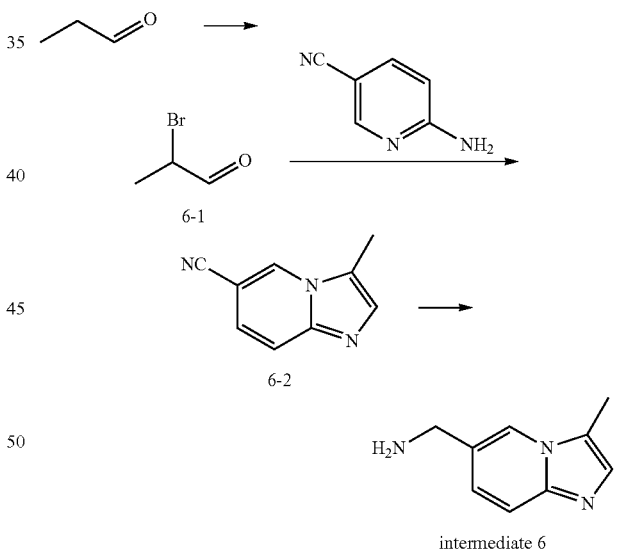

2-Bromopropanal (6-1)

To a solution of propionaldehyde (20 mL, 265 mmol) in 25 mL of dioxane at 000° C. was added bromine (13.5 mL, 265 mmol) within 1 h. The reaction mixture was allowed to continue stirring for an additional 10 min until the reaction became colorless. The mixture was diluted with 200 mL of ether, and washed with aqueous $NaHSO_4$, $NaHCO_3$ and brine. The aqueous layer was extracted with ether. The combined organic layer was dried over $Na_2SO_4$ and concentrated. The resulting oil was further purified by distillation under vacuum to afford the title compound (8.5 g).

3-Methylimidazo[1,2-a]pyridine-6-carbonitrile (6-2)

To a solution of 6-aminonicotinonitrile (1.2 g, 10.1 mmol) in ethanol (80 mL) was added 2-bromopropanal (6-1) (6.9 g, 50.5 mmol). The reaction mixture was stirred at 80° C. overnight. The solution was concentrated, diluted with water (20 mL) and adjusted to PH>7 with saturated aqueous NaHCO$_3$ solution. The precipitate was collected to afford the title compound (430 mg). MS (m/z): 158 (M+H)$^+$.

(3-Methylimidazo[1,2-a]pyridin-6-yl)methanamine (Intermediate 6)

To a solution of 3-methylimidazo[1,2-a]pyridine-6-carbonitrile (6-2) (200 mg, 1.27 mmol) in methanol (30 mL) were added Raney nickel (slurry in water, 100 mg) and 1N ammonia. The reaction mixture was stirred under H$_2$ for 2 h, then filtered and concentrated to afford the title compound (200 mg). MS (m/z): 162 (M+H)$^+$

Intermediate 7

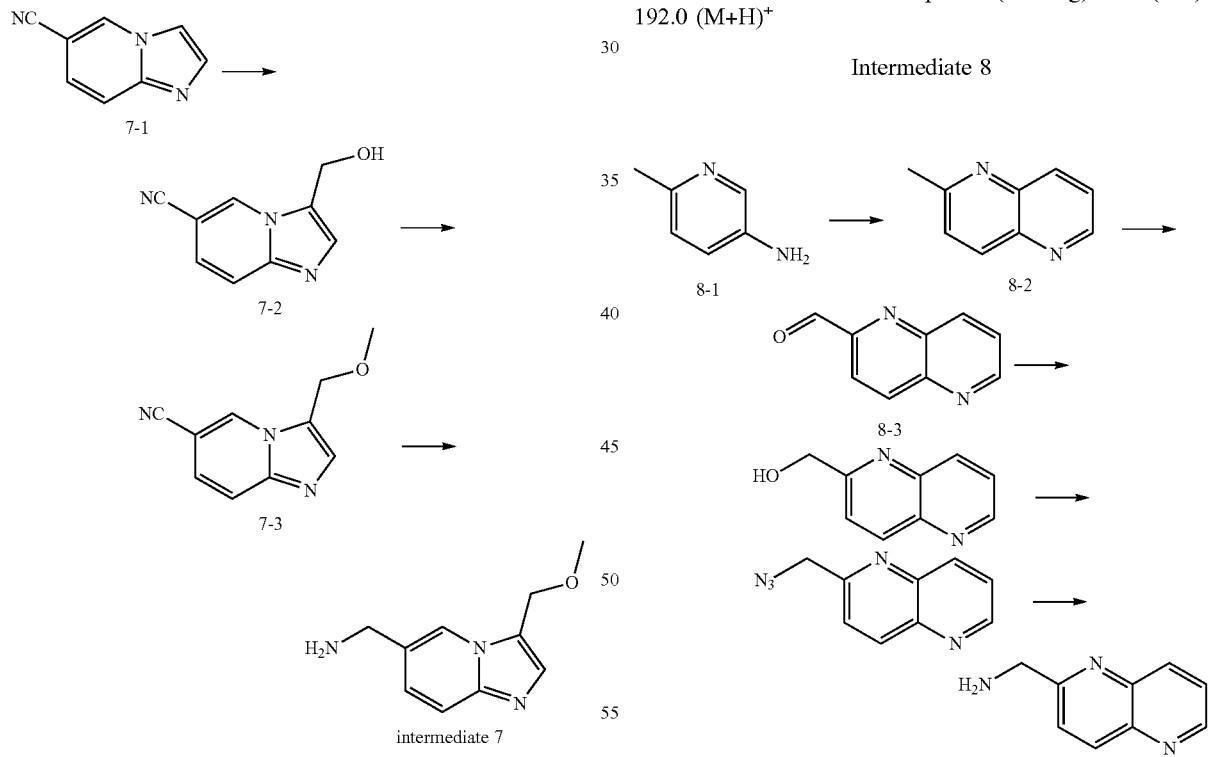

intermediate 7

3-(Hydroxymethyl)imidazo[1,2-a]pyridine-6-carbonitrile (7-2)

To a solution of imidazo[1,2-a]pyridine-6-carbonitrile (7-1) (1.43 g, 10 mmol) in 3 mL of acetic acid were added sodium acetate (3.03 g, 37 mmol) and then formaldehyde (6 mL, 37% in water). The reaction mixture was stirred at 100° C. overnight. After cooled to room temperature, the mixture was adjusted to pH>7 with aqueous Na$_2$CO$_3$. The precipitate was collected to afford the title compound (1.4 g). MS (m/z): 174.0 (M+H)$^+$

3-(Methoxymethyl)imidazo[1,2-a]pyridine-6-carbonitrile (7-3)

To a solution of 3-(hydroxymethyl)-imidazo[1,2-a]pyridine-6-carbonitrile (7-2) (346 mg, 2 mmol) in 20 mL of THF was added sodium hydride (240 mg, 60% in oil) at 0° C. The reaction mixture was stirred at 0° C. for 1 h, then methyl iodide (615 mg, 4.3 mmol) was added. The reaction was stirred at room temperature overnight. The mixture was treated with aqueous Na$_2$CO$_3$, then concentrated. The residue was diluted with water and extracted with EtOAc. The combined organics were dried over Na$_2$SO$_4$ and concentrated to afford the title compound (300 mg). MS (m/z): 188.0 (M+H)$^+$

(3-(Methoxymethyl)imidazo[1,2-a]pyridin-6-yl)methanamine (Intermediate 7)

To a solution of 3-(methoxymethyl)imidazo[1,2-a]pyridine-6-carbonitrile (7-3) (300 mg, 1.6 mmol) in methanol (30 mL) were added Raney nickel (slurry in water, 150 mg) and 1N ammonia. The reaction mixture was stirred under H$_2$ for 2 h. The mixture was filtered. The filtrate was concentrated to afford the title compound (300 mg). MS (m/z): 192.0 (M+H)$^+$

Intermediate 8

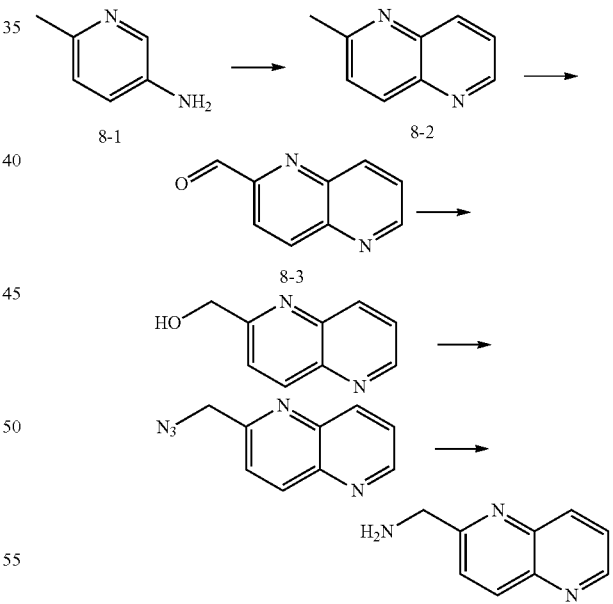

intermediate 8

2-Methyl-1,5-naphthyridine (8-2)

A mixture of 6-methylpyridin-3-amine (8-1) (4.8 g, 44.4 mmol) and propane-1,2,3-triol (20 g, 222 mmol) in 5 mL of H$_2$O was stirred at room temperature for 5 min, then concentrated H$_2$SO$_4$ (47 g, 488 mmol) was added dropwise within 20 min at room temperature. After addition, the reaction mixture was stirred at 150° C. for 30 min. After cooled to room temperature, the mixture was poured into water, adjusted with 6 N NaOH to pH 13, then extracted with ethyl acetate. The combined organic layers were washed with brine, dried over Na$_2$SO$_4$, concentrated and purified by chromatography on silica gel to afford the title compound (2.9 g). MS: 145 (M+1)$^+$.

1,5-Naphthyridine-2-carbaldehyde (8-3)

A mixture of 2-methyl-1,5-naphthyridine (8-2) (2.9 g, 20.1 mmol) and SeO$_2$ (2.2 g, 20.1 mmol) in 40 mL of dioxane was refluxed for 3 h. After cooled to room temperature, the reaction mixture was concentrated. The residue was treated with brine and extracted with DCM/i-PrOH=4/1. The organic layer was washed with brine, dried over Na$_2$SO$_4$, concentrated and purified by chromatography on silica gel to afford the title compound (1.81 g).

(1,5-Naphthyridin-2-yl)methanol (8-4)

To a solution of 1,5-naphthyridine-2-carbaldehyde (8-3) (1.0 g, 6.32 mmol) in MeOH (15 mL) and THF (15 mL) was added NaBH$_4$ (84 mg, 2.21 mmol). The reaction mixture was stirred at 0° C. for 0.5 h. The mixture was concentrated and purified by chromatography on silica gel to afford the title compound (790 mg).

(1,5-Naphthyridin-2-yl)methanamine (Intermediate 8)

Intermediate 8 was prepared from (1,5-naphthyridin-2-yl)methanol (8-4) following the procedures similar to the procedure for synthesizing intermediate D from D-3. MS (m/z): 160 (M+1)+.

Intermediate 9

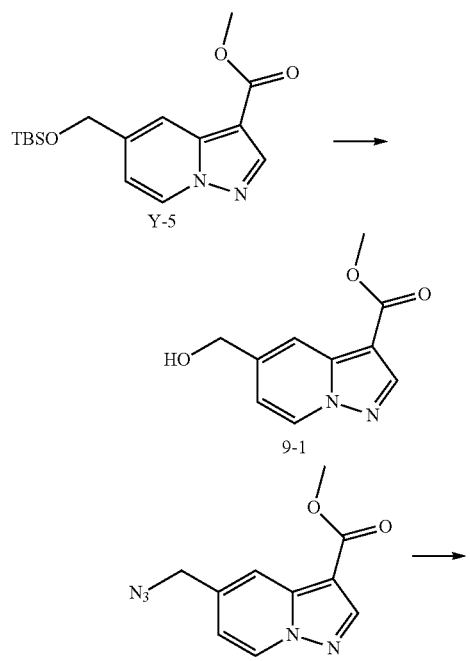

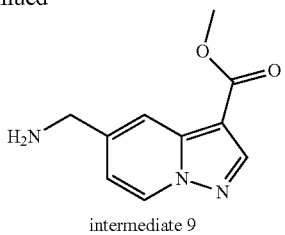

intermediate 9

Methyl 5-(hydroxymethyl)pyrazolo[1,5-a]pyridine-3-carboxylate (9-1)

To a solution of methyl 5-((tert-butyldimethylsilyloxy)methyl)pyrazolo[1,5-a]pyridine-3-carboxylate (Y-5) (2.9 g, 9.1 mmol) in anhydrous THF (20 mL) was added TBAF (3.5 g, 13.7 mmol). The reaction mixture was stirred at room temperature for 10 min, then treated with ethyl acetate (50 mL). The resulting mixture was washed with brine, dried over Na$_2$SO$_4$ and concentrated to afford the title compound (1.9 g).

Methyl 5-(aminomethyl)pyrazolo[1,5-a]pyridine-3-carboxylate (intermediate 9)

Intermediate 9 was prepared from methyl 5-(hydroxymethyl)pyrazolo[1,5-a]pyridine-3-carboxylate (9-1) following the procedures similar to the procedure of synthesizing intermediate D from D-3. MS (m/z): 148 (M+1)$^+$.

Intermediate 10

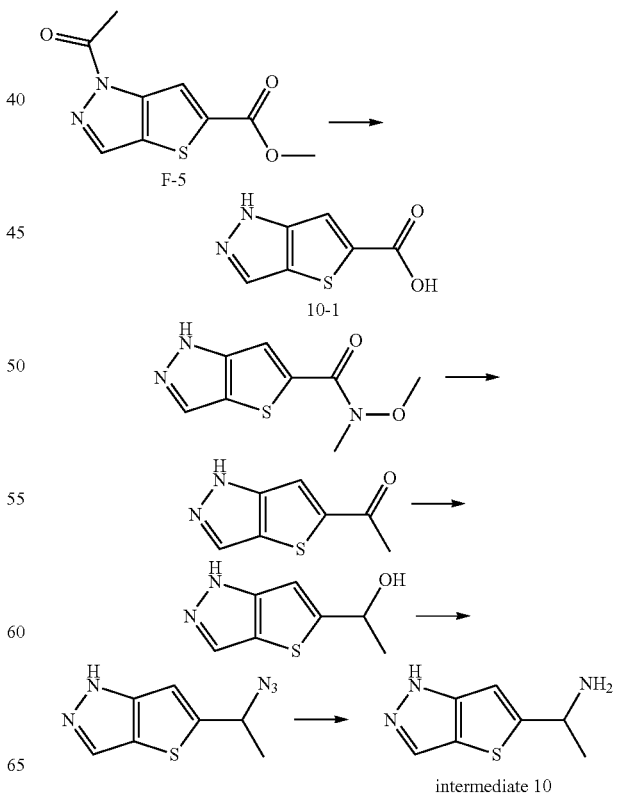

intermediate 10

1H-Thieno[3,2-c]pyrazole-5-carboxylic acid (10-1)

To a solution of methyl 1H-thieno[3,2-c]pyrazole-5-carboxylate (F-5) (4.2 g, 18.7 mmol) in MeOH (50 mL) was added a solution of LiOH.H$_2$O (3.1 g, 74.8 mmol) in water (5 mL). The reaction mixture was stirred at room temperature overnight. Then 1N HCl was added to adjust to pH to 5, the resulting precipitate was collected and dried to afford the title compound.

1-(1H-thieno[3,2-c]pyrazol-5-yl)ethanamine (intermediate 10)

Intermediate 10 was prepared from 1H-thieno[3,2-c]pyrazole-5-carboxylic acid (10-1) following similar procedures for synthesizing intermediate T' from T-1. MS (m/z): 168 (M+1)$^+$.

Intermediate 11

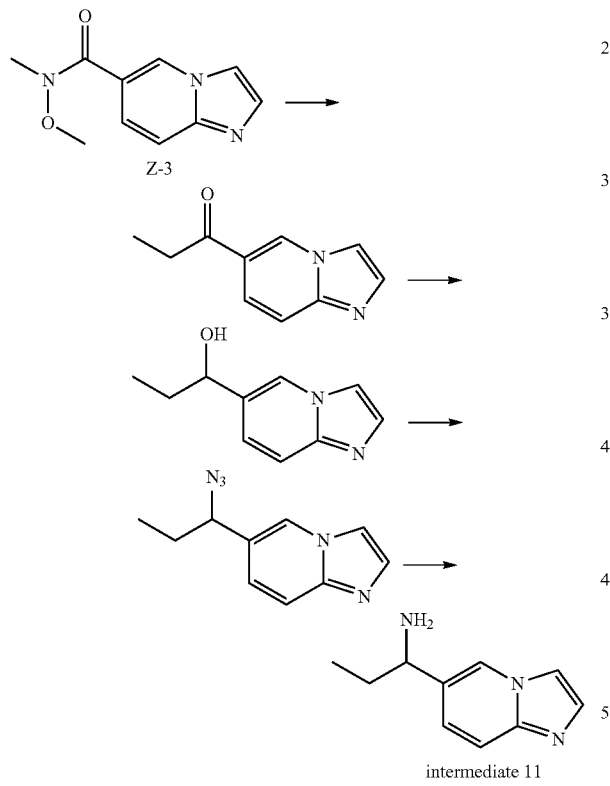

1-(imidazo[1,2-a]pyridin-6-yl)propan-1-amine

Intermediate 11 was prepared from Z-3 following similar procedures for synthesizing intermediate Z from Z-3.

Example 1. Preparation of Compounds 1-332

Compounds of the present invention can be made according to the following examples. It will be understood by those skilled in the art that the following examples do not limit the invention. For example, it may be possible to alter exact solvents, conditions, quantities, or utilize the equivalent reagents and intermediates with appropriate protecting groups.

Compound 1, 1-((1H-Pyrrolo[2,3-b]pyridin-3-yl)methyl)-6-(1-methyl-1H-pyrazol-4-yl)-1H-[1,2,3]-triazolo[4,5-b]pyrazine

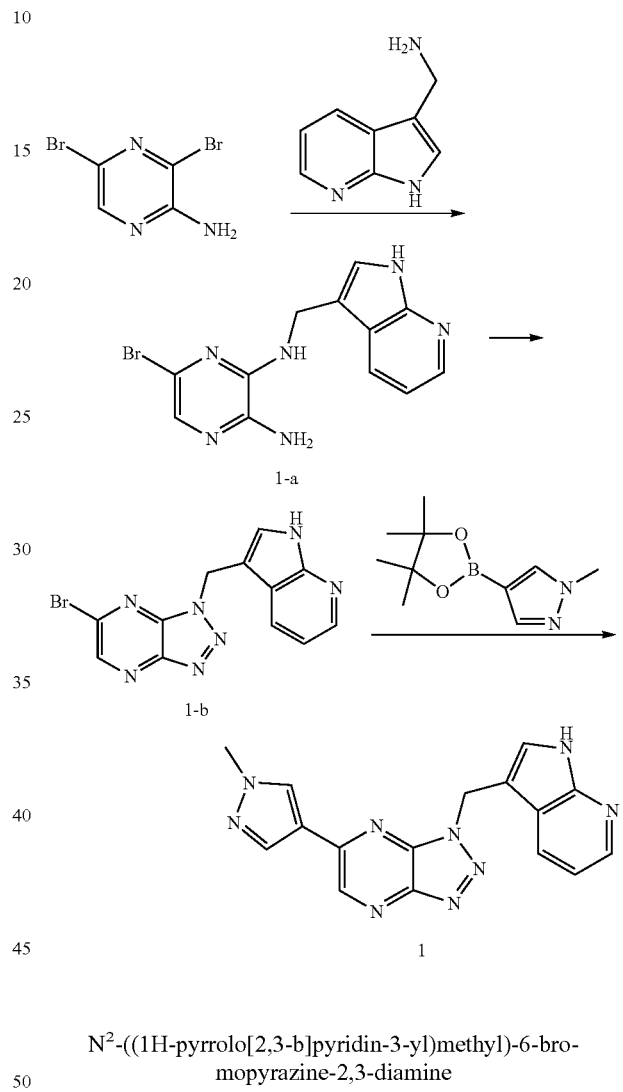

N$^2$-((1H-pyrrolo[2,3-b]pyridin-3-yl)methyl)-6-bromopyrazine-2,3-diamine

A mixture of (1H-pyrrolo[2,3-b]pyridin-3-yl)methanamine (intermediate A) (442 mg, 3.0 mmol), 3,5-dibromopyrazin-2-amine (758 mg, 3.0 mmol) and N-ethyl-N-isopropylpropan-2-amine (1160 mg, 9.0 mmol) in EtOH (70 mL) was stirred at 150° C. overnight. After being cooled to room temperature, it was concentrated and purified by chromatography to afford the title compound (70 mg) MS (m/z): 319 (M+1)$^+$.

1-((1H-Pyrrolo[2,3-b]pyridin-3-yl)methyl)-6-bromo-1H-[1,2,3]triazolo[4,5-b]pyrazine To the ice-cooled mixture of N$^2$-((1H-pyrrolo[2,3-b]pyridin-3-yl)methyl)-6-bromopyrazine-2,3-diamine (48 mg, 0.15 mmol) in HOAc/H$_2$O (1.5 mL/1.5 mL) was added NaNO$_2$ (31 mg, 0.45 mmol) in water (0.2 mL). The reaction was stirred for 1.5 h in an ice bath, then aqueous $H_2SO_4$ (49%, 0.1 mL) was added. The resulting mixture was allowed to warm to room temperature and stir overnight, then was adjusted to pH>8 with 3 N aqueous NaOH solution, and extracted with EtOAc. The combined organics were dried over $Na_2SO_4$, filtered and concentrated to give the title compound (46 mg) MS (m/z): 332 (M+1)+.

1-((1H-Pyrrolo[2,3-b]pyridin-3-yl)methyl)-6-(1-methyl-1H-pyrazol-4-yl)-1H-[1,2,3]-triazolo[4,5-b]pyrazine The mixture of 1-((1H-pyrrolo[2,3-b]pyridin-3-yl)methyl)-6-bromo-1H-[1,2,3]triazolo-[4,5-b]pyrazine (46 mg, 0.14 mmol), 1-methyl-4-(4,4,5,5-tetramethyl-1,3,2-dioxaborolan-2-yl)-1H-pyrazole (77 mg, 0.35 mmol), $PdCl_2$ (dppf) (12 mg, 0.014 mmol) and $Cs_2CO_3$ (137 mg, 0.42 mmol) in dioxane/$H_2O$ (10:1, 8 mL) was stirred at 80° C. overnight. After being cooled to room temperature, the mixture was concentrated and purified by chromatography to afford the title compound (18 mg) MS (m/z): 332 (M+H).

Compounds 2-59, 265-269, 272, 274-277, 279-290, 293-296, 298-299, 301-305, 308-310, 316-317, 326, 328-329, 331

The following compounds 2-59, 265-269, 272, 274-277, 279-290, 293-296, 298-299, 301-305, 308-310, 316-317, 326, 328-329, 331 were prepared according to the procedures of Compound 1 using the corresponding intermediates and boronic acid or ester under appropriate conditions that will be recognized by one skilled in the art:

TABLE 1

| Compound | Structure | LC/MS data |
|---|---|---|
| 2 | 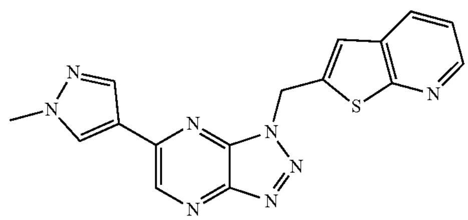 [SMILES: Cn1cc(-c2cnc3nnn(Cc4cc5cccnc5s4)c3n2)cn1] | 349 (M + 1)+ |
| 3 | 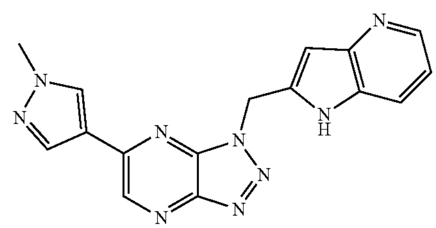 [SMILES: Cn1cc(-c2cnc3nnn(Cc4cc5ncccc5[nH]4)c3n2)cn1] | 332 (M + 1)+ |
| 4 | 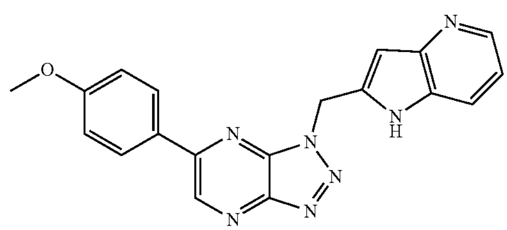 [SMILES: COc1ccc(-c2cnc3nnn(Cc4cc5ncccc5[nH]4)c3n2)cc1] | 358 (M + 1)+ |
| 5 | 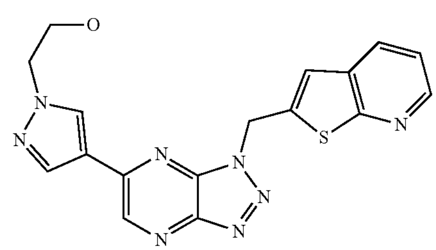 [SMILES: OCCn1cc(-c2cnc3nnn(Cc4cc5cccnc5s4)c3n2)cn1] | 379 (M + 1)+ |
| 6 | 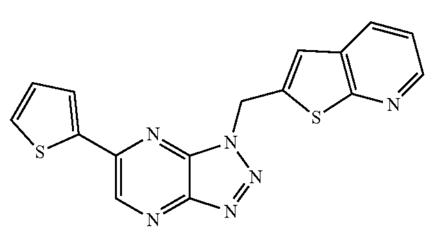 [SMILES: c1csc(-c2cnc3nnn(Cc4cc5cccnc5s4)c3n2)c1] | 351 (M + 1)+ |

TABLE 1-continued

| Compound | Structure | LC/MS data |
|---|---|---|
| 7 | 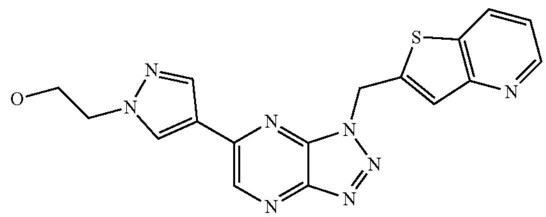 [SMILES: OCCn1cc(-c2cnc3nnn(Cc4cc5ncccc5s4)c3n2)cn1] | 379 (M + 1)+ |
| 8 | 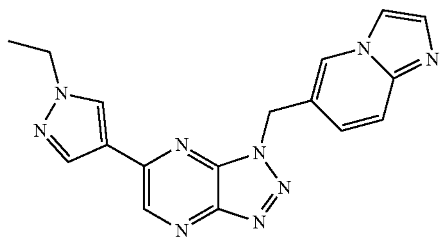 [SMILES: CCn1cc(-c2cnc3nnn(Cc4ccc5nccn5c4)c3n2)cn1] | 346 (M + 1)+ |
| 9 | 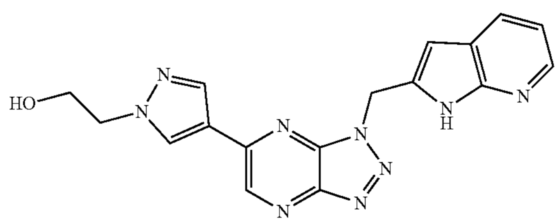 [SMILES: OCCn1cc(-c2cnc3nnn(Cc4cc5cccnc5[nH]4)c3n2)cn1] | 362 (M + 1)+ |
| 10 | 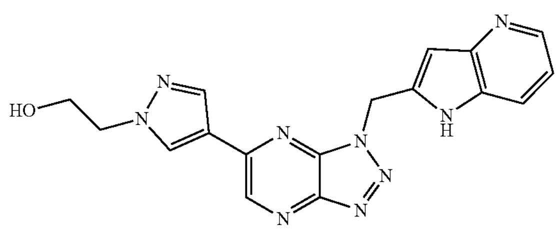 [SMILES: OCCn1cc(-c2cnc3nnn(Cc4cc5ncccc5[nH]4)c3n2)cn1] | 362 (M + 1)+ |
| 11 | 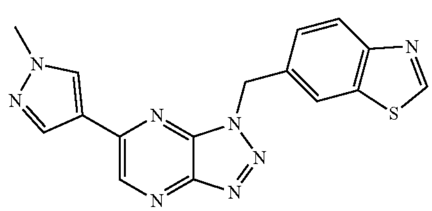 [SMILES: Cn1cc(-c2cnc3nnn(Cc4ccc5ncsc5c4)c3n2)cn1] | 349 (M + 1)+ |
| 12 | 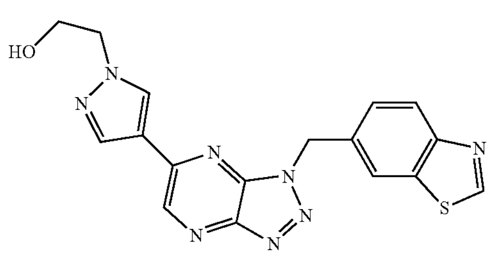 [SMILES: OCCn1cc(-c2cnc3nnn(Cc4ccc5ncsc5c4)c3n2)cn1] | 379 (M + 1)+ |

TABLE 1-continued

| Compound | Structure | LC/MS data |
|---|---|---|
| 13 | 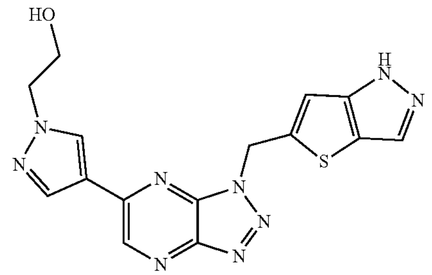 [SMILES: OCCn1cc(-c2cnc3nnn(Cc4cc5[nH]ncc5s4)c3n2)cn1] | 367.4 (M)+ |
| 14 | 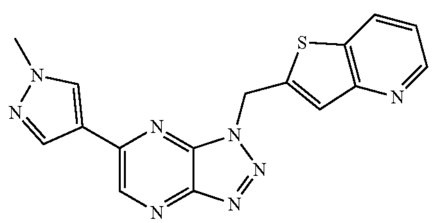 [SMILES: Cn1cc(-c2cnc3nnn(Cc4cc5ncccc5s4)c3n2)cn1] | 348 (M)+ |
| 15 | 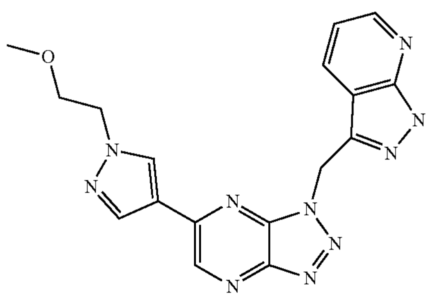 [SMILES: COCCn1cc(-c2cnc3nnn(Cc4n[nH]c5ncccc45)c3n2)cn1] | 377 (M + 1)+ |
| 16 | 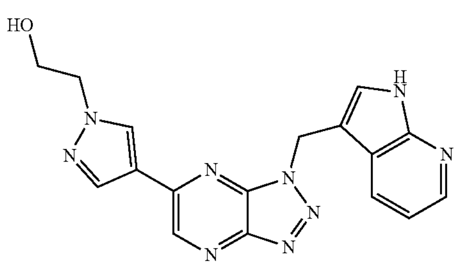 [SMILES: OCCn1cc(-c2cnc3nnn(Cc4c[nH]c5ncccc45)c3n2)cn1] | 362 (M + 1)+ |
| 17 | 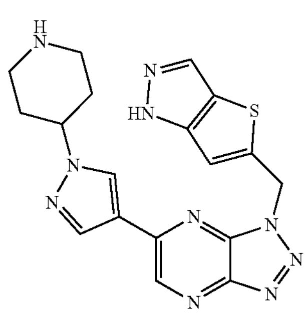 [SMILES: c1nn(C2CCNCC2)cc1-c1cnc2nnn(Cc3cc4[nH]ncc4s3)c2n1] | 407 (M + 1)+ |

TABLE 1-continued
| Compound | Structure | LC/MS data |
|---|---|---|
| 18 | 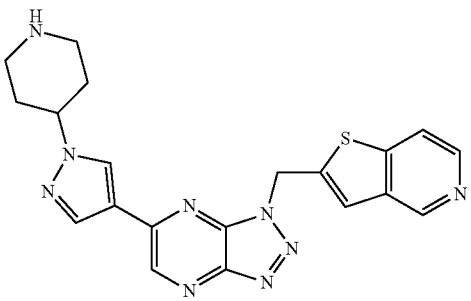 [SMILES: c1cc2sc(Cn3nnc4ncc(-c5cnn(C6CCNCC6)c5)nc43)cc2cn1] | 418 (M + 1)+ |
| 19 | 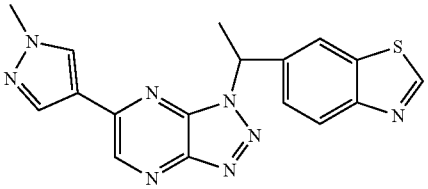 [SMILES: CC(c1ccc2ncsc2c1)n1nnc2ncc(-c3cnn(C)c3)nc21] | 363 (M + 1)+ |
| 20 | 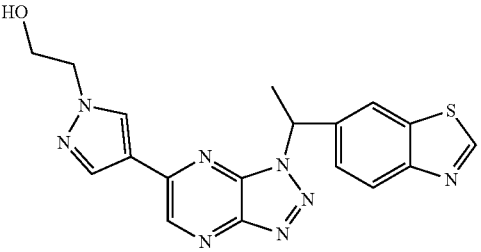 [SMILES: CC(c1ccc2ncsc2c1)n1nnc2ncc(-c3cnn(CCO)c3)nc21] | 393 (M + 1)+ |
| 21 | 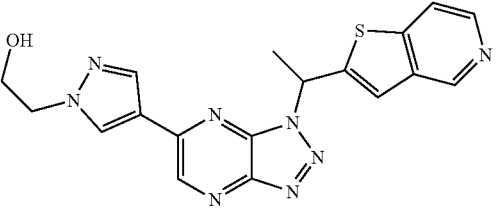 [SMILES: CC(c1cc2cnccc2s1)n1nnc2ncc(-c3cnn(CCO)c3)nc21] | 393 (M + 1)+ |
| 22 | 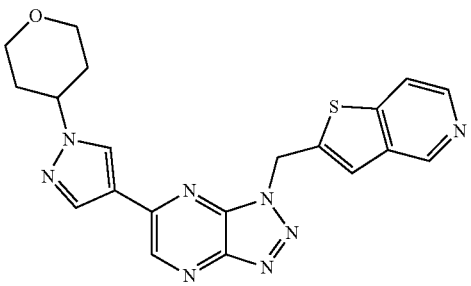 [SMILES: c1cc2sc(Cn3nnc4ncc(-c5cnn(C6CCOCC6)c5)nc43)cc2cn1] | 419 (M + 1)+ |
| 23 | 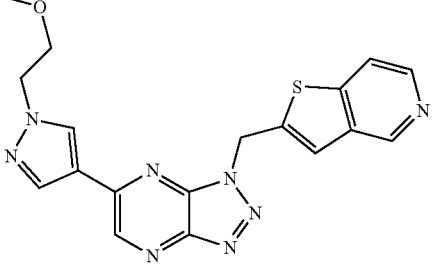 | 393 (M + 1)+ |

TABLE 1-continued

| Compound | Structure | LC/MS data |
|---|---|---|
| 24 | 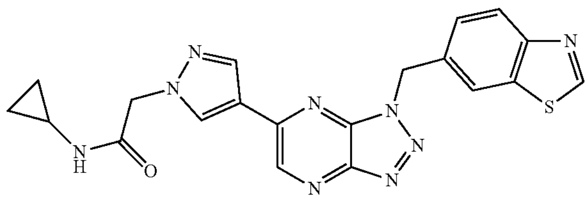 [SMILES: O=C(Cn1cc(-c2cnc3nnn(Cc4ccc5ncsc5c4)c3n2)cn1)NC1CC1] | 432 (M + 1)⁺ |
| 25 | 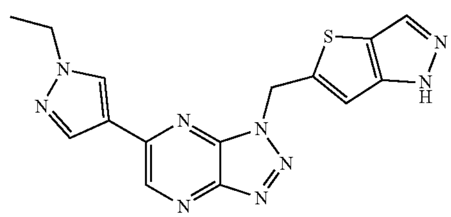 [SMILES: CCn1cc(-c2cnc3nnn(Cc4cc5[nH]ncc5s4)c3n2)cn1] | 352 (M + 1)⁺ |
| 26 | 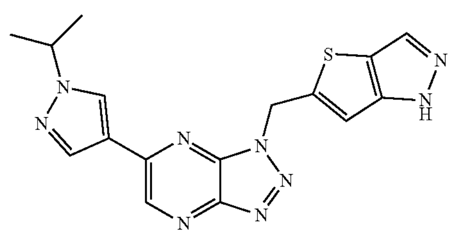 [SMILES: CC(C)n1cc(-c2cnc3nnn(Cc4cc5[nH]ncc5s4)c3n2)cn1] | 366 (M + 1)⁺ |
| 27 | 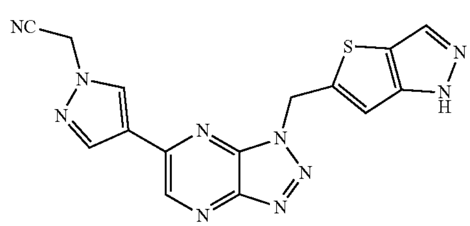 [SMILES: N#CCn1cc(-c2cnc3nnn(Cc4cc5[nH]ncc5s4)c3n2)cn1] | 363 (M + 1)⁺ |
| 28 | 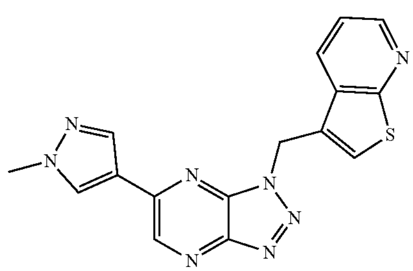 [SMILES: Cn1cc(-c2cnc3nnn(Cc4csc5ncccc45)c3n2)cn1] | 349 (M + 1)⁺ |
| 29 | 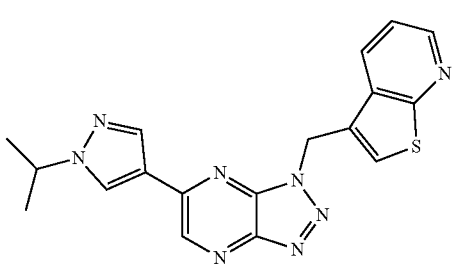 [SMILES: CC(C)n1cc(-c2cnc3nnn(Cc4csc5ncccc45)c3n2)cn1] | 377 (M + 1)⁺ |

TABLE 1-continued

| Compound | Structure | LC/MS data |
| --- | --- | --- |
| 30 | 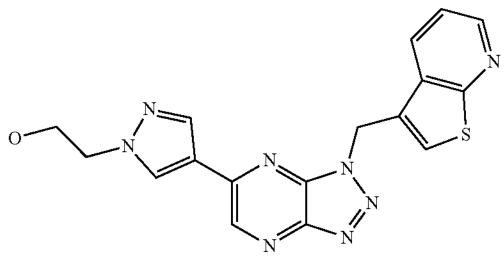 [SMILES: OCCn1cc(-c2cnc3nnn(Cc4csc5ncccc45)c3n2)cn1] | 379 (M + 1)+ |
| 31 | 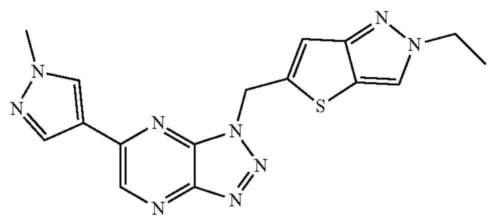 [SMILES: CCn1cc2sc(Cn3nnc4ncc(-c5cnn(C)c5)nc43)cc2n1] | 366 (M + 1)+ |
| 32 | 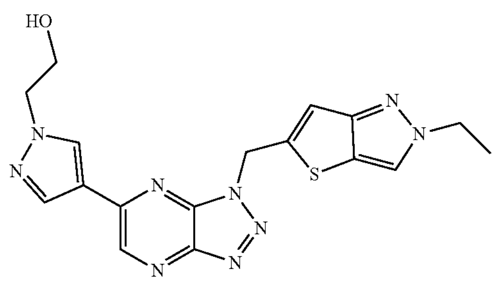 [SMILES: CCn1cc2sc(Cn3nnc4ncc(-c5cnn(CCO)c5)nc43)cc2n1] | 396.7 (M + 1)+ |
| 33 | 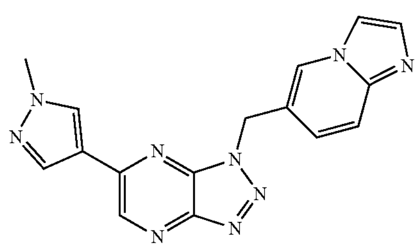 [SMILES: Cn1cc(-c2cnc3nnn(Cc4ccc5nccn5c4)c3n2)cn1] | 332 (M + 1)+ |
| 34 | 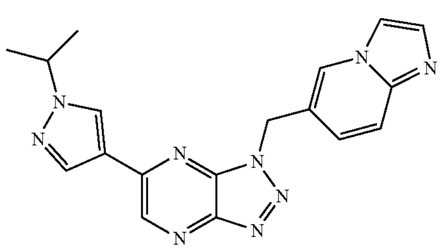 [SMILES: CC(C)n1cc(-c2cnc3nnn(Cc4ccc5nccn5c4)c3n2)cn1] | 360 (M + 1)+ |
| 35 | 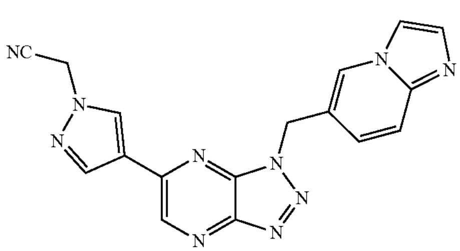 [SMILES: N#CCn1cc(-c2cnc3nnn(Cc4ccc5nccn5c4)c3n2)cn1] | 357 (M + 1)+ |

TABLE 1-continued

| Compound | Structure | LC/MS data |
| --- | --- | --- |
| 36 | 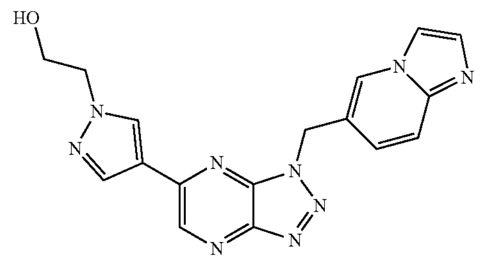 [SMILES: OCCn1cc(-c2cnc3nnn(Cc4ccc5nccn5c4)c3n2)cn1] | 362 (M + 1)+ |
| 37 | 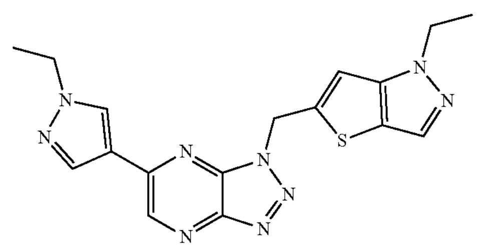 [SMILES: CCn1cc(-c2cnc3nnn(Cc4cc5c(cnn5CC)s4)c3n2)cn1] | 380 (M + 1)+ |
| 38 | 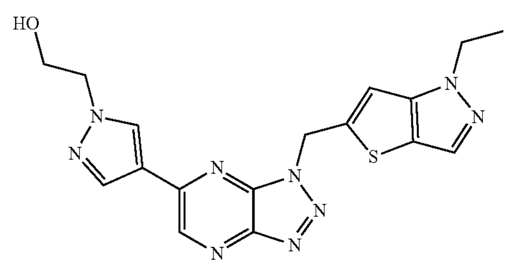 [SMILES: CCn1ncc2sc(Cn3nnc4ncc(-c5cnn(CCO)c5)nc43)cc21] | 396 (M + 1)+ |
| 39 | 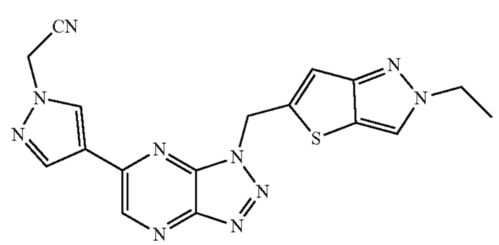 [SMILES: CCn1cc2sc(Cn3nnc4ncc(-c5cnn(CC#N)c5)nc43)cc2n1] | 391.7 (M + 1)+ |
| 40 | 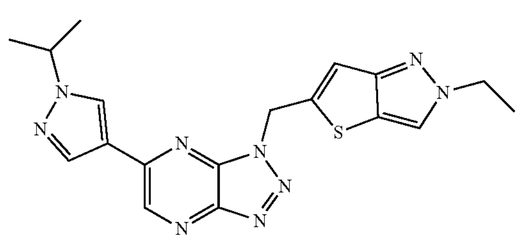 [SMILES: CCn1cc2sc(Cn3nnc4ncc(-c5cnn(C(C)C)c5)nc43)cc2n1] | 394.5 (M + 1)+ |
| 41 | 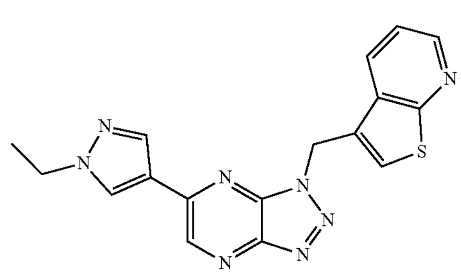 [SMILES: CCn1cc(-c2cnc3nnn(Cc4csc5ncccc45)c3n2)cn1] | 363 (M + 1)+ |

TABLE 1-continued

| Compound | Structure | LC/MS data |
|---|---|---|
| 42 | 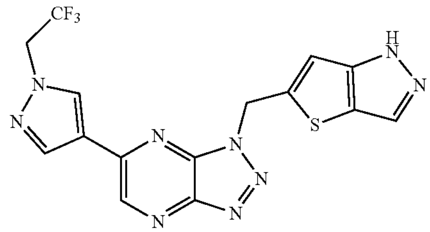 [SMILES: FC(F)(F)Cn1cc(-c2cnc3nnn(Cc4cc5[nH]ncc5s4)c3n2)cn1] | 406.9 (M + 1)+ |
| 43 | 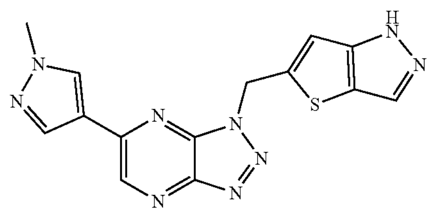 [SMILES: Cn1cc(-c2cnc3nnn(Cc4cc5[nH]ncc5s4)c3n2)cn1] | 338 (M + 1)+ |
| 44 | 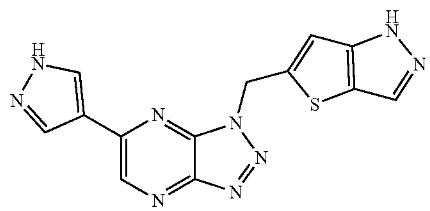 [SMILES: c1n[nH]cc1-c1cnc2nnn(Cc3cc4[nH]ncc4s3)c2n1] | 324 (M + 1)+ |
| 45 | 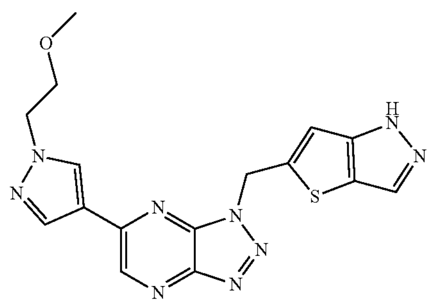 [SMILES: COCCn1cc(-c2cnc3nnn(Cc4cc5[nH]ncc5s4)c3n2)cn1] | 382 (M + 1)+ |
| 46 | 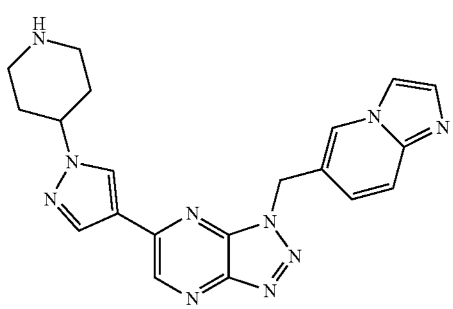 [SMILES: c1cn2cc(Cn3nnc4ncc(-c5cnn(C6CCNCC6)c5)nc43)ccc2n1] | 401 (M + 1)+ |
| 47 | 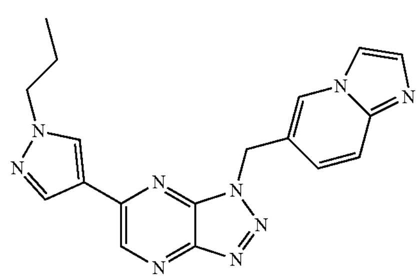 [SMILES: CCCn1cc(-c2cnc3nnn(Cc4ccc5nccn5c4)c3n2)cn1] | 360 (M + 1)+ |

TABLE 1-continued

| Compound | Structure | LC/MS data |
|---|---|---|
| 48 | 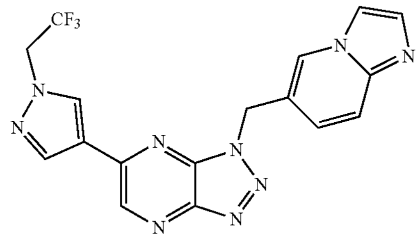 [SMILES: FC(F)(F)Cn1cc(-c2cnc3nnn(Cc4ccc5nccn5c4)c3n2)cn1] | 400 (M + 1)+ |
| 49 | 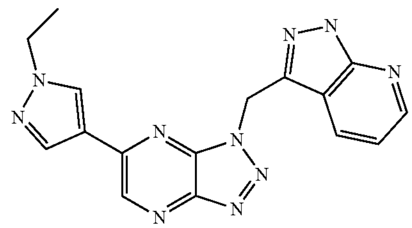 [SMILES: CCn1cc(-c2cnc3nnn(Cc4n[nH]c5ncccc45)c3n2)cn1] | 347 (M + 1)+ |
| 50 | 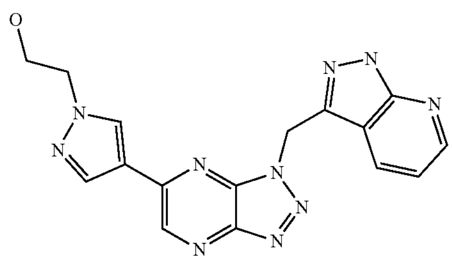 [SMILES: OCCn1cc(-c2cnc3nnn(Cc4n[nH]c5ncccc45)c3n2)cn1] | 363 (M + 1)+ |
| 51 | 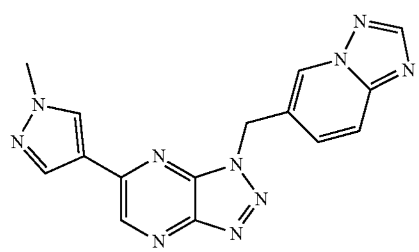 [SMILES: Cn1cc(-c2cnc3nnn(Cc4ccc5ncnn5c4)c3n2)cn1] | 333 (M + 1)+ |
| 52 | 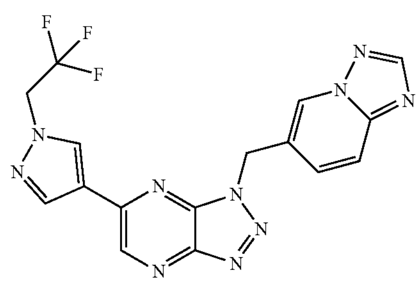 [SMILES: FC(F)(F)Cn1cc(-c2cnc3nnn(Cc4ccc5ncnn5c4)c3n2)cn1] | 401 (M + 1)+ |
| 53 | 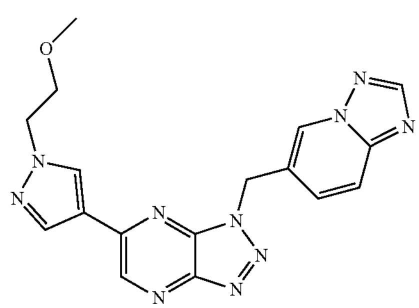 [SMILES: COCCn1cc(-c2cnc3nnn(Cc4ccc5ncnn5c4)c3n2)cn1] | 377 (M + 1)+ |

TABLE 1-continued

| Compound | Structure | LC/MS data |
|---|---|---|
| 54 | 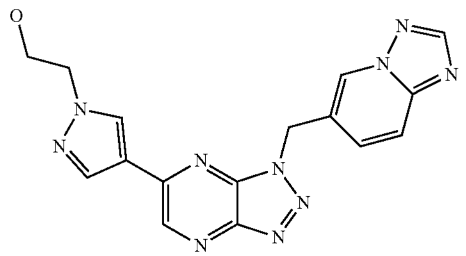 [SMILES: OCCn1cc(-c2cnc3nnn(Cc4ccc5ncnn5c4)c3n2)cn1] | 363 (M + 1)+ |
| 55 | 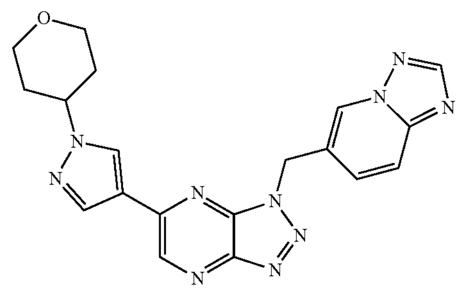 [SMILES: c1nc2ccc(Cn3nnc4ncc(-c5cnn(C6CCOCC6)c5)nc43)cn2n1] | 403 (M + 1)+ |
| 56 | 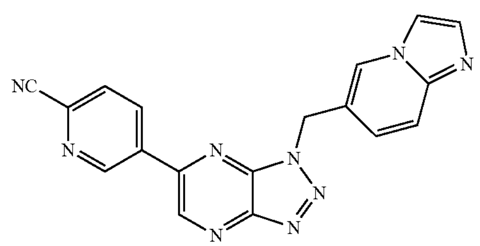 [SMILES: N#Cc1ccc(-c2cnc3nnn(Cc4ccc5nccn5c4)c3n2)cn1] | 354 (M + 1)+ |
| 57 | 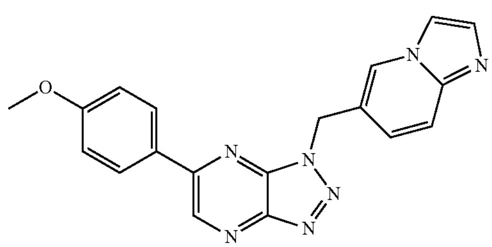 [SMILES: COc1ccc(-c2cnc3nnn(Cc4ccc5nccn5c4)c3n2)cc1] | 358 (M + 1)+ |
| 58 | 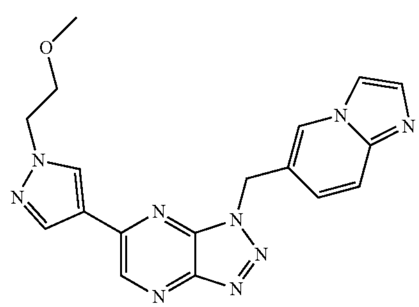 [SMILES: COCCn1cc(-c2cnc3nnn(Cc4ccc5nccn5c4)c3n2)cn1] | 376 (M + 1)+ |
| 59 | 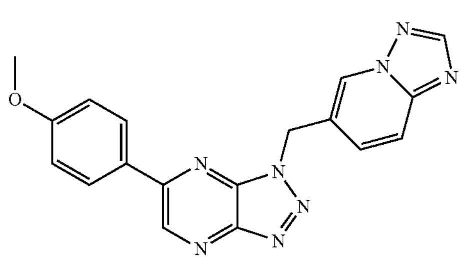 [SMILES: COc1ccc(-c2cnc3nnn(Cc4ccc5ncnn5c4)c3n2)cc1] | 359 (M + 1)+ |

TABLE 1-continued

| Compound | Structure | LC/MS data |
| --- | --- | --- |
| 265 | 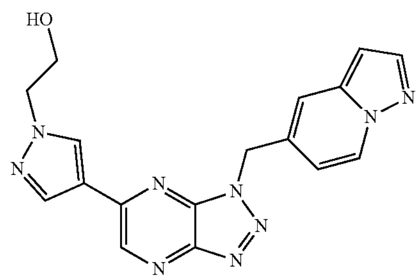 [SMILES: OCCn1cc(-c2cnc3nnn(Cc4ccn5nccc5c4)c3n2)cn1] | 362 (M + 1)+ |
| 266 | 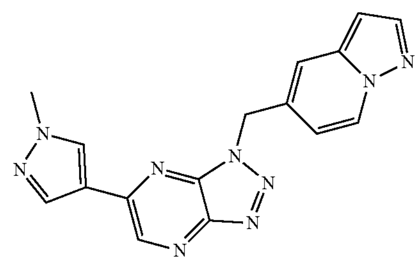 [SMILES: Cn1cc(-c2cnc3nnn(Cc4ccn5nccc5c4)c3n2)cn1] | 332 (M + 1)+ |
| 267 | 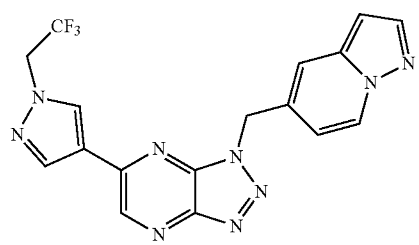 | 400 (M + 1)+ |
| 268 | 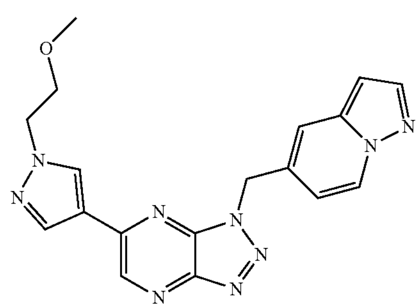 [SMILES: COCCn1cc(-c2cnc3nnn(Cc4ccn5nccc5c4)c3n2)cn1] | 376 (M + 1)+ |
| 269 | 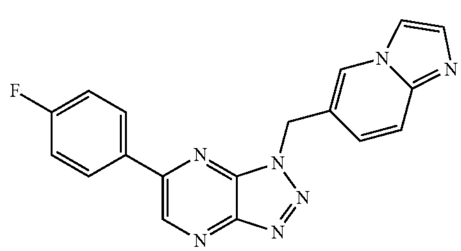 [SMILES: Fc1ccc(-c2cnc3nnn(Cc4ccc5nccn5c4)c3n2)cc1] | 346 (M + 1)+ |

TABLE 1-continued
| Compound | Structure | LC/MS data |
|---|---|---|
| 272* | 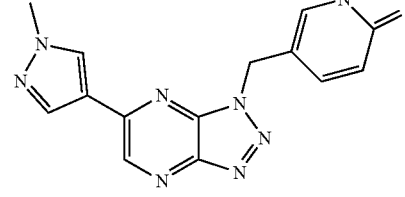 | 362 (M + 1)+ |
| 274 | 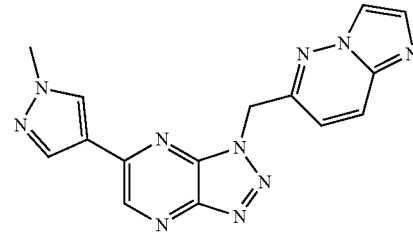 | 333.1 (M + 1)+ |
| 275 | 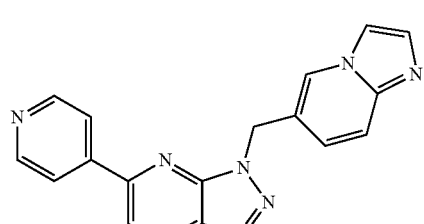 | 329.1 (M + 1)+ |
| 276 | 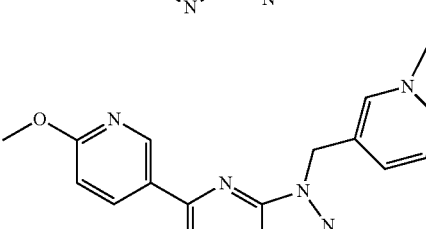 | 359 (M + 1)+ |
| 277 | 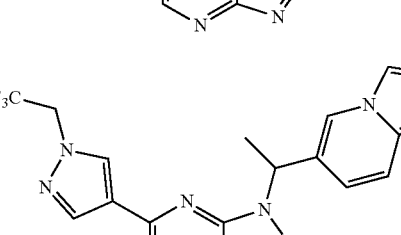 | 413.9 (M + 1)+ |
| 279 | 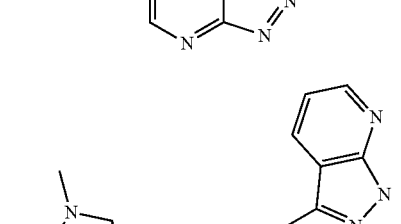 | 333 (M + 1)+ |

TABLE 1-continued

| Compound | Structure | LC/MS data |
| --- | --- | --- |
| 280 | 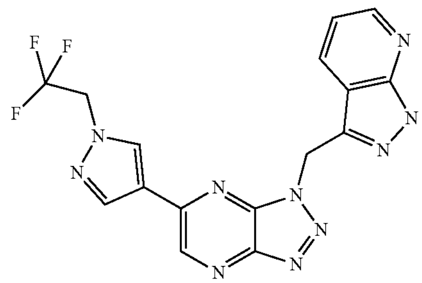 [SMILES: FC(F)(F)Cn1cc(-c2cnc3nnn(Cc4n[nH]c5ncccc45)c3n2)cn1] | 401 (M + 1)+ |
| 281 | 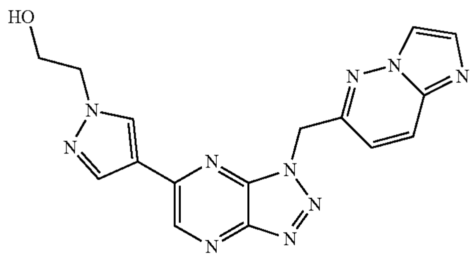 [SMILES: OCCn1cc(-c2cnc3nnn(Cc4ccc5nccn5n4)c3n2)cn1] | 363.1 (M + 1)+ |
| 282 | 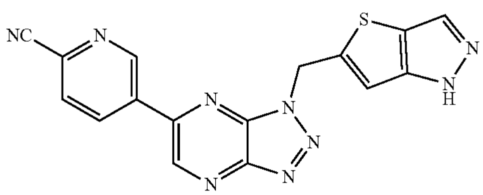 [SMILES: N#Cc1ccc(-c2cnc3nnn(Cc4cc5[nH]ncc5s4)c3n2)cn1] | 360.1 (M + 1)+ |
| 283 | 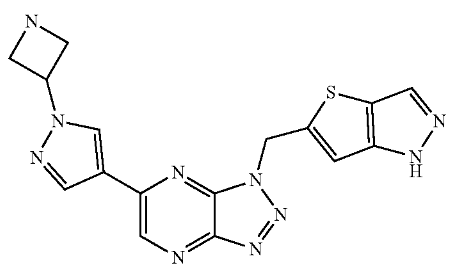 [SMILES: c1nn(C2CNC2)cc1-c1cnc2nnn(Cc3cc4[nH]ncc4s3)c2n1] | 379.0 (M + 1)+ |
| 284 | 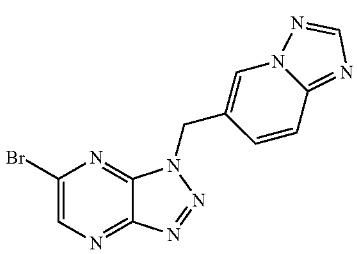 [SMILES: Brc1cnc2nnn(Cc3ccc4ncnn4c3)c2n1] | 332.9 (M + 1)+ |
| 285 | 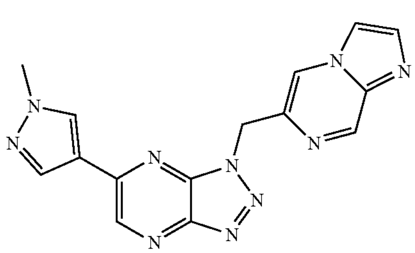 [SMILES: Cn1cc(-c2cnc3nnn(Cc4cn5ccnc5cn4)c3n2)cn1] | 333 (M + 1)+ |

TABLE 1-continued

| Compound | Structure | LC/MS data |
|---|---|---|
| 286 | 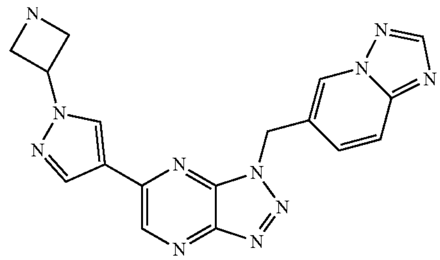 [SMILES: c1nc2ccc(Cn3nnc4ncc(-c5cnn(C6CNC6)c5)nc43)cn2n1] | 374.1 (M + 1)+ |
| 287 | 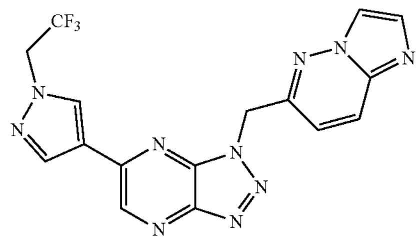 [SMILES: FC(F)(F)Cn1cc(-c2cnc3nnn(Cc4ccc5nccn5n4)c3n2)cn1] | 400.9 (M + 1)+ |
| 288 | 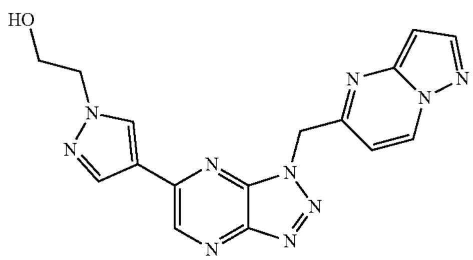 [SMILES: OCCn1cc(-c2cnc3nnn(Cc4ccn5nccc5n4)c3n2)cn1] | 363.0 (M + 1)+ |
| 289 | 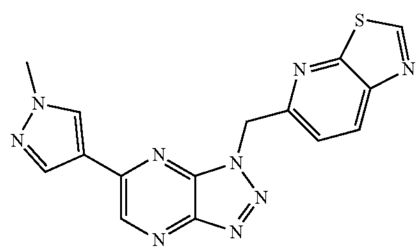 [SMILES: Cn1cc(-c2cnc3nnn(Cc4ccc5ncsc5n4)c3n2)cn1] | 350 (M + 1)+ |
| 290 | 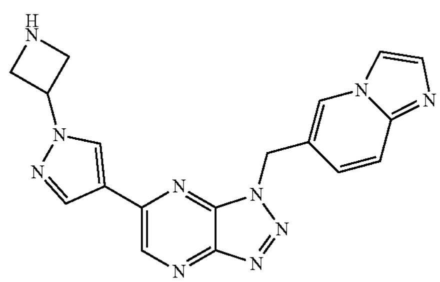 [SMILES: c1cn2cc(Cn3nnc4ncc(-c5cnn(C6CNC6)c5)nc43)ccc2n1] | 373 (M + 1)+ |
| 293 | 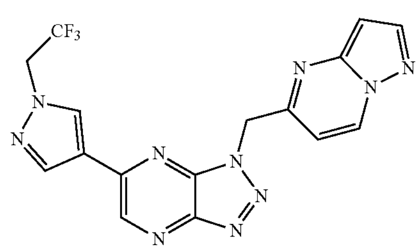 [SMILES: FC(F)(F)Cn1cc(-c2cnc3nnn(Cc4ccn5nccc5n4)c3n2)cn1] | 401 (M + 1)+ |

TABLE 1-continued

| Compound | Structure | LC/MS data |
|---|---|---|
| 294 | 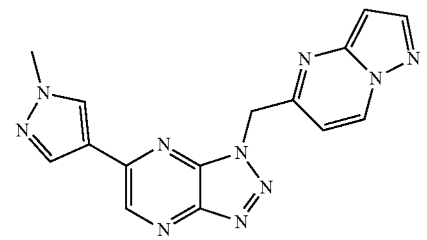 [SMILES: Cn1cc(-c2cnc3nnn(Cc4ccn5nccc5n4)c3n2)cn1] | 333 (M + 1)+ |
| 295 | 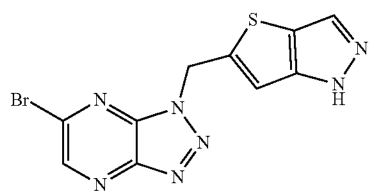 [SMILES: Brc1cnc2nnn(Cc3cc4[nH]ncc4s3)c2n1] | 335.9 (M + 1)+ |
| 296 | 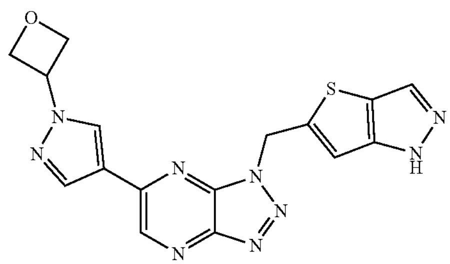 [SMILES: c1nn(C2COC2)cc1-c1cnc2nnn(Cc3cc4[nH]ncc4s3)c2n1] | 380.0 (M + 1)+ |
| 298 | 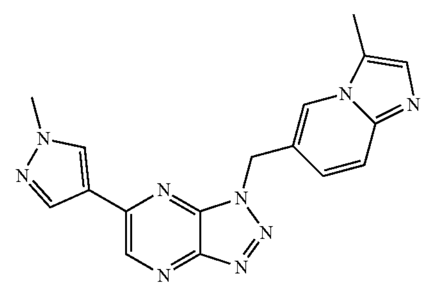 [SMILES: Cc1cnc2ccc(Cn3nnc4ncc(-c5cnn(C)c5)nc43)cn12] | 346 (M + 1)+ |
| 299 | 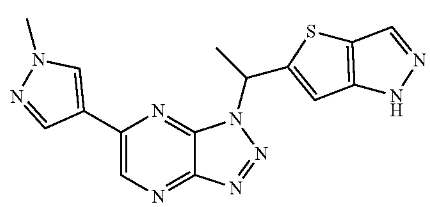 [SMILES: CC(c1cc2[nH]ncc2s1)n1nnc2ncc(-c3cnn(C)c3)nc21] | 351.9 (M + 1)+ |
| 301 | 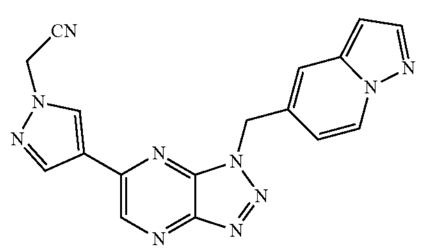 [SMILES: N#CCn1cc(-c2cnc3nnn(Cc4ccn5nccc5c4)c3n2)cn1] | 357.0 (M + 1)+ |

TABLE 1-continued

| Compound | Structure | LC/MS data |
|---|---|---|
| 302 | 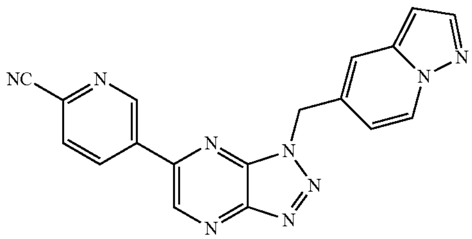 [SMILES: N#Cc1ccc(-c2cnc3nnn(Cc4ccn5nccc5c4)c3n2)cn1] | 354.1 (M + 1)+ |
| 303 | 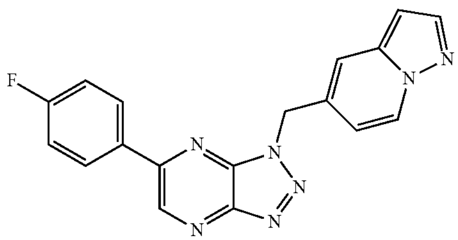 [SMILES: Fc1ccc(-c2cnc3nnn(Cc4ccn5nccc5c4)c3n2)cc1] | 346.1 (M + 1)+ |
| 304 | 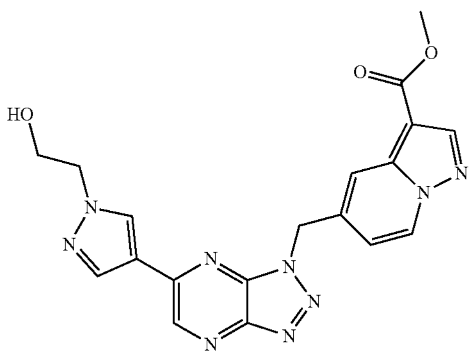 [SMILES: COC(=O)c1cnn2ccc(Cn3nnc4ncc(-c5cnn(CCO)c5)nc43)cc12] | 420.0 (M + 1)+ |
| 305 | 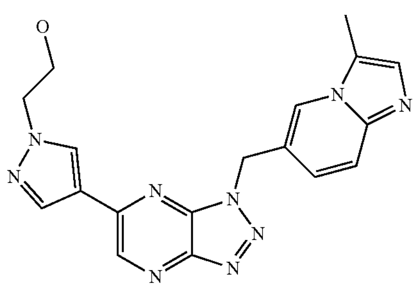 [SMILES: Cc1cnc2ccc(Cn3nnc4ncc(-c5cnn(CCO)c5)nc43)cn12] | 376.0 (M + 1)+ |
| 308 | 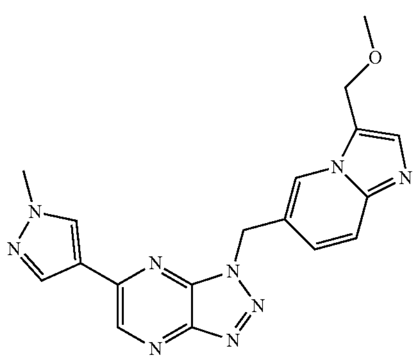 [SMILES: COCc1cnc2ccc(Cn3nnc4ncc(-c5cnn(C)c5)nc43)cn12] | 376.0 (M + 1)+ |

TABLE 1-continued

| Compound | Structure | LC/MS data |
|---|---|---|
| 309 | 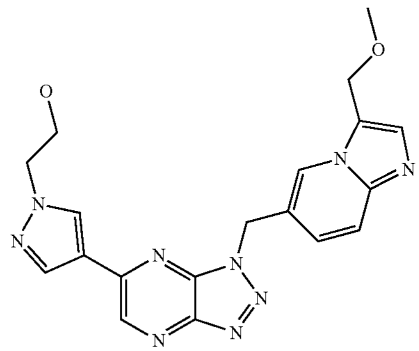 [SMILES: COCc1cnc2ccc(Cn3nnc4ncc(-c5cnn(CCO)c5)nc43)cn12] | 405.9 (M + 1)+ |
| 310 | 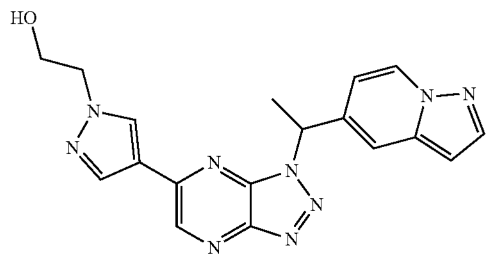 [SMILES: CC(c1ccn2nccc2c1)n1nnc2ncc(-c3cnn(CCO)c3)nc21] | 375.9 (M + 1)+ |
| 316 | 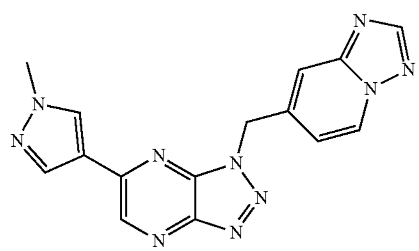 [SMILES: Cn1cc(-c2cnc3nnn(Cc4ccn5ncnc5c4)c3n2)cn1] | 333.0 (M + 1)+ |
| 317 | 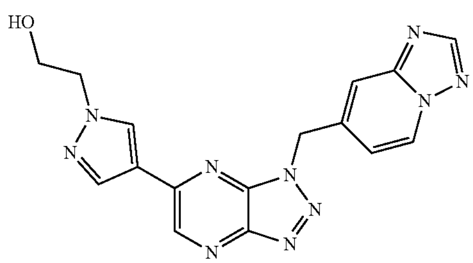 [SMILES: OCCn1cc(-c2cnc3nnn(Cc4ccn5ncnc5c4)c3n2)cn1] | 362.9 (M + 1)+ |
| 326 | 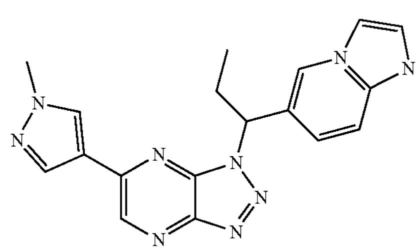 | 360.1 (M + 1)+ |
| 328 | 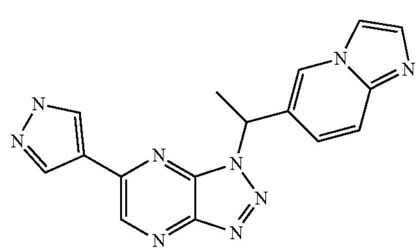 [SMILES: CC(c1ccc2nccn2c1)n1nnc2ncc(-c3cn[nH]c3)nc21] | 332.1 (M + 1)+ |

TABLE 1-continued

| Compound | Structure | LC/MS data |
|---|---|---|
| 329 | 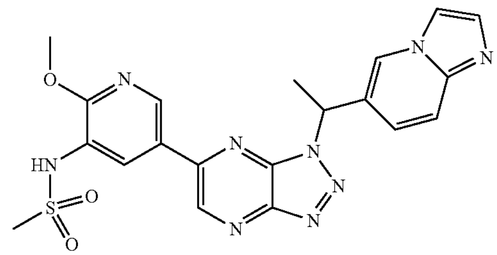 [SMILES: COc1ncc(-c2cnc3nnn(C(C)c4ccc5nccn5c4)c3n2)cc1NS(C)(=O)=O] | 466.1 (M + 1)+ |
| 331 | 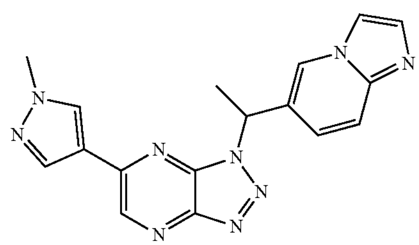 [SMILES: CC(c1ccc2nccn2c1)n1nnc2ncc(-c3cnn(C)c3)nc21] | 346 (M + 1)+ |

*Compound 272 was prepared from Compound 33 by the following procedure:

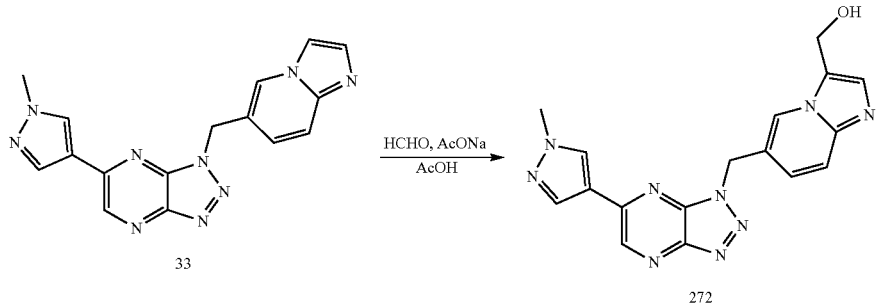 [SMILES: "AcOH" ; Cn1cc(-c2cnc3nnn(Cc4ccc5nccn5c4)c3n2)cn1 ; Cn1cc(-c2cnc3nnn(Cc4ccc5ncc(CO)n5c4)c3n2)cn1]

To a solution of compound 33 (66 mg, 0.2 mmol) in 0.1 mL of acetic acid were added sodium acetate (60 mg, 0.73 mmol) and an aqueous solution of formaldehyde (37%, 0.2 mL, 2.8 mmol). The reaction mixture was stirred at 100° C. overnight. After cooled to room temperature, the reaction mixture was diluted with water and basified with a saturated sodium carbonate aqueous solution. The resulting precipitate was filtered. The filtrate was purified by chromatography to afford compound 272 (30 mg).

Compound 60

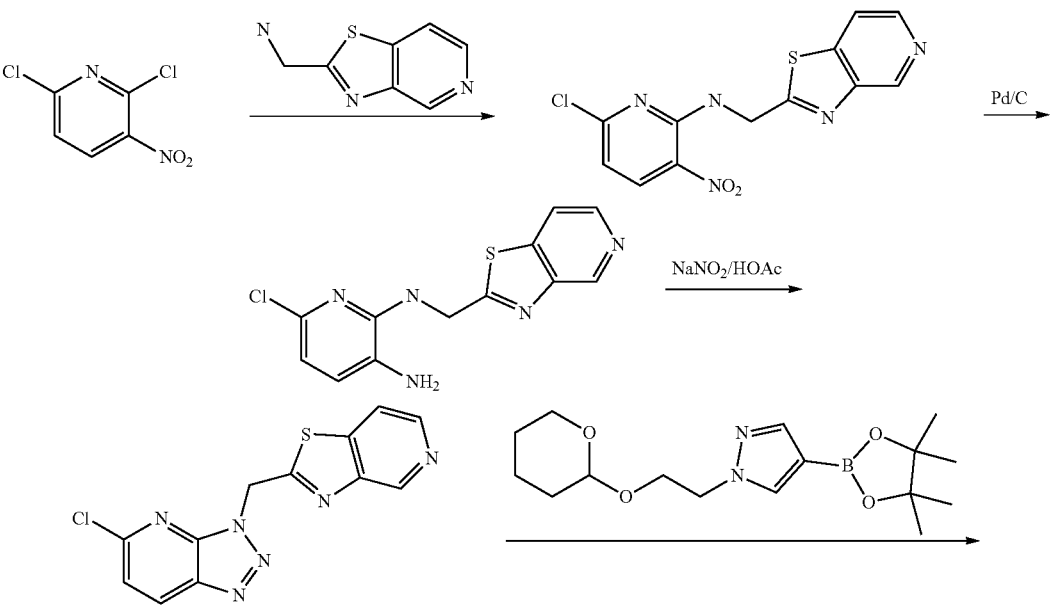

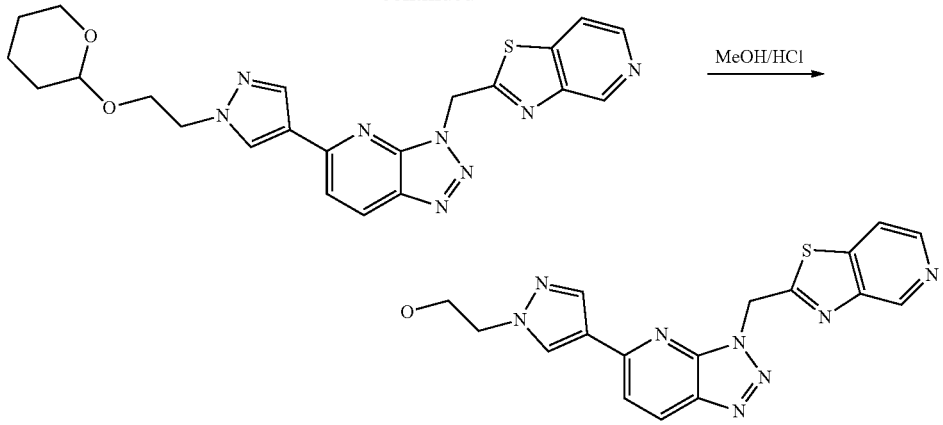

3-Nitro-6-chloro-N-(thiazolo[4,5-c]pyridin-2-ylmethyl)pyridin-2-amine

To a solution of 3-nitro-2,6-dichloropyridine (106 mg, 0.55 mmol) in isopropanol (3 mL) was sequentially added Na$_2$CO$_3$ (116 mg, 1.1 mmol) and intermediate R (100 mg, 0.61 mmol). The reaction mixture was stirred at room temperature overnight, and then concentrated. The residue was extracted with EtOAc. The organic layer was separated, concentrated, and purified by chromatography on silica gel to afford the title compound. MS (m/z): 322 (M)$^+$.

6-Chloro-N$^2$-(thiazolo[4,5-c]pyridin-2-ylmethyl)pyridine-2,3-diamine

10% Pd/C (20 mg) was added to a solution of 3-nitro-6-chloro-N-(thiazolo[4,5-c]pyridin-2-ylmethyl)pyridin-2-amine (100 mg, 0.31 mmol) in MeOH (2 mL) and THF (10 mL). The mixture was stirred at room temperature under 1 atm of H$_2$ for 1 h, and then filtered. The filtrate was concentrated and purified by chromatography on silica gel to afford the title compound. MS (m/z): 292 (M+1)$^+$.

5-Chloro-3-(thiazolo[4,5-c]pyridin-2-ylmethyl)-3H-[1,2,3]triazolo[4,5-b]pyridine A solution of NaNO$_2$ (42.5 mg, 0.62 mmol) in H$_2$O (0.5 mL) was added dropwise to a solution of 6-chloro-N$^2$-(thiazolo[4,5-c]pyridin-2-ylmethyl)pyridine-2,3-diamine (90 mg, 0.31 mmol) in AcOH (1 mL) and H$_2$O (1 mL) at 0° C. The reaction solution was stirred at 0° C. for 1 h, then basified with 30% aqueous NaOH to pH 9. The resulting precipitate was collected by filtration to afford the title compound. MS (m/z): 303 (M+1)$^+$.

5-(1-(2-(Tetrahydro-2H-pyran-2-yloxy)ethyl)-1H-pyrazol-4-yl)-3-(thiazolo[4,5-c]pyridin-2-ylmethyl)-3H-[1,2,3]triazolo[4,5-b]pyridine To a solution of intermediate X (75 mg, 0.23 mmol), 5-chloro-3-(thiazolo[4,5-c]pyridin-2-ylmethyl)-3H-[1,2,3]triazolo[4,5-b]pyridine (64 mg, 0.21 mmol) in dioxane (1.5 mL) and H$_2$O (0.15 mL) were added Pd(dppf)Cl$_2$ (32.7 mg, 0.04 mmol) and Cs$_2$CO$_3$ (98 mg, 0.3 mmol) under N$_2$. The resulting mixture was stirred at 120° C. overnight under N$_2$, and then concentrated. The residue was purified by chromatography to afford the title compound. MS (m/z): 463 (M+1)$^+$.

2-(4-(3-(Thiazolo[4,5-c]pyridin-2-ylmethyl)-3H-[1,2,3]triazolo[4,5-b]pyridin-5-yl)-1H-pyrazol-1-yl)ethanol 5-(1-(2-(tetrahydro-2H-pyran-2-yloxy)ethyl)-1H-pyrazol-4-yl)-3-(thiazolo[4,5-c]pyridin-2-ylmethyl)-3H-[1,2,3]triazolo[4,5-b]pyridine (20 mg, 0.04 mmol) was dissolved in MeOH/HCl (2 mL). The reaction mixture was stirred at room temperature for 1 h, and then concentrated. The residue was purified by chromatography to afford the title compound. MS (m/z): 379 (M+1)$^+$.

Compounds 61-76, 79, 81-151, 273, 291, 292, 297, 332

The following compounds 61-76, 79, 81-151, 273, 291, 292, 297, 332 were prepared according to the procedures of Compound 60 using the corresponding intermediates and boronic acid or ester under appropriate conditions that will be recognized by one skilled in the art:

TABLE 2

| Compound | Structure | LC/MS data |
| --- | --- | --- |
| 61 | 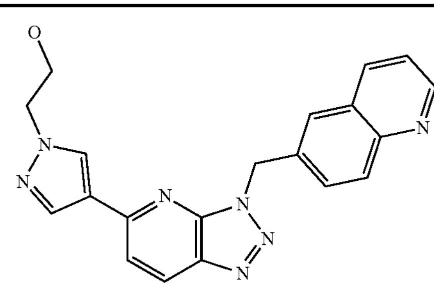 | 372 (M + 1)$^+$ |

TABLE 2-continued

| Compound | Structure | LC/MS data |
|---|---|---|
| 62 | 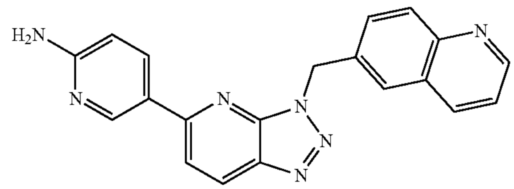 [SMILES: Nc1ccc(-c2ccc3nnn(Cc4ccc5ncccc5c4)c3n2)cn1] | 354 (M + 1)+ |
| 63 | 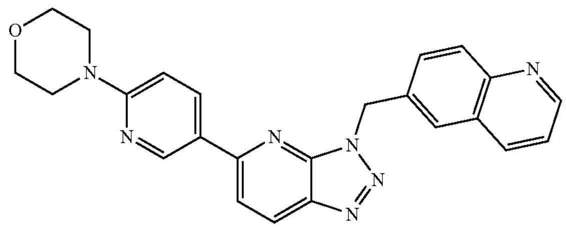 [SMILES: c1cnc2ccc(Cn3nnc4ccc(-c5ccc(N6CCOCC6)nc5)nc43)cc2c1] | 424 (M + 1)+ |
| 64 | 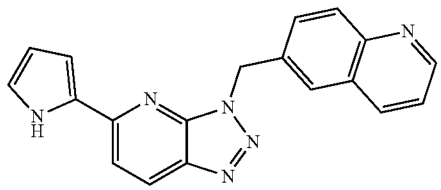 [SMILES: c1c[nH]c(-c2ccc3nnn(Cc4ccc5ncccc5c4)c3n2)c1] | 327 (M + 1)+ |
| 65 | 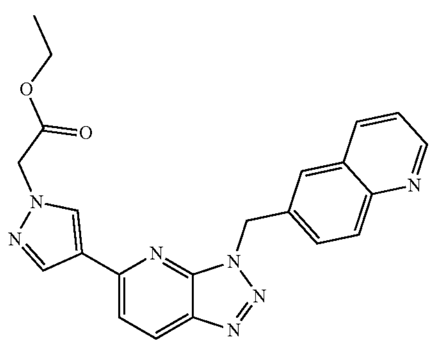 [SMILES: CCOC(=O)Cn1cc(-c2ccc3nnn(Cc4ccc5ncccc5c4)c3n2)cn1] | 414 (M + 1)+ |
| 66 | 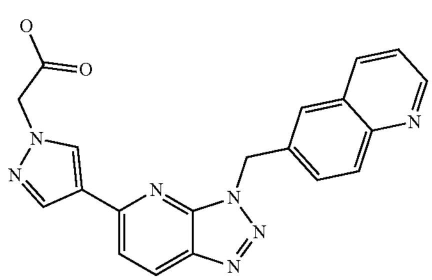 [SMILES: O=C(O)Cn1cc(-c2ccc3nnn(Cc4ccc5ncccc5c4)c3n2)cn1] | 386 (M + 1)+ |
| 67 | 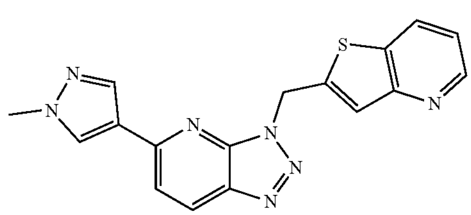 [SMILES: Cn1cc(-c2ccc3nnn(Cc4cc5ncccc5s4)c3n2)cn1] | 348 (M + 1)+ |

TABLE 2-continued

| Compound | Structure | LC/MS data |
|---|---|---|
| 68 | 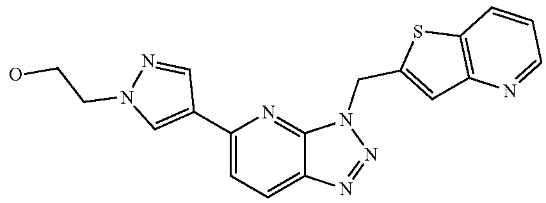 [SMILES: OCCn1cc(-c2ccc3nnn(Cc4cc5ncccc5s4)c3n2)cn1] | 378 (M + 1)+ |
| 69 | 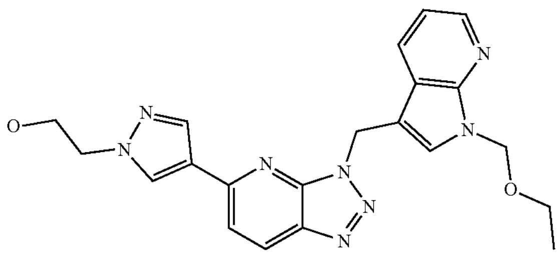 [SMILES: CCOCn1cc(Cn2nnc3ccc(-c4cnn(CCO)c4)nc32)c2cccnc21] | 419 (M + 1)+ |
| 70 | 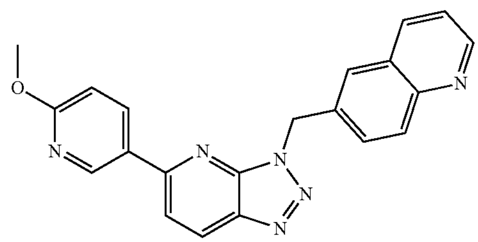 [SMILES: COc1ccc(-c2ccc3nnn(Cc4ccc5ncccc5c4)c3n2)cn1] | 369 (M + 1)+ |
| 71 | 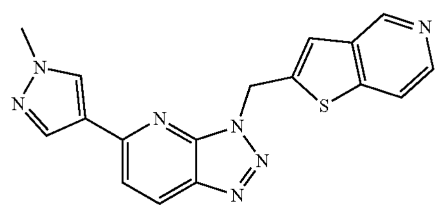 [SMILES: Cn1cc(-c2ccc3nnn(Cc4cc5cnccc5s4)c3n2)cn1] | 348 (M + 1)+ |
| 72 | 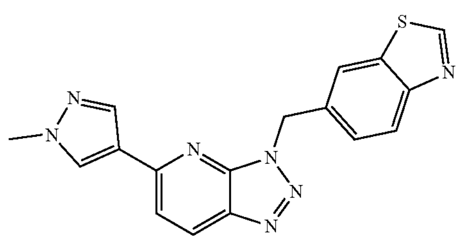 [SMILES: Cn1cc(-c2ccc3nnn(Cc4ccc5ncsc5c4)c3n2)cn1] | 348 (M + 1)+ |
| 73 | 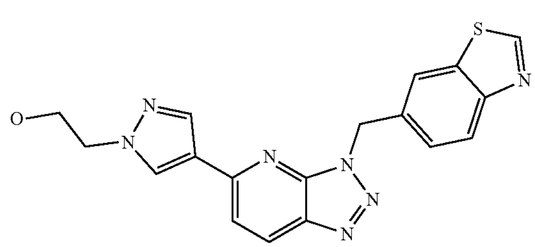 [SMILES: OCCn1cc(-c2ccc3nnn(Cc4ccc5ncsc5c4)c3n2)cn1] | 378 (M + 1)+ |

TABLE 2-continued

| Compound | Structure | LC/MS data |
|---|---|---|
| 74 | 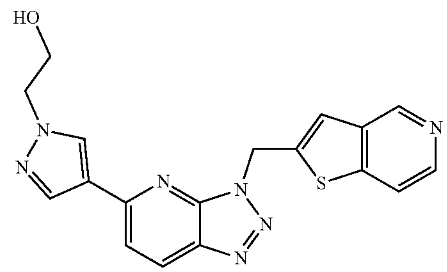 [SMILES: OCCn1cc(-c2ccc3nnn(Cc4cc5cnccc5s4)c3n2)cn1] | 378 (M + 1)+ |
| 75 | 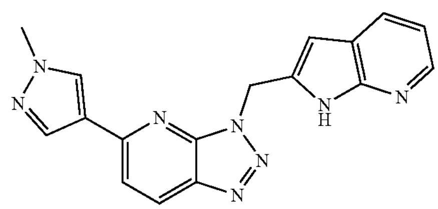 [SMILES: Cn1cc(-c2ccc3nnn(Cc4cc5cccnc5[nH]4)c3n2)cn1] | 331 (M + 1)+ |
| 76 | 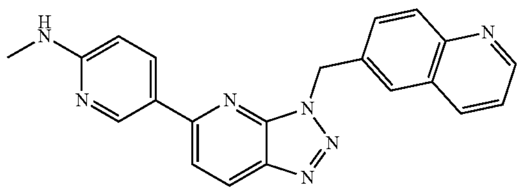 [SMILES: CNc1ccc(-c2ccc3nnn(Cc4ccc5ncccc5c4)c3n2)cn1] | 368 (M + 1)+ |
| 79 | 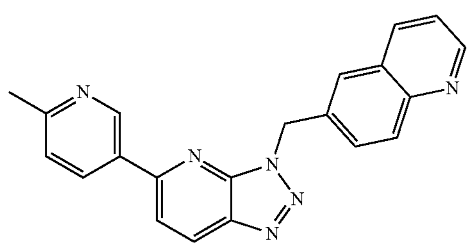 [SMILES: Cc1ccc(-c2ccc3nnn(Cc4ccc5ncccc5c4)c3n2)cn1] | 353 (M + 1)+ |
| 81 | 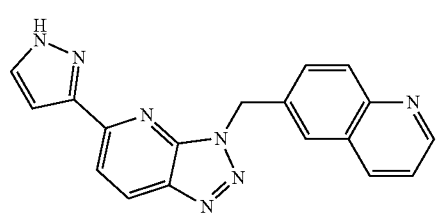 [SMILES: c1cnc2ccc(Cn3nnc4ccc(-c5cc[nH]n5)nc43)cc2c1] | 328 (M + 1)+ |
| 82 | 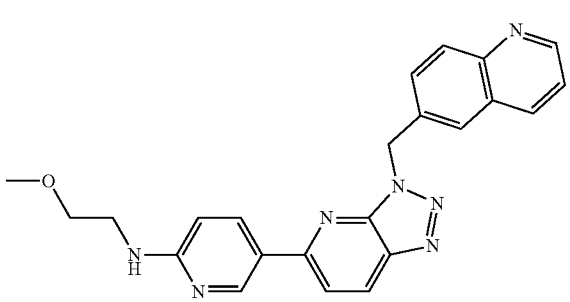 [SMILES: COCCNc1ccc(-c2ccc3nnn(Cc4ccc5ncccc5c4)c3n2)cn1] | 412 (M + 1)+ |

TABLE 2-continued
| Compound | Structure | LC/MS data |
|---|---|---|
| 83 | 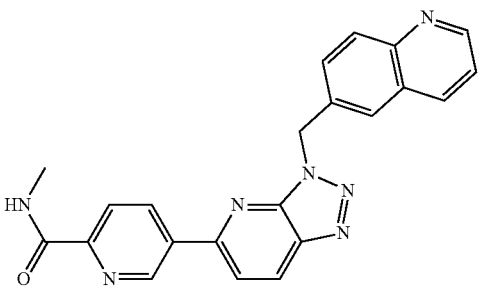 [SMILES: CNC(=O)c1ccc(-c2ccc3nnn(Cc4ccc5ncccc5c4)c3n2)cn1] | 396 (M + 1)+ |
| 84 | 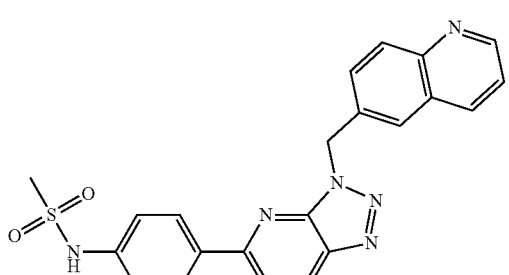 | 431 (M + 1)+ |
| 85 | 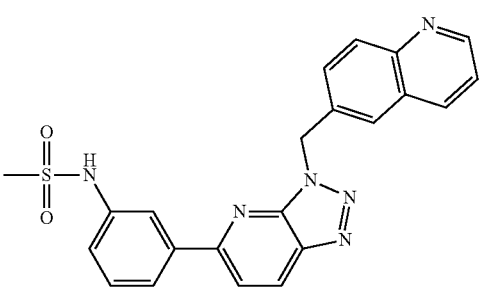 [SMILES: CS(=O)(=O)Nc1cccc(-c2ccc3nnn(Cc4ccc5ncccc5c4)c3n2)c1] | 431 (M + 1)+ |
| 86 | 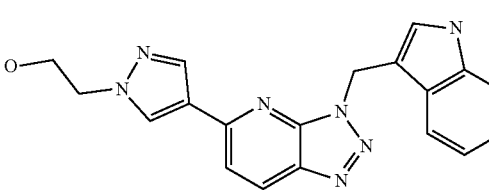 | 361 (M + 1)+ |
| 87 | 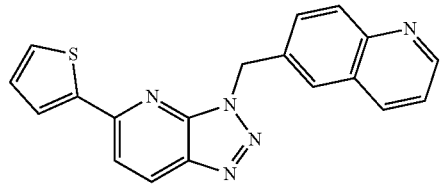 [SMILES: c1csc(-c2ccc3nnn(Cc4ccc5ncccc5c4)c3n2)c1] | 344 (M + 1)+ |
| 88 | 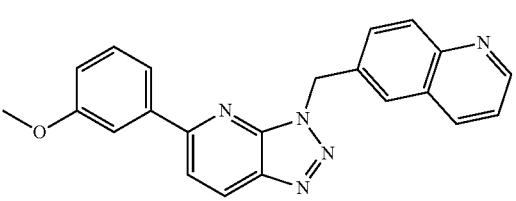 [SMILES: COc1cccc(-c2ccc3nnn(Cc4ccc5ncccc5c4)c3n2)c1] | 368 (M + 1)+ |

TABLE 2-continued

| Compound | Structure | LC/MS data |
|---|---|---|
| 90 | 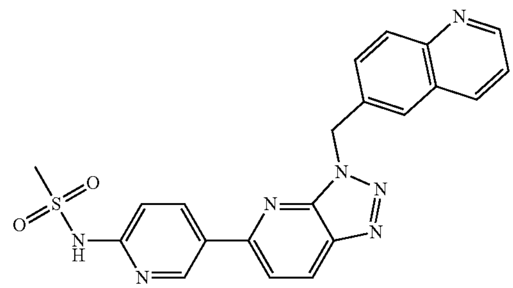 [SMILES: CS(=O)(=O)Nc1ccc(-c2ccc3nnn(Cc4ccc5ncccc5c4)c3n2)cn1] | 432 (M + 1)+ |
| 91 | 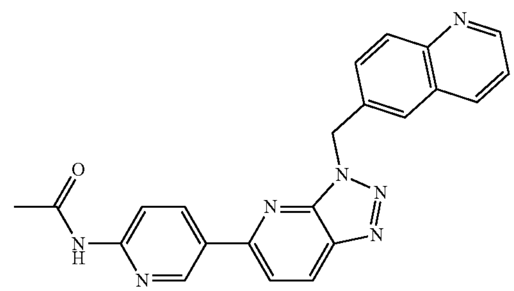 [SMILES: CC(=O)Nc1ccc(-c2ccc3nnn(Cc4ccc5ncccc5c4)c3n2)cn1] | 396 (M + 1)+ |
| 92 | 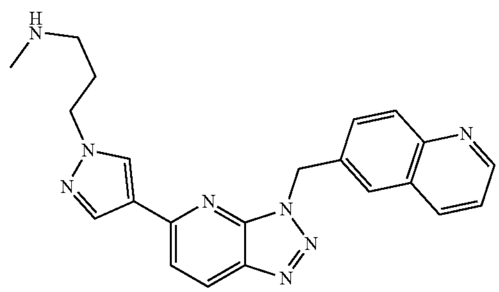 [SMILES: CNCCCn1cc(-c2ccc3nnn(Cc4ccc5ncccc5c4)c3n2)cn1] | 399 (M + 1)+ |
| 93 | 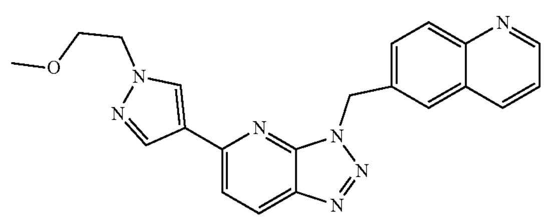 [SMILES: COCCn1cc(-c2ccc3nnn(Cc4ccc5ncccc5c4)c3n2)cn1] | 386 (M + 1)+ |
| 94[1] | 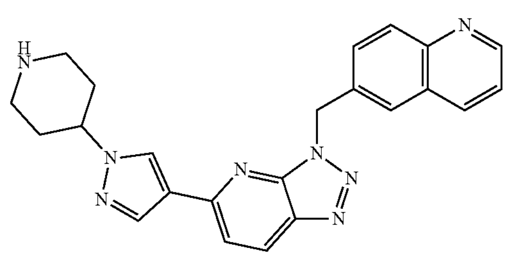 [SMILES: c1cnc2ccc(Cn3nnc4ccc(-c5cnn(C6CCNCC6)c5)nc43)cc2c1] | 411 (M + 1)+ |
| 95 | 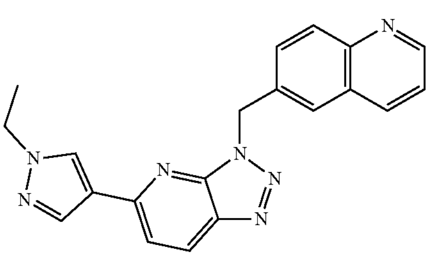 [SMILES: CCn1cc(-c2ccc3nnn(Cc4ccc5ncccc5c4)c3n2)cn1] | 356 (M + 1)+ |

TABLE 2-continued

| Compound | Structure | LC/MS data |
|---|---|---|
| 96 | 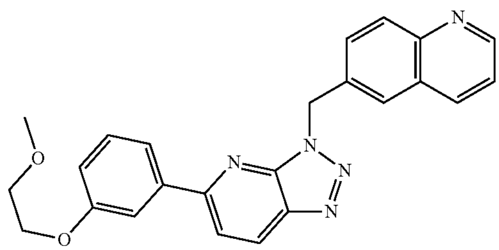 [SMILES: COCCOc1cccc(-c2ccc3nnn(Cc4ccc5ncccc5c4)c3n2)c1] | 412 (M + 1)+ |
| 97 | 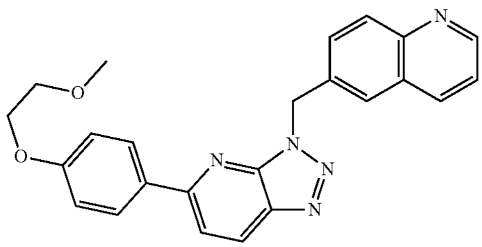 [SMILES: COCCOc1ccc(-c2ccc3nnn(Cc4ccc5ncccc5c4)c3n2)cc1] | 412 (M + 1)+ |
| 98[2] | 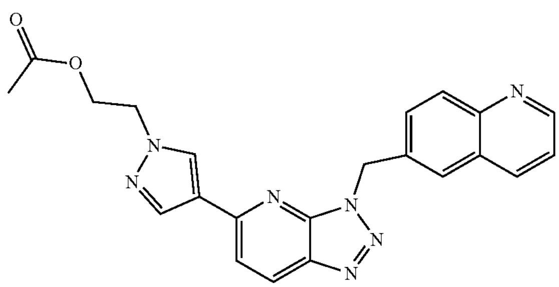 [SMILES: CC(=O)OCCn1cc(-c2ccc3nnn(Cc4ccc5ncccc5c4)c3n2)cn1] | 414 (M + 1)+ |
| 99 | 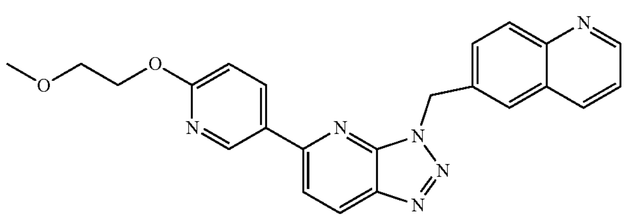 [SMILES: COCCOc1ccc(-c2ccc3nnn(Cc4ccc5ncccc5c4)c3n2)cn1] | 413 (M + 1)+ |
| 100 | 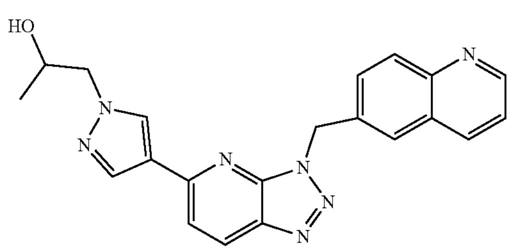 [SMILES: CC(O)Cn1cc(-c2ccc3nnn(Cc4ccc5ncccc5c4)c3n2)cn1] | 386 (M + 1)+ |
| 101[3] | 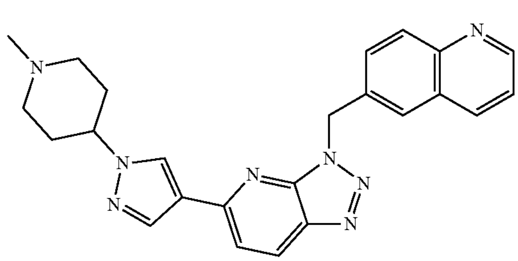 [SMILES: CN1CCC(n2cc(-c3ccc4nnn(Cc5ccc6ncccc6c5)c4n3)cn2)CC1] | 425 (M + 1)+ |

TABLE 2-continued
| Compound | Structure | LC/MS data |
|---|---|---|
| 102 | 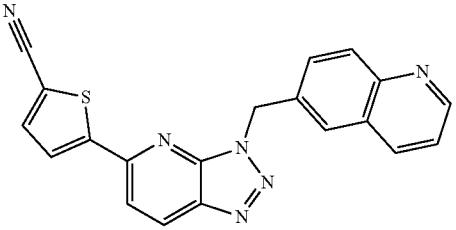 [SMILES: N#Cc1ccc(-c2ccc3nnn(Cc4ccc5ncccc5c4)c3n2)s1] | 369 (M + 1)+ |
| 103 | 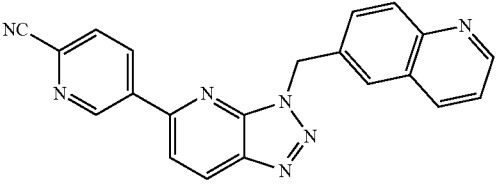 [SMILES: N#Cc1ccc(-c2ccc3nnn(Cc4ccc5ncccc5c4)c3n2)cn1] | 364 (M + 1)+ |
| 104[4] | 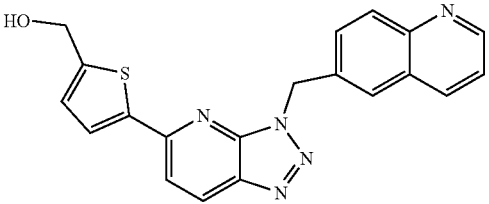 [SMILES: OCc1ccc(-c2ccc3nnn(Cc4ccc5ncccc5c4)c3n2)s1] | 374 (M + 1)+ |
| 105[5] | 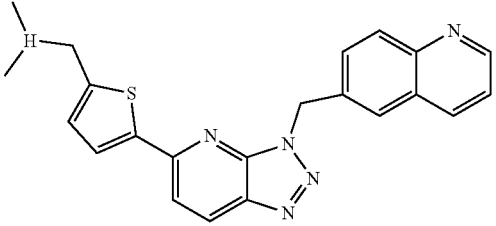 | 401 (M + 1)+ |
| 106 | 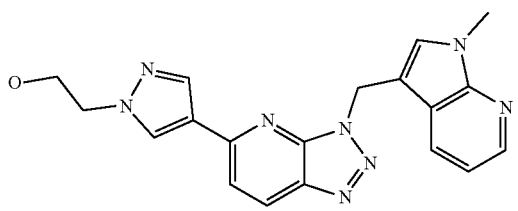 [SMILES: Cn1cc(Cn2nnc3ccc(-c4cnn(CCO)c4)nc32)c2cccnc21] | 375 (M + 1)+ |
| 107 | 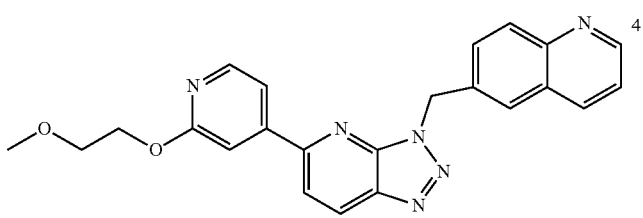 | 413 (M + 1)+ |
| 108[6] | 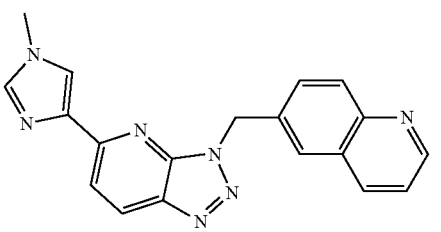 [SMILES: Cn1cnc(-c2ccc3nnn(Cc4ccc5ncccc5c4)c3n2)c1] | 342 (M + 1)+ |

TABLE 2-continued

| Compound | Structure | LC/MS data |
|---|---|---|
| 109[6] | 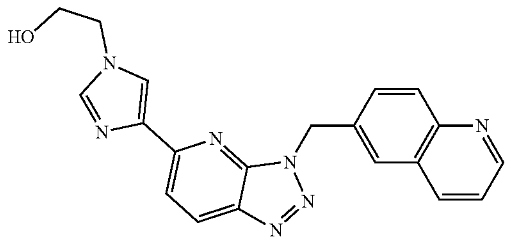 [SMILES: OCCn1cnc(-c2ccc3nnn(Cc4ccc5ncccc5c4)c3n2)c1] | 372 (M + 1)+ |
| 110 | 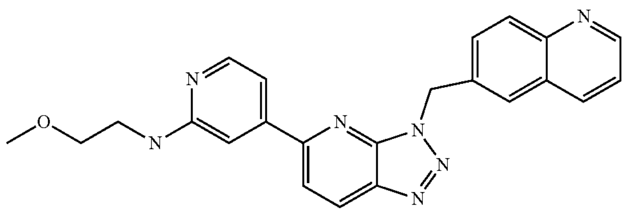 [SMILES: COCCNc1cc(-c2ccc3nnn(Cc4ccc5ncccc5c4)c3n2)ccn1] | 412 (M + 1)+ |
| 111 | 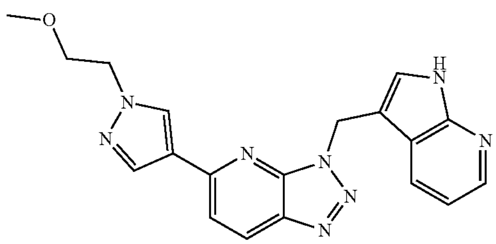 [SMILES: COCCn1cc(-c2ccc3nnn(Cc4c[nH]c5ncccc45)c3n2)cn1] | 375 (M + 1)+ |
| 112 | 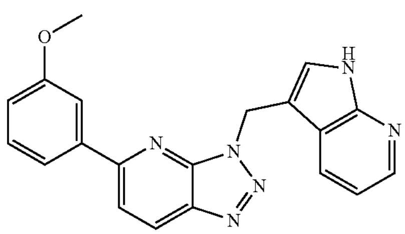 [SMILES: COc1cccc(-c2ccc3nnn(Cc4c[nH]c5ncccc45)c3n2)c1] | 357 (M + 1)+ |
| 113 | 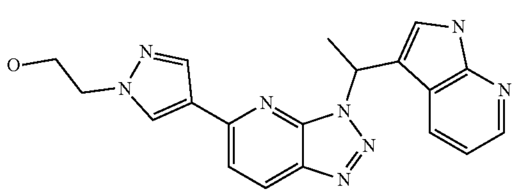 [SMILES: CC(c1c[nH]c2ncccc12)n1nnc2ccc(-c3cnn(CCO)c3)nc21] | 375 (M + 1)+ |
| 114 | 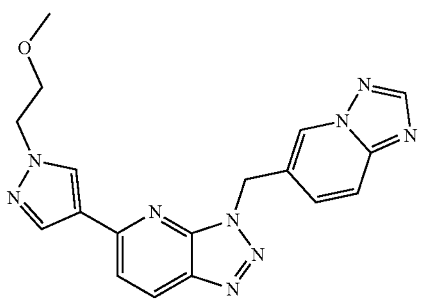 [SMILES: COCCn1cc(-c2ccc3nnn(Cc4ccc5ncnn5c4)c3n2)cn1] | 376 (M + 1)+ |

TABLE 2-continued

| Compound | Structure | LC/MS data |
|---|---|---|
| 115 | 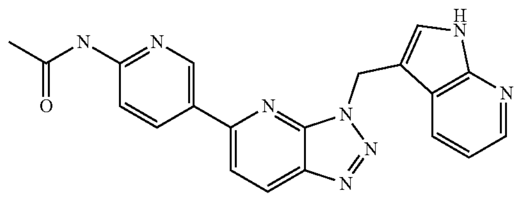 [SMILES: CC(=O)Nc1ccc(-c2ccc3nnn(Cc4c[nH]c5ncccc45)c3n2)cn1] | 385 (M + 1)+ |
| 116[7] | 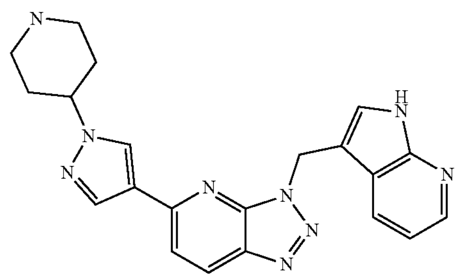 [SMILES: c1cnc2[nH]cc(Cn3nnc4ccc(-c5cnn(C6CCNCC6)c5)nc43)c2c1] | 400 (M + 1)+ |
| 117 | 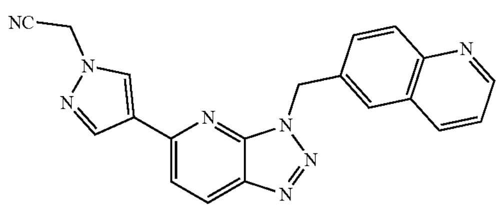 [SMILES: N#CCn1cc(-c2ccc3nnn(Cc4ccc5ncccc5c4)c3n2)cn1] | 367 (M + 1)+ |
| 118 | 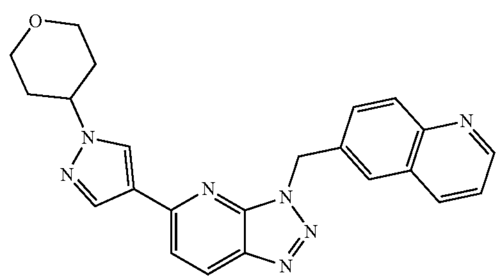 [SMILES: c1cnc2ccc(Cn3nnc4ccc(-c5cnn(C6CCOCC6)c5)nc43)cc2c1] | 412 (M + 1)+ |
| 119 | 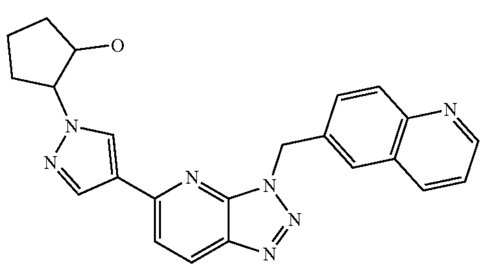 [SMILES: OC1CCCC1n1cc(-c2ccc3nnn(Cc4ccc5ncccc5c4)c3n2)cn1] | 412 (M + 1)+ |
| 120 | 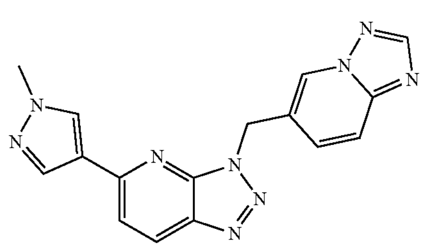 [SMILES: Cn1cc(-c2ccc3nnn(Cc4ccc5ncnn5c4)c3n2)cn1] | 332 (M + 1)+ |

TABLE 2-continued

| Compound | Structure | LC/MS data |
|---|---|---|
| 121 | 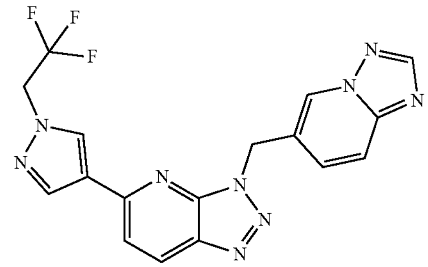 [SMILES: FC(F)(F)Cn1cc(-c2ccc3nnn(Cc4ccc5ncnn5c4)c3n2)cn1] | 400 (M + 1)+ |
| 122 | 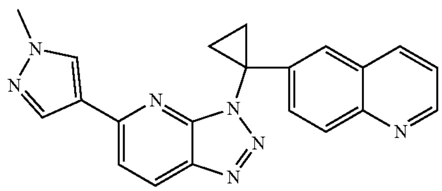 [SMILES: Cn1cc(-c2ccc3nnn(C4(c5ccc6ncccc6c5)CC4)c3n2)cn1] | 368 (M + 1)+ |
| 123 | 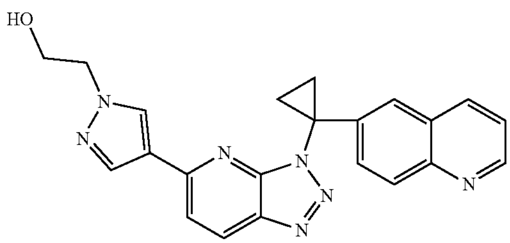 [SMILES: OCCn1cc(-c2ccc3nnn(C4(c5ccc6ncccc6c5)CC4)c3n2)cn1] | 398 (M + 1)+ |
| 124 | 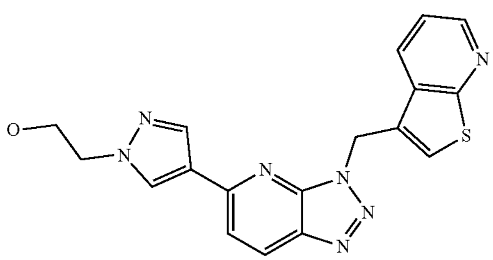 [SMILES: OCCn1cc(-c2ccc3nnn(Cc4csc5ncccc45)c3n2)cn1] | 378 (M + 1)+ |
| 125 | 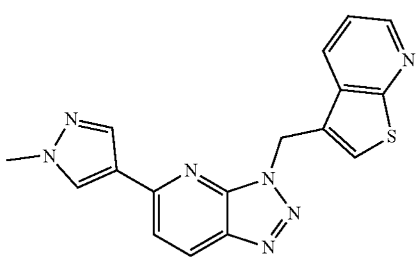 [SMILES: Cn1cc(-c2ccc3nnn(Cc4csc5ncccc45)c3n2)cn1] | 348 (M + 1)+ |
| 126 | 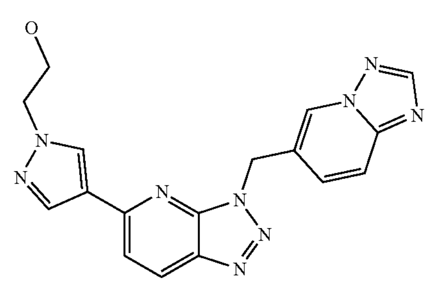 [SMILES: OCCn1cc(-c2ccc3nnn(Cc4ccc5ncnn5c4)c3n2)cn1] | 362 (M + 1)+ |

TABLE 2-continued
| Compound | Structure | LC/MS data |
|---|---|---|
| 127 | 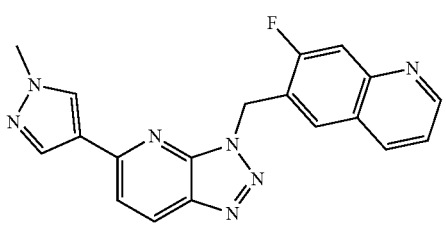 [SMILES: Cn1cc(-c2ccc3nnn(Cc4cc5cccnc5cc4F)c3n2)cn1] | 360 (M + 1)+ |
| 128 | 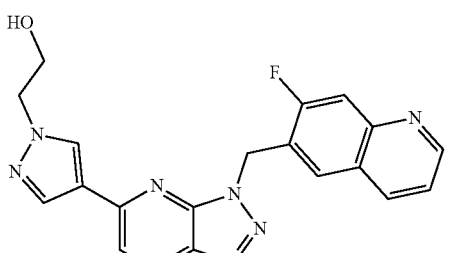 | 390 (M + 1)+ |
| 129 | 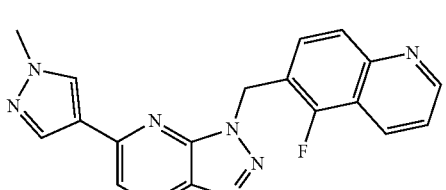 | 360 (M + 1)+ |
| 130 | 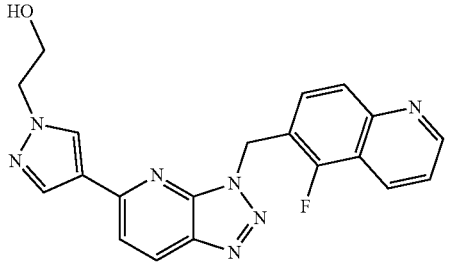 [SMILES: OCCn1cc(-c2ccc3nnn(Cc4ccc5ncccc5c4F)c3n2)cn1] | 390 (M + 1)+ |
| 131 | 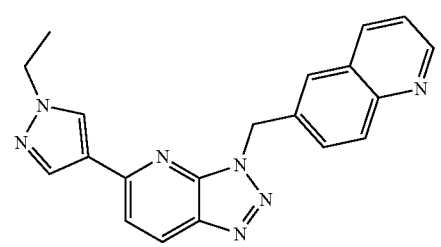 [SMILES: CCn1cc(-c2ccc3nnn(Cc4ccc5ncccc5c4)c3n2)cn1] | 356 (M + 1)+ |
| 132 | 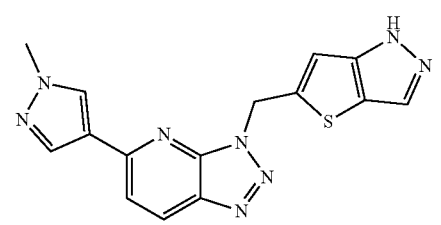 [SMILES: Cn1cc(-c2ccc3nnn(Cc4cc5[nH]ncc5s4)c3n2)cn1] | 337 (M + 1)+ |

TABLE 2-continued

| Compound | Structure | LC/MS data |
|---|---|---|
| 133 | 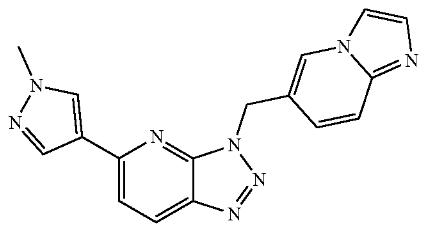 [SMILES: Cn1cc(-c2ccc3nnn(Cc4ccc5nccn5c4)c3n2)cn1] | 331 (M + 1)+ |
| 134 | 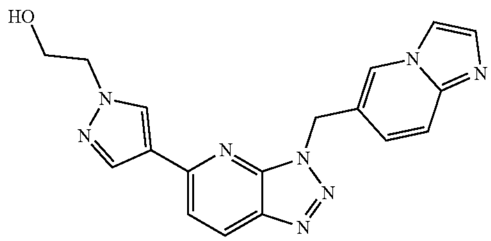 [SMILES: OCCn1cc(-c2ccc3nnn(Cc4ccc5nccn5c4)c3n2)cn1] | 361 (M + 1)+ |
| 135 | 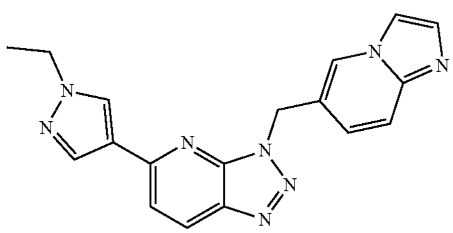 [SMILES: CCn1cc(-c2ccc3nnn(Cc4ccc5nccn5c4)c3n2)cn1] | 345 (M + 1)+ |
| 136 | 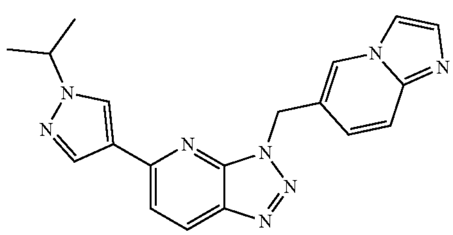 [SMILES: CC(C)n1cc(-c2ccc3nnn(Cc4ccc5nccn5c4)c3n2)cn1] | 359 (M + 1)+ |
| 137 | 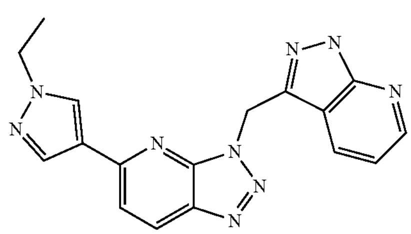 [SMILES: CCn1cc(-c2ccc3nnn(Cc4n[nH]c5ncccc45)c3n2)cn1] | 346 (M + 1)+ |
| 138[g] | | 362 (M + 1)+ |

TABLE 2-continued

| Compound | Structure | LC/MS data |
| --- | --- | --- |
| 139 | 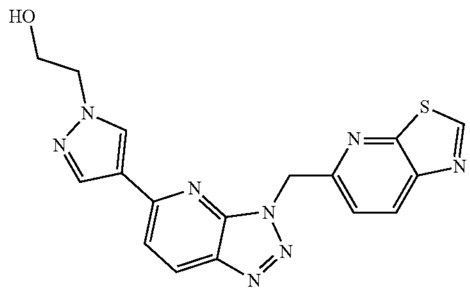 [SMILES: OCCn1cc(-c2ccc3nnn(Cc4ccc5ncsc5n4)c3n2)cn1] | 379 (M + 1)+ |
| 140 | 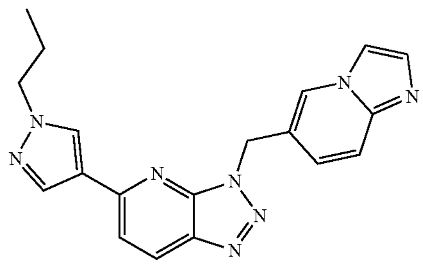 [SMILES: CCCn1cc(-c2ccc3nnn(Cc4ccc5nccn5c4)c3n2)cn1] | 359 (M + 1)+ |
| 141 | 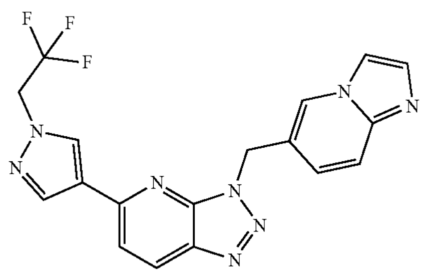 [SMILES: FC(F)(F)Cn1cc(-c2ccc3nnn(Cc4ccc5nccn5c4)c3n2)cn1] | 399 (M + 1)+ |
| 142 | 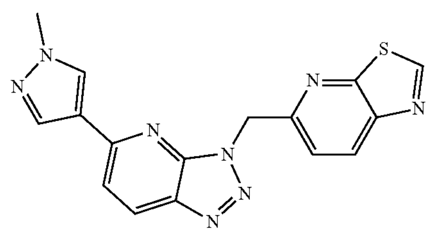 [SMILES: Cn1cc(-c2ccc3nnn(Cc4ccc5ncsc5n4)c3n2)cn1] | 349 (M + 1)+ |
| 143 | 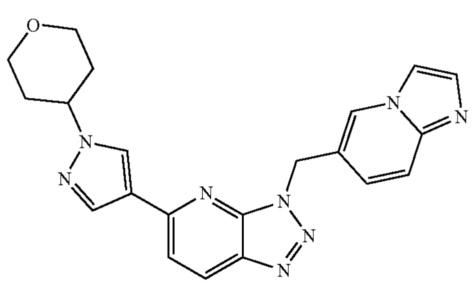 [SMILES: c1cn2cc(Cn3nnc4ccc(-c5cnn(C6CCOCC6)c5)nc43)ccc2n1] | 401 (M + 1)+ |
| 144 | 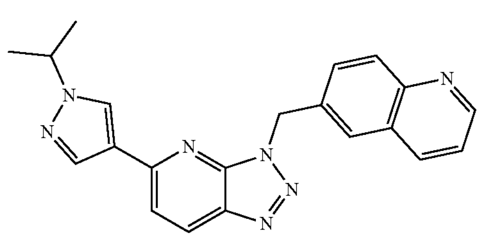 [SMILES: CC(C)n1cc(-c2ccc3nnn(Cc4ccc5ncccc5c4)c3n2)cn1] | 370 (M + 1)+ |

TABLE 2-continued

| Compound | Structure | LC/MS data |
|---|---|---|
| 145 | 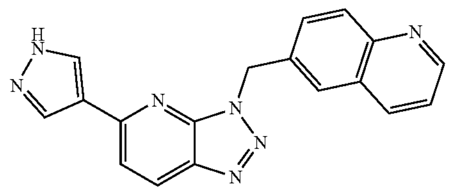 [SMILES: c1cnc2ccc(Cn3nnc4ccc(-c5cn[nH]c5)nc43)cc2c1] | 328 (M + 1)+ |
| 146 | 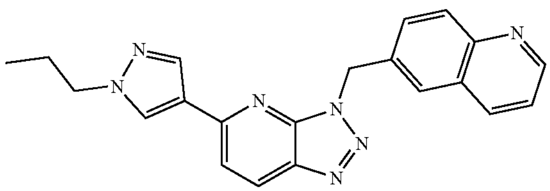 [SMILES: CCCn1cc(-c2ccc3nnn(Cc4ccc5ncccc5c4)c3n2)cn1] | 370 (M + 1)+ |
| 147 | 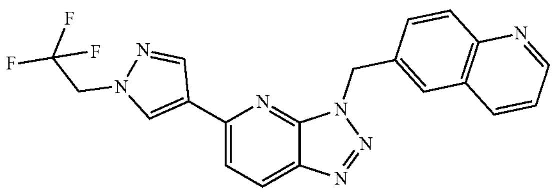 [SMILES: FC(F)(F)Cn1cc(-c2ccc3nnn(Cc4ccc5ncccc5c4)c3n2)cn1] | 410 (M + 1)+ |
| 148[9] | 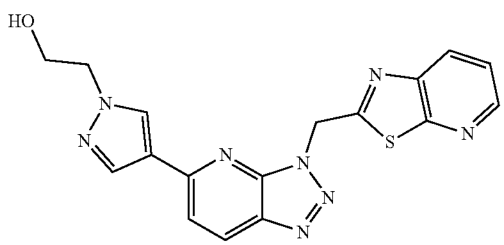 [SMILES: OCCn1cc(-c2ccc3nnn(Cc4nc5cccnc5s4)c3n2)cn1] | 379 (M + 1)+ |
| 149[9] | 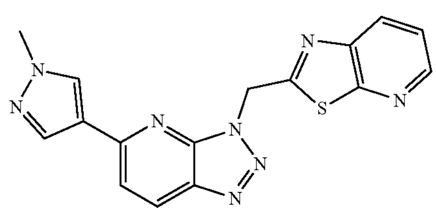 [SMILES: Cn1cc(-c2ccc3nnn(Cc4nc5cccnc5s4)c3n2)cn1] | 349 (M + 1)+ |
| 150 | 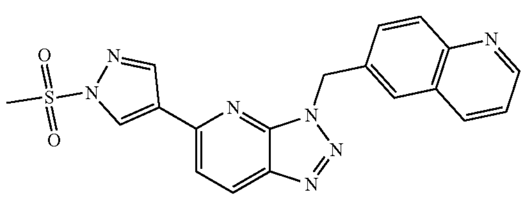 [SMILES: CS(=O)(=O)n1cc(-c2ccc3nnn(Cc4ccc5ncccc5c4)c3n2)cn1] | 406 (M + 1)+ |

TABLE 2-continued

| Compound | Structure | LC/MS data |
|---|---|---|
| 151 | 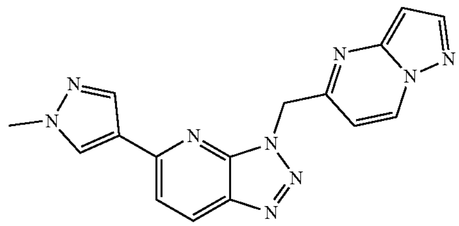 [SMILES: Cn1cc(-c2ccc3nnn(Cc4ccn5nccc5n4)c3n2)cn1] | 332 (M + 1)+ |
| 273 | 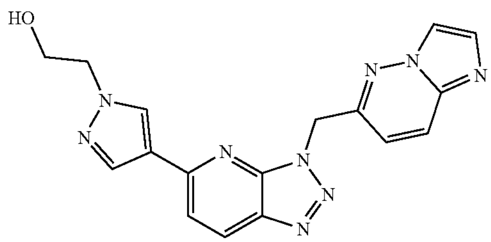 [SMILES: OCCn1cc(-c2ccc3nnn(Cc4ccc5nccn5n4)c3n2)cn1] | 362.1 (M + 1)+ |
| 291 | 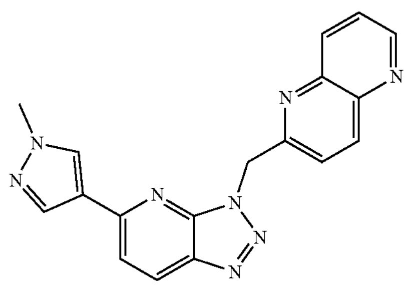 [SMILES: Cn1cc(-c2ccc3nnn(Cc4ccc5ncccc5n4)c3n2)cn1] | 343.1 (M + 1)+ |
| 292 | 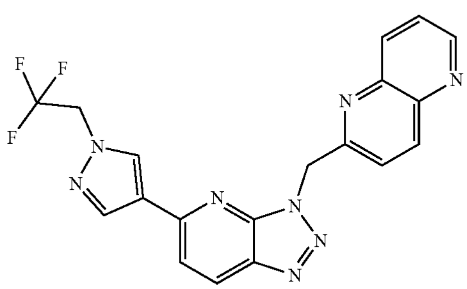 [SMILES: FC(F)(F)Cn1cc(-c2ccc3nnn(Cc4ccc5ncccc5n4)c3n2)cn1] | 411 (M + 1)+ |
| 297 | 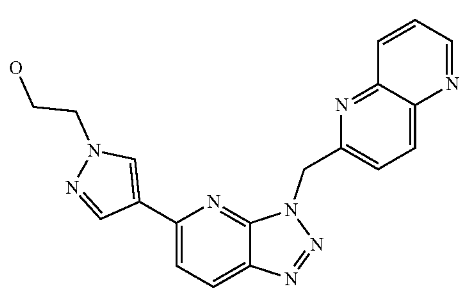 [SMILES: OCCn1cc(-c2ccc3nnn(Cc4ccc5ncccc5n4)c3n2)cn1] | 373.1 (M + 1)+ |

| Compound | Structure | LC/MS data |
|---|---|---|
| 332 | 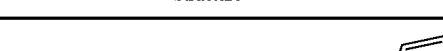 | 386 (M + 1)+ |

[1] Using the following procedure, Compound 94 was synthesized from intermediate 94-a that was prepared according to the procedures of Compound 60 using the corresponding intermediates and boronic acid or ester under appropriate conditions that will be recognized by one skilled in the art. :

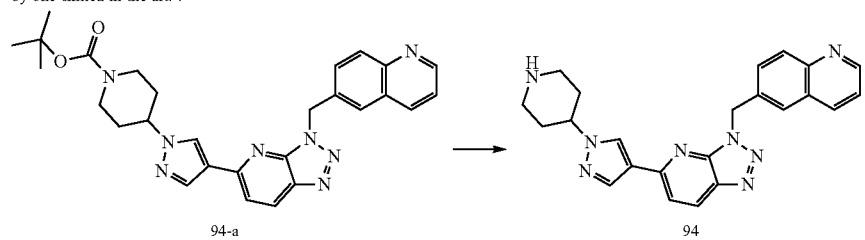

94-a → 94

A solution of 94-a (30 mg, 0.06 mmol) in TFA (2 mL) and DCM (2 mL) was stirred at room tempature overnight, then concentrated. The residue was dissolved in aqueous sodium bicarbonate solution and extracted with EtOAc. The organic layer was concentrated and purified on silica gel to afford Compound 94.

[2] Compound 98 was prepared from Compound 61 using the following procedure:

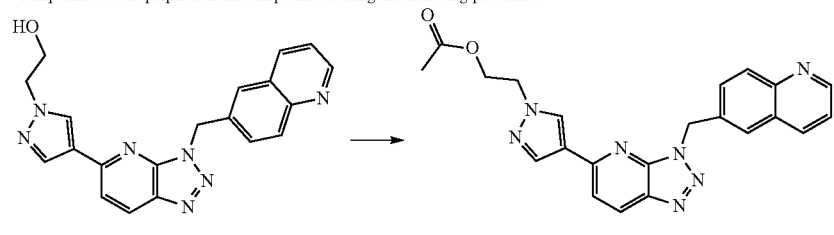

61 → 98

A solution of Compound 61 in DCM was treated with Et₃N and acetyl chloride at room temparature for 3 h. It was then treated with water and extracted with DCM (15 mL × 2). The combined organic extracts were dried, concentrated and the residue was purified on silica to afford Compound 98.

[3] Compound 101 was prepared from Compound 94 using the following procedure: To a solutoin of Compound 94 (18 mg, 0.044 mmol) in anhydrous DCM (2 mL) was added Et₃N (12.2 uL, 0.088 mmol), followed by CH₃I (2.4 uL, 0.048 mmol) at 0° C. The reaction mixture was warmed to room tempature, and stirred for over 1 h. A saturated sodium bicarbonate aqueous solution was added to the mixture. The organic layer was separated, and the aqueous layer was extracted with EtOAc. The combined extracts were dried over Na₂SO₄ and concentrated. The resulting residue was purified on silica to afford Compound 101.

[4] Compound 104 was prepared according to the procedure of Intermediates W-1 to W using Intermediate 104-a that was prepared according to the procedures of Compound 60.

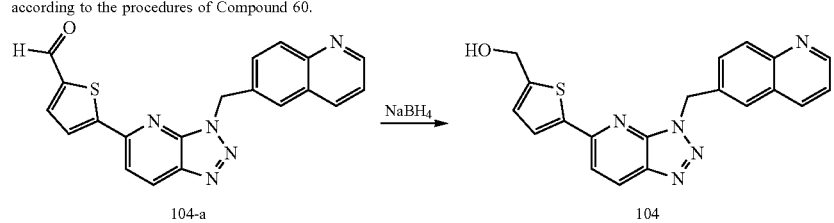

104-a → 104

[5] Compound 105 was prepared from intermediate 104-a by the following procedure

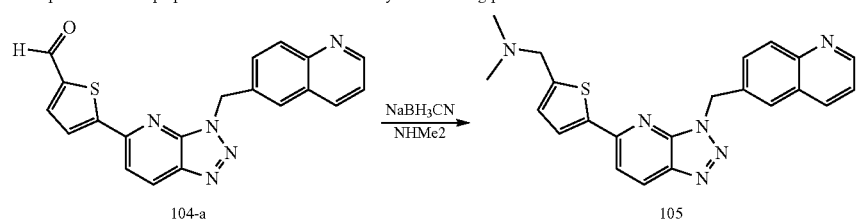

104-a → 105

A mixture of intermediate 104-a (37 mg, 0.1 mmol) and exessive amount of dimethylamine in methanol (5 mL) was stirred at room temperature for 1 h. Sodium cyano borohydride (12 mg) was added. The resulting mixture was stirred at room temperature for 16 h, then concentrated. The residue was treated with saturated aqueous sodium bicarbonate and DCM. The organic layer was separated, concentrated. The residue was purified on silica to afford Compound 105 (8 mg).

TABLE 2-continued

| Compound | Structure | LC/MS data |
|---|---|---|

[6]Under similar conditions of Compound 60, Compound 108 was prepared by using Intermediate 108-a that was prepared according to the procedure of intermediates U-3 to U

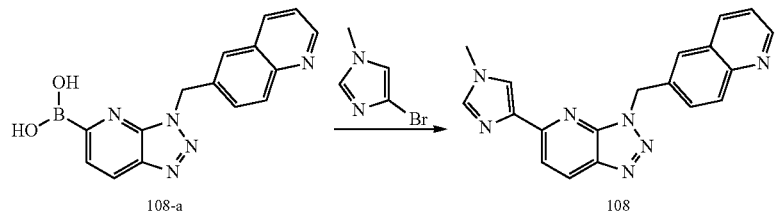

108-a          108

Compound 109 was prepared similar to Compound 108

[7]Compound 116 was prepared according to the procedures of Compound 94.

[8]P(t-Bu)$_3$HBF$_4$ and Pd$_2$(dba)$_3$ were used instead of Pd(dppf)Cl$_2$ in the procedure of Compound 138.
[9]Compounds 148 was prepared by the following route using similar conditions described for Compound 60.

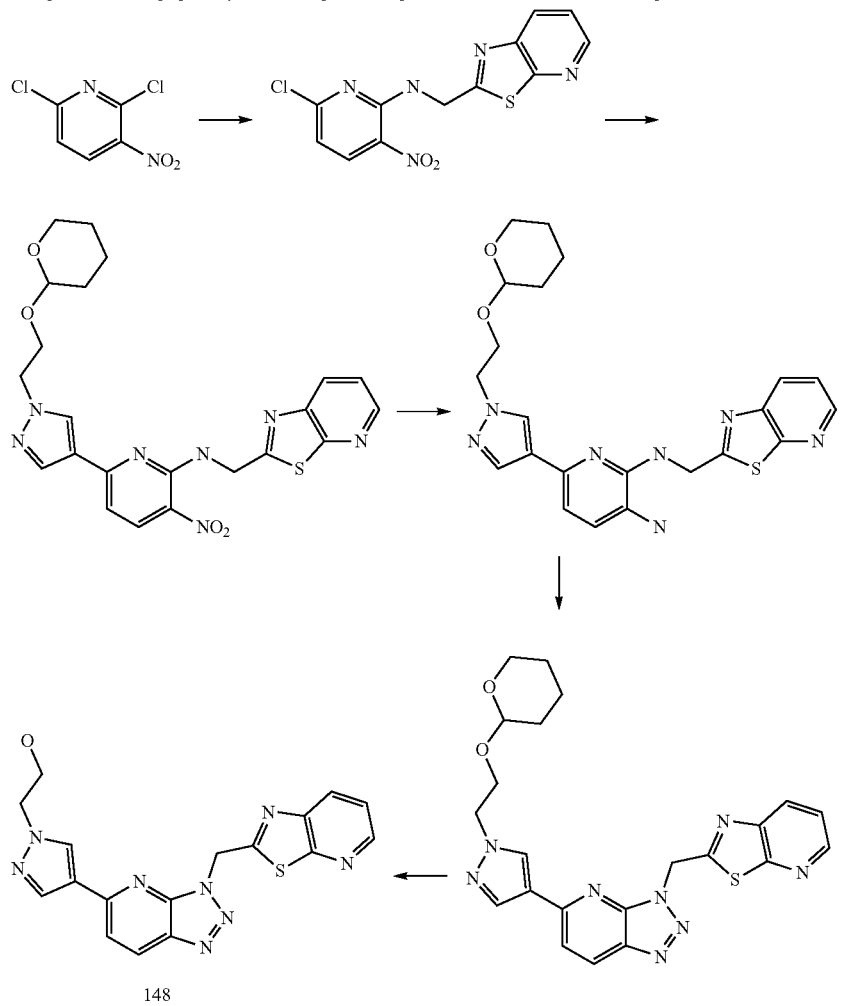

148

According to the procedure of Compound 148, Compound 149 was prepared using the corresponding intermediates and reagents under appropriate conditions that will be recognized by one skilled in the art:

135

Compound 152: N-(1-methyl-1H-pyrazol-3-yl)-1-(quinolin-6-ylmethyl)-1H-[1,2,3]triazolo-[4,5-b]pyrazin-6-amine

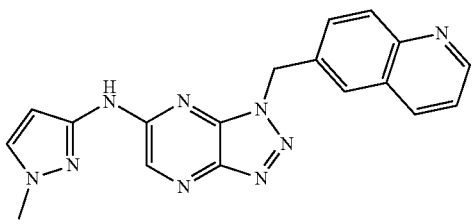 [SMILES: Cn1ccc(Nc2cnc3nnn(Cc4ccc5ncccc5c4)c3n2)n1]

To a suspension of 6-((6-bromo-1H-[1,2,3]triazolo[4,5-b]pyrazin-1-yl)methyl)quinoline (68 mg, 0.2 mmol) (prepared from quinolin-6-ylmethanamine following the procedures of Compound 1) and 1-methyl-1H-pyrazol-3-amine (20 mg, 0.22 mmol) in dioxane (5 mL) were added $Cs_2CO_3$ (72 mg, 0.22 mmol) and $H_2O$ (0.5 mL). The mixture was degassed and charged with $N_2$ three times, then $Pd_2(dba)_3$ (0.02 mmol, 18 mg) and xantphos (0.04 mmol, 23 mg) were added. The resulting mixture was stirred at 120° C. under one atmosphere of $N_2$ overnight, then concentrated. The resulting residue was purified by chromatography to afford the title compound (10 mg). MS (m/z): 358 (M+1)$^+$.

Compounds 80, 153-240

The following compounds 80, 153-240 were prepared according to the procedure of Compound 152 using the corresponding intermediates and amines under appropriate conditions that will be recognized by one skilled in the art:

TABLE 3

| Compound | Structure | LC/MS data |
| --- | --- | --- |
| 80 | 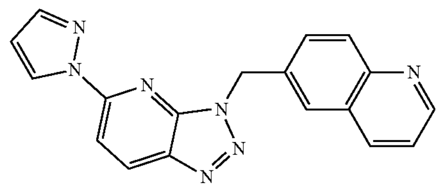 [SMILES: c1cnc2ccc(Cn3nnc4ccc(-n5cccn5)nc43)cc2c1] | 328 (M + 1)$^+$ |
| 153 | 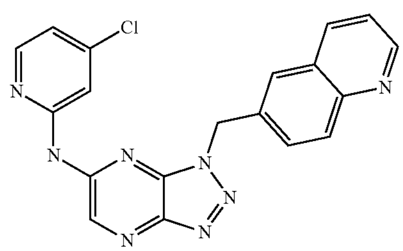 [SMILES: Clc1ccnc(Nc2cnc3nnn(Cc4ccc5ncccc5c4)c3n2)c1] | 389 (M + 1)$^+$ |
| 154[10] | | 383 (M + 1)$^+$ |
| 155 | 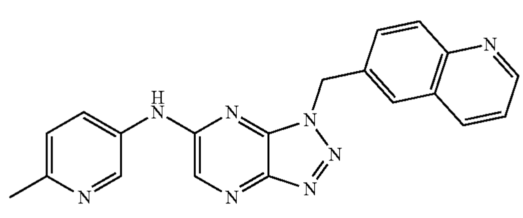 [SMILES: Cc1ccc(Nc2cnc3nnn(Cc4ccc5ncccc5c4)c3n2)cn1] | 369 (M + 1)$^+$ |
| 156 | 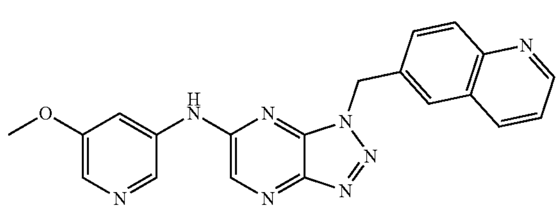 [SMILES: COc1cncc(Nc2cnc3nnn(Cc4ccc5ncccc5c4)c3n2)c1] | 385 (M + 1)$^+$ |

TABLE 3-continued

| Compound | Structure | LC/MS data |
|---|---|---|
| 157 | 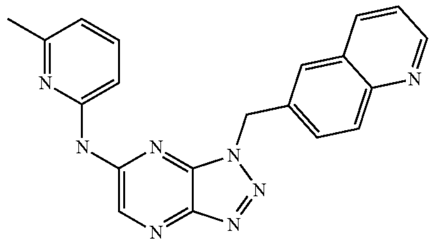 [SMILES: Cc1cccc(Nc2cnc3nnn(Cc4ccc5ncccc5c4)c3n2)n1] | 369 (M + 1)⁺ |
| 158 | 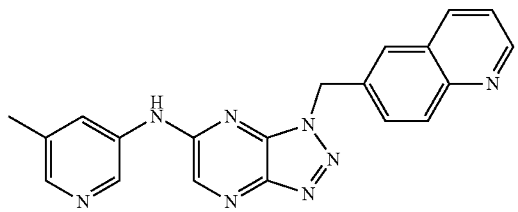 [SMILES: Cc1cncc(Nc2cnc3nnn(Cc4ccc5ncccc5c4)c3n2)c1] | 369 (M + 1)⁺ |
| 159 | 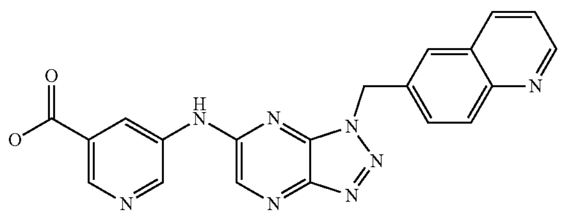 [SMILES: O=C(O)c1cncc(Nc2cnc3nnn(Cc4ccc5ncccc5c4)c3n2)c1] | 399 (M + 1)⁺ |
| 160 | 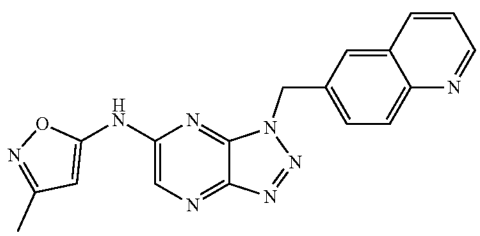 [SMILES: Cc1cc(Nc2cnc3nnn(Cc4ccc5ncccc5c4)c3n2)on1] | 359 (M + 1)⁺ |
| 161 | 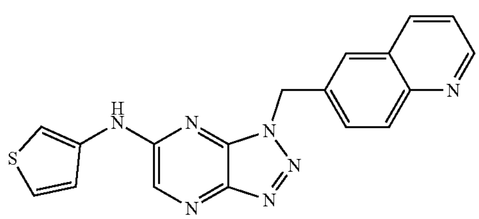 [SMILES: c1cnc2ccc(Cn3nnc4ncc(Nc5ccsc5)nc43)cc2c1] | 360 (M + 1)⁺ |
| 162 | 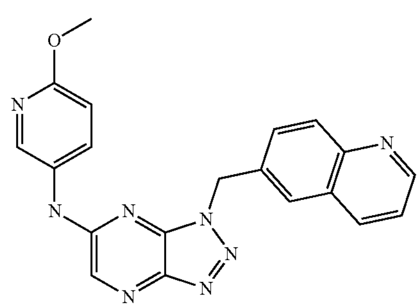 [SMILES: COc1ccc(Nc2cnc3nnn(Cc4ccc5ncccc5c4)c3n2)cn1] | 385 (M + 1)⁺ |

TABLE 3-continued

| Compound | Structure | LC/MS data |
|---|---|---|
| 163 | 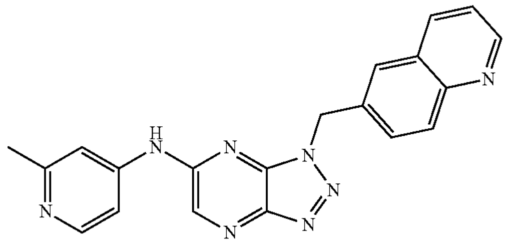 [SMILES: Cc1cc(Nc2cnc3nnn(Cc4ccc5ncccc5c4)c3n2)ccn1] | 369 (M + 1)+ |
| 164 | 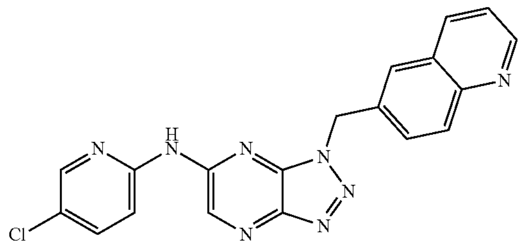 [SMILES: Clc1ccc(Nc2cnc3nnn(Cc4ccc5ncccc5c4)c3n2)nc1] | 389 (M + 1)+ |
| 165 | 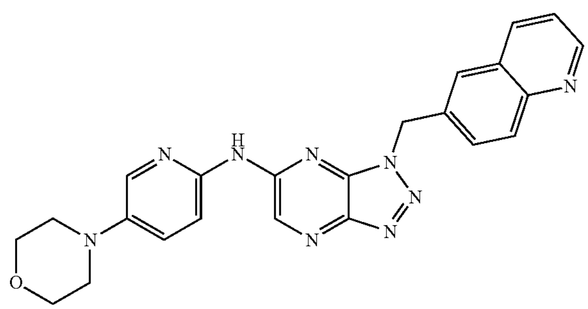 [SMILES: c1cnc2ccc(Cn3nnc4ncc(Nc5ccc(N6CCOCC6)cn5)nc43)cc2c1] | 440 (M + 1)+ |
| 166 | 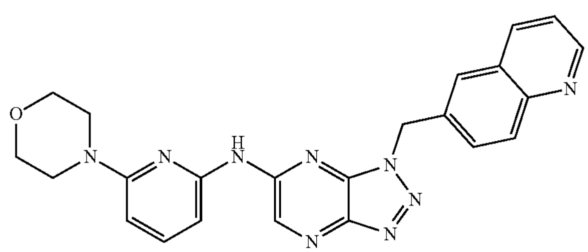 [SMILES: c1cc(Nc2cnc3nnn(Cc4ccc5ncccc5c4)c3n2)nc(N2CCOCC2)c1] | 440 (M + 1)+ |
| 167 | 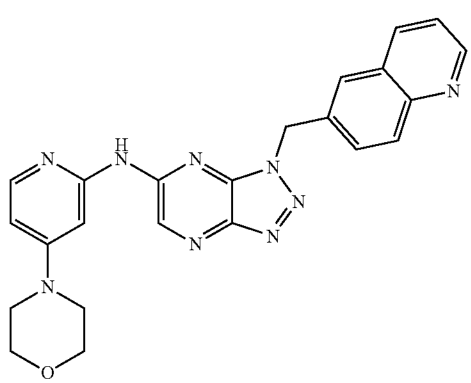 [SMILES: c1cnc2ccc(Cn3nnc4ncc(Nc5cc(N6CCOCC6)ccn5)nc43)cc2c1] | 440 (M + 1)+ |

TABLE 3-continued

| Compound | Structure | LC/MS data |
|---|---|---|
| 168 | 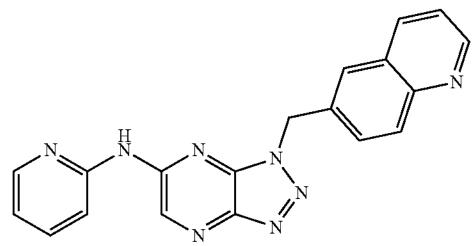 [SMILES: c1ccc(Nc2cnc3nnn(Cc4ccc5ncccc5c4)c3n2)nc1] | 355 (M + 1)+ |
| 169 | 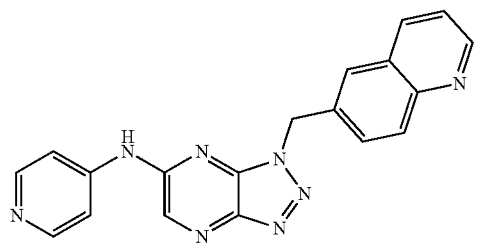 | 355 (M + 1)+ |
| 170 | 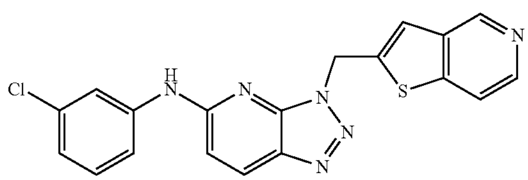 [SMILES: Clc1cccc(Nc2ccc3nnn(Cc4cc5cnccc5s4)c3n2)c1] | 393 (M + 1)+ |
| 171 | 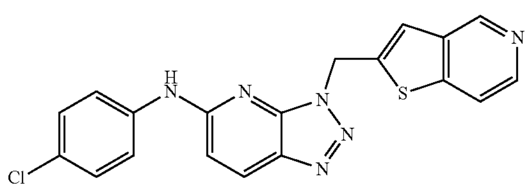 [SMILES: Clc1ccc(Nc2ccc3nnn(Cc4cc5cnccc5s4)c3n2)cc1] | 393 (M + 1)+ |
| 172 | 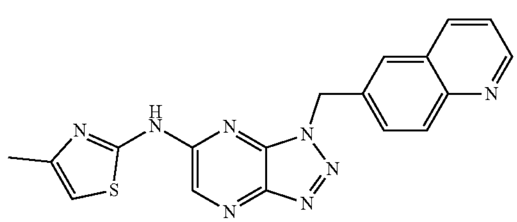 [SMILES: Cc1csc(Nc2cnc3nnn(Cc4ccc5ncccc5c4)c3n2)n1] | 375 (M + 1)+ |
| 173 | 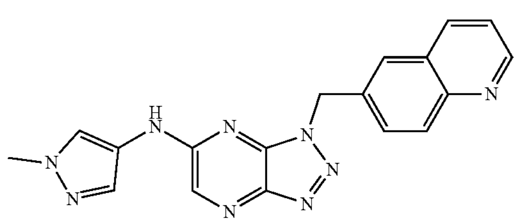 [SMILES: Cn1cc(Nc2cnc3nnn(Cc4ccc5ncccc5c4)c3n2)cn1] | 358 (M + 1)+ |

TABLE 3-continued

| Compound | Structure | LC/MS data |
|---|---|---|
| 174 | 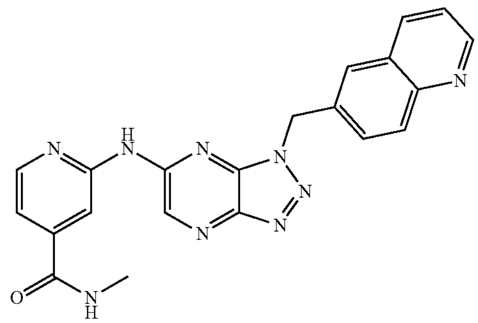 [SMILES: CNC(=O)c1ccnc(Nc2cnc3nnn(Cc4ccc5ncccc5c4)c3n2)c1] | 412 (M + 1)+ |
| 175 | 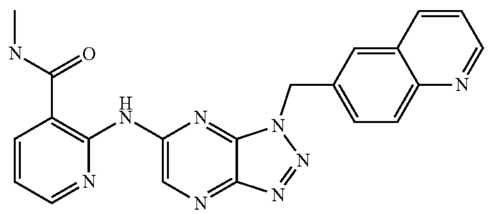 [SMILES: CNC(=O)c1cccnc1Nc1cnc2nnn(Cc3ccc4ncccc4c3)c2n1] | 412 (M + 1)+ |
| 176 | 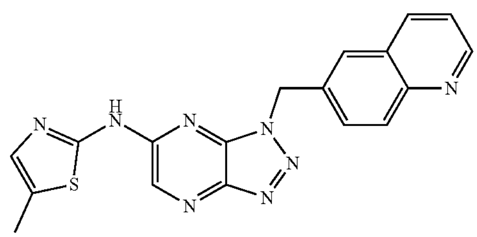 [SMILES: Cc1cnc(Nc2cnc3nnn(Cc4ccc5ncccc5c4)c3n2)s1] | 375 (M + 1)+ |
| 177[10] | 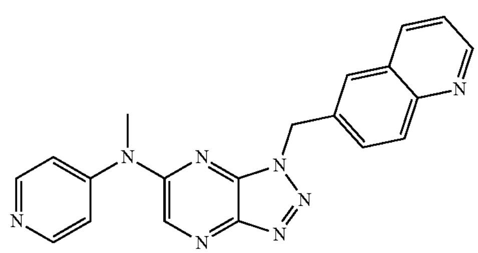 [SMILES: CN(c1ccncc1)c1cnc2nnn(Cc3ccc4ncccc4c3)c2n1] | 369 (M + 1)+ |
| 178 | 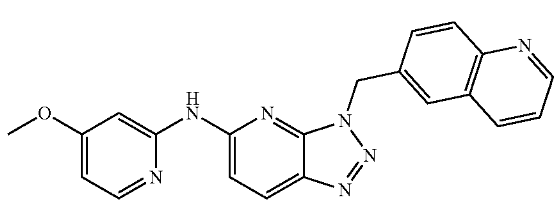 [SMILES: COc1ccnc(Nc2ccc3nnn(Cc4ccc5ncccc5c4)c3n2)c1] | 384 (M + 1)+ |
| 179 | 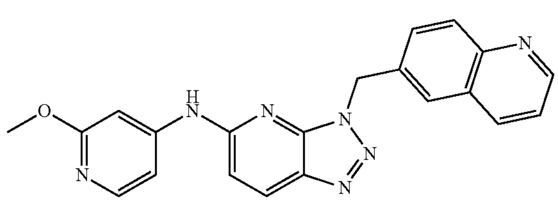 [SMILES: COc1cc(Nc2ccc3nnn(Cc4ccc5ncccc5c4)c3n2)ccn1] | 384 (M + 1)+ |

TABLE 3-continued

| Compound | Structure | LC/MS data |
|---|---|---|
| 180 | 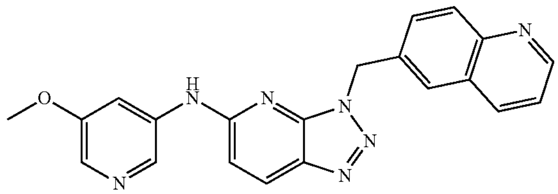 | 384 (M + 1)+ |
| 181 | 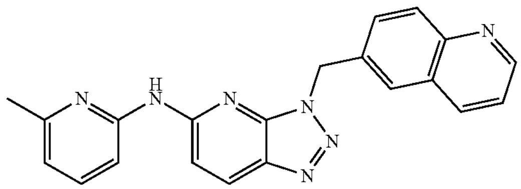 [SMILES: Cc1cccc(Nc2ccc3nnn(Cc4ccc5ncccc5c4)c3n2)n1] | 368 (M + 1)+ |
| 182 | 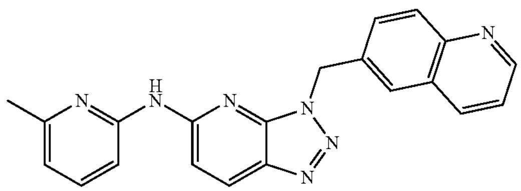 [SMILES: Cc1cccc(Nc2ccc3nnn(Cc4ccc5ncccc5c4)c3n2)n1] | 368 (M + 1)+ |
| 183 | 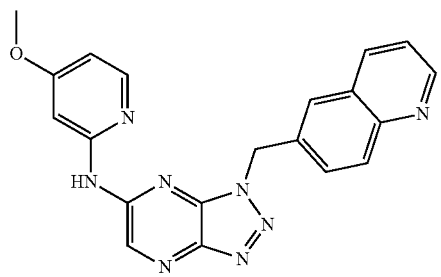 [SMILES: COc1ccnc(Nc2cnc3nnn(Cc4ccc5ncccc5c4)c3n2)c1] | 385 (M + 1)+ |
| 185 | 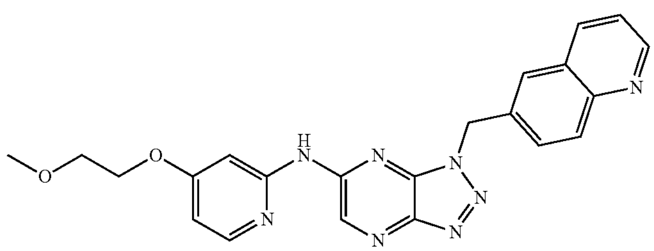 [SMILES: COCCOc1ccnc(Nc2cnc3nnn(Cc4ccc5ncccc5c4)c3n2)c1] | 429 (M + 1)+ |
| 186 | 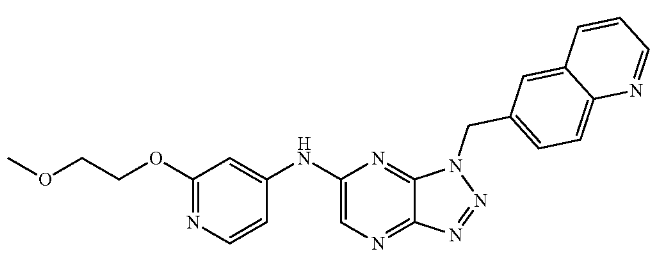 [SMILES: COCCOc1cc(Nc2cnc3nnn(Cc4ccc5ncccc5c4)c3n2)ccn1] | 429 (M + 1)+ |
| 187 | 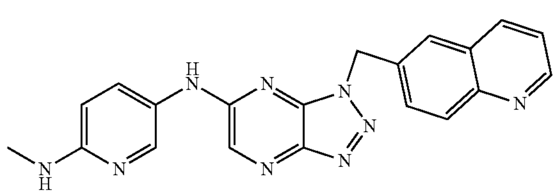 [SMILES: CNc1ccc(Nc2cnc3nnn(Cc4ccc5ncccc5c4)c3n2)cn1] | 384 (M + 1)+ |

TABLE 3-continued

| Compound | Structure | LC/MS data |
| --- | --- | --- |
| 188 | 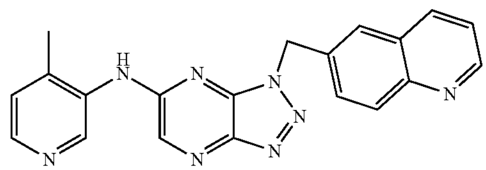 [SMILES: Cc1ccncc1Nc1cnc2nnn(Cc3ccc4ncccc4c3)c2n1] | 369 (M + 1)+ |
| 189 | 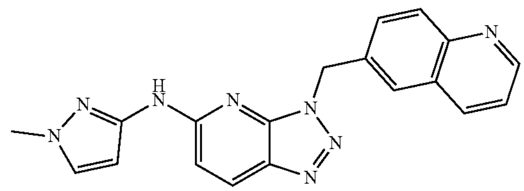 [SMILES: Cn1ccc(Nc2ccc3nnn(Cc4ccc5ncccc5c4)c3n2)n1] | 357 (M + 1)+ |
| 190 | 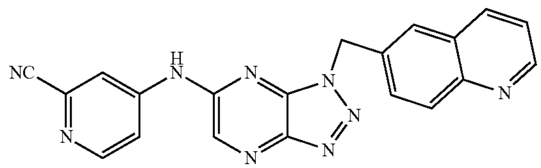 [SMILES: N#Cc1cc(Nc2cnc3nnn(Cc4ccc5ncccc5c4)c3n2)ccn1] | 380 (M + 1)+ |
| 191 | 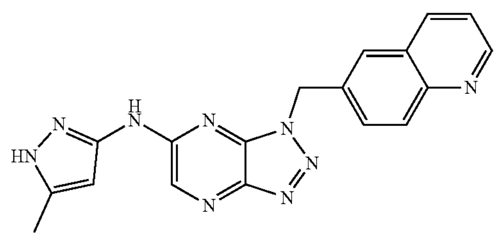 [SMILES: Cc1cc(Nc2cnc3nnn(Cc4ccc5ncccc5c4)c3n2)n[nH]1] | 358 (M + 1)+ |
| 192 | 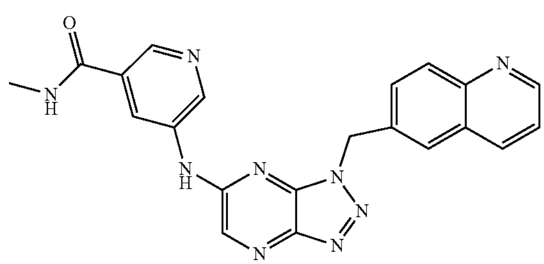 [SMILES: CNC(=O)c1cncc(Nc2cnc3nnn(Cc4ccc5ncccc5c4)c3n2)c1] | 412 (M + 1)+ |
| 193 | 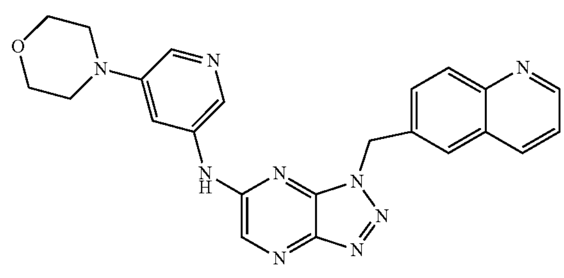 [SMILES: c1cnc2ccc(Cn3nnc4ncc(Nc5cncc(N6CCOCC6)c5)nc43)cc2c1] | 440 (M + 1)+ |
| 194 | 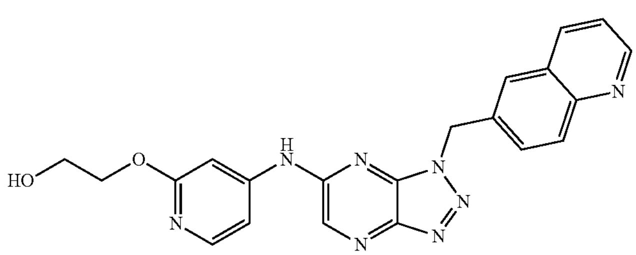 [SMILES: OCCOc1cc(Nc2cnc3nnn(Cc4ccc5ncccc5c4)c3n2)ccn1] | 415 (M + 1)+ |

TABLE 3-continued

| Compound | Structure | LC/MS data |
| --- | --- | --- |
| 195 | 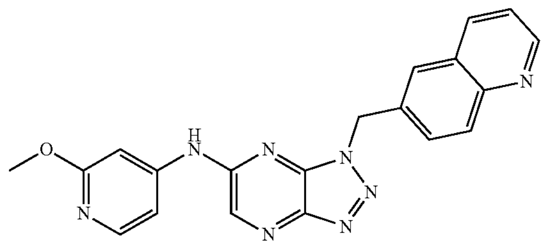 [SMILES: COc1cc(Nc2cnc3nnn(Cc4ccc5ncccc5c4)c3n2)ccn1] | 385 (M + 1)+ |
| 196 | 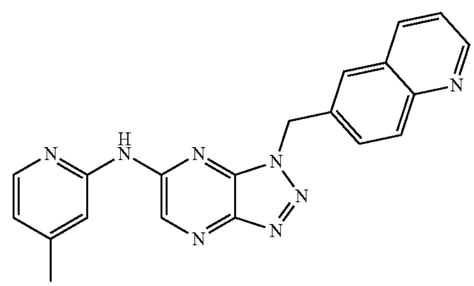 [SMILES: Cc1ccnc(Nc2cnc3nnn(Cc4ccc5ncccc5c4)c3n2)c1] | 369 (M + 1)+ |
| 197 | 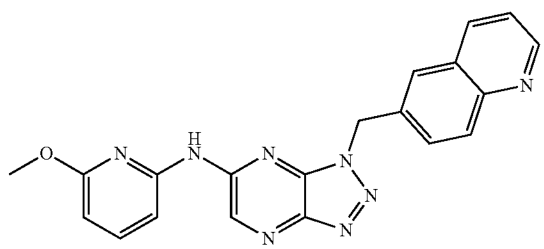 [SMILES: COc1cccc(Nc2cnc3nnn(Cc4ccc5ncccc5c4)c3n2)n1] | 385 (M + 1)+ |
| 198 | 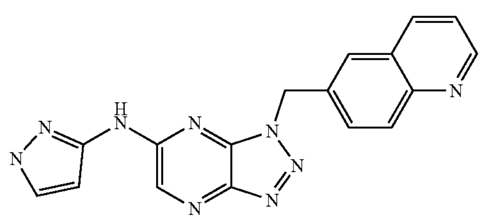 [SMILES: c1cnc2ccc(Cn3nnc4ncc(Nc5cc[nH]n5)nc43)cc2c1] | 344 (M + 1)+ |
| 199 | 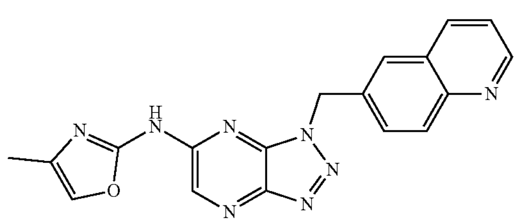 | 359 (M + 1)+ |
| 200 | 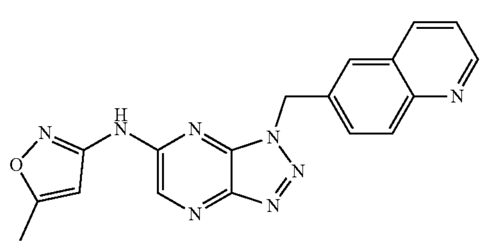 [SMILES: Cc1cc(Nc2cnc3nnn(Cc4ccc5ncccc5c4)c3n2)no1] | 359 (M + 1)+ |

TABLE 3-continued

| Compound | Structure | LC/MS data |
|---|---|---|
| 201 | 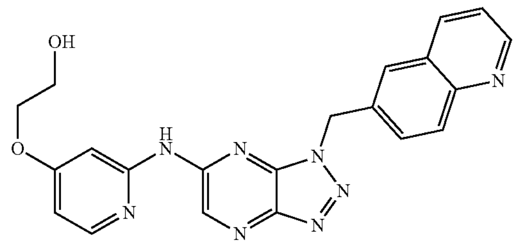 [SMILES: OCCOc1ccnc(Nc2cnc3nnn(Cc4ccc5ncccc5c4)c3n2)c1] | 415 (M + 1)+ |
| 202 | 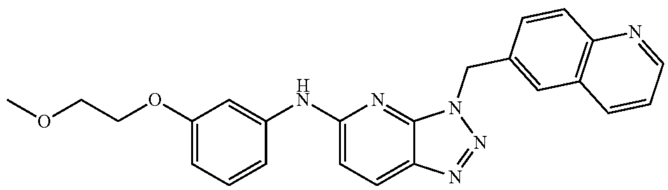 [SMILES: COCCOc1cccc(Nc2ccc3nnn(Cc4ccc5ncccc5c4)c3n2)c1] | 427 (M + 1)+ |
| 203 | 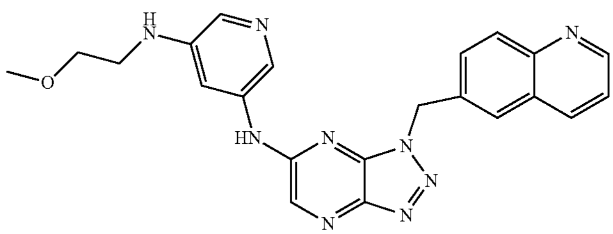 [SMILES: COCCNc1cncc(Nc2cnc3nnn(Cc4ccc5ncccc5c4)c3n2)c1] | 428 (M + 1)+ |
| 204 | 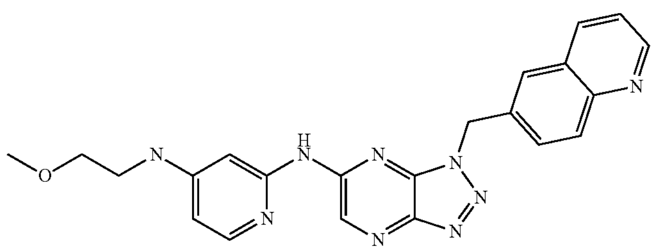 [SMILES: COCCNc1ccnc(Nc2cnc3nnn(Cc4ccc5ncccc5c4)c3n2)c1] | 428 (M + 1)+ |
| 205 | 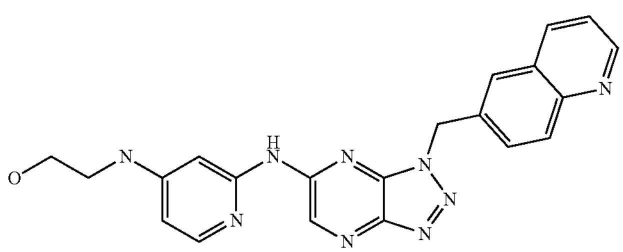 [SMILES: OCCNc1ccnc(Nc2cnc3nnn(Cc4ccc5ncccc5c4)c3n2)c1] | 414 (M + 1)+ |
| 206 | 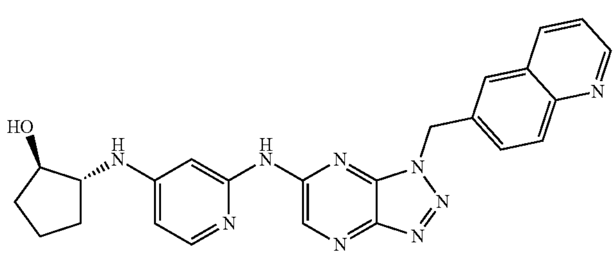 [SMILES: O[C@@H]1CCC[C@H]1Nc1ccnc(Nc2cnc3nnn(Cc4ccc5ncccc5c4)c3n2)c1] | 454 (M + 1)+ |

TABLE 3-continued

| Compound | Structure | LC/MS data |
|---|---|---|
| 207 | 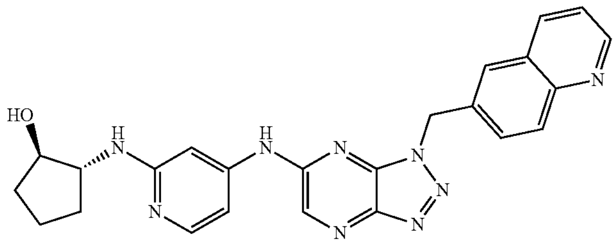 [SMILES: O[C@@H]1CCC[C@H]1Nc1cc(Nc2cnc3nnn(Cc4ccc5ncccc5c4)c3n2)ccn1] | 454 (M + 1)+ |
| 208 | 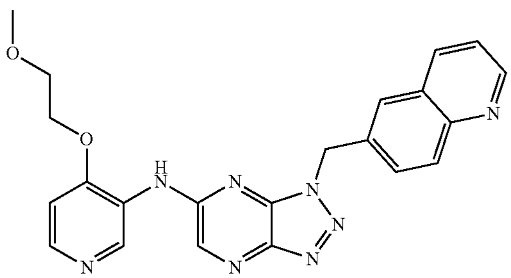 [SMILES: COCCOc1ccncc1Nc1cnc2nnn(Cc3ccc4ncccc4c3)c2n1] | 429 (M + 1)+ |
| 209 | 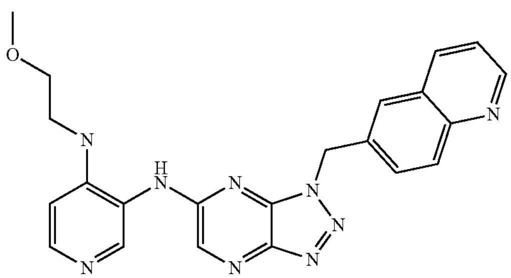 [SMILES: COCCNc1ccncc1Nc1cnc2nnn(Cc3ccc4ncccc4c3)c2n1] | 428 (M + 1)+ |
| 210 | 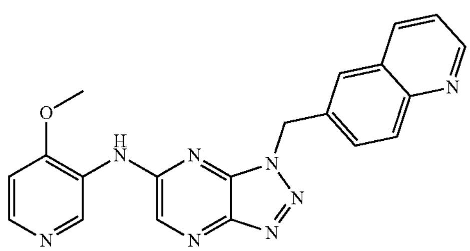 [SMILES: COc1ccncc1Nc1cnc2nnn(Cc3ccc4ncccc4c3)c2n1] | 385 (M + 1)+ |
| 211 | 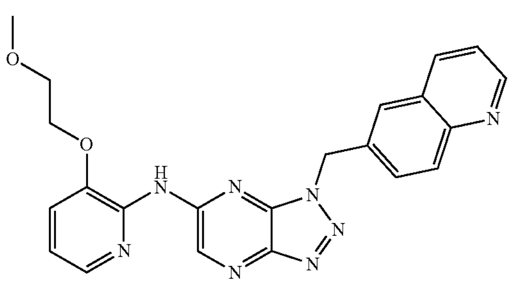 [SMILES: COCCOc1cccnc1Nc1cnc2nnn(Cc3ccc4ncccc4c3)c2n1] | 429 (M + 1)+ |
| 212 | 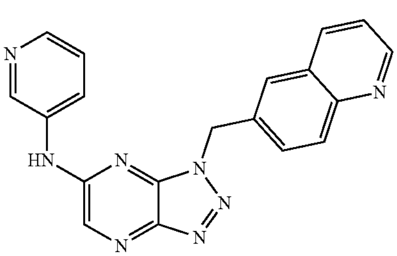 [SMILES: c1cncc(Nc2cnc3nnn(Cc4ccc5ncccc5c4)c3n2)c1] | 355 (M + 1)+ |

TABLE 3-continued

| Compound | Structure | LC/MS data |
|---|---|---|
| 213 | 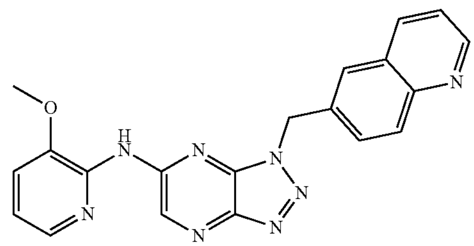 [SMILES: COc1cccnc1Nc1cnc2nnn(Cc3ccc4ncccc4c3)c2n1] | 385 (M + 1)+ |
| 214 | 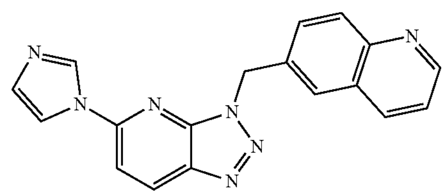 [SMILES: c1cnc2ccc(Cn3nnc4ccc(-n5ccnc5)nc43)cc2c1] | 328 (M + 1)+ |
| 215 | 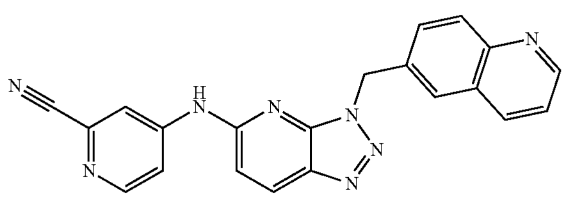 [SMILES: N#Cc1cc(Nc2ccc3nnn(Cc4ccc5ncccc5c4)c3n2)ccn1] | 379 (M + 1)+ |
| 216 | 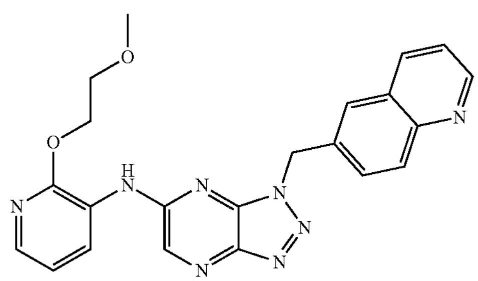 [SMILES: COCCOc1ncccc1Nc1cnc2nnn(Cc3ccc4ncccc4c3)c2n1] | 429 (M + 1)+ |
| 217 | Chiral | 441 (M + 1)+ |
| 218 | Chiral | 441 (M + 1)+ |

TABLE 3-continued
| Compound | Structure | LC/MS data |
|---|---|---|
| 219 | 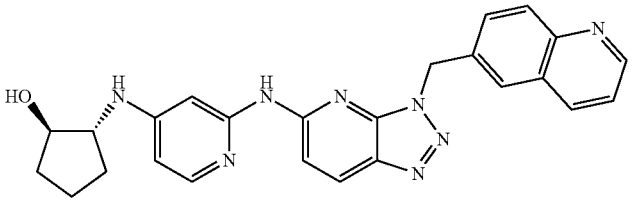 [SMILES: O[C@@H]1CCC[C@H]1Nc1ccnc(Nc2ccc3nnn(Cc4ccc5ncccc5c4)c3n2)c1] | 453 (M + 1)+ |
| 220 | 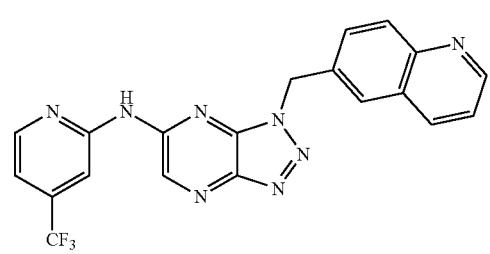 [SMILES: FC(F)(F)c1ccnc(Nc2cnc3nnn(Cc4ccc5ncccc5c4)c3n2)c1] | 423 (M + 1)+ |
| 221 | 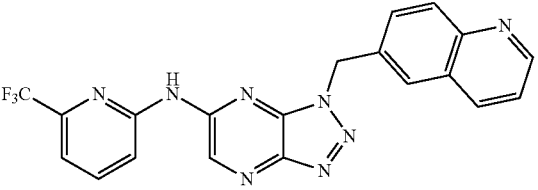 [SMILES: FC(F)(F)c1cccc(Nc2cnc3nnn(Cc4ccc5ncccc5c4)c3n2)n1] | 423 (M + 1)+ |
| 222 | 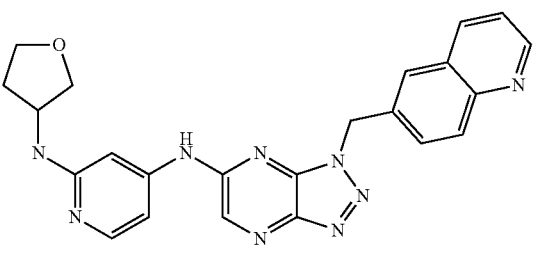 [SMILES: c1cnc2ccc(Cn3nnc4ncc(Nc5ccnc(NC6CCOC6)c5)nc43)cc2c1] | 440 (M + 1)+ |
| 223 | 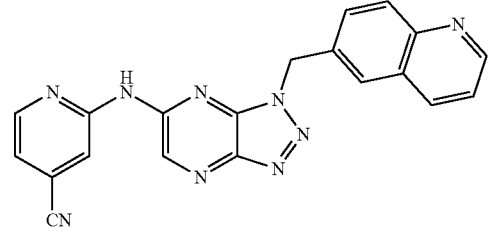 [SMILES: N#Cc1ccnc(Nc2cnc3nnn(Cc4ccc5ncccc5c4)c3n2)c1] | 380 (M + 1)+ |
| 224 | 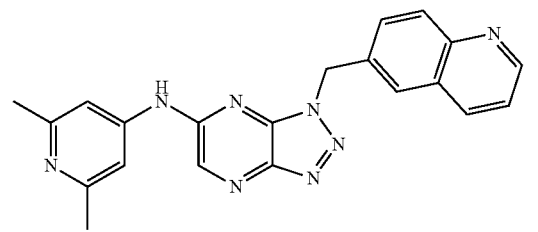 [SMILES: Cc1cc(Nc2cnc3nnn(Cc4ccc5ncccc5c4)c3n2)cc(C)n1] | 383 (M + 1)+ |

TABLE 3-continued

| Compound | Structure | LC/MS data |
| --- | --- | --- |
| 225 | 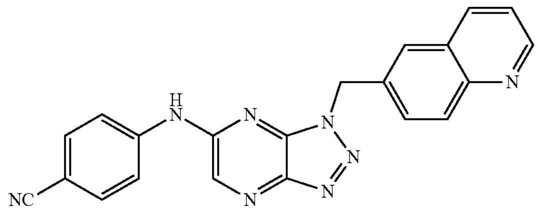 [SMILES: N#Cc1ccc(Nc2cnc3nnn(Cc4ccc5ncccc5c4)c3n2)cc1] | 379 (M)+ |
| 226 | 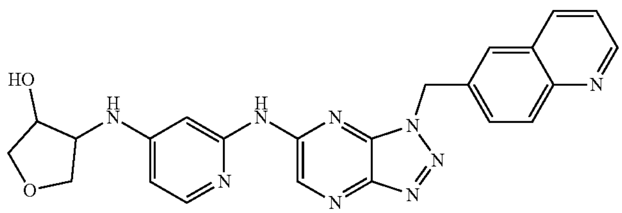 [SMILES: OC1COCC1Nc1ccnc(Nc2cnc3nnn(Cc4ccc5ncccc5c4)c3n2)c1] | 455 (M + 1)+ |
| 227 | 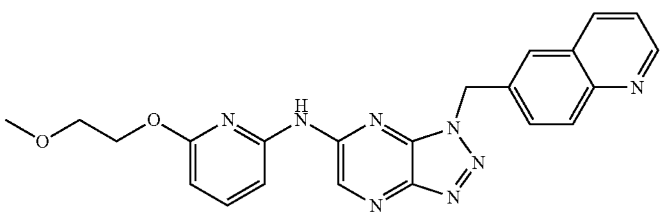 [SMILES: COCCOc1cccc(Nc2cnc3nnn(Cc4ccc5ncccc5c4)c3n2)n1] | 428 (M)+ |
| 228 | 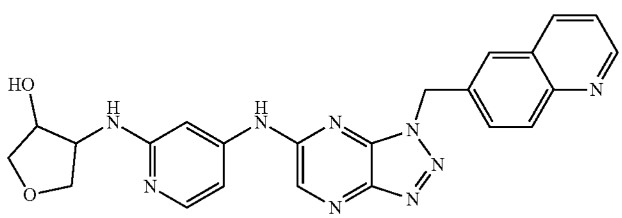 [SMILES: OC1COCC1Nc1cc(Nc2cnc3nnn(Cc4ccc5ncccc5c4)c3n2)ccn1] | 456 (M + 1)+ |
| 229 | 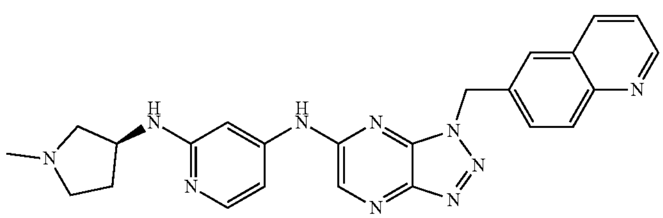 [SMILES: CN1CC[C@H](Nc2cc(Nc3cnc4nnn(Cc5ccc6ncccc6c5)c4n3)ccn2)C1] | 453 (M + 1)+ |
| 230 | 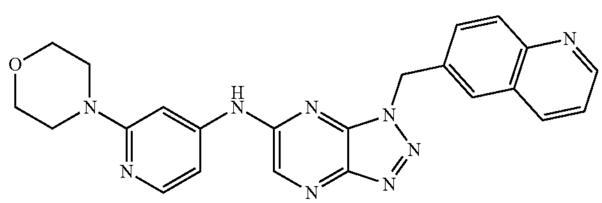 [SMILES: c1cnc2ccc(Cn3nnc4ncc(Nc5ccnc(N6CCOCC6)c5)nc43)cc2c1] | 440 (M + 1)+ |
| 231 | 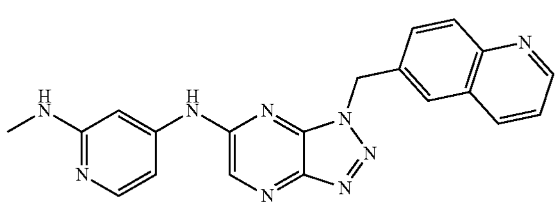 [SMILES: CNc1cc(Nc2cnc3nnn(Cc4ccc5ncccc5c4)c3n2)ccn1] | 384 (M + 1)+ |

TABLE 3-continued

| Compound | Structure | LC/MS data |
| --- | --- | --- |
| 232 | 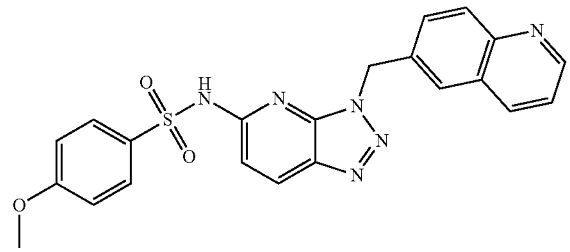 [SMILES: COc1ccc(S(=O)(=O)Nc2ccc3nnn(Cc4ccc5ncccc5c4)c3n2)cc1] | 447 (M + 1)+ |
| 233 | 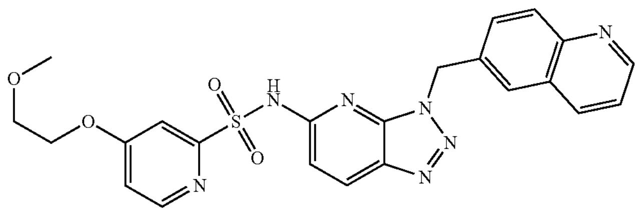 [SMILES: COCCOc1ccnc(S(=O)(=O)Nc2ccc3nnn(Cc4ccc5ncccc5c4)c3n2)c1] | 427 (M)+ |
| 234 | 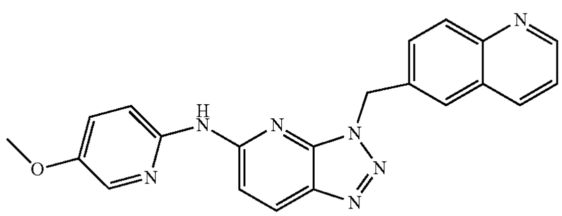 [SMILES: COc1ccc(Nc2ccc3nnn(Cc4ccc5ncccc5c4)c3n2)nc1] | 384 (M + 1)+ |
| 235 | 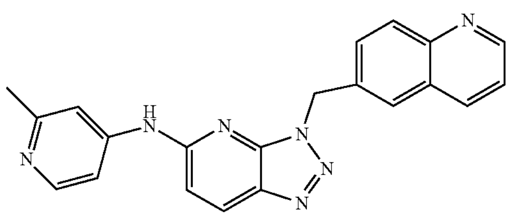 [SMILES: Cc1cc(Nc2ccc3nnn(Cc4ccc5ncccc5c4)c3n2)ccn1] | 368 (M + 1)+ |
| 236 | 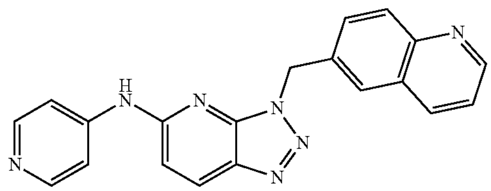 [SMILES: c1cnc2ccc(Cn3nnc4ccc(Nc5ccncc5)nc43)cc2c1] | 354 (M + 1)+ |
| 237 | 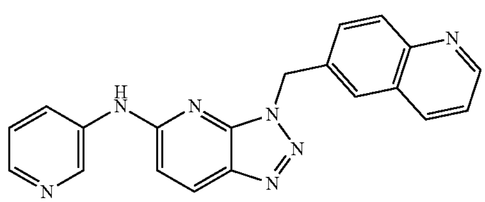 [SMILES: c1cncc(Nc2ccc3nnn(Cc4ccc5ncccc5c4)c3n2)c1] | 354 (M + 1)+ |
| 238 | 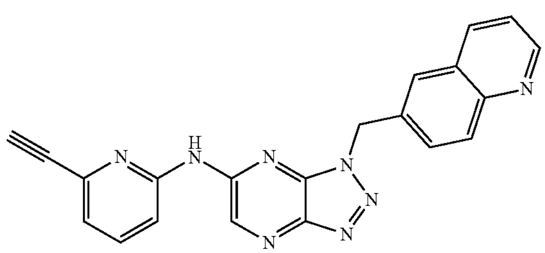 [SMILES: C#Cc1cccc(Nc2cnc3nnn(Cc4ccc5ncccc5c4)c3n2)n1] | 379 (M + 1)+ |

TABLE 3-continued

| Compound | Structure | | LC/MS data |
|---|---|---|---|
| 239[10] | 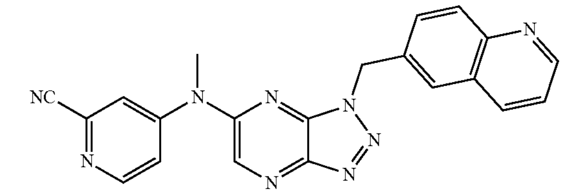 [SMILES: CN(c1ccnc(C#N)c1)c1cnc2nnn(Cc3ccc4ncccc4c3)c2n1] | | 394 (M + 1)+ |
| 240 | 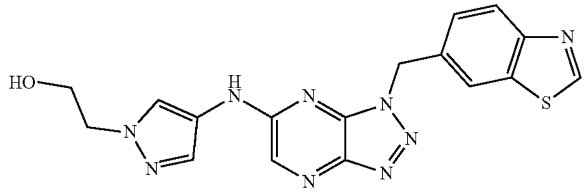 [SMILES: OCCn1cc(Nc2cnc3nnn(Cc4ccc5ncsc5c4)c3n2)cn1] | | 394 (M + 1)+ |
| 241 | 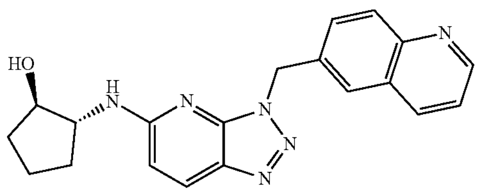 | Chiral | 361 (M + 1)+ |
| 242 | 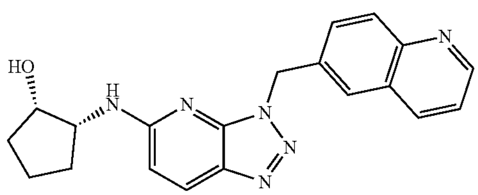 | Chiral | 361 (M + 1)+ |
| 243 | 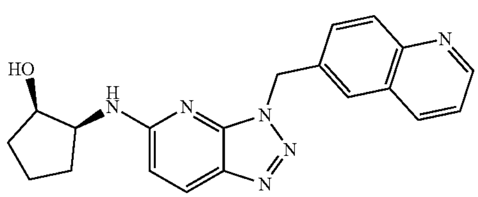 | Chiral | 361 (M + 1)+ |

[10]Under similar conditions described in Compound 152, Compound 154 was synthesized by using Intermediate 154-a that was prepared according to the procedure of Compound 244, under appropriate conditions that will be recognized by one skilled in the art.

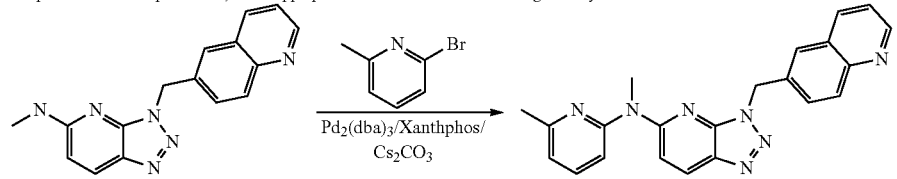

According to the procedure of Compound 154, Compound 177 and 239 were prepared using the corresponding intermediates and reagents under appropriate conditions that will be recognized by one skilled in the art.

165

Compound 244: 6-((6-(Pyridin-4-ylthio)-1H-[1,2,3]triazolo[4,5-b]pyrazin-1-yl)methyl)-quinoline

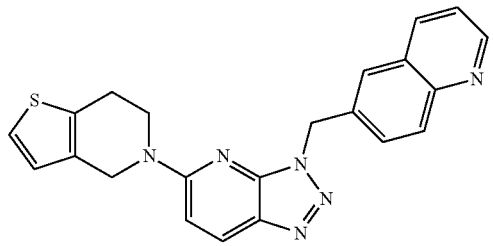 [SMILES: c1cnc2ccc(Cn3nnc4ccc(N5CCc6sccc6C5)nc43)cc2c1]

166

The mixture 6-((5-chloro-3H-[1,2,3]triazolo[4,5-b]pyridin-3-yl)methyl)quinoline (60 mg, 0.2 mmol) (prepared according to Compound 60), $Cs_2CO_3$ (195 mg, 0.6 mmol) and 4,5,6,7-tetrahydrothieno[3,2-c]pyridine hydrochloride (52 mg, 0.3 mmol) in DMF (1.5 mL) was stirred at 120° C. overnight, then concentrated. The residue was purified by chromatography to afford the title compound MS (m/z): 399 (M+1)$^+$.

Compounds 245-260

The following compounds 245-260 were prepared according to the procedures of Compound 244 using the corresponding intermediates under similar conditions that will be recognized by one skilled in the art.

TABLE 4

| Compound | Structure | LC/MS data |
|---|---|---|
| 245 | 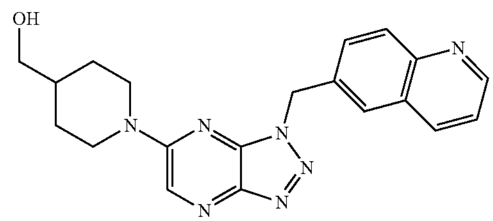 [SMILES: OCC1CCN(c2cnc3nnn(Cc4ccc5ncccc5c4)c3n2)CC1] | 375 (M + 1)$^+$ |
| 246 | 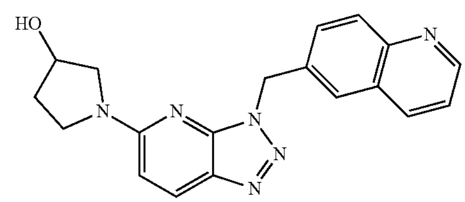 [SMILES: OC1CCN(c2ccc3nnn(Cc4ccc5ncccc5c4)c3n2)C1] | 347 (M + 1)$^+$ |
| 247 | 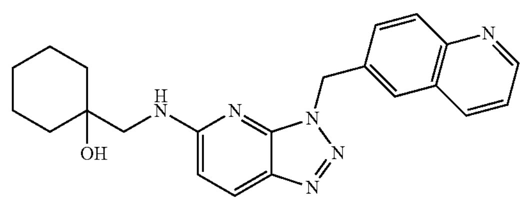 [SMILES: OC1(CNc2ccc3nnn(Cc4ccc5ncccc5c4)c3n2)CCCCC1] | 389 (M + 1)$^+$ |
| 248 | 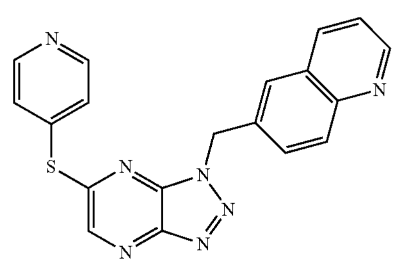 [SMILES: c1cnc2ccc(Cn3nnc4ncc(Sc5ccncc5)nc43)cc2c1] | 372 (M + 1)$^+$ |
| 249 | 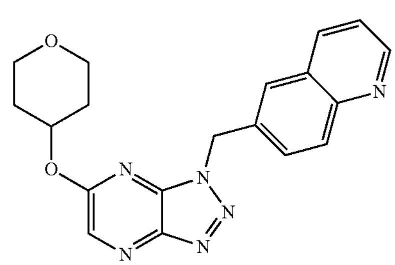 [SMILES: c1cnc2ccc(Cn3nnc4ncc(OC5CCOCC5)nc43)cc2c1] | 362 (M + 1)$^+$ |

TABLE 4-continued

| Compound | Structure | LC/MS data |
|---|---|---|
| 250 | 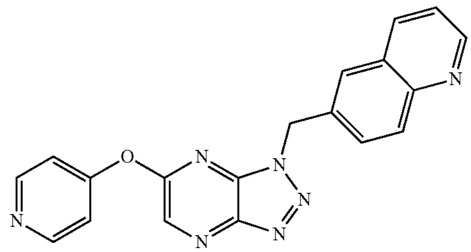 [SMILES: c1cnc2ccc(Cn3nnc4ncc(Oc5ccncc5)nc43)cc2c1] | 356 (M + 1)+ |
| 252 | 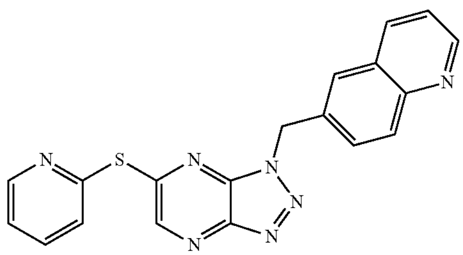 [SMILES: c1ccc(Sc2cnc3nnn(Cc4ccc5ncccc5c4)c3n2)nc1] | 372 (M + 1)+ |
| 253 | 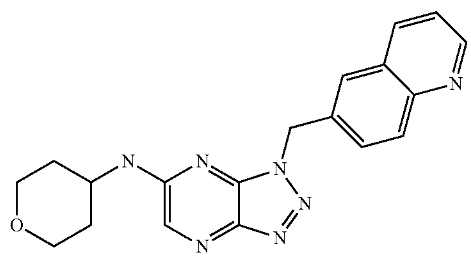 [SMILES: c1cnc2ccc(Cn3nnc4ncc(NC5CCOCC5)nc43)cc2c1] | 361 (M + 1)+ |
| 254 | 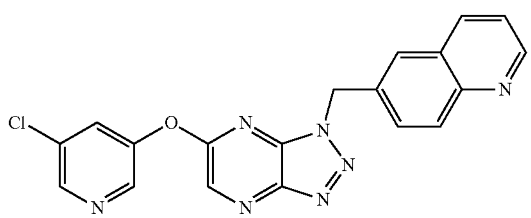 [SMILES: Clc1cncc(Oc2cnc3nnn(Cc4ccc5ncccc5c4)c3n2)c1] | 389 (M)+ |
| 255 | 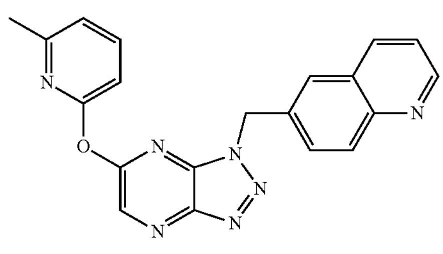 [SMILES: Cc1cccc(Oc2cnc3nnn(Cc4ccc5ncccc5c4)c3n2)n1] | 370 (M + 1)+ |
| 256 | 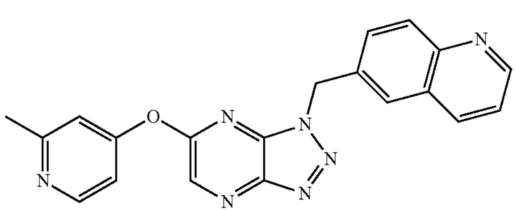 [SMILES: Cc1cc(Oc2cnc3nnn(Cc4ccc5ncccc5c4)c3n2)ccn1] | 370 (M + 1)+ |

TABLE 4-continued
| Compound | Structure | LC/MS data |
|---|---|---|
| 257 | 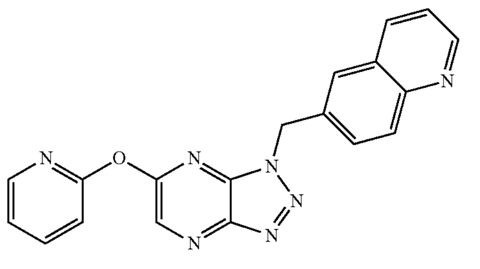 [SMILES: c1ccc(Oc2cnc3nnn(Cc4ccc5ncccc5c4)c3n2)nc1] | 356 (M + 1)+ |
| 258 | 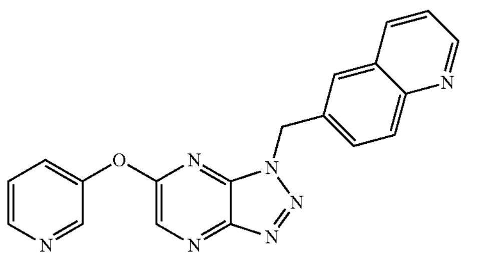 [SMILES: c1cncc(Oc2cnc3nnn(Cc4ccc5ncccc5c4)c3n2)c1] | 356 (M + 1)+ |
| 259 | 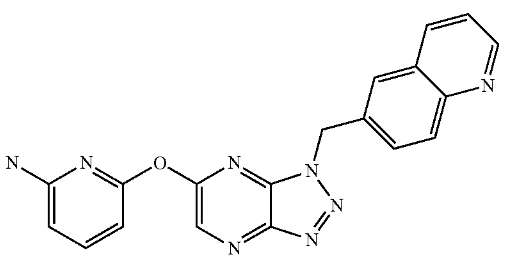 [SMILES: Nc1cccc(Oc2cnc3nnn(Cc4ccc5ncccc5c4)c3n2)n1] | 371 (M + 1)+ |
| 260 | 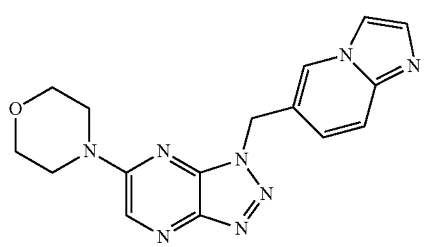 [SMILES: c1cn2cc(Cn3nnc4ncc(N5CCOCC5)nc43)ccc2n1] | 337 (M + 1)+ |
Compound 261: N-(5-(1-methyl-1H-pyrazol-4-yl)-3-(quinolin-6-ylmethyl)-3H-[1,2,3]triazolo[4,5-b]pyridin-7-yl)acetamide
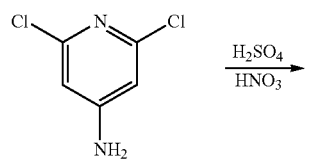
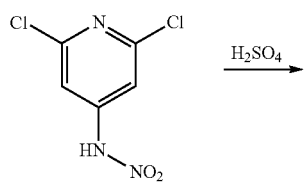
-continued
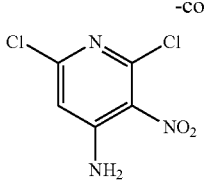
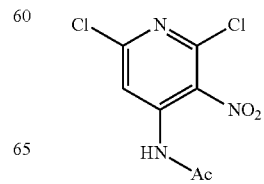
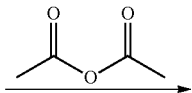

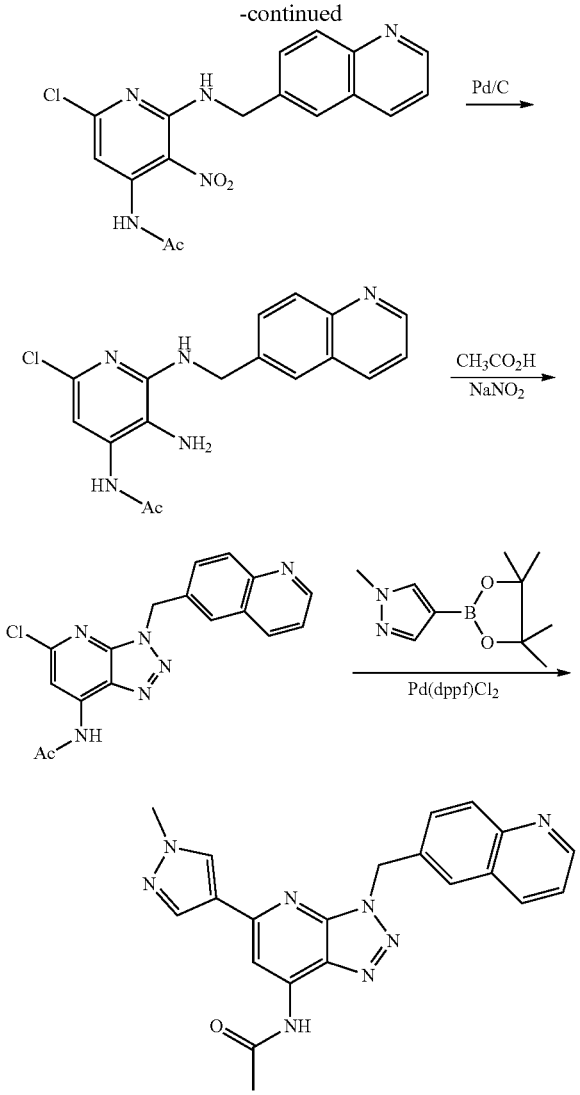

N-(2,6-Dichloropyridin-4-yl)nitramide 2,6-Dichloropyridin-4-amine (3.0 g, 18 mmol) was carefully added to concentrated sulfuric acid (20 mL). The mixture was cooled in an ice bath, and fuming nitric acid (2.6 mL) was added dropwise via pipette. The mixture was warmed to room temperature and stirred for 1 h, then poured onto crushed ice, resulting in a white precipitate. The white precipitate was collected by filtration, washed with cold water, and dried to afford the title compound (3.7 g), which was used for next step without further purification.

2,6-Dichloro-3-nitropyridin-4-amine

N-(2,6-Dichloropyridin-4-yl)nitramide (3.7 g, 18 mmol) was added to concentrated sulfuric acid (5 mL), and the reaction mixture was heated at 60° C. for 30 mins After cooled to room temperature, the reaction mixture was poured onto crushed ice, and concentrated ammonium hydroxide was added until the pH reached about 7. The precipitate was collected by filtration, washed with ice cold water, and dried to afford the title compound (2.5 g). MS (m/z): 208 (M+1)$^+$.

N-(2,6-Dichloro-3-nitropyridin-4-yl)acetamide 2,6-Dichloro-3-nitropyridin-4-amine (208 mg, 1 mmol) was added to acetic anhydride (2 mL), and the reaction mixture was refluxed overnight. After cooled to room temperature, the reaction mixture was basified with aqueous Na$_2$CO$_3$ until the pH was 8. The resulting mixture was then extracted with CH$_2$Cl$_2$. The organic layer was separated, dried over Na$_2$SO$_4$, and concentrated to afford the title compound (240 mg), which was used for the next step without further purification. MS (m/z): 250 (M+1)$^+$.

N-(6-Chloro-3-nitro-2-(quinolin-6-ylmethylamino) pyridin-4-yl)acetamide

To a mixture of N-(2,6-dichloro-3-nitropyridin-4-yl)acetamide (240 mg, 0.96 mmol) and quinolin-6-ylmethanamine (150 mg, 0.96 mmol) in CH$_3$CN (10 mL) was added Et$_3$N (0.5 mL). The reaction mixture was stirred at 80° C. for 1 h. After being cooled to room temperature, the mixture was purified by chromatography on silica gel eluting with DCM/MeOH=50/1 to afford the title compound (220 mg). MS (m/z): 372 (M+1)$^+$.

N-(3-Amino-6-chloro-2-(quinolin-6-yl methylamino)pyridin-4-yl)acetamide

To a solution of N-(6-chloro-3-nitro-2-(quinolin-6-ylmethylamino)pyridin-4-yl)acetamide (220 mg, 0.593 mmol) in methanol (5 mL) and CH$_2$Cl$_2$ (5 mL) was added 10% catalytical amount Pd/C. The reaction mixture was stirred at room temperature under 1 atm of H$_2$ for 1 h, then filtered. The filtrate was concentrated to afford the title compound, which was used for the next step without further purification. MS (m/z): 342 (M+1)$^+$.

N-(5-Chloro-3-(quinolin-6-ylmethyl)-3H-[1,2,3]triazolo[4,5-b]pyridin-7-yl)acetamide N-(3-amino-6-chloro-2-(quinolin-6-ylmethylamino)pyridin-4-yl)acetamide was added to a solution of acetic acid (2 mL) and water (2 mL) at 0° C., followed by the addition of NaNO$_2$ (180 mg, 2.6 mmol) in H$_2$O (0.2 mL). The reaction was stirred at 0° C. for 1 h, and then basified with 30% NaOH to pH=7. The resulting precipitate was collected by filtration to afford the title compound (80 mg), which was used for the next step without further purification. MS (m/z): 353 (M+1)$^+$.

N-(5-(1-Methyl-1H-pyrazol-4-yl)-3-(quinolin-6-ylmethyl)-3H-[1,2,3]triazolo[4,5-b]pyridin-7-yl)acetamide To a mixture of N-(5-chloro-3-(quinolin-6-ylmethyl)-3H-[1,2,3]triazolo[4,5-b]pyridin-7-yl)acetamide (80 mg, 0.227 mmol), 1-methyl-4-(4,4,5,5-tetramethyl-1,3,2-dioxaborolan-2-yl)-1H-pyrazole (50 mg, 0.24 mmol) and Na$_2$CO$_3$ (48 mg, 0.25 mmol) in dioxane (10 mL) and H$_2$O (1 mL) under N$_2$ was added Pd(dppf)Cl$_2$ (20 mg, 0.02 mmol). The reaction mixture was stirred at 100° C. under N$_2$ overnight. After cooled to room temperature, the reaction mixture was concentrated and purified by chromatography to afford the title compound (7 mg). MS: 400 (M+1)+.

Compound 262: 5-(1-Methyl-1H-pyrazol-4-yl)-3-(quinolin-6-ylmethyl)-3H-[1,2,3]triazolo-[4,5-b]pyridin-7-ol

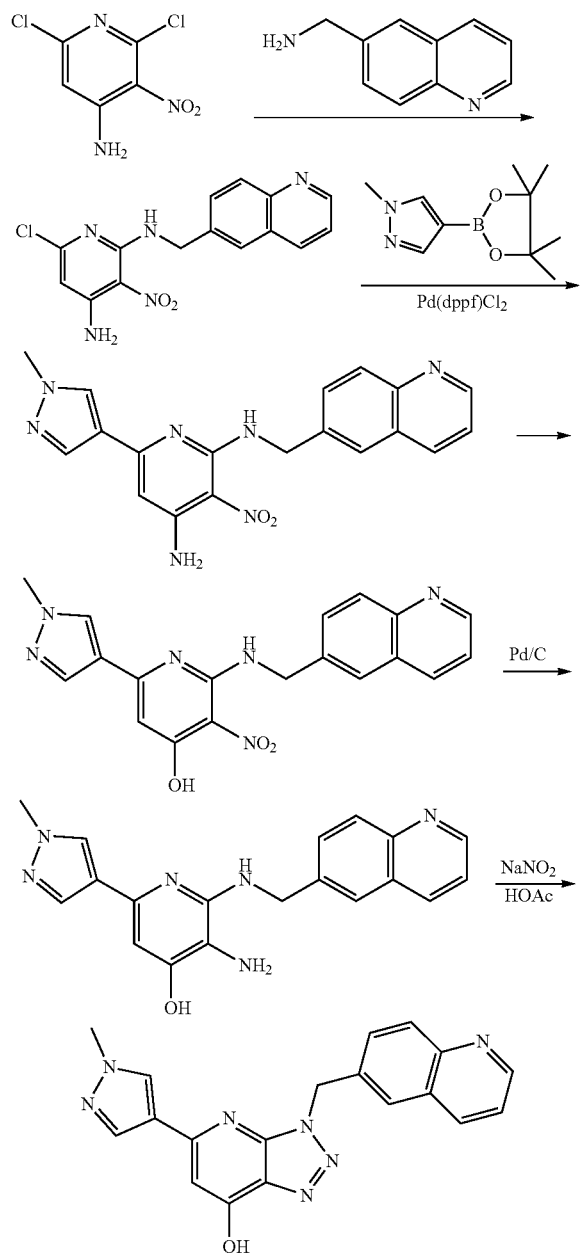

6-Chloro-3-nitro-N2-(quinolin-6-ylmethyl)pyridine-2,4-diamine

To a mixture of 2,6-dichloro-3-nitropyridin-4-amine (624 mg, 3 mmol) and quinolin-6-ylmethanamine (316 mg, 2 mmol) in CH$_3$CN (10 mL) was added Et$_3$N (0.5 mL). The reaction mixture was stirred at 80° C. for 1 h. After cooled to room temperature, the mixture was concentrated to afford the title compound (658 mg). MS (m/z): 330 (M+1)+.

6-(1-Methyl-1H-pyrazol-4-yl)-3-nitro-N2-(quinolin-6-ylmethyl) pyridine-2,4-diamine To a mixture of 6-chloro-3-nitro-N2-(quinolin-6-ylmethyl)pyridine-2,4-diamine (658 mg, 2 mmol), 1-methyl-4-(4,4,5,5-tetramethyl-1,3,2-dioxaborolan-2-yl)-1H-pyrazole (500 mg, 2.4 mmol) and Na$_2$CO$_3$ (424 mg, 4 mmol) in dioxane (20 mL) and H$_2$O (2 mL) under N$_2$ was added Pd(dppf)Cl$_2$ (160 mg, 0.2 mmol). The reaction mixture was stirred at 100° C. under N$_2$ overnight. After cooled to room temperature, the mixture was concentrated and purified by chromatography to afford the title compound (300 mg). MS (m/z): 376 (M+1)+.

6-(1-Methyl-1H-pyrazol-4-yl)-3-nitro-2-(quinolin-6-yl methylamino)pyridin-4-ol

To a mixture of 6-(1-methyl-1H-pyrazol-4-yl)-3-nitro-N$^2$-(quinolin-6-ylmethyl) pyridine-2,4-diamine (260 mg, 0.69 mmol) in HBF4 (5 mL) at 0° C. was added HNO$_2$ (96 mg, 1.4 mmol) in H$_2$O (0.5 mL). The reaction mixture was stirred at 0° C. overnight, then basified with aqueous NaHCO$_3$ to pH=6-7. The resulting mixture was filtered. The filtrate was concentrated and purified by chromatography on silica gel to afford the title compound (200 mg). MS (m/z): 377 (M+1)+.

3-Amino-6-(1-methyl-1H-pyrazol-4-yl)-2-(quinolin-6-ylmethylamino) pyridin-4-ol

To a solution of 6-(1-methyl-1H-pyrazol-4-yl)-3-nitro-N2-(quinolin-6-ylmethyl)pyridine-2,4-diamine (200 mg, 0.53 mmol) in methanol (10 mL) was added 10% Pd/C (20 mg, 0.1 eq). The reaction mixture was stirred at room temperature under 1 atm of H$_2$ for 2 h, then filtered. The filtrate was concentrated to afford the title compound (170 mg), which was used for the next step without further purification. MS (m/z): 347 (M+1)+.

5-(1-Methyl-1H-pyrazol-4-yl)-3-(quinolin-6-yl methyl)-3H-[1,2,3]triazolo[4,5-b]pyridin-7-ol 3-amino-6-(1-methyl-1H-pyrazol-4-yl)-2-(quinolin-6-ylmethylamino)pyridin-4-ol (170 mg, 0.49 mmol) was added to a solution of acetic acid (3 mL) and H$_2$O (3 mL) at 0° C., followed by the addition of NaNO$_2$ (69 mg, 10 mmol) in H$_2$O (0.3 mL). The reaction mixture was stirred at 0° C. for 1 h, then basified with aqueous 30% NaOH to pH=6-7 and purified by chromatography to afford the title compound (120 mg). MS (m/z): 358 (M+1)+.

Compound 263: 6-((7-Chloro-5-(1-methyl-1H-pyrazol-4-yl)-3H-[1,2,3]triazolo[4,5-b]pyridin-3-yl)methyl)quinoline

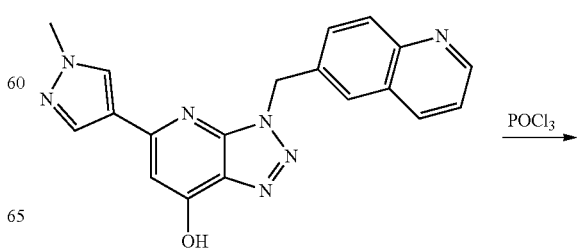

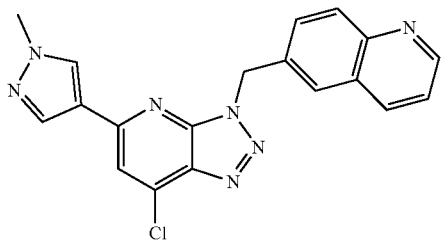

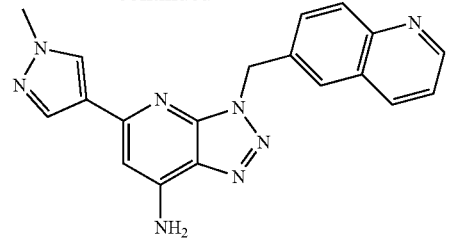

5-(1-Methyl-1H-pyrazol-4-yl)-3-(quinolin-6-ylmethyl)-3H-[1,2,3]triazolo[4,5-b]pyridin-7-ol (120 mg, 0.336 mmol) was dissolved in POCl₃ (2 ml). The reaction mixture was stirred at 110° C. for 1 h. After cooled to 0° C., the mixture was basified with aqueous NaHCO₃ to pH=7, and extracted with EtOAc. The organic layer was separated, dried over anhydrous Na₂SO₄, concentrated, and purified by chromatography to afford the title compound (25 mg). MS: 376 (M+1)⁺.

Compound 264: 5-(1-Methyl-1H-pyrazol-4-yl)-3-(quinolin-6-ylmethyl)-3H-[1,2,3]triazolo-[4,5-b]pyridin-7-amine

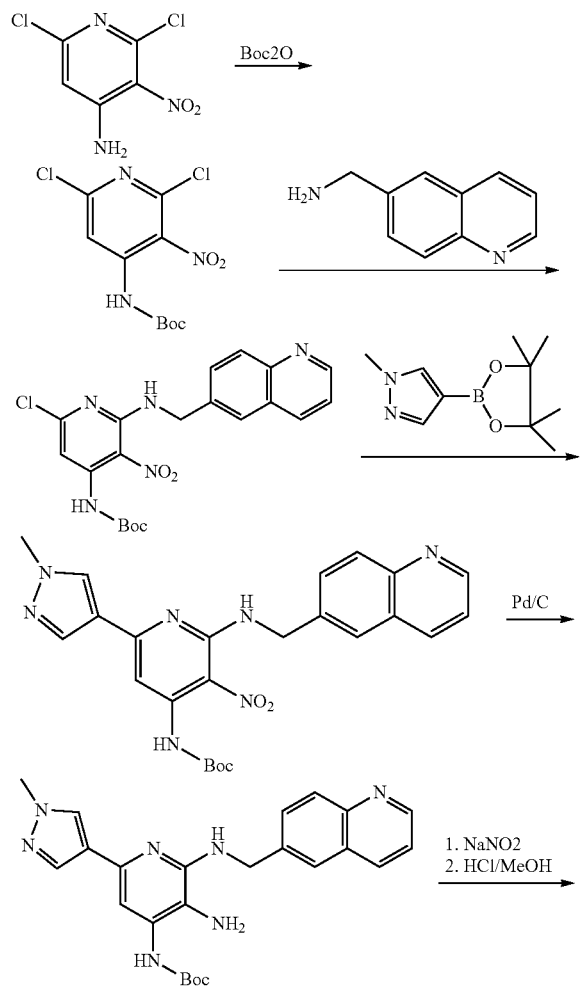

tert-Butyl 2,6-dichloro-3-nitropyridin-4-ylcarbamate

To a solution of 2,6-dichloro-3-nitropyridin-4-amine (832 mg. 4 mmol) in THF (10 mL) was added DMAP (50 mg, 0.4 mmol) and (Boc)₂O (1.0 g, 4.6 mmol) in that order. The reaction mixture was stirred at room temperature for 2 h, then concentrated. The residue was purified by chromatography on silica gel eluting with Pet/EtOAc=50/1 to afford the title compound (1.20 g).

tert-Butyl 6-chloro-3-nitro-2-(quinolin-6-ylmethylamino) pyridin-4-ylcarbamate

A solution of tert-butyl 2,6-dichloro-3-nitropyridin-4-ylcarbamate (1.2 g, 3.9 mmol) and quinolin-6-ylmethanamine (616 mg, 3.9 mmol) in CH₃CN (15 mL) and Et₃N (1 mL) was stirred at 80° C. for 1 h. After cooled to room temperature, the mixture was concentrated. The residue was purified by chromatography to afford the title compound (1.60 g). MS (m/z): 430 (M+1)⁺.

tert-Butyl 6-(1-methyl-1H-pyrazol-4-yl)-3-nitro-2-(quinolin-6-ylmethylamino) pyridin-4-ylcarbamate To a mixture of tert-butyl 6-chloro-3-nitro-2-(quinolin-6-ylmethylamino)pyridin-4-ylcarbamate (860 mg, 2 mmol), 1-methyl-4-(4,4,5,5-tetramethyl-1,3,2-dioxaborolan-2-yl)-1H-pyrazole (416 mg, 2 mmol) and Na₂CO₃ (424 mg, 4 mmol) in dioxane (20 mL) and H₂O (2 mL) under N₂ was added Pd(dppf)Cl₂ (163 mg, 0.2 mmol). The reaction was stirred at 80° C. under N₂ overnight. After cooled to room temperature, the mixture was concentrated and purified by chromatography to afford the title compound (950 mg). MS (m/z): 476 (M+1)⁺.

tert-Butyl 3-amino-6-(1-methyl-1H-pyrazol-4-yl)-2-(quinolin-6-ylmethylamino) pyridin-4-ylcarbamate To a solution of tert-butyl 6-(1-methyl-1H-pyrazol-4-yl)-3-nitro-2-(quinolin-6-ylmethylamino)pyridin-4-ylcarbamate (950 mg, 2 mmol) in methanol (10 mL) was added 10% Pd/C (95 mg, 0.1 eq). The reaction was stirred at room temperature under 1 atm of H₂ for 1 h, then filtered. The filtrate was concentrated to afford the title compound (890 mg), which was used for the next step without further purification. MS (m/z): 446 (M+1)⁺.

5-(1-Methyl-1H-pyrazol-4-yl)-3-(quinolin-6-yl methyl)-3H-[1,2,3]triazolo[4,5-b]pyridin-7-amine tert-Butyl 3-amino-6-(1-methyl-1H-pyrazol-4-yl)-2-(quinolin-6-ylmethylamino)pyridin-4-ylcarbamate (890 mg, 2 mmol) was added to a solution of acetic acid (5 mL) and water (5 mL) at 0° C., followed by the addition of NaNO₂

(300 mg, 4 mmol) in H₂O (0.5 mL). The reaction was stirred at 0° C. for 1 h, then basified with 30% NaOH to pH=8. The resulting mixture was filtered to afford a solid. The solid was treated with TFA (3 mL), and then stirred at room temperature for another 0.5 h, before treated with aqueous Na₂CO₃ to adjust the pH to 8. The resulting mixture was purified by chromatography to afford the title compound (190 mg). MS: 358 (M+1)⁺.

Compound 278: 1-((3-Bromoimidazo[1,2-a]pyridin-6-yl)methyl)-6-(1-methyl-1H-pyrazol-4-yl)-1H-[1,2,3]triazolo[4,5-b]pyrazine

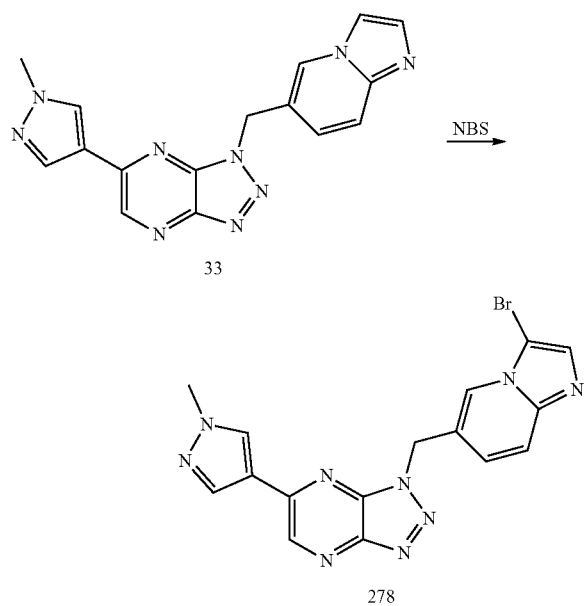

To a solution of Compound 33 (10 mg, 0.03 mmol) in CHCl₃ (3 mL) was added NBS (5.4 mg, 0.031 mmol). The reaction mixture was stirred at room temperature overnight. The solvent was evaporated, and the residue was purified by chromatography to afford the title compound (11 mg). MS (m/z): 411.7 (M+1)⁺.

Compound 300

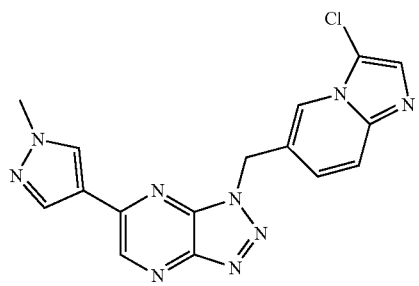 [SMILES: Cn1cc(-c2cnc3nnn(Cc4ccc5ncc(Cl)n5c4)c3n2)cn1]

Compound 300 was prepared with NCS according to the procedure of Compound 278. MS (m/z): 365.9 (M+1)⁺.

Compound 306: 2-(4-(1-((3-(Hydroxymethyl)imidazo[1,2-a]pyridin-6-yl)methyl)-1H-[1,2,3]triazolo[4,5-b]pyrazin-6-yl)-1H-pyrazol-1-yl)ethanol

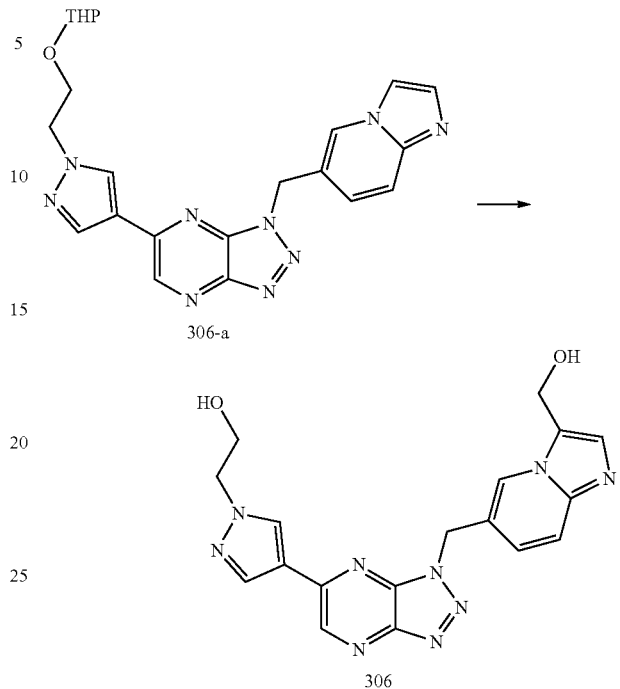

To a solution of 306-a (60 mg, 0.13 mmol) (prepared according to the procedure of Compound 1) in 0.1 mL of acetic acid were added sodium acetate (39 mg, 0.48 mmol) and then formaldehyde (0.13 mL, 37% in water). The mixture was stirred at 100° C. overnight. After cooled, the mixture was adjusted to pH>7 with aqueous NaOH. The resulting precipitate was collected and purified by chromatography to afford the title compound (10 mg). MS (m/z): 392.0 (M+H)⁺

Compound 307:6-((6-(1-Methyl-1H-pyrazol-4-yl)-1H-[1,2,3]triazolo[4,5-b]pyrazin-1-yl)methyl)-imidazo[1,2-a]pyridine-3-carbaldehyde

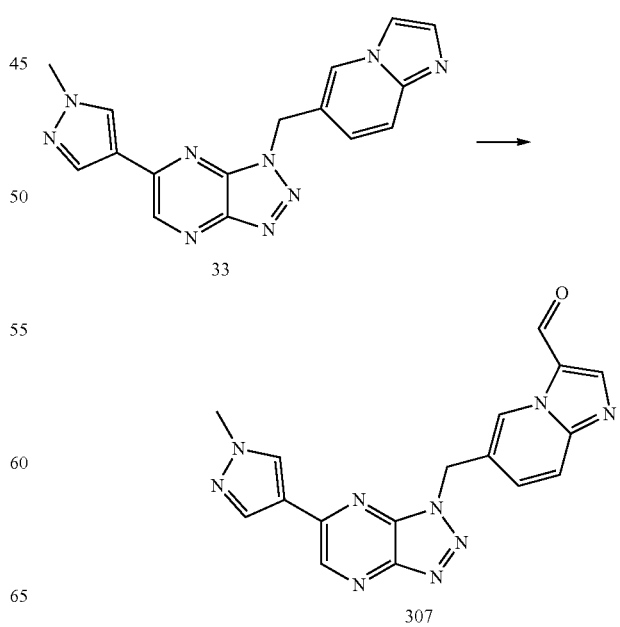

To a mixture of Compound 33 (33 mg, 0.1 mmol) in 0.2 mL of acetic acid and 0.4 Compound 1) in 0.1 mL of water was added hexamethylenetetramine (16 mg, 0.11 mmol). The mixture was stirred at 120° C. overnight. After cooled, the mixture was adjusted to pH7 with aqueous NaOH and purified by chromatography to afford the title compound (5 mg). MS (m/z): 360.0 (M+H)$^+$.

Compound 311: 2-(4-(1-(Pyrazolo[1,5-a]pyridin-5-ylmethyl)-1H-[1,2,3]triazolo[4,5-b]pyrazin-6-yl)-1H-pyrazol-1-yl)ethanol

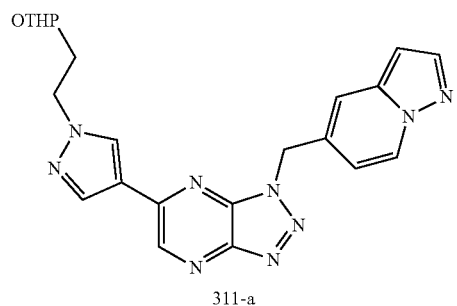

311-a

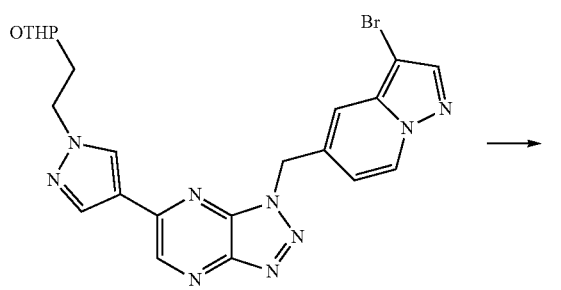

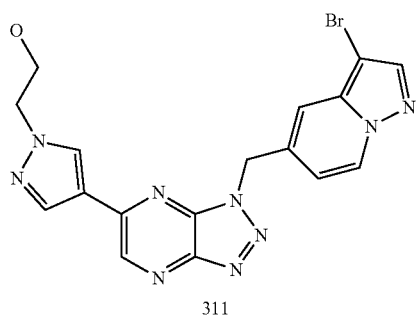

311

To a solution of 1-(pyrazolo[1,5-a]pyridin-5-ylmethyl)-6-(1-(2-(tetrahydro-2H-pyran-2-yloxy)ethyl)-1H-pyrazol-4-yl)-1H-[1,2,3]triazolo[4,5-b]pyrazine 311-a (10 mg, 0.022 mmol) (prepared according to the procedure of Compound 1) in CHCl$_3$ was added NBS (4.4 mg, 0.025 mmol). The reaction mixture was stirred at rt for 1 h, then concentrated. The resulting residue was dissolved in CHCl$_3$ (2 mL) and MeOH (2 mL), followed by the addition of 6N HCl in MeOH. The resulting mixture was stirred for 30 min, then treated with NH3.H2O to bring pH to 8. The mixture was concentrated and purified by prep-TLC to afford the title compound. MS (m/z): 439.9 (M+1)$^+$.

Compound 312: 5-((6-(1-(2-Hydroxyethyl)-1H-pyrazol-4-yl)-1H-[1,2,3]triazolo[4,5-b]pyrazin-1-yl)methyl)pyrazolo[1,5-a]pyridine-3-carbaldehyde

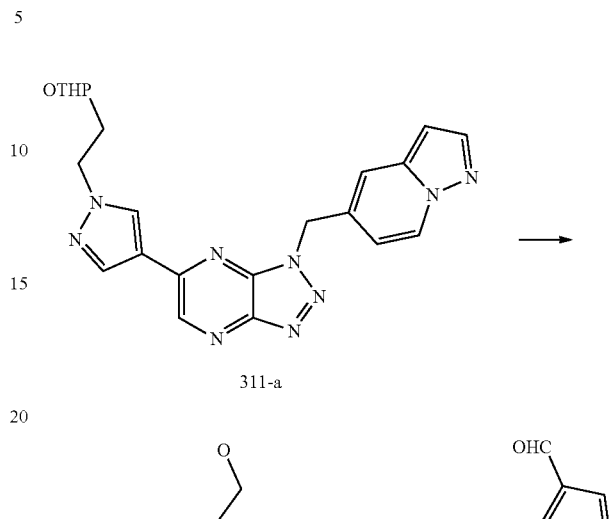

To a solution of 1-(pyrazolo[1,5-a]pyridin-5-ylmethyl)-6-(1-(2-(tetrahydro-2H-pyran-2-yloxy)ethyl)-1H-pyrazol-4-yl)-1H-[1,2,3]triazolo[4,5-b]pyrazine 311-a (125 mg, 0.28 mmol) in AcOH/H$_2$O (2 mL/1 mL) was added HMTA (79 mg, 0.56 mmol). The reaction mixture was stirred at 110° C. for 2 h, then treated with NH$_3$.H$_2$O to bring pH to 8. The resulting mixture was then concentrated and purified by prep-TLC to afford the title compound (67 mg). MS (m/z): 389.37 (M+1)$^+$.

Compound 313: 2-(4-(1-((3-(Hydroxymethyl)pyrazolo[1,5-a]pyridin-5-yl)methyl)-1H-[1,2,3]triazolo[4,5-b]pyrazin-6-yl)-1H-pyrazol-1-yl)ethanol

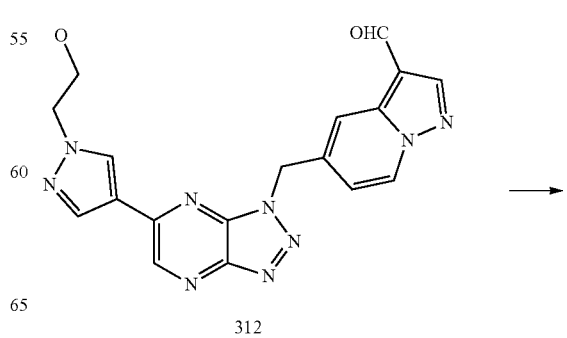

312

-continued

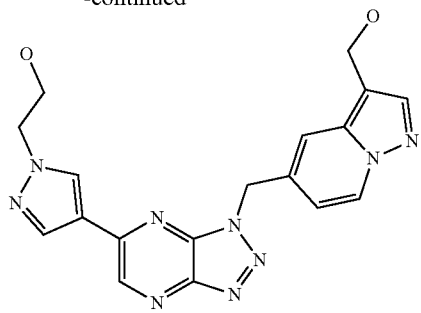

313

To a solution of compound 312 (10 mg, 0.025 mmol) in MeOH was added NaBH$_4$ (4 mg, 0.051 mmol). The reaction was stirred at room temperature for 1 h, then concentrated and purified by prep-TLC to afford the title compound.

Compound 318: 1-(1-(3-(methoxymethyl)imidazo[1,2-a]pyridin-6-yl)ethyl)-6-(1-methyl-1H-pyrazol-4-yl)-1H-[1,2,3]triazolo[4,5-b]pyrazine

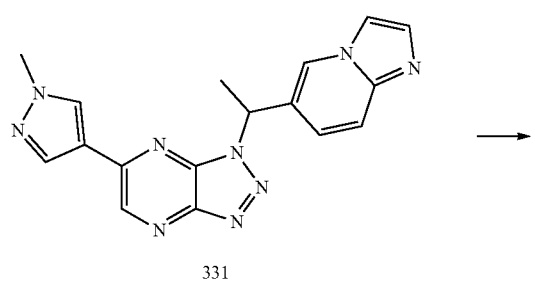

331

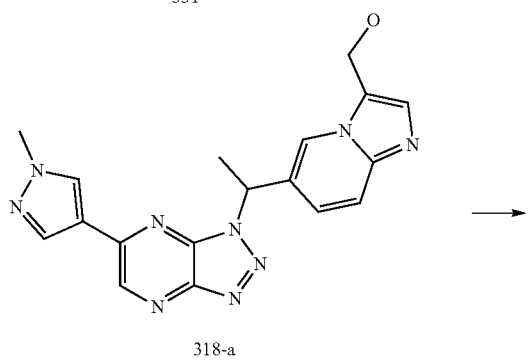

318-a

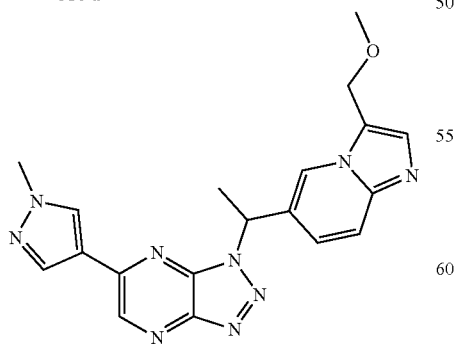

318

Intermediate 318-a was prepared according to the procedure of Compound 306 by using Compound 331.

To a mixture of (6-(1-(6-(1-methyl-1H-pyrazol-4-yl)-1H-[1,2,3]triazolo[4,5-b]pyrazin-1-yl)ethyl)H-imidazo[1,2-a]pyridin-3-yl)methanol 318-a (40 mg, 0.11 mmol) in 30 mL of THF was added sodium hydride (22 mg, 0.53 mmol, 60% in mineral oil) at 0° C. The mixture was stirred at 0° C. for 1 h, then iodomethane (60 mg, 0.43 mmol) was added. The mixture was stirred at room temperature overnight, then treated with sat. Na$_2$CO$_3$, then concentrated. The residue was diluted with water, and extracted with ethyl acetate. The combined organic layers were dried over Na$_2$SO$_4$, concentrated and purified by chromatography on silica gel to afford the title compound (30 mg) MS (m/z): 389.9 (M+H)$^+$ Compounds 319 and 320

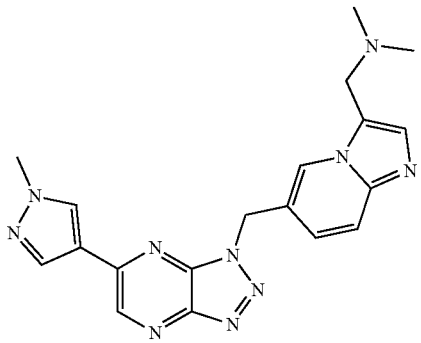

319

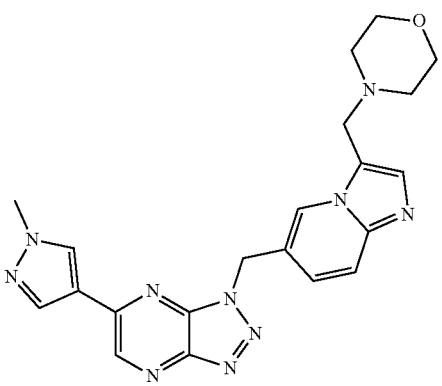

320

Compounds 319 and 320 were prepared according to the procedure of Compound 327. Compound 319: MS: 388.9 (M+1)$^+$; Compound 320 MS: 431 (M+1) Compounds 321:

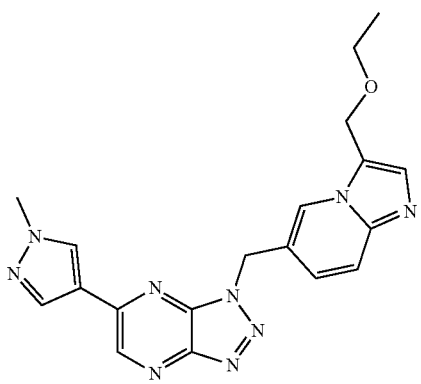

321

Compound 321 was prepared according to the procedure of Compound 318 starting from Compound 272. MS: 389.9 (M+1)$^+$.

Compound 322

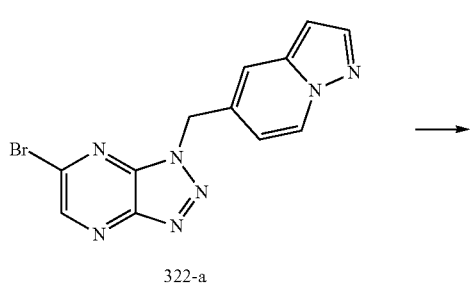

322-a

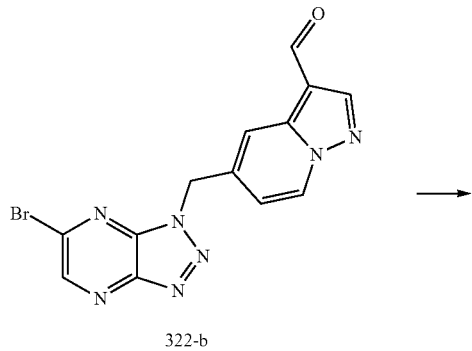

322-b

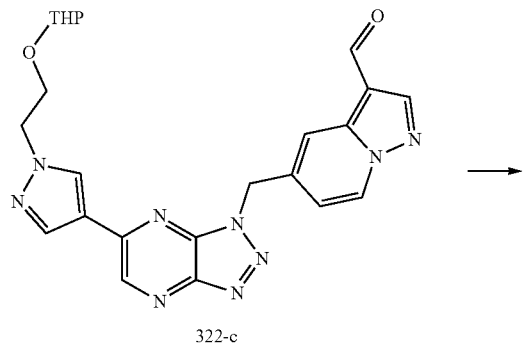

322-c

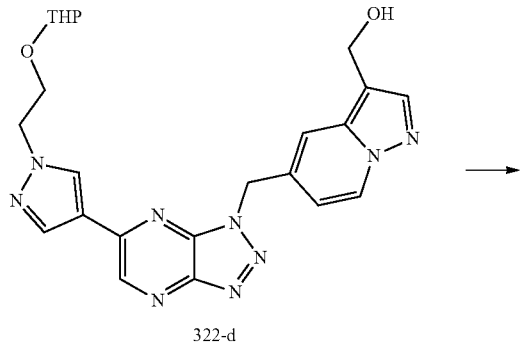

322-d

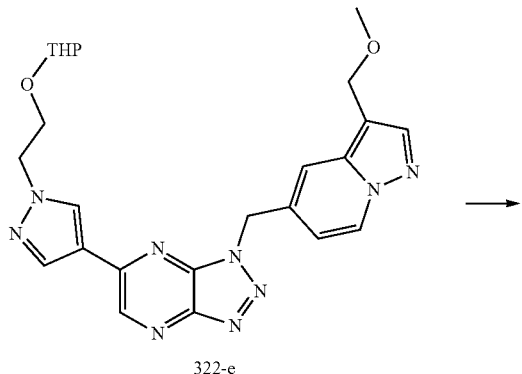

322-e

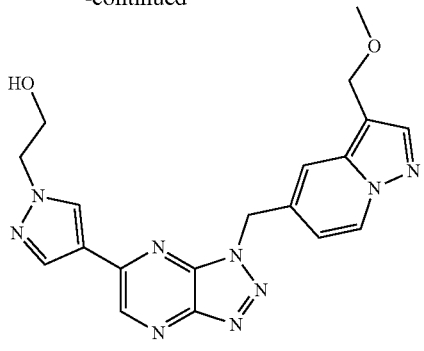

322

5-((6-Bromo-1H-[1,2,3]triazolo[4,5-b]pyrazin-1-yl)methyl)pyrazolo[1,5-a]pyridine-3-carbaldehyde (322-b)

The title compound (Intermediate 322-b) was prepared according to the procedure of Compound 307.

5-((6-(1-(2-(Tetrahydro-2H-pyran-2-yloxy)ethyl)-1H-pyrazol-4-yl)-1H-[1,2,3]triazolo[4,5-b]pyrazin-1-yl)methyl)pyrazolo[1,5-a]pyridine-3-carbaldehyde (322-c)

The title compound (Intermediate 322-c) was prepared from 322-b according to the procedure of Compound 1.

(5-((6-(1-(2-(Tetrahydro-2H-pyran-2-yloxy)ethyl)-1H-pyrazol-4-yl)-1H-[1,2,3]triazolo[4,5-b]pyrazin-1-yl)methyl)pyrazolo[1,5-a]pyridin-3-yl)methanol (332-d)

The title compound (Intermediate 322-d) was prepared from 322-c according to the procedure of Compound 313. MS (m/z): 476.1 (M+H)$^+$.

1-((3-(Methoxymethyl)pyrazolo[1,5-a]pyridin-5-yl)methyl)-6-(1-(2-(tetrahydro-2H-pyran-2-yloxy)ethyl)-1H-pyrazol-4-yl)-1H-[1,2,3]triazolo[4,5-b]pyrazine (332-e)

The title compound (Intermediate 322-e) was prepared from 322-d according to the procedure of Compound 318.

2-(4-(1-((3-(Methoxymethyl)pyrazolo[1,5-a]pyridin-5-yl)methyl)-1H-[1,2,3]triazolo[4,5-b]pyrazin-6-yl)-1H-pyrazol-1-yl)ethanol (compound 322)

To a mixture of 322-e (40 mg, 0.082 mmol) in methanol (15 mL) was added a solution of HCl in methanol (0.5 mL, 5 N). The mixture was stirred at 0° C. for 1 h, then treated with ammonia to adjust pH to >7. The resulting solution was concentrated and purified by chromatography to afford the title compound (15 mg).

Compounds 323

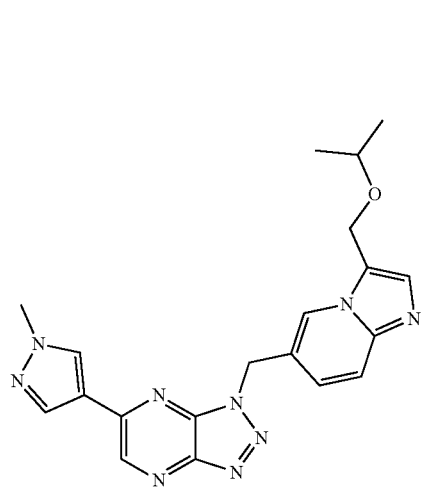

323

Compound 323 was prepared from compound 272 according to the procedure of Compound 318. MS: 403.9 (M+1)⁺

Compound 327: N-methyl-1-(6-((6-(1-methyl-1H-pyrazol-4-yl)-1H-[1,2,3]triazolo[4,5-b]pyrazin-1-yl)methyl)imidazo[1,2-a]pyridin-3-yl)methanamine

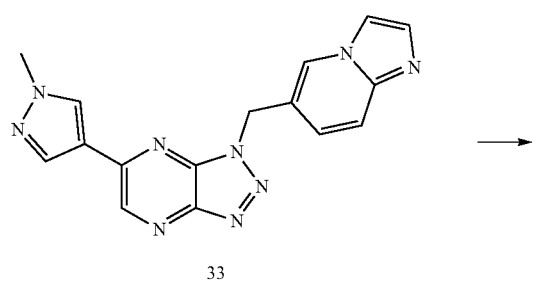

33

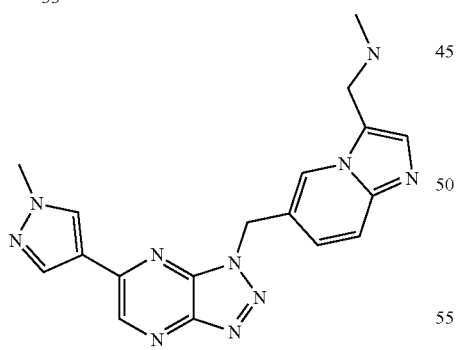

327

To a mixture of compound 33 (50 mg, 0.15 mmol) in acetic acid (0.5 mL) were added ammonium chloride (61 mg, 0.9 mmol) and formaldehyde (61 mg, 0.75 mmol, 37% in water). The mixture was stirred at 55° C. for 24 h. The reaction was treated with ammonia to adjust the pH to >7, then concentrated and purified by chromatography to afford the title compound (15 mg). MS (m/z): 374.8 (M+H)⁺.

Compound 330

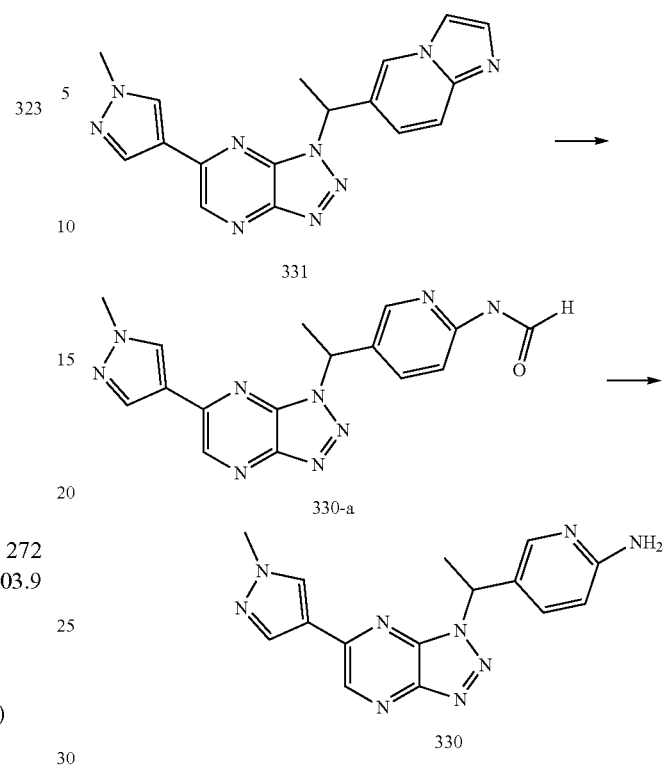

N-(5-(1-(6-(1-Methyl-1H-pyrazol-4-yl)-1H-[1,2,3]triazolo[4,5-b]pyrazin-1-yl)ethyl)pyridin-2-yl)formamide (330-a)

To a solution of the compound 331 (1.0 g) in 100 mL of CH₂Cl₂ was bubbled O₃ at −60-−70° C. for 30 mins, then N₂ for 10 mins. The reaction mixture was treated with Na₂SO₃ solution, and stirred for 10 mins. The resulting mixture was extracted with CH₂Cl₂. The organic layer was concentrated and purified by chromatography to afford the title compound as a solid (300 mg). MS (m/z): 322 (M+H)⁺.

5-(1-(6-(1-Methyl-1H-pyrazol-4-yl)-1H-[1,2,3]triazolo[4,5-b]pyrazin-1-yl)ethyl)pyridin-2-amine (Compound 330)

A solution of compound 330-a (300 mg) in 10 mL of HCl/CH₃OH was stirred overnight, then concentrated and basified with Na₂CO₃ solution. The resulting mixture was purified by chromatography to afford the title compound as a solid, 155 mg.

Compound 77 and 78

Compound 77

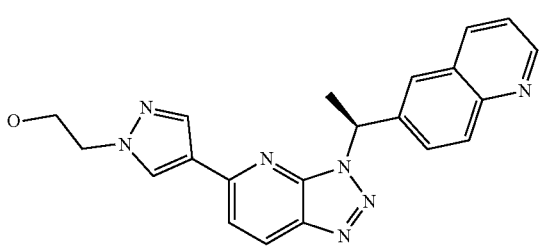

Compound 78

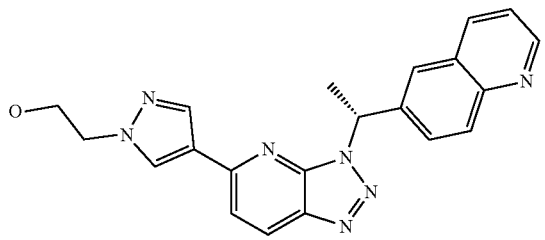

The racemic Compound 332 (4 mg) was resolved by chiral HPLC to produce the optically pure enantiomers Compound 77 (0.7 mg) and 78 (1.1 mg) (HPLC conditions: Gilson system, Column: Dicel IA 4.6×250 mm; mobile phase: n-hexane/i-PrOH/DEA=70/30/0.1; flow rate, 1 mL/min; detector: UV 254 nm). Compound 77 is the first eluent with at least 98% ee, MS (m/z): 386 (M+1)$^+$. Compound 78 is the second eluent with at least 98% ee, MS (m/z): 386 (M+1)$^+$.

Compound 270 and 271

Compound 270

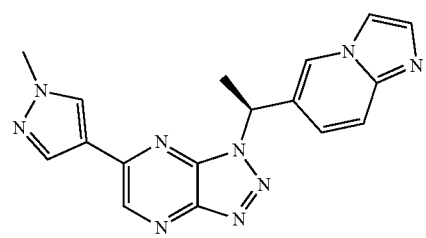

Compound 271

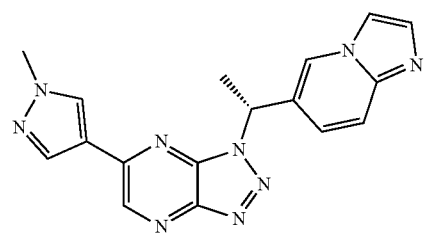

The racemic compound 331 (3 mg) was resolved by chiral HPLC to produce the optically pure enantiomers Compound 270 (0.9 mg) and 271 (1.1 mg). (HPLC conditions: Gilson system, column: Dicel IA 20×250 mm; mobile phase: EtOH/CH$_3$CN=9/1; flow rate=8 mL/min; detector: UV 254 nm), Compound 270 is the first eluent with at least 98% ee, MS (m/z): 346 (M+1)$^+$. and Compound 271 is the second eluent with 93% ee, MS (m/z): 346 (M+1)$^+$.

Compounds 314 and 315

314

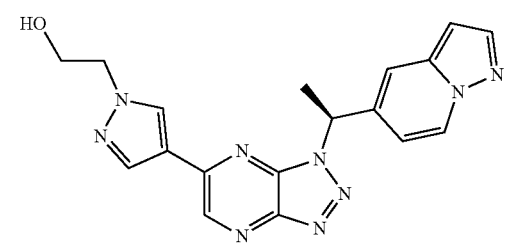

315

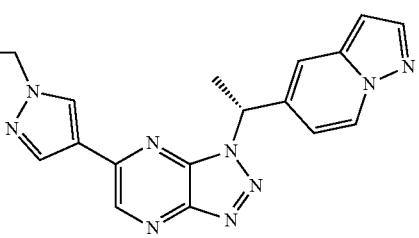

The racemic compound 310 (5 mg) was resolved by chiral HPLC to produce optically pure enantiomers Compound 314 (1.0 mg) and Compound 315 (1.9 mg). (HPLC conditions: Gilson system, Column: Dicel IA 20×250 mm; Mobile phase: n-Hexane/i-PrOH/DEA=6/4/0.1; Flow rate: 8 ml/min; Detector: 254 nm;). Compound 314 is the first eluent with 95% ee, MS (m/z): 376 (M+1)$^+$. Compound 315 is the second eluent with 80% ee, MS (m/z): 376 (M+1)$^+$.

Compounds 324 and 325

324

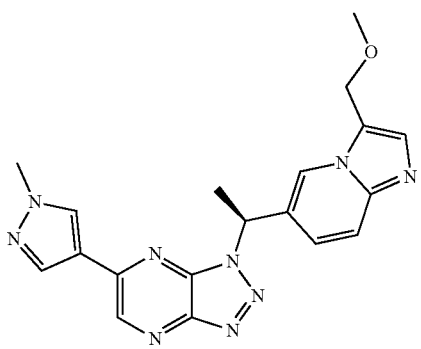

325

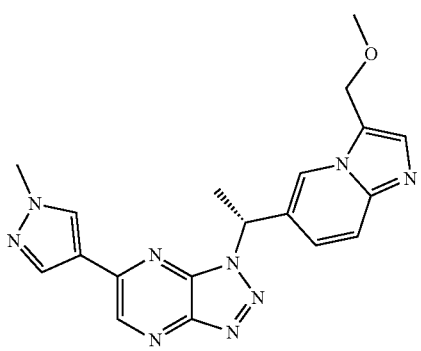

Racemic Compound 318 (50 mg) was resolved by chiral HPLC to produce enantiomeic Compounds 324 (15 mg) and 325 (8 mg). (HPLC conditions: Gilson system; column: dicel IA, 20×250 mm IA; mobile phase: ethanol/methanol/DEA=70/30/0.1; detector: UV 254 nm). Compound 324 is the first eluent with at least 98% ee, MS (m/z): 390 (M+1)$^+$. Compound 325 is the second eluent with at least 90% ee, MS (m/z): 390 (M+1)$^+$.

Example 2: Inhibition of c-Met Kinase Activity Using Transcreener FP Assay

1. Reagents

Transcreenen™ KINASE Assay kit: Bellbrook Labs., 3003-10K;
Recombinant human Met: Invitrogen, PV3143;
Poly E4Y (substrate): Sigma, P0275; 5 mg/mL, dissolved in H$_2$O;

Assay buffer: 67 mM HEPES, 0.013% Triton X-100, 27 mM MgCl$_2$, 0.67 mM MnCl$_2$, 1.25 mM DTT, PH 7.4;
10 mM ATP: Invitrogene, PV3227;
500 mM EDTA: Invitrogene, 15575-038;
96 well black Greiner plate: Greiner, 675076.

2. Solution Preparation

Compound dilution: dilute test articles to 5 folds of the testing concentration using 20% DMSO.

Prepare Enzyme/Substrate stock: dilute recombinant human c-Met and Poly E4Y in assay buffer to 0.5 µg/mL for c-Met, and 62.5 µg/mL for Poly E4Y. The mixture is kept on ice until use;

Prepare ATP Diluent: dilute 10 mM ATP stock to 25 µM with assay buffer;

Prepare ADP Diluent: dilute 500 µM ADP stock to 25 µM with assay buffer;

Prepare ATP standard curve stock as following:

| Column | ADP diluent (uL) | ATP diluent (uL) |
|---|---|---|
| 1 | 50 | 0 |
| 2 | 25 | 25 |
| 3 | 10 | 40 |
| 4 | 5 | 45 |
| 5 | 5 | 95 |
| 6 | 5 | 195 |
| 7 | 5 | 495 |
| 8 | 4 | 496 |
| 9 | 3 | 497 |
| 10 | 2 | 498 |
| 11 | 1 | 499 |
| 12 | 1 | 999 |

3. Enzymatic Reaction: In 96-Well Reaction Plate

Add 5 µL of test article or 5 µL of 20% DMSO or 5 µL of 500 mM EDTA;
Add 10 µL of Enzyme/Substrate stock;
Add 10 µL of ATP Diluent to begin the enzyme reaction and mix on plate shaker;
Add 5 µL of 20% DMSO, 10 µL of assay buffer and 10 µL of ATP standard curve stock into standard curve wells;
Gently shake at 28° C. for 45 min.

4. Stop Reaction and Detect ADP

Prepare Detection Mix: According to the procedures described in the Assay kit, Alexa633 tracer, ADP antibody and stop & detect buffer were added into H$_2$O and mixed thoroughly.

Prepare Tracer Only control: According to the procedures described in the Assay kit, ADP Alexa633 tracer and stop & detect buffer were added to H$_2$O and mixed thoroughly.

Prepare No Tracer control: According to the procedures described in the Assay kit, the stop & detect buffer was diluted with H$_2$O;

Add 25 µL of detection mix, Tracer Only control and No Tracer control into corresponding wells, respectively;

The reaction plate was gently shaken at 28° C. for 1 h;

Florescence polarization (FP) was measured on TECAN F500. Excitation wavelength: 610 nm, Emission wavelength: 670 nm.

5. Data Analysis $$\text{Inhibition (\%)} = 100 - \frac{\text{Compound well [ADP]}}{\text{Positive control well [ADP]}} \times 100$$

Where:
Compound well [ADP] represents the ADP concentration of the compound well.
Positive control well [ADP] represents the ADP concentration of the 20% DMSO well.

Conversion of mP value to ADP concentration is based on the formula which is determined by standard curve. Measurement of mP value follows the suggestion of the instructions provided by BellBrook Labs (www.bellbrooklabs.com).

IC$_{50}$: calculated using XL-Fit 2.0 software.

IC$_{50}$ values of compounds 7, 8, 11, 12, 16, 19, 20, 25, 33, 34, 35, 36, 42, 43, 44, 45, 47, 48, 49, 50, 56, 57, 77, 127, 128, 129, 153, 156, 158, 161, 163, 169, 190, 192, 193, 195, 197, 198, 203, 207, 210, 212, 220, 222, 223, 224, 225, 227, 228, 229, 230, 254, 265, 269, 270, 278, 279, 280, 300, 301, 303, 308, 309, 314, 318, 325, 328, 332, 1, 13, 14, 15, 21, 24, 26, 27, 46, 51, 52, 54, 58, 59, 61, 62, 63, 65, 70, 72, 76, 81, 82, 83, 84, 85, 86, 87, 88, 89, 90, 91, 95, 97, 102, 104, 111, 112, 113, 115, 117, 130, 131, 132, 133, 134, 135, 136, 137, 140, 141, 144, 145, 146, 147, 150, 152, 155, 157, 160, 162, 164, 165, 166, 168, 172, 173, 176, 177, 179, 180, 182, 183, 185, 186, 188, 189, 191, 194, 196, 199, 200, 202, 213, 214, 215, 217, 218, 221, 226, 235, 237, 238, 239, 240, 245, 246, 248, 250, 252, 253, 255, 258, 259, 266, 267, 268, 271, 272, 274, 275, 276, 277, 281, 282, 283, 287, 290, 295, 298, 302, 304, 305, 306, 307, 310, 311, 312, 313, 315, 319, 321, 322, 323, 324, 326, 327, 329, 331 are in the range of 0.001 to less than 0.1 uM.

IC$_{50}$ values of compounds 2, 5, 6, 9, 17, 18, 22, 23, 28, 30, 37, 38, 41, 53, 55, 64, 66, 71, 73, 74, 78, 79, 80, 92, 93, 94, 96, 98, 99, 100, 101, 103, 105, 107, 108, 109, 110, 116, 118, 119, 120, 121, 122, 123, 126, 138, 142, 143, 154, 170, 174, 181, 187, 201, 204, 205, 206, 208, 209, 216, 219, 231, 234, 236, 241, 244, 247, 249, 257, 260, 261, 263, 273, 284, 285, 286, 288, 289, 292, 293, 294, 296, 299, 316, 317, 320, are from 0.1 uM to less than 1 uM.

What is claimed:

1. A compound of formula 1:

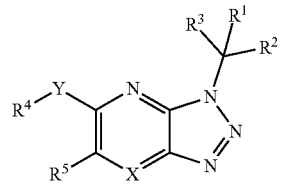

a pharmaceutically acceptable salt thereof wherein
X is C(R$^6$), Y is selected from —O—, and —N(R$^7$)— or Y is absent, and R$^1$ is 8-10 membered heteroaryl optionally substituted with one or more groups selected from halo, —CF$_3$, —CF$_2$H, cycloalkyl, —C(O)R$^{11}$, —C(O)OR$^{11}$, —CN, —C(O)NR$^{13}$R$^{14}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —NO$_2$, —S(O)$_n$R$^{12}$, —S(O)$_n$NR$^{13}$R$^{14}$, heterocycle, heteroaryl, aryl, alkenyl, alkynyl, lower alkyl, lower alkyl substituted with hydroxy, lower alkyl substituted with lower alkoxy, lower alkyl substituted with —NR$^{13}$R$^{14}$, and lower alkyl substituted with heterocycle;

R$^2$ and R$^3$ are independently selected from hydrogen, and alkyl, or R$^2$ and R$^3$, together with the carbon to which they are attached, form a ring chosen from 3- to 7-membered cycloalkyl and 3- to 7-membered heterocycle;

R⁴ is selected from halo, alkyl, cycloalkyl, heterocycle, aryl and heteroaryl, each of which, except for halo, is optionally substituted with one or more groups selected from:
lower alkyl optionally substituted with one or more groups selected from hydroxy, lower alkoxy, cyano, halo, —C(O)OR¹¹, —C(O)NR¹³R¹⁴, —NR¹³R¹⁴, —OC(O)R¹¹, —NR¹³C(O)R¹¹, —NR¹³S(O)ₙR¹², —NR¹³S(O)ₙNR¹³R¹⁴, —NR¹³C(O)OR¹², and —NR¹³C(O)NR¹³R¹⁴,
lower alkoxy optionally substituted with one or more groups selected from halo, hydroxy, and lower alkoxy;
cycloalkoxy optionally substituted with one or more groups selected from halo, hydroxy, and lower alkoxy;
heterocycloalkoxy optionally substituted with one or more groups selected from halo, hydroxy, and lower alkoxy;
heterocycle optionally substituted with one or more groups selected from lower alkyl, halo, hydroxy, and lower alkoxy;
heteroaryloxy optionally substituted with one or more groups selected from lower alkyl, halo, hydroxy, and lower alkoxy;
aryl optionally substituted with one or more groups selected from lower alkyl, halo, hydroxy, and lower alkoxy;
heteroaryl optionally substituted with one or more groups selected from lower alkyl, halo, hydroxy, and lower alkoxy;
halo, cyano, —C(O)R¹¹, —C(O)OR¹¹, —NR¹³R¹⁴, —NR¹³C(O)R¹¹, —NR¹³S(O)ₙR¹², —NR¹³S(O)ₙNR¹³R¹⁴, —NR¹³C(O)OR¹², —NR¹³C(O)NR¹³R¹⁴, —C(O)NR¹³R¹⁴, —S(O)ₙR¹², and —S(O)ₙNR¹³R¹⁴;
R⁵ is selected from hydrogen, halo, OH, NH₂, CF₃, —CF₂H, alkyl, alkenyl, and alkynyl;
R⁶ is selected from hydrogen, —OH, —NH₂, —NHC(O)R¹¹, halo and alkyl;
R⁷ is selected from hydrogen and lower alkyl;
each n is independently 0, 1, or 2;
R¹¹, R¹², R¹³, and R¹⁴ are independently selected from hydrogen, alkyl, alkenyl, alkynyl, cycloalkyl, aryl, heteroaryl, and heterocycle, each of which except for hydrogen, is optionally substituted with one or more groups selected from halo, lower alkyl, hydroxy, and lower alkoxy, or R¹³ and R¹⁴, with the nitrogen to which they are attached, combine to form a heterocycle ring, which is optionally substituted with one or more groups selected from halo, lower alkyl, hydroxy, and lower alkoxy and further optionally includes one or two additional heteroatoms in the heterocycle ring wherein the one or two additional heteroatoms are selected from —O—, —S—, and —N(R¹⁵)—; and
R¹⁵ is selected from hydrogen, lower alkyl, —C(O)R¹¹, —C(O)OR¹¹, —C(O)NR¹³R¹⁴, —S(O)ₙR¹², and —S(O)ₙNR¹³R¹⁴;
provided that R¹ is not optionally substituted phenyl or optionally substituted 4-pyridinyl.

2. The compound of claim 1, or a pharmaceutically acceptable salt thereof, wherein R⁶ is selected from hydrogen and lower alkyl.

3. The compound of claim 2, or a pharmaceutically acceptable salt thereof, wherein R⁶ is hydrogen.

4. The compound of claim 1, or a pharmaceutically acceptable salt thereof, wherein Y is —O—.

5. The compound of claim 1, or a pharmaceutically acceptable salt thereof, wherein Y is —N(R⁷)—.

6. The compound of claim 5, or a pharmaceutically acceptable salt thereof, wherein R⁷ is hydrogen or methyl.

7. The compound of claim 1, or a pharmaceutically acceptable salt thereof, wherein Y is absent.

8. The compound of claim 1, or a pharmaceutically acceptable salt thereof, wherein R¹ is a ring system selected from

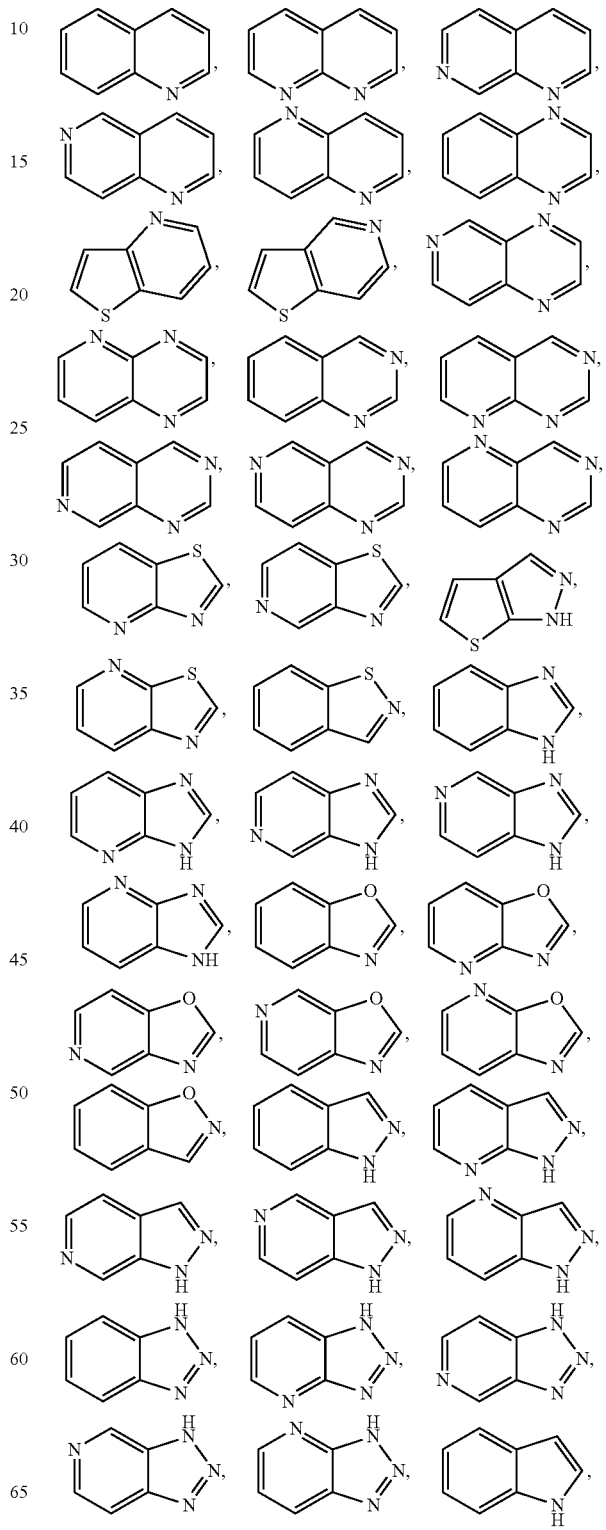

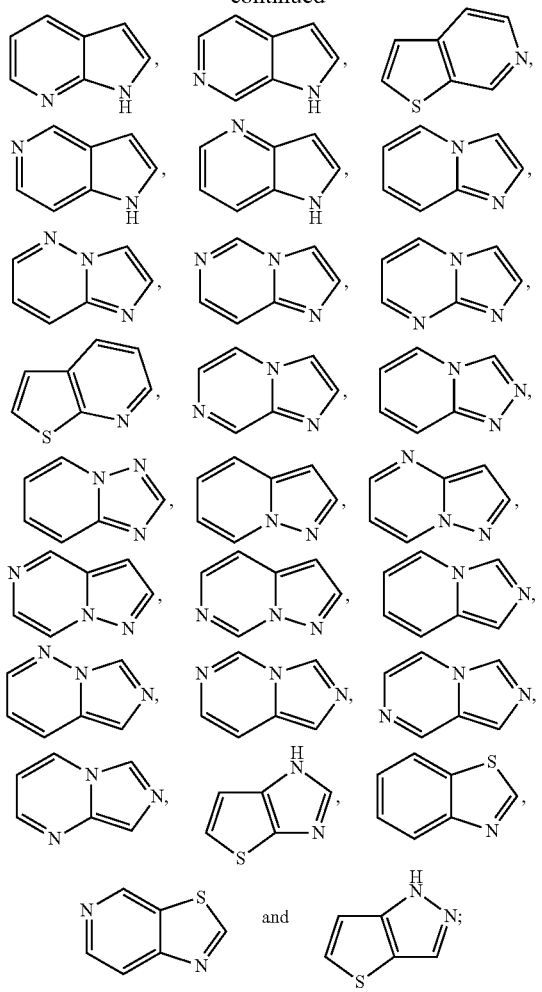

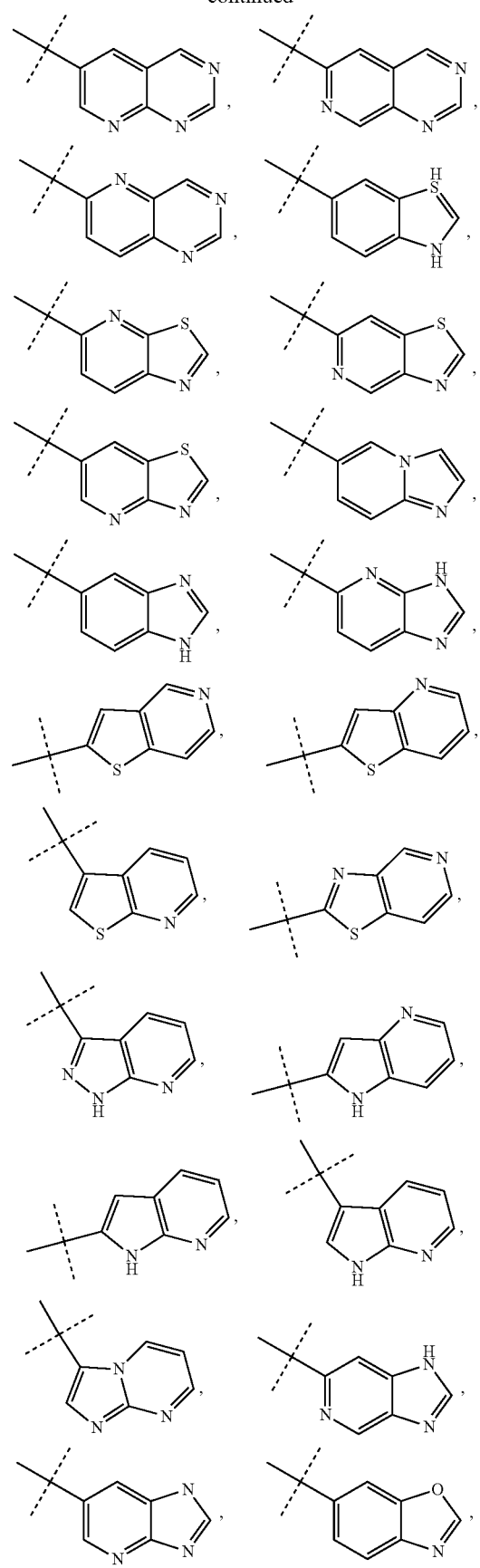

wherein each of said ring systems is optionally substituted with one or more groups selected from halo, $CF_3$, —$CF_2H$, cycloalkyl, —$C(O)R^{11}$, $C(O)OR^{11}$, —CN, —$C(O)NR^{13}R^{14}$, —$NR^{13}R^{14}$, —$NR^{13}C(O)R^{11}$, —$NR^{13}S(O)_nR^{12}$, —$NR^{13}S(O)_nNR^{13}R^{14}$, —$NR^{13}C(O)OR^{12}$, —$NR^{13}C(O)NR^{13}R^{14}$, —$NO_2$, —$S(O)_nR^{12}$, —$S(O)_nNR^{13}R^{14}$, heterocycle, heteroaryl, aryl, alkenyl, alkynyl, lower alkyl, lower alkyl substituted with hydroxy, lower alkyl substituted with lower alkoxy, lower alkyl substituted with —$NR^{13}R^{14}$, and lower alkyl substituted with heterocycle.

9. The compound of claim 1, or a pharmaceutically acceptable salt thereof, wherein $R^1$ is a ring system selected from

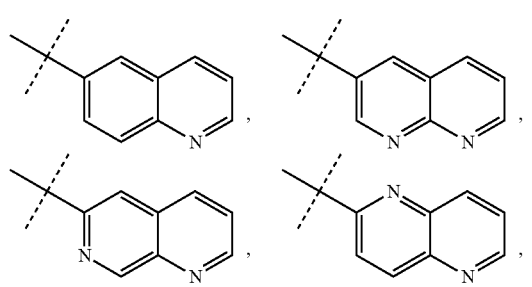

-continued

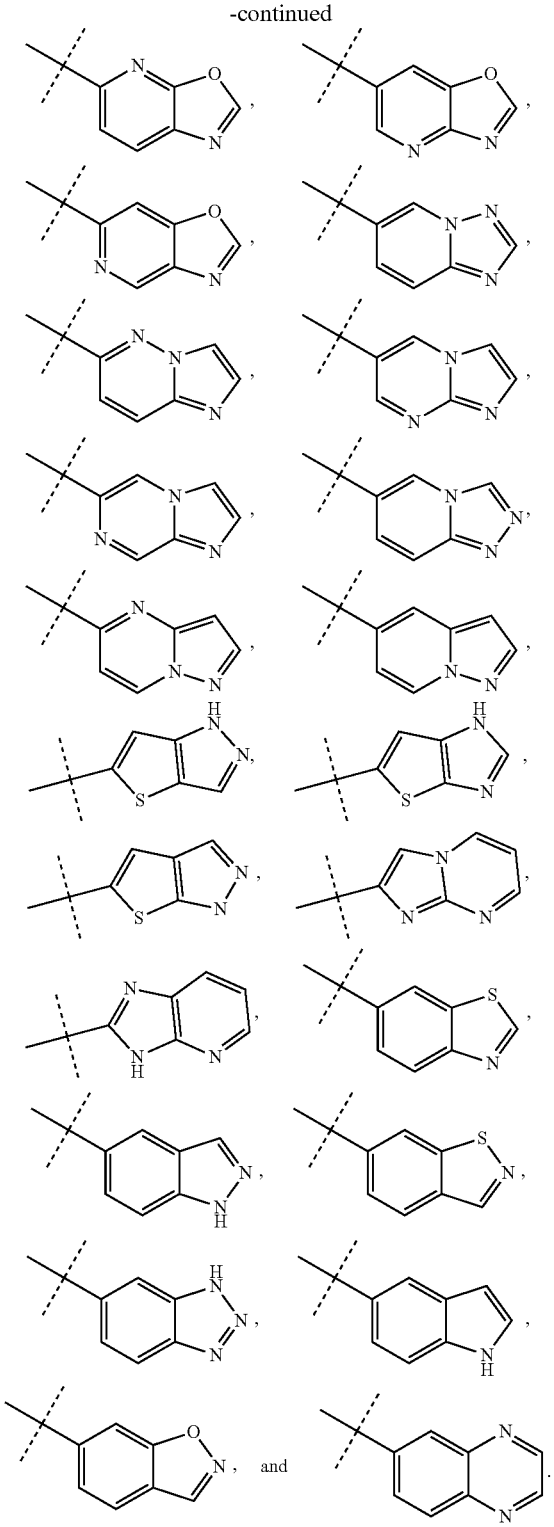

10. The compound of claim 1, or a pharmaceutically acceptable salt thereof, wherein $R^2$ and $R^3$ are independently selected from hydrogen and $C_1$-$C_6$ alkyl or $R^2$ and $R^3$, together with the carbon to which they are attached, form a 3-membered cycloalkyl.

11. The compound of claim 1, or a pharmaceutically acceptable salt thereof, wherein $R^5$ is hydrogen.

12. The compound of claim 1, or a pharmaceutically acceptable salt thereof, wherein $R^4$ is aryl optionally substituted with one or more groups selected from:
lower alkyl optionally substituted with one or more groups selected from hydroxy, lower alkoxy, cyano, halo, —C(O)OR$^{11}$, —C(O)NR$^{13}$R$^{14}$, —NR$^{13}$R$^{14}$, —OC(O)R$^{11}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, and —NR$^{13}$C(O)NR$^{13}$R$^{14}$;
lower alkoxy optionally substituted with one or more groups selected from halo, hydroxy, and lower alkoxy;
heterocycle optionally substituted with one or more groups selected from lower alkyl, halo, hydroxy, and lower alkoxy;
heteroaryloxy optionally substituted with one or more groups selected from lower alkyl, halo, hydroxy, and lower alkoxy;
aryl optionally substituted with one or more groups selected from lower alkyl, halo, hydroxy, and lower alkoxy;
heteroaryl optionally substituted with one or more groups selected from lower alkyl, halo, hydroxy, and lower alkoxy; and
halo, cyano, —C(O)R$^{11}$, —C(O)OR$^{11}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —C(O)NR$^{13}$R$^{14}$, —S(O)$_n$R$^{12}$, and —S(O)$_n$NR$^{13}$R$^{14}$.

13. The compound of claim 1, or a pharmaceutically acceptable salt thereof, wherein $R^4$ is heterocycle optionally substituted with one or more groups selected from:
lower alkyl optionally substituted with one or more groups selected from hydroxy, lower alkoxy, cyano, halo, —C(O)OR$^{11}$, —C(O)NR$^{13}$R$^{14}$, —NR$^{13}$R$^{14}$, —OC(O)R$^{11}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, and —NR$^{13}$C(O)NR$^{13}$R$^{14}$;
lower alkoxy optionally substituted with one or more groups selected from halo, hydroxy, and lower alkoxy;
heterocycle optionally substituted with one or more groups selected from lower alkyl, halo, hydroxy, and lower alkoxy; and
halo, cyano, —C(O)R$^{11}$, —C(O)OR$^{11}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —C(O)NR$^{13}$R$^{14}$, —S(O)$_n$R$^{12}$, and —S(O)$_n$NR$^{13}$R$^{14}$.

14. The compound of claim 13, or a pharmaceutically acceptable salt thereof, wherein $R^4$ is selected from pyrrolidin-1-yl, piperidin-1-yl, tetrahydro-2H-pyran-4-yl, morpholin-4-yl, and 6,7-dihydrothieno[3,2-c]pyridin-5(4H)-yl, each of which is optionally substituted with one or more groups selected from;
lower alkyl optionally substituted with one or more groups selected from hydroxy, lower alkoxy, cyano, halo, —C(O)OR$^{11}$, —C(O)NR$^{13}$R$^{14}$, —NR$^{13}$R$^{14}$, —OC(O)R$^{11}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, and —NR$^{13}$C(O)NR$^{13}$R$^{14}$;
lower alkoxy optionally substituted with one or more groups selected from halo, hydroxy, and lower alkoxy;
heterocycle optionally substituted with one or more groups selected from lower alkyl, halo, hydroxy, and lower alkoxy; and
halo, cyano, —C(O)R$^{11}$, —C(O)OR$^{11}$, —NR$^{13}$R$^{14}$, —NR$^{13}$C(O)R$^{11}$, —NR$^{13}$S(O)$_n$R$^{12}$, —NR$^{13}$S(O)$_n$NR$^{13}$R$^{14}$, —NR$^{13}$C(O)OR$^{12}$, —NR$^{13}$C(O)NR$^{13}$R$^{14}$, —C(O)NR$^{13}$R$^{14}$, —S(O)$_n$R$^{12}$, and —S(O)$_n$NR$^{13}$R$^{14}$.

15. The compound of claim 1, or a pharmaceutically acceptable salt thereof, wherein $R^4$ is heteroaryl optionally substituted with one or more groups selected from:
  lower alkyl optionally substituted with one or more groups selected from hydroxy, lower alkoxy, cyano, halo, $-C(O)OR^{11}$, $-C(O)NR^{13}R^{14}$, $-NR^{13}R^{14}$, $-OC(O)R^{11}$, $-NR^{13}C(O)R^{11}$, $-NR^{13}S(O)_nR^{12}$, $-NR^{13}S(O)_nNR^{13}R^{14}$, $-NR^{13}C(O)OR^{12}$, and $-NR^{13}C(O)NR^{13}R^{14}$;
  lower alkoxy optionally substituted with one or more groups selected from halo, hydroxy, and lower alkoxy;
  heterocycle optionally substituted with one or more groups selected from lower alkyl, halo, hydroxy, and lower alkoxy; and
  halo, cyano, $-C(O)R^{11}$, $-C(O)OR^{11}$, $-NR^{13}R^{14}$, $-NR^{13}C(O)R^{11}$, $-NR^{13}S(O)_nR^{12}$, $-NR^{13}S(O)_nNR^{13}R^{14}$, $-NR^{13}C(O)OR^{12}$, $-NR^{13}C(O)NR^{13}R^{14}$, $-C(O)NR^{13}R^{14}$, $-S(O)_nR^{12}$, and $-S(O)_nNR^{13}R^{14}$.

16. The compound of claim 15, or a pharmaceutically acceptable salt thereof, wherein $R^4$ is selected from 1H-pyrazol-1-yl, 1H-pyrazol-3-yl, 1H-pyrazol-4-yl, 1H-imidazol-1-yl, 1H-imidazol-4-yl, oxazol-2-yl, thiazol-2-yl, isoxazol-3-yl, isoxazol-5-yl, 1H-pyrrol-2-yl, 1H-pyrrol-3-yl, thiophen-2-yl, thiophen-3-yl, pyridin-2-yl, pyridin-3-yl, and pyridin-4-yl, each of which is optionally substituted with one or more groups selected from:
  lower alkyl optionally substituted with one or more groups selected from hydroxy, lower alkoxy, cyano, halo, $-C(O)OR^{11}$, $-C(O)NR^{13}R^{14}$, $-NR^{13}R^{14}$, $-OC(O)R^{11}$, $-NR^{13}C(O)R^{11}$, $-NR^{13}S(O)_nR^{12}$, $-NR^{13}S(O)_nNR^{13}R^{14}$, $-NR^{13}C(O)OR^{12}$, and $-NR^{13}C(O)NR^{13}R^{14}$;
  lower alkoxy optionally substituted with one or more groups selected from halo, hydroxy, and lower alkoxy;
  heterocycle optionally substituted with one or more groups selected from lower alkyl, halo, hydroxy, and lower alkoxy; and
  halo, cyano, $-C(O)R^{11}$, $-C(O)OR^{11}$, $-NR^{13}R^{14}$, $-NR^{13}C(O)R^{11}$, $-NR^{13}S(O)_nR^{12}$, $-NR^{13}S(O)_nNR^{13}R^{14}$, $-NR^{13}C(O)OR^{12}$, $-NR^{13}C(O)NR^{13}R^{14}$, $-C(O)NR^{13}R^{14}$, $-S(O)_nR^{12}$, and $-S(O)_nNR^{13}R^{14}$.

17. A compound of claim 1 or a one pharmaceutically acceptable salt thereof, selected from
  2-(4-(3-(thiazolo[4,5-c]pyridin-2-ylmethyl)-3H-[1,2,3]triazolo[4,5-b]pyridin-5-yl)-1H-pyrazol-1-yl)ethanol;
  2-(4-(3-(quinolin-6-ylmethyl)-3H-[1,2,3]triazolo[4,5-b]pyridin-5-yl)-1H-pyrazol-1-yl)ethanol;
  5-(3-(quinolin-6-ylmethyl)-3H-[1,2,3]triazolo[4,5-b]pyridin-5-yl)pyridin-2-amine;
  4-(5-(3-(quinolin-6-ylmethyl)-3H-[1,2,3]triazolo[4,5-b]pyridin-5-yl)pyridin-2-yl)morpholine;
  6-((5-(1H-pyrrol-2-yl)-3H-[1,2,3]triazolo[4,5-b]pyridin-3-yl)methyl)quinolone;
  ethyl 2-(4-(3-(quinolin-6-ylmethyl)-3H-[1,2,3]triazolo[4,5-b]pyridin-5-yl)-1H-pyrazol-1-yl)acetate;
  2-(4-(3-(quinolin-6-ylmethyl)-3H-[1,2,3]triazolo[4,5-b]pyridin-5-yl)-1H-pyrazol-1-yl)acetic acid;
  2-((5-(1-methyl-1H-pyrazol-4-yl)-3H-[1,2,3]triazolo[4,5-b]pyridin-3-yl)methyl)thieno[3,2-b]pyridine;
  2-(4-(3-(thieno[3,2-b]pyridin-2-ylmethyl)-3H-[1,2,3]triazolo[4,5-b]pyridin-5-yl)-1H-pyrazol-1-yl)ethanol hydrochloride;
  2-(4-(3-((1-(ethoxymethyl)-1H-pyrrolo[2,3-b]pyridin-3-yl)methyl)-3H-[1,2,3]triazolo[4,5-b]pyridin-5-yl)-1H-pyrazol-1-yl)ethanol;
  6-((5-(6-methoxypyridin-3-yl)-3H-[1,2,3]triazolo[4,5-b]pyridin-3-yl)methyl)quinolone;
  2-((5-(1-methyl-1H-pyrazol-4-yl)-3H-[1,2,3]triazolo[4,5-b]pyridin-3-yl)methyl)thieno[3,2-c]pyridine;
  6-((5-(1-methyl-1H-pyrazol-4-yl)-3H-[1,2,3]triazolo[4,5-b]pyridin-3-yl)methyl)benzo[d]thiazole;
  2-(4-(3-(benzo[d]thiazol-6-ylmethyl)-3H-[1,2,3]triazolo[4,5-b]pyridin-5-yl)-1H-pyrazol-1-yl)ethanol;
  2-(4-(3-(thieno[3,2-c]pyridin-2-ylmethyl)-3H-[1,2,3]triazolo[4,5-b]pyridin-5-yl)-1H-pyrazol-1-yl)ethanol;
  3-((1H-pyrrolo[2,3-b]pyridin-2-yl)methyl)-5-(1-methyl-1H-pyrazol-4-yl)-3H-[1,2,3]triazolo[4,5-b]pyridine;
  N-methyl-5-(3-(quinolin-6-ylmethyl)-3H-[1,2,3]triazolo[4,5-b]pyridin-5-yl)pyridin-2-amine;
  (S)-2-(4-(3-(1-(quinolin-6-yl)ethyl)-3H-[1,2,3]triazolo[4,5-b]pyridin-5-yl)-1H-pyrazol-1-yl)ethanol;
  (R)-2-(4-(3-(1-(quinolin-6-yl)ethyl)-3H-[1,2,3]triazolo[4,5-b]pyridin-5-yl)-1H-pyrazol-1-yl)ethanol;
  6-((5-(6-methylpyridin-3-yl)-3H-[1,2,3]triazolo[4,5-b]pyridin-3-yl)methyl)quinolone;
  6-((5-(1H-pyrazol-1-yl)-3H-[1,2,3]triazolo[4,5-b]pyridin-3-yl)methyl)quinolone;
  6-((5-(1H-pyrazol-3-yl)-3H-[1,2,3]triazolo[4,5-b]pyridin-3-yl)methyl)quinolone;
  N-(2-methoxyethyl)-5-(3-(quinolin-6-ylmethyl)-3H-[1,2,3]triazolo[4,5-b]pyridin-5-yl)pyridin-2-amine;
  N-methyl-5-(3-(quinolin-6-ylmethyl)-3H-[1,2,3]triazolo[4,5-b]pyridin-5-yl)picolinamide;
  N-(4-(3-(quinolin-6-ylmethyl)-3H-[1,2,3]triazolo[4,5-b]pyridin-5-yl)phenyl)methanesulfonamide;
  N-(3-(3-(quinolin-6-ylmethyl)-3H-[1,2,3]triazolo[4,5-b]pyridin-5-yl)phenyl)methanesulfonamide;
  2-(4-(3-((1H-pyrrolo[2,3-b]pyridin-3-yl)methyl)-3H-[1,2,3]triazolo[4,5-b]pyridin-5-yl)-1H-pyrazol-1-yl)ethanol;
  6-((5-(thiophen-2-yl)-3H-[1,2,3]triazolo[4,5-b]pyridin-3-yl)methyl)quinolone;
  6-((5-(3-methoxyphenyl)-3H-[1,2,3]triazolo[4,5-b]pyridin-3-yl)methyl)quinolone;
  N-(5-(3-(quinolin-6-ylmethyl)-3H-[1,2,3]triazolo[4,5-b]pyridin-5-yl)pyridin-2-yl)methanesulfonamide;
  N-(5-(3-(quinolin-6-ylmethyl)-3H-[1,2,3]triazolo[4,5-b]pyridin-5-yl)pyridin-2-yl)acetamide;
  N-methyl-3-(4-(3-(quinolin-6-ylmethyl)-3H-[1,2,3]triazolo[4,5-b]pyridin-5-yl)-1H-pyrazol-1-yl)propan-1-amine;
  6-((5-(1-(2-methoxyethyl)-1H-pyrazol-4-yl)-3H-[1,2,3]triazolo[4,5-b]pyridin-3-yl)methyl)quinolone;
  6-((5-(1-(piperidin-4-yl)-1H-pyrazol-4-yl)-3H-[1,2,3]triazolo[4,5-b]pyridin-3-yl)methyl)quinolone;
  6-((5-(1-ethyl-1H-pyrazol-4-yl)-3H-[1,2,3]triazolo[4,5-b]pyridin-3-yl)methyl)quinolone;
  6-((5-(3-(2-methoxyethoxy)phenyl)-3H-[1,2,3]triazolo[4,5-b]pyridin-3-yl)methyl)quinolone;
  6-((5-(4-(2-methoxyethoxy)phenyl)-3H-[1,2,3]triazolo[4,5-b]pyridin-3-yl)methyl)quinolone;
  2-(4-(3-(quinolin-6-ylmethyl)-3H-[1,2,3]triazolo[4,5-b]pyridin-5-yl)-1H-pyrazol-1-yl)ethyl acetate;
  6-((5-(6-(2-methoxyethoxy)pyridin-3-yl)-3H-[1,2,3]triazolo[4,5-b]pyridin-3-yl)methyl)quinolone;
  1-(4-(3-(quinolin-6-ylmethyl)-3H-[1,2,3]triazolo[4,5-b]pyridin-5-yl)-1H-pyrazol-1-yl)propan-2-ol;
  6-((5-(1-(1-methylpiperidin-4-yl)-1H-pyrazol-4-yl)-3H-[1,2,3]triazolo[4,5-b]pyridin-3-yl)methyl)quinolone;
  5-(3-(quinolin-6-ylmethyl)-3H-[1,2,3]triazolo[4,5-b]pyridin-5-yl)thiophene-2-carbonitrile;
  5-(3-(quinolin-6-ylmethyl)-3H-[1,2,3]triazolo[4,5-b]pyridin-5-yl)picolinonitrile;

(5-(3-(quinolin-6-ylmethyl)-3H-[1,2,3]triazolo[4,5-b]pyridin-5-yl)thiophen-2-yl)methanol;
N,N-dimethyl-1-(5-(3-(quinolin-6-ylmethyl)-3H-[1,2,3]triazolo[4,5-b]pyridin-5-yl)thiophen-2-yl)methanamine;
2-(4-(3-((1-methyl-1H-pyrrolo[2,3-b]pyridin-3-yl)methyl)-3H-[1,2,3]triazolo[4,5-b]pyridin-5-yl)-1H-pyrazol-1-yl)ethanol;
6-((5-(2-(2-methoxyethoxy)pyridin-4-yl)-3H-[1,2,3]triazolo[4,5-b]pyridin-3-yl)methyl)quinolone;
6-((5-(1-methyl-1H-imidazol-4-yl)-3H-[1,2,3]triazolo[4,5-b]pyridin-3-yl)methyl)quinolone;
2-(4-(3-(quinolin-6-ylmethyl)-3H-[1,2,3]triazolo[4,5-b]pyridin-5-yl)-1H-imidazol-1-yl)ethanol;
N-(2-methoxyethyl)-4-(3-(quinolin-6-ylmethyl)-3H-[1,2,3]triazolo[4,5-b]pyridin-5-yl)pyridin-2-amine;
3-((1H-pyrrolo[2,3-b]pyridin-3-yl)methyl)-5-(1-(2-methoxyethyl)-1H-pyrazol-4-yl)-3H-[1,2,3]triazolo[4,5-b]pyridine;
3-((1H-pyrrolo[2,3-b]pyridin-3-yl)methyl)-5-(3-methoxyphenyl)-3H-[1,2,3]triazolo[4,5-b]pyridine;
2-(4-(3-(1-(1H-pyrrolo[2,3-b]pyridin-3-yl)ethyl)-3H-[1,2,3]triazolo[4,5-b]pyridin-5-yl)-1H-pyrazol-1-yl)ethanol;
3-([1,2,4]triazolo[1,5-a]pyridin-6-ylmethyl)-5-(1-(2-methoxyethyl)-1H-pyrazol-4-yl)-3H-[1,2,3]triazolo[4,5-b]pyridine
N-(5-(3-((1H-pyrrolo[2,3-b]pyridin-3-yl)methyl)-3H-[1,2,3]triazolo[4,5-b]pyridin-5-yl)pyridin-2-yl)acetamide;
3-((1H-pyrrolo[2,3-b]pyridin-3-yl)methyl)-5-(1-(piperidin-4-yl)-1H-pyrazol-4-yl)-3H-[1,2,3]triazolo[4,5-b]pyridine;
2-(4-(3-(quinolin-6-ylmethyl)-3H-[1,2,3]triazolo[4,5-b]pyridin-5-yl)-1H-pyrazol-1-yl)acetonitrile;
6-((5-(1-(tetrahydro-2H-pyran-4-yl)-1H-pyrazol-4-yl)-3H-[1,2,3]triazolo[4,5-b]pyridin-3-yl)methyl)quinolone;
2-(4-(3-(quinolin-6-ylmethyl)-3H-[1,2,3]triazolo[4,5-b]pyridin-5-yl)-1H-pyrazol-1-yl)cyclopentanol;
3-([1,2,4]triazolo[1,5-a]pyridin-6-ylmethyl)-5-(1-methyl-1H-pyrazol-4-yl)-3H-[1,2,3]triazolo[4,5-b]pyridine;
3-([1,2,4]triazolo[1,5-a]pyridin-6-ylmethyl)-5-(1-(2,2,2-trifluoroethyl)-1H-pyrazol-4-yl)-3H-[1,2,3]triazolo[4,5-b]pyridine;
6-(1-(5-(1-methyl-1H-pyrazol-4-yl)-3H-[1,2,3]triazolo[4,5-b]pyridin-3-yl)cyclopropyl)quinolone;
2-(4-(3-(1-(quinolin-6-yl)cyclopropyl)-3H-[1,2,3]triazolo[4,5-b]pyridin-5-yl)-1H-pyrazol-1-yl)ethanol;
2-(4-(3-(thieno[2,3-b]pyridin-3-ylmethyl)-3H-[1,2,3]triazolo[4,5-b]pyridin-5-yl)-1H-pyrazol-1-yl)ethanol;
3-((5-(1-methyl-1H-pyrazol-4-yl)-3H-[1,2,3]triazolo[4,5-b]pyridin-3-yl)methyl)thieno[2,3-b]pyridine;
2-(4-(3-([1,2,4]triazolo[1,5-a]pyridin-6-ylmethyl)-3H-[1,2,3]triazolo[4,5-b]pyridin-5-yl)-1H-pyrazol-1-yl)ethanol;
7-fluoro-6-((5-(1-methyl-1H-pyrazol-4-yl)-3H-[1,2,3]triazolo[4,5-b]pyridin-3-yl)methyl)quinolone;
2-(4-(3-((7-fluoroquinolin-6-yl)methyl)-3H-[1,2,3]triazolo[4,5-b]pyridin-5-yl)-1H-pyrazol-1-yl)ethanol hydrochloride;
5-fluoro-6-((5-(1-methyl-1H-pyrazol-4-yl)-3H-[1,2,3]triazolo[4,5-b]pyridin-3-yl)methyl)quinolone;
2-(4-(3-((5-fluoroquinolin-6-yl)methyl)-3H-[1,2,3]triazolo[4,5-b]pyridin-5-yl)-1H-pyrazol-1-yl)ethanol hydrochloride;
6-((5-(1-ethyl-1H-pyrazol-4-yl)-3H-[1,2,3]triazolo[4,5-b]pyridin-3-yl)methyl)quinolone;
5-((5-(1-methyl-1H-pyrazol-4-yl)-3H-[1,2,3]triazolo[4,5-b]pyridin-3-yl)methyl)-1H-thieno[3,2-c]pyrazole;
3-(imidazo[1,2-a]pyridin-6-ylmethyl)-5-(1-methyl-1H-pyrazol-4-yl)-3H-[1,2,3]triazolo[4,5-b]pyridine;
2-(4-(3-(imidazo[1,2-a]pyridin-6-ylmethyl)-3H-[1,2,3]triazolo[4,5-b]pyridin-5-yl)-1H-pyrazol-1-yl)ethanol;
5-(1-ethyl-1H-pyrazol-4-yl)-3-(imidazo[1,2-a]pyridin-6-ylmethyl)-3H-[1,2,3]triazolo[4,5-b]pyridine;
3-(imidazo[1,2-a]pyridin-6-ylmethyl)-5-(1-isopropyl-1H-pyrazol-4-yl)-3H-[1,2,3]triazolo[4,5-b]pyridine;
3-((1H-pyrazolo[3,4-b]pyridin-3-yl)methyl)-5-(1-ethyl-1H-pyrazol-4-yl)-3H-[1,2,3]triazolo[4,5-b]pyridine;
2-(4-(3-((1H-pyrazolo[3,4-b]pyridin-3-yl)methyl)-3H-[1,2,3]triazolo[4,5-b]pyridin-5-yl)-1H-pyrazol-1-yl)ethanol;
2-(4-(3-(thiazolo[5,4-b]pyridin-5-ylmethyl)-3H-[1,2,3]triazolo[4,5-b]pyridin-5-yl)-1H-pyrazol-1-yl)ethanol;
3-(imidazo[1,2-a]pyridin-6-ylmethyl)-5-(1-propyl-1H-pyrazol-4-yl)-3H-[1,2,3]triazolo[4,5-b]pyridine;
3-(imidazo[1,2-a]pyridin-6-ylmethyl)-5-(1-(2,2,2-trifluoroethyl)-1H-pyrazol-4-yl)-3H-[1,2,3]triazolo[4,5-b]pyridine;
5-((5-(1-methyl-1H-pyrazol-4-yl)-3H-[1,2,3]triazolo[4,5-b]pyridin-3-yl)methyl)thiazolo[5,4-b]pyridine;
3-(imidazo[1,2-a]pyridin-6-ylmethyl)-5-(1-(tetrahydro-2H-pyran-4-yl)-1H-pyrazol-4-yl)-3H-[1,2,3]triazolo[4,5-b]pyridine;
6-((5-(1-isopropyl-1H-pyrazol-4-yl)-3H-[1,2,3]triazolo[4,5-b]pyridin-3-yl)methyl)quinolone;
6-((5-(1H-pyrazol-4-yl)-3H-[1,2,3]triazolo[4,5-b]pyridin-3-yl)methyl)quinolone;
6-((5-(1-propyl-1H-pyrazol-4-yl)-3H-[1,2,3]triazolo[4,5-b]pyridin-3-yl)methyl)quinolone;
6-((5-(1-(2,2,2-trifluoroethyl)-1H-pyrazol-4-yl)-3H-[1,2,3]triazolo[4,5-b]pyridin-3-yl)methyl)quinolone;
2-(4-(3-(thiazolo[5,4-b]pyridin-2-ylmethyl)-3H-[1,2,3]triazolo[4,5-b]pyridin-5-yl)-1H-pyrazol-1-yl)ethanol;
2-((5-(1-methyl-1H-pyrazol-4-yl)-3H-[1,2,3]triazolo[4,5-b]pyridin-3-yl)methyl)thiazolo[5,4-b]pyridine;
6-((5-(1-(methylsulfonyl)-1H-pyrazol-4-yl)-3H-[1,2,3]triazolo[4,5-b]pyridin-3-yl)methyl)quinolone;
5-(1-methyl-1H-pyrazol-4-yl)-3-(pyrazolo[1,5-a]pyrimidin-5-ylmethyl)-3H-[1,2,3]triazolo[4,5-b]pyridine;
N-(3-chlorophenyl)-3-(thieno[3,2-c]pyridin-2-ylmethyl)-3H-[1,2,3]triazolo[4,5-b]pyridin-5-amine;
N-(4-chlorophenyl)-3-(thieno[3,2-c]pyridin-2-ylmethyl)-3H-[1,2,3]triazolo[4,5-b]pyridin-5-amine;
N-(4-methoxypyridin-2-yl)-3-(quinolin-6-ylmethyl)-3H-[1,2,3]triazolo[4,5-b]pyridin-5-amine;
N-(2-methoxypyridin-4-yl)-3-(quinolin-6-ylmethyl)-3H-[1,2,3]triazolo[4,5-b]pyridin-5-amine;
N-(5-methoxypyridin-3-yl)-3-(quinolin-6-ylmethyl)-3H-[1,2,3]triazolo[4,5-b]pyridin-5-amine;
N-(6-methylpyridin-2-yl)-3-(quinolin-6-ylmethyl)-3H-[1,2,3]triazolo[4,5-b]pyridin-5-amine;
N-(5-methylpyridin-3-yl)-3-(quinolin-6-ylmethyl)-3H-[1,2,3]triazolo[4,5-b]pyridin-5-amine;
N-(1-methyl-1H-pyrazol-3-yl)-3-(quinolin-6-ylmethyl)-3H-[1,2,3]triazolo[4,5-b]pyridin-5-amine;
N-(3-(2-methoxyethoxy)phenyl)-3-(quinolin-6-ylmethyl)-3H-[1,2,3]triazolo[4,5-b]pyridin-5-amine;
6-((5-(1H-imidazol-1-yl)-3H-[1,2,3]triazolo[4,5-b]pyridin-3-yl)methyl)quinolone;
4-((3-(quinolin-6-ylmethyl)-3H-[1,2,3]triazolo[4,5-b]pyridin-5-yl)amino)picolinonitrile;

(1R,2R)-2-((2-((3-(quinolin-6-ylmethyl)-3H-[1,2,3]triazolo[4,5-b]pyridin-5-yl)amino)pyridin-4-yl)amino)cyclopentanol;

4-methoxy-N-(3-(quinolin-6-ylmethyl)-3H-[1,2,3]triazolo[4,5-b]pyridin-5-yl)benzenesulfonamide;

N-(4-(2-methoxyethoxy)pyridin-2-yl)-3-(quinolin-6-ylmethyl)-3H-[1,2,3]triazolo[4,5-b]pyridin-5-amine;

N-(5-methoxypyridin-2-yl)-3-(quinolin-6-ylmethyl)-3H-[1,2,3]triazolo[4,5-b]pyridin-5-amine;

N-(2-methylpyridin-4-yl)-3-(quinolin-6-ylmethyl)-3H-[1,2,3]triazolo[4,5-b]pyridin-5-amine;

N-(pyridin-4-yl)-3-(quinolin-6-ylmethyl)-3H-[1,2,3]triazolo[4,5-b]pyridin-5-amine;

N-(pyridin-3-yl)-3-(quinolin-6-ylmethyl)-3H-[1,2,3]triazolo[4,5-b]pyridin-5-amine;

(1R,2R)-2-((3-(quinolin-6-ylmethyl)-3H-[1,2,3]triazolo[4,5-b]pyridin-5-yl)amino)cyclopentanol;

(1S,2R)-2-((3-(quinolin-6-ylmethyl)-3H-[1,2,3]triazolo[4,5-b]pyridin-5-yl)amino)cyclopentanol;

(1R,2S)-2-((3-(quinolin-6-ylmethyl)-3H-[1,2,3]triazolo[4,5-b]pyridin-5-yl)amino)cyclopentanol;

5-(3-(quinolin-6-ylmethyl)-3H-[1,2,3]triazolo[4,5-b]pyridin-5-yl)-4,5,6,7-tetrahydrothieno[3,2-c]pyridine;

(1-(3-(quinolin-6-ylmethyl)-3H-[1,2,3]triazolo[4,5-b]pyridin-5-yl)piperidin-4-yl)methanol;

1-(3-(quinolin-6-ylmethyl)-3H-[1,2,3]triazolo[4,5-b]pyridin-5-yl)pyrrolidin-3-ol;

1-(((3-(quinolin-6-ylmethyl)-3H-[1,2,3]triazolo[4,5-b]pyridin-5-yl)amino)methyl)cyclohexanol;

6-((5-((tetrahydro-2H-pyran-4-yl)oxy)-3H-[1,2,3]triazolo[4,5-b]pyridin-3-yl)methyl)quinolone;

3-(quinolin-6-ylmethyl)-N-(tetrahydro-2H-pyran-4-yl)-3H-[1,2,3]triazolo[4,5-b]pyridin-5-amine;

N-(5-(1-methyl-1H-pyrazol-4-yl)-3-(quinolin-6-ylmethyl)-3H-[1,2,3]triazolo[4,5-b]pyridin-7-yl)acetamide;

5-(1-methyl-1H-pyrazol-4-yl)-3-(quinolin-6-ylmethyl)-3H-[1,2,3]triazolo[4,5-b]pyridin-7-ol;

6-((7-chloro-5-(1-methyl-1H-pyrazol-4-yl)-3H-[1,2,3]triazolo[4,5-b]pyridin-3-yl)methyl)quinolone;

5-(1-methyl-1H-pyrazol-4-yl)-3-(quinolin-6-ylmethyl)-3H-[1,2,3]triazolo[4,5-b]pyridin-7-amine;

2-(4-(3-(imidazo[1,2-b]pyridazin-6-ylmethyl)-3H-[1,2,3]triazolo[4,5-b]pyridin-5-yl)-1H-pyrazol-1-yl)ethanol;

2-((5-(1-methyl-1H-pyrazol-4-yl)-3H-[1,2,3]triazolo[4,5-b]pyridin-3-yl)methyl)-1,5-naphthyridine;

2-((5-(1-(2,2,2-trifluoroethyl)-1H-pyrazol-4-yl)-3H-[1,2,3]triazolo[4,5-b]pyridin-3-yl)methyl)-1,5-naphthyridine;

2-(4-(3-(1,5-naphthyridin-2-yl)methyl)-3H-[1,2,3]triazolo[4,5-b]pyridin-5-yl)-1H-pyrazol-1-yl)ethanol; and 2-(4-)3-(1-(quinolin-6-yl)ethyl)-3H-[1,2,3]triazolo[4,5-b]pyridin-5-yl)-1H-pyrazol-1-yl)ethanol.

18. A pharmaceutical composition comprising a compound of claim 1, or a pharmaceutically acceptable salt thereof and at least one pharmaceutically acceptable carrier.

* * * * *